(12) United States Patent
Bohlmann et al.

(10) Patent No.: US 8,889,381 B2
(45) Date of Patent: Nov. 18, 2014

(54) DITERPENE SYNTHASES AND METHOD FOR PRODUCING DITERPENOIDS

(71) Applicants: Joerg Bohlmann, Vancouver (CA); Philipp Zerbe, North Vancouver (CA)

(72) Inventors: Joerg Bohlmann, Vancouver (CA); Philipp Zerbe, North Vancouver (CA)

(73) Assignee: University of British Columbia, Vancouver (CA)

( * ) Notice: Subject to any disclaimer, the term of this patent is extended or adjusted under 35 U.S.C. 154(b) by 0 days.

(21) Appl. No.: 13/694,350

(22) Filed: Nov. 21, 2012

(65) Prior Publication Data

US 2013/0224809 A1    Aug. 29, 2013

Related U.S. Application Data

(60) Provisional application No. 61/562,280, filed on Nov. 21, 2011.

(51) Int. Cl.
| | |
|---|---|
| *C07H 21/04* | (2006.01) |
| *C12N 9/88* | (2006.01) |
| *C07D 307/77* | (2006.01) |
| *C12P 7/02* | (2006.01) |
| *C12N 15/52* | (2006.01) |
| *C12P 15/00* | (2006.01) |

(52) U.S. Cl.
CPC ........... *C12N 9/88* (2013.01); *C12Y 402/03018* (2013.01); *C07D 307/77* (2013.01); *C12P 7/02* (2013.01); *C12N 15/52* (2013.01); *C12P 15/00* (2013.01); *C12Y 402/03032* (2013.01)
USPC ..... 435/127; 435/155; 435/320.1; 435/252.3; 435/252.33; 435/254.11; 435/254.2; 435/257.2; 435/325; 435/348; 435/410; 435/419; 536/23.2

(58) Field of Classification Search
None
See application file for complete search history.

(56) References Cited

U.S. PATENT DOCUMENTS

| | | | | |
|---|---|---|---|---|
| 4,952,496 | A | 8/1990 | Studier et al. | 435/91 |
| 5,177,306 | A * | 1/1993 | Whitaker | 800/317.3 |
| 5,525,728 | A | 6/1996 | Schneider et al. | 549/299 |
| 6,531,303 | B1 | 3/2003 | Millis et al. | 435/155 |
| 6,689,593 | B2 | 2/2004 | Millis et al. | 435/155 |
| 7,238,514 | B2 | 7/2007 | Matsuda et al. | 435/252.3 |
| 7,838,279 | B2 | 11/2010 | Millis et al. | 435/254.2 |
| 7,842,497 | B2 | 11/2010 | Millis et al. | 435/254.2 |

(Continued)

FOREIGN PATENT DOCUMENTS

| | | |
|---|---|---|
| EP | 2 363 458 | 9/2011 |
| WO | WO 2008/007031 | 1/2008 |

(Continued)

OTHER PUBLICATIONS

Guo et al., "Protein tolerance to random amino acid change", Proceedings of the National Academy of Sciences USA, vol. 101, No. 25, pp. 9205-9210, 2004.*

(Continued)

*Primary Examiner* — Rebecca Prouty
*Assistant Examiner* — Richard Ekstrom
(74) *Attorney, Agent, or Firm* — McKenna Long & Aldridge LLP; Stephanie Seidman

(57) ABSTRACT

Provided herein are diterpene synthases (diTPS) and methods for producing diterpenoids. Also provided herein are nucleic acid sequences encoding diTPS, diTPS amino acid sequences, diTPS proteins, vectors, cells, transgenic organisms, uses, compositions, methods, processes, and kits thereof.

22 Claims, 12 Drawing Sheets

(56) References Cited

U.S. PATENT DOCUMENTS

| | | | |
|---|---|---|---|
| 7,906,710 B2 | 3/2011 | Karunanandaa et al. | 800/306 |
| 2004/0249219 A1 | 12/2004 | Saucy | 568/388 |
| 2008/0281135 A1 | 11/2008 | Tissier et al. | 585/240 |
| 2009/0123984 A1 | 5/2009 | Chappell et al. | 435/166 |
| 2010/0297722 A1 | 11/2010 | Anterola et al. | 435/167 |
| 2011/0041218 A1 | 2/2011 | Schalk | 800/298 |
| 2011/0189717 A1 | 8/2011 | Ajikumar et al. | 435/29 |
| 2011/0280960 A1* | 11/2011 | Rubens et al. | 424/641 |
| 2012/0208173 A1 | 8/2012 | Zulak et al. | 435/4 |
| 2013/0189677 A1 | 7/2013 | Breuil et al. | 435/6.11 |

FOREIGN PATENT DOCUMENTS

| | | |
|---|---|---|
| WO | WO 2009/044336 | 4/2009 |
| WO | WO 2009/095366 | 8/2009 |
| WO | WO 2009/101126 | 8/2009 |
| WO | WO 2013/075239 | 5/2013 |
| WO | WO 2013/110191 | 8/2013 |

OTHER PUBLICATIONS

International Search Report and Written Opinion, issued Feb. 6, 2013, in connection with corresponding International Patent Application No. PCT/CA2012/050837, 16 pages.

Altschul et al., "Basic local alignment search tool," J. Molec. Biol. 215(3):403-410 (1990).

Altschul et al., "Gapped BLAST and PSI-BLAST: a new generation of protein database search programs," Nucleic Acids Res. 25:3389-3402 (1997).

Barrero et al., "Synthesis of Ambrox® from (−)-sclareol and (+)-cis-abienol," Tetrahedron 49(45):10405-10412 (1993).

Barrero et al., "Synthesis of nor-ambreinolide from (+)-cis-abienol," Tetrahedron 50(22):6653-6662 (1994).

Barrero et al., "Degradation of the side chain of (−)-sclareol: a very short synthesis of nor-ambreinolide and Ambrox," Synth. Comm. 34(19):3631-3643 (2004).

Beier and Young, "Characterization of a regulatory region upstream of the ADR2 locus of S. cerevisiae," Nature 300:724-728 (1982).

Bleeker et al., "RNA-seq discovery, functional characterization, and comparison of sesquiterpene synthases from Solanum lycopersicum and Solanum habrochaites trichomes," Plant Mol. Biol. 77:323-336 (2011).

Bohlmann et al., "Terpenoid-based defenses in conifers: cDNA cloning, characterization, and functional expression of wound-inducible (E)-α-bisabolene synthase from grand fir (Abies grandis)," Proc. Natl. Acad. Sci. U.S.A. 95:6756-6761 (1993).

Bohlmann et al., "Monoterpene synthases from grand fir (Abies grandis)," J. Biol. Chem. 272:21784-21792 (1997).

Bohlmann et al., "Plant terpenoid synthases: molecular biology and phylogenetic analysis," Proc. Natl. Acad. Sci. U.S.A. 95:4126-4133 (1998).

Bohlmann et al., "cDNA cloning, characterization, and functional expression of four new monoterpene synthase members of the Tpsd gene family from Grand Fir (Abies grandis)," Arch. Biochem. Biophys. 368(2):232-243 (1999).

Bohlmann et al., "Terpenoid biomaterials," Plant J. 54(4):656-669 (2008).

Bohlmann, "Terpenoid synthases—from chemical ecology and forest fires to biofuels and bioproducts," Structure 19(12):1730-1731 (2011).

Bohlmann, "Pine terpenoid defences in the mountain pine beetle epidemic and in other conifer pest interactions: specialized enemies are eating holes into a diverse, dynamic and durable defence system," Tree Physiol. 943-945 (2012).

Brodelius et al., "Fusion of farnesyldiphosphate synthase and epi-aristolochene synthase, a sesquiterpene cyclase involved in capsidiol biosynthesis in Nicotiana tabacum," Eur. J. Biochem. 269:3570-3577 (2002).

Caniard et al., "Discovery and functional characterization of two diterpene synthases for sclareol biosynthesis in Salvia sclarea (L.) and their relevance for perfume manufacture," BMC Plant Biol. 12:119 (2012).

Carman et al., "The biosynthesis of labdanoids. The optical purity of naturally occurring manool and abienol," Aust. J. Chem. 46:1105-1114 (1993).

Chen et al., "The family of terpene synthases in plants: a mid-size family of genes for specialized metabolism that is highly diversified throughout the kingdom," Plant J. 66:212-229 (2011).

de Boer et al., "The tac promoter: a functional hybrid derived from the trp and lac promoters," Proc. Natl. Acad. Sci. U.S.A. 80:21-25 (1983).

de la Bastide et al., "Assembling genomic DNA sequences with PHRAP," Curr. Protoc. Bioinformatics Ch. 11:Unit 11.4 (2007).

Ding et al., "Quantification of cis-Abienol in oriental tobacco leaves by LC," Chromatographia 66:529-532 (2007).

Falara et al, "A copal-8-ol diphosphate synthase from the angiosperm Cistus creticus subsp. Creticus is a putative key enzyme for the formation of pharmacologically active, oxygen-containing labdane-type diterpenes," Plant Physiol. 154(1):301-310 (2010).

Fleer et al., "High-level secretion of correctly processed recombinant human interleukin-1β in Kluyveromyces lactis," Gene 107:285-295 (1991).

Franceschi et al., "Anatomical and chemical defenses of conifer bark against bark beetles and other pests," New Phytol. 167:353-375 (2005).

Gambliel and Croteau, "Pinene cyclases I and II. Two enzymes from sage (Salvia officinalis) which catalyze sterospecific cyclizations of geranyl pyrophosphate to monoterpene olefins of opposite configuration," J. Biol. Chem . 259:740-748 (1984).

Genbank Accession No. AY779541, "Pinus taeda diterpene synthase mRNA, complete cds," Published on Jun. 2, 2005 [online][ retrieved on Feb. 19, 2013] Retrieved from:<URL: ncbi.nlm.nih.gov/nuccore/AY779541 [2 pages].

Genbank Accession No. AAC49310, "taxadiene synthase [Taxus brevifolia]," Published on Jun. 5, 1993 [online][retrieved on Feb. 19, 2013] Retrieved from:<URL: ncbi.nlm.nih.gov/protein/AAC49310 [2 pages].

Genbank Accession No. AAK83563, "abietadiene synthase [Abies grandis]," Published on Aug. 3, 2001 [online][ Feb. 19, 2013] Retrieved from:<URL: ncbi.nlm.nih.gov/protein/AAK83563 [2 pages].

Genbank Accession No. AAL09965, "levopimaradiene synthase [Ginkgo biloba]," Published on Oct. 3, 2001 [online][retrieved on Feb. 20, 2013] Retrieved from:<URL: ncbi.nlm.nih.gov/protein/15865065 [2 pages].

Genbank Accession No. AAS18603, "taxadiene synthase [Taxus x media]," Published on Aug. 17, 2007 [online][retrieved on Feb. 19, 2013] Retrieved from:<URL: ncbi.nlm.nih.gov/protein/Aas18603 [2 pages].

Genbank Accession No. AAS47690, "isopimaradiene synthase [Picea abies]," Published on Apr. 8, 2009 [online][ retrieved on Feb. 19, 2013] Retrieved from:<URL: ncbi.nlm.nih.gov/protein/AAS47690 [2 pages].

Genbank Accession No. AAS47691.1, "levopimaradiene/abietadiene synthase [Picea abies]," Published on Aug. 4, 2009 [online][retrieved on Mar. 19, 2012] Retrieved from:<URL:ncbi.nlm.nih.gov/protein/AAS47691.1, 2 pages.

Genbank Accession No. ABW82997, "taxadiene synthase [Taxus cuspidata var. nana]," Published on Aug. 13, 2009 [online][ retrieved on Feb. 19, 2013] Retrieved from:<URL: ncbi.nlm.nih.gov/protein/ABW82997 [1 page].

Genbank Accession No. ADZ45512, "isopimaradiene synthase [Picea sitchensis]," Published on Mar. 16, 2011 [online][ retrieved on Feb. 19, 2013] Retrieved from:<URL: ncbi.nlm.nih.gov/protein/ADZ45512 [2 pages].

Genbank Accession No. ADZ45517, "levopimaradiene/abietadiene synthase [Picea sitchensis]," Published on Mar. 16, 2011 [online][ retrieved on Feb. 19, 2013] Retrieved from:<URL: ncbi.nlm.nih.gov/protein/ADZ45517 [2 pages].

(56) References Cited

OTHER PUBLICATIONS

Genbank Accession No. BAF61135, "ent-kaurene synthase [*Physcomitrella patens*]," Published on May 9, 2007 [online][ retrieved on Feb. 19, 2013] Retrieved from:<URL: ncbi.nlm.nih.gov/protein/BAF61135 [2 pages].
Gilbert et al., "Useful proteins from recombinant bacteria," Sci. Am. 242(3):74-94 (1980).
Gray et al., "The isolation of abienol from Canada Balsam, the oleoresin of *Abies balsamea* (L.) Mill.," J. Chem. Soc. 5822-5825 (1964).
Greenhagen et al., "Identifying and manipulating structural determinates linking catalytic specificities in terpene synthases," Proc. Natl. Acad. Sci. U.S.A. 103:9826-9831 (2006).
Guindon et al., "New algorithms and methods to estimate maximum-likelihood phylogenies: assessing the performance of PhyML3.0," Syst. Biol. 59(3):307-321 (2010).
Guo et al., "Biosynthesis of the diterpene cis-abienol in cell-free extracts of tobacco trichomes," Arch. Biochem. Biophys. 308:103-108 (1994).
Guo et al., "Biosynthesis of labdenediol and sclareol in cell-free extracts from trichomes of *Nicotiana glutinosa*," Planta 197:627-632 (1995).
Hall et al., "Evolution of conifer diterpene synthases: diterpene resin acid biosynthesis in odgepole pine and jack pine involves monofunctional and bifunctional diterpene synthases," Plant Physiol. 161(2):600-616 (2013).
Hamberger et al., "Cytochrome P450 mono-oxygenases in conifer genomes: discovery of members of the terpenoid oxygenase superfamily in spruce and pine," Biochem. Soc. Trans. 34(6):1209-1214 (2006).
Hamberger et al., "Evolution of diterpene metabolism: Sitka spruce CYP720B4 catalyzes multiple oxidations in resin acid biosynthesis of conifer defense against insects," Plant Physiol. 157:1677-1695 (2011).
Hayashi et al., "Identification and functional analysis of bifunctional ent-kaurene synthase from the moss *Physcomitrella patens*," FEBS Lett. 580:6175-6181 (2006).
Hess et al., "Cooperation of glycolytic enzymes," Adv. Enzyme Reg. 7:149-167 (1969).
Hillwig et al., "Diterpenoid biopolymers: new directions for renewable materials engineering," Biopolymers 95(2):71-76 (2010).
Hitzeman et al., "Isolation and characterization of the yeast 3-phosphoglycerokinase gene (PGK) by an immunological screening technique," J. Biol. Chem. 255:12073-12080 (1980).
Holland and Holland, "Isolation and identification of yeast messenger ribonucleic acids coding for enolase, glyceraldehyde-3-phosphate dehydrogenase, and phosphoglycerate kinase," Biochem. 17:4900-4907 (1978).
Holm et al., "DaliLite workbench for protein structure comparison," Bioinformatics 16(6):566-567 (2000).
IUPAC-IUB Commission on Biochemical Nomenclature, "A one-letter notation for amino acid sequences. Tentative rules," J. Biol. Chem. 243(13):3557-3559 (1968).
IUPAC-IUB Commission on Bio-Chemical Nomenclature Symbols for Amino-Acid Derivatives and Peptides, "Recommendations," Biochem. 11(9):1726-1732 (1972).
Jay et al., "Construction of a general vector for efficient expression of mammalian proteins in bacteria: use of a synthetic ribosome binding site," Proc. Natl. Acad. Sci. U.S.A. 78(9):5543-5548 (1981).
Jones, "Isolation of cDNAs and functional characterisation of two multi-product terpene synthase enzymes from sandalwood, *Santalum album* L.," Arch. Biochem. Biophys. 477(1):121-130 (2008).
Jones et al., "Sandalwood fragrance biosynthesis involves sesquiterpene synthases of both the terpene synthase (TPS)-a and TPS-b subfamilies, including santalene synthases," J. Biol. Chem. 286(20):17445-17454 (2011).
Kawaide et al., "Identification of the single amino acid involved in quenching the ent-kauranyl cation by a water molecule in ent-kaurene synthase of *Physcomitrella patens*," FEBS J. 278(1):123133 (2011).
Keeling et al., "Diterpene resin acids in conifers," Phytochem. 67:2415-2423 (2006).
Keeling et al., "Genes, enzymes and chemicals of terpenoid diversity in the constitutive and induced defence of conifers against insects and pathogens," New Phytol. 170:657-675 (2006).
Keeling et al., "Functional plasticity of paralogous diterpene synthases involved in conifer defense,"Proc. Natl. Acad. Sci. U.S.A. 105(3):1085-1090 (2008).
Keeling et al., "Identification and functional characterization of monofunctional ent-copalyl diphosphate and ent-kaurene synthases in white spruce reveal different patterns for diterpene synthase evolution for primary and secodary metabolism in gymnosperms," Plant Physiol. 152(3):1 197-1208 (2010).
Keeling et al., "Transcriptome mining, functional characterization, and phylogeny of a large terpene synthase gene family in spruce (*Picea* spp.)," BMC Plant Biol. 11:43 (2011).
Keeling et al., "The primary diterpene synthase products of *Picea abies* levopimaradiene/abietadiene synthase (PaLAS) are epimers of a thermally unstable diterpenol," J. Biol. Chem. 286(24):21145-21153 (2011).
Kasai et al., "Taxadiene synthase structure and evolution of modular architecture in terpene biosynthesis," Nature 469:116-120 (2011).
Kolosova et al., "Isolation of high-quality RNA from gymnosperm and angiosperm trees," Biotechniques 36(5):821-824 (2004).
Kopper et al., "Effects of diterpene acids on components of a conifer bark beetle-fungal interaction: tolerance by Ips pini and sensitivity by its associate *Ophiostoma* ips," Environ. Entomol. 34(2): 486-493, (2005).
Laskowski et al., "PROCHECK: a program to check the stereochemical quality of protein structures," J. Appl. Cryst. 26:283-291 (1993).
Leonard et al., "Combining metabolic and protein engineering of a terpenoid biosynthetic pathway for overproduction and selectivity control," Proc. Natl. Acad. Sci. U.S.A. 107(31):13654-13659 (2010).
Lesburg et al., "Managing and manipulating carbocations in biology: terpenoid cyclase structure and mechanism," Curr. Opin. Struc. Biol. 8:695-703 (1998).
Lewinsohn et al., "Oleoresinosis in grand fir (*Abies grandis*) saplings and mature trees," Plant Physiol. 101:1021-1028 (1993).
Mafu et al., "A novel labda-7,13E-dien-15-ol-producing bifunctional diterpene synthase from *Selaginella moellendorffii*," Chem BioChem 12:1984-1987 (2011).
Martin et al., "Functional characterization of nine Norway spruce TPS genes and evolution of gymnosperm terpene synthases of the TPS-d subfamily," Plant Physiol. 135:1908-1927 (2004).
Martin et al., "Identification of Vitis vinifera (−)-alpha-terpineol synthase by in silico screening of full-length cDNA ESTs and functional characterization of recombinant terpene synthase," Phytochem. 65(9):1223-1229 (2004).
Mau and West, "Cloning of casbene synthase cDNA: evidence for conserved structural features among terpenoid cyclases in plants," Proc. Natl. Acad. Sci. U.S.A. 91:8497-8501 (1994).
Mayfield et al., "Expression and assembly of a fully active antibody in algae," Proc. Natl. Acad. Sci. U.S.A. 100(2):438-442 (2003).
Miller et al., "Insect-induced conifer defense. White pine weevil and methyl jasmonate induce traumatic resinosis, de novo formed volatile emissions, and accumulation of terpenoid synthase and putative octadecanoid pathway transcripts in Sitka spruce," Plant Physiol. 137:369-382 (2005).
Miroux et al., "Over-production of proteins in *Escherichia coli*: mutant hosts that allow synthesis of some membrane proteins and globular proteins at high levels," J. Mol. Biol. 260(3):289-298 (1996).
Miyazawa et al., "Characteristic odor components in the essential oil from yacon tubers (*Polymnia sonchifolia* Poepp. Et Endl.)," J. Essent. Oil Res. 20:12-14 (2008).
Muneta et al., "Large-scale production of porcine mature interleukin-18 (IL-18) in silkworms using a hybrid baculovirus expression system," J. Vet. Med. Sci. 65(2):219-223 (2003).

(56) References Cited

OTHER PUBLICATIONS

Nielsen et al., "CPHmodels-3.0—remote homology modeling using structure-guided sequence profiles," Nucleic Acids Res. 38:W576-W581 (2010).

Peralta-Yahya et al., "Identification and microbial production of a terpene-based advanced biofuel," Nature Comm. 2:483 (2011).

Peters et al., "Abietadiene synthase from grand fir (*Abies grandis*): characterization and mechanism of action of the "pseudomature" recombinant enzyme," Biochem. 39:15592-15602 (2000).

Peters et al., "Bifunctional abietadiene synthase: free diffusive transfer of the (+)-copalyl diphosphate intermediate between two distinct active sites," J. Am. Chem. Soc. 123:8974-8978 (2001).

Peters et al., "Abietadiene synthase catalysis: mutational analysis of a prenyl diphosphate ionization-initiated cyclization and rearrangement," Proc. Natl. Acad. Sci. U.S.A. 99(2):580-584 (2002).

Peters et al., "Abietadiene synthase catalysis: conserved residues involved in protonation-initiated cyclization of geranylgeranyl diphosphate to (+)-copalyl diphosphate," Biochem. 41:1836-1842 (2002).

Peters et al., "Bifunctional abietadiene synthase: mutual structural dependence of the active sites for protonation-initiated and ionization-initiated cyclizations," Biochem. 42:2700-2707 (2003).

Pham et al., "Large-scale transient transfection of serum-free suspension-growing HEK293 EBNA1 cells: peptone additives improve cell growth and transfection efficiency," Biotechnol. Bioeng. 84(3):332-342 (2003).

Ralph et al., "A conifer genomics resource of 200,000 spruce (*Picea* spp.) ESTs and 6,464 high-quality, sequence-finished full-length cDNAs for Sitka spruce (*Picea sitchensis*)," BMC Genomics 9:484 (2008).

Ro et al., "Loblolly pine abietadienol/abietadienal oxidase PtAO (CYP720B1) is a multifunctional, multisubstrate cytochrome P450 monooxygenase," Proc. Natl. Acad. Sci. U.S.A. 102(22):8060-8065 (2005).

Ro et al., "Diterpene resin acid biosynthesis in loblolly pine (*Pinus taeda*): functional characterization of abietadiene/levopimaradiene synthase (PtTPS-LAS) cDNA and subcellular targeting of PtTPS-LAS and abietadienol/abietadienal oxidase (PtAO, CYP720B1)," Phytochem. 67:1572-1578 (2006).

Russell et al., "Nucleotide sequence of the yeast alcohol dehydrogenase II gene," J. Biol. Chem . 258:2674-2682 (1982).

Schardl et al., "Design and construction of a versatile system for the expression of foreign genes in plants," Gene 61(1):1-11 (1987).

Schüttelkopf et al., "PRODRG: a tool for high-throughput crystallography of protein-ligand complexes," Acta Crystallogr. D Biol. Crystallogr. 60:1355-1363 (2004).

Severson et al., "Quantitation of the major cuticular components from green leaf of different tobacco types," J. Agric. Food Chem. 32:566-570 (1984).

Tholl, "Terpene synthases and the regulation, diversity and biological roles of terpene metabolism," Curr. Opin. Plant Biol. 9(3):297-304 (2006).

Thomsen et al., "MolDock: a new technique for high-accuracy molecular docking," J. Med. Chem. 49:3315-3321 (2006).

Trapp et al., "Defensive resin biosynthesis in conifers," Annu. Rev. Plant Physiol. Plant Mol. Biol. 52:689-724 (2001).

Turner and Croteau, "Organization of monoterpene biosynthesis in Mentha. Immunocytochemical localizations of geranyl diphosphate synthase, limonene-6-hydroxylase, isopiperitenol dehydrogenase, and pulegone reductase," Plant Physiol. 136:4215-4227 (2004).

van den Berg et al., "Kluyveromyces as a host for heterologous gene expression: expression and secretion of prochymosin," Biotechnol. 8:135-139 (1990).

Vlad et al., "Mass-spectrometric invstigation of the abienols-diterpene alcohols," Khimiya Prirodnykh Soedinenii 1:30-35 (1974) [English translation].

Vogel et al., "Abietadiene synthase from grand fir (*Abies grandis*)," J. Biol. Chem. 271:23262-23268 (1996).

Watson et al., "Molecular Biology of the Gene," 4th Edition, Benjamin/Cummings, p. 224 (1987).

Wiederstein et al., "ProSA-web: interactive web service for the recognition of errors in three-dimensional structures of proteins," Nucleic Acids Res. 35:W407-W410 (2007).

Wilderman et al., "A single residue switch converts abietadiene synthase into a pimaradiene specific cyclase," J. Am. Chem. Soc. 129:15736-15737 (2007).

Zerbe et al., "Mutational analysis of white spruce (*Picea glauca*) ent-kaurene synthase (PgKS) reveals common and distinct mechanisms of conifer diterpene synthases of general and specialized metabolism," Phytochem. 74:30-39 (2012).

Zerbe et al., "Bifunctional cis-abienol synthase from *Abies balsamea* discovered by transcriptome sequencing and its implications for diterpenoid fragrance production," J. Biol. Chem. 287(15):12121-12131(2012).

Zhou et al., "Investigating the conservation pattern of a putative second terpene synthase divalent metal binding motif in plants," Phytochem. 70:366-369 (2009).

Zulak et al., "Targeted proteomics using selected reaction monitoring reveals the induction of specific terpene synthases in a multi-level study of methyl jasmonate-treated Norway spruce (*Picea abies*)," Plant J. 60:1015-1030 (2009).

Zulak et al., "Terpenoid biosynthesis and specialized vascular cells of conifer defense," J. Integr. Plant Biol. 52(1):86-97 (2010).

Letter/Written Disclosure of the Supplemental Disclosure Statement for the above-referenced application, mailed on the same day herewith, 2 pages.

Response to Written Opinion, submitted Sep. 19, 2013, in connection with corresponding International Patent Application No. PCT/CA2012/050837, 34 pages.

Letter/Written Disclosure of the Supplemental Information Disclosure Statement for the above-referenced application, mailed Apr. 29, 2014, 2 pages.

International Preliminary Report on Patentability, issued Feb. 28, 2014, in connection with corresponding International Patent Application No. PCT/CA2012/050837, 16 pages.

\* cited by examiner

DITERPENE SYNTHASES AND METHOD FOR PRODUCING DITERPENOIDS

RELATED APPLICATIONS

Benefit of priority is claimed to U.S. Provisional Application Ser. No. 61/562,280, filed Nov. 21, 2011, entitled "Diterpene Synthases and Method for Producing Diterpenoids." The subject matter of the above-noted application is incorporated by reference in its entirety.

This application is related to International PCT Application No. PCT/CA2012/050837, filed the same day herewith, entitled "Diterpene Synthases and Method for Producing Diterpenoids," which claims priority to U.S. Provisional Application Ser. No. 61/562,280.

The subject matter of each of the above-noted applications is incorporated by reference in its entirety.

INCORPORATION BY REFERENCE OF SEQUENCE LISTING PROVIDED ON COMPACT DISCS

An electronic version on compact disc (CD-R) of the Sequence Listing is filed herewith in duplicate (labeled Copy #1 Replacement and Copy #2 Replacement), the contents of which are incorporated by reference in their entirety. The computer-readable file on each of the aforementioned compact discs, created on Feb. 27, 2013, is identical, 200 kilobytes in size, and titled 234SEQ.002.txt.

FIELD OF THE INVENTION

Provided herein are diterpene synthases (diTPS) and methods for producing diterpenoids. Also provided herein are nucleic acid sequences encoding diTPS, diTPS amino acid sequences, diTPS proteins, vectors, cells, transgenic organisms, uses, compositions, methods, processes, and kits thereof.

BACKGROUND

Conifers produce a diverse array of diterpenoids as major oleoresin components that play a role in the chemical defense against herbivores and pathogens, such as bark beetles and their associated fungi (Trapp et al. (2001) *Annu. Rev. Plant Physiol. Plant Mol. Biol.*, 52:689-724; Keeling et al. (2006) *Phytochemistry*, 67:2415-2423; Keeling et al. (2006) *New Phytol.*, 170:657-675). Oleoresin diterpenoids are also used as large-volume, renewable raw material for the production of a suite of industrial resins and coatings, and other bioproducts (Bohlmann et al. (2008) *Plant J.*, 54:656-669; Hillwig et al. (2011) *Biopolymer*, 95:71-76). There is a need for alternative methods for producing diterpenoids.

SUMMARY

Provided herein are methods for producing diterpenoids. Also provided herein are nucleic acids encoding diterpene synthase (diTPS), diTPS amino acid sequences, and vectors, hosts containing diTPS and that can be used to produce diterpenoids. More specifically, the methods provided herein relate to the production of bicyclic tertiary diterpene alcohols such as for example cis-abienol and the production of diterpene olefins such as for example abietadiene, levopimaradiene, palustradiene or neoabietadiene. The production can be in vivo or in vitro. Also provided herein are methods for expression of an enzyme with diTPS activity in a host organism.

Also provided herein are diTPS nucleic acid sequences, diTPS amino acid sequences, proteins, vectors, cells, transgenic organisms, uses, compositions, methods, processes, and kits thereof. For example, a diterpene synthase (diTPS) polypeptide having the sequence set forth in SEQ ID NO:1; SEQ ID NO:3, SEQ ID NO: 5, SEQ ID NO: 7, an active fragment thereof, or sequence substantially identical thereto are provided. Furthermore, provided herein is a nucleic acid encoding the polypeptide sequence set forth in SEQ ID NO:1; SEQ ID NO:3, SEQ ID NO: 5 or SEQ ID NO: 7. The nucleic acid can have the sequence set forth in SEQ ID NO: 2; SEQ ID NO: 4, SEQ ID NO: 6, SEQ ID NO: 8 or a sequence substantially identical thereto. Also provided herein is a nucleic acid encoding the polypeptide sequence as set forth in SEQ ID NO: 7, an active fragment thereof, or sequence substantially identical thereto, wherein the nucleotide at position 621 is replaced by A, the nucleotide at position 402 is replaced by A, the nucleotide at position 404 is replaced by A or a combination thereof. Also provided herein is a diterpene synthase with an active site as disclosed in FIG. 6.

Provided herein is a method for producing diterpenoids that includes providing a host containing a nucleotide sequence encoding a diterpene synthase (diTPS), the nucleotide sequence operatively linked with a regulatory region that is active in the host, and growing the host thereby expressing the nucleotide sequence and producing diterpenoids.

Also provided herein is a method for producing one or more diterpenoids by introducing into a host capable of producing (E,E,E)-geranylgeranyl diphosphate (GGPP) one or more nucleotide sequence encoding a diterpene synthase (diTPS), the nucleotide sequence operatively linked with a regulatory region that is active in the host, and growing the host thereby expressing the nucleotide sequence and producing diterpenoids. The diTPS can contain a bifunctional class I/II diTPS.

Also provided is a method for producing one or more diterpenoids by contacting (E,E,E)-geranylgeranyl diphosphate (GGPP) with at least one polypeptide having a diterpene synthase (diTPS) activity under conditions effective to produce diterpenoids. Optionally, the diterpenoids produced can be isolated. The diTPS can contain a bifunctional class I/II diTPS.

Also provided herein is a method for producing diterpenoids by contacting (E,E,E)-geranylgeranyl diphosphate (GGPP) with at least one polypeptide having a diterpene synthase (diTPS) activity under conditions effective to produce diterpenoids and optionally, isolating the produced diterpenoids.

In one example, provided herein is an isolated nucleic acid molecule containing a sequence of nucleotides encoding a bifunctional class I/II cis-abienol synthase (CAS) polypeptide or an active fragment, wherein the encoded polypeptide or active fragment comprises a class II active site comprising a DxDD motif and a class I active site comprising a DDxxD motif; and the encoded polypeptide or active fragment catalyzes the formation of cis-abienol from geranylgeranyl diphosphate (GGPP). For example, the isolated nucleic acid molecule has a sequence of nucleotides encoding a cis-abienol synthase (CAS) polypeptide set forth in SEQ ID NO:7, an active fragment thereof, or a sequence that exhibits at least 75% sequence identity to SEQ ID NO:7, wherein the encoded polypeptide or active fragment catalyzes the formation of cis-abienol from geranylgeranyl diphosphate (GGPP). The sequence of nucleotides that encodes a CAS polypeptide exhibits at least 80%, 85%, 90%, 95% or 98% sequence identity to SEQ ID NO:7. In some examples, the sequence of nucleotides encodes a polypeptide that has the sequence of amino acids set forth in SEQ ID NO:7 or an active fragment thereof. In other examples, the sequence of nucleotides encodes a polypeptide that is the sequence of amino acids set forth in SEQ ID NO:7 or an active fragment thereof. In any of the above examples, the active fragment is a pseudomature form.

For example, in any of the examples of an isolated nucleic acid molecule encoding a bifunctional class I/II cis-abienol synthase (CAS) polypeptide or an active fragment, the nucleic acid molecule contains the sequence of nucleotides set forth in SEQ ID NO:8 or a sequence of nucleotides that exhibits at least 75% sequence identity to SEQ ID NO:8 or the complement thereof, wherein the sequence of nucleotides encodes a polypeptide or active fragment that catalyzes the formation of cis-abienol from geranylgeranyl diphosphate (GGPP). For example, the sequence of nucleotides exhibits at least 80%, 85%, 90%, 95% or 98% sequence identity to SEQ ID NO:8 or the complement thereof. In some examples, the nucleic acid molecule contains the sequence of nucleotides set forth in SEQ ID NO:8, an active fragment thereof or the complement thereof. In other examples, the nucleic acid molecule has the sequence of nucleotides set forth in SEQ ID NO:8, an active fragment thereof or the complement thereof.

Also provided herein is a cis-abienol synthase (CAS) polypeptide encoded by any of the nucleic acid molecules provided herein above encoding a bifunctional class I/II cis-abienol synthase (CAS) polypeptide or an active fragment thereof.

Also provided herein is a vector containing any of the nucleic acid molecules provided herein above encoding a bifunctional class I/II cis-abienol synthase (CAS) polypeptide or an active fragment thereof. Also provided is a host cell containing such a vector. The host cell can be a prokaryotic or eukaryotic host cell. For example, the host cell is a bacterial, fungal, plant, insect, amphibian or animal cell, such as an *E. coli* cell or a yeast cell. In examples herein, the host cell is one that produces GGPP. For example, the host cell is transformed with one or more sequences that result in production of GGPP.

Also provided herein are methods for producing a bicyclic tertiary diterpene alcohol, by i) contacting (E,E,E)-geranylgeranyl diphosphate (GGPP) with a bifunctional class I/II synthase polypeptide having a diterpene synthase (diTPS) activity under conditions effective to produce bicyclic tertiary diterpene alcohols, wherein the bifunctional class I/II synthase is a conifer synthase; and ii) optionally, isolating the diterpenoids produced in step i). Also provided herein are methods for producing cis-abienol, by i) contacting (E,E,E)-geranylgeranyl diphosphate (GGPP) with a bifunctional class I/II synthase polypeptide having a diterpene synthase (diTPS) activity under conditions effective to produce cis-abienol; ii) optionally, isolating the cis-abienol produced in step i). In the above provided methods, the bifunctional class I/II synthase has a class II active site containing a DxDD motif and a class I active site containing a DDxxD motif. In particular examples of any of the above provided methods, the bifunctional class I/II synthase is a cis-abienol synthase (CAS) polypeptide or active fragment that catalyzes the formation of cis-abienol from geranylgeranyl diphosphate (GGPP).

For example, in the above provided methods, the bifunctional class I/II synthase is a CAS polypeptide or active fragment that contains the sequence of amino acids set forth in SEQ ID NO:7, an active fragment thereof, or a sequence that exhibits at least 75% sequence identity to SEQ ID NO:7, wherein the encoded polypeptide or active fragment catalyzes the formation of cis-abienol from geranylgeranyl diphosphate (GGPP). For example, the sequence of amino acids exhibits at least 80%, 85%, 90%, 95% or 98% sequence identity to SEQ ID NO:7. In some examples, the CAS polypeptide contains the sequence of amino acids set forth in SEQ ID NO:7 or an active fragment thereof. In other examples, the CAS polypeptide is the sequence of amino acids set forth in SEQ ID NO:7 or an active fragment thereof. In any of the above examples, the active fragment is a pseudomature form.

In any of the above examples of methods herein, the CAS polypeptide is encoded by the sequence of nucleotides set forth in SEQ ID NO:8 or a sequence of nucleotides that exhibits at least 75% sequence identity to SEQ ID NO:8 or the complement thereof, wherein the sequence of nucleotides encodes a polypeptide or active fragment that catalyzes the formation of cis-abienol from geranylgeranyl diphosphate (GGPP). For example, the sequence of nucleotides exhibits at least 80%, 85%, 90%, 95% or 98% sequence identity to SEQ ID NO:8 or the complement thereof. In some examples, the sequence of nucleotides contains the sequence of nucleotides set forth in SEQ ID NO:8, an active fragment thereof or the complement thereof. In other examples, the sequence of nucleotides is set forth in SEQ ID NO:8, an active fragment thereof or the complement thereof.

In any of the above methods of producing a bicyclic tertiary diterpene alcohol or cis-abienol, the step of contacting (E,E,E)-geranylgeranyl diphosphate (GGPP) with a bifunctional class I/II synthase polypeptide is effected in vitro or in vivo. In examples of methods herein, the bicyclic tertiary diterpene alcohol or cis-abienol is further isolated. For example, the cis-abienol is used to produce (−)-ambroxide.

Also provided herein is an isolated nucleic acid molecule containing the sequence of nucleotides encoding a levopimaradiene/abietadiene synthase (LAS) set forth in SEQ ID NO: 1, an active fragment thereof, or a sequence that exhibits greater than 99% sequence identity to SEQ ID NO:1, wherein the encoded polypeptide or active fragment catalyzes the formation of epimers of 13-hydroxy-8(14)-abietene from geranylgeranyl diphosphate (GGPP), such as any one or more of abietadiene, levopimaradiene, neoabietadiene and palustradiene. For example, the sequence of nucleotides encodes a polypeptide that contains the sequence of amino acids set forth in SEQ ID NO: 1 or an active fragment thereof. In other examples, the sequence of nucleotides encodes a polypeptide that has the sequence of amino acids set forth in SEQ ID NO:1 or an active fragment thereof. In any of the above examples, the active fragment is a pseudomature form.

For example, in any of the examples of an isolated nucleic acid molecule encoding a levopimaradiene/abietadiene synthase (LAS), the nucleic acid molecule contains the sequence of nucleotides set forth in SEQ ID NO:2 or a sequence of nucleotides that exhibits greater than 99% sequence identity to SEQ ID NO:2 or the complement thereof, wherein the sequence of nucleotides encodes a polypeptide or active fragment that catalyzes the formation of epimers of 13-hydroxy-8(14)-abietene from geranylgeranyl diphosphate (GGPP). In one example, the isolated nucleic acid molecule contains the sequence of nucleotides set forth in SEQ ID NO:2, an active fragment thereof or the complement thereof. In another example, the isolated nucleic acid molecule has the sequence of nucleotides set forth in SEQ ID NO:1, an active fragment thereof or the complement thereof.

Also provided herein is a levopimaradiene/abietadiene synthase (LAS) polypeptide encoded by any of the nucleic acid molecules provided above encoding a levopimaradiene/ abietadiene synthase (LAS) or an active fragment thereof.

Also provided herein is a vector containing any of the nucleic acid molecules provided herein above encoding a levopimaradiene/abietadiene synthase (LAS) or an active fragment thereof. Also provided is a host cell containing such a vector. The host cell can be a prokaryotic or eukaryotic host cell. For example, the host cell is a bacterial, fungal, plant, insect, amphibian or animal cell, such as an *E. coli* cell or a yeast cell. In examples herein, the host cell is one that produces GGPP. For example, the host cell is transformed with one or more sequences that result in production of GGPP.

Also provided herein is a method of producing an epimer of 13-hydroxy-8(14)-abietene, such as any one or more of abietadiene, levopimaradiene, neoabietadiene and palustradiene, by i) contacting (E,E,E)-geranylgeranyl diphosphate (GGPP) with a levopimaradiene/abietadiene synthase (LAS) polypeptide encoded by any of the nucleic acid molecules provided herein encoding a levopimaradiene/abietadiene synthase (LAS) or an active fragment thereof under conditions effective to produce an epimer of 13-hydroxy-8(14)-abietene; and ii) optionally, isolating the epimer of 13-hydroxy-8(14)-abietene produced in step i), such as any one or more of abietadiene, levopimaradiene, neoabietadiene and palustradiene. In examples of the methods provided herein, the step of contacting (E,E,E)-geranylgeranyl diphosphate (GGPP) with a levopimaradiene/abietadiene synthase (LAS) polypeptide is effected in vitro or in vivo. In examples of the methods herein, the method further includes isolating one or more of the diterpenes selected from among abietadiene, levopimaradiene, neoabietadiene and palustradiene.

Also provided herein is an isolated nucleic acid molecule containing the sequence of nucleotides encoding a isopimaradiene synthase (Iso) polypeptide set forth in SEQ ID NO: 3, an active fragment thereof, or a sequence that exhibits at least 95% sequence identity to SEQ ID NO:3, wherein the encoded polypeptide or active fragment catalyzes the formation of isopimaradiene from geranylgeranyl diphosphate (GGPP). For example, the sequence of nucleotides encodes a polypeptide that exhibits at least 96%, 97%, 98%, 99% or more sequence identity to SEQ ID NO:3. In one example, the sequence of nucleotides encodes a polypeptide that contains the sequence of amino acids set forth in SEQ ID NO: 3 or an active fragment thereof. In another example, the sequence of nucleotides encodes a polypeptide that has the sequence of amino acids set forth in SEQ ID NO:3 or an active fragment thereof. In any of the above examples, the active fragment is a pseudomature form.

For example, in any of the examples of an isolated nucleic acid molecule encoding isopimaradiene synthase (Iso) polypeptide, the nucleic acid molecule contains the sequence of nucleotides set forth in SEQ ID NO:4 or a sequence of nucleotides that exhibits at least 95% sequence identity to SEQ ID NO:4 or the complement thereof, wherein the sequence of nucleotides encodes a polypeptide or active fragment that catalyzes the formation of isopimaradiene from geranylgeranyl diphosphate (GGPP). For example, the sequence of nucleotides exhibits at least 96%, 97%, 98%, 99% or more sequence identity to SEQ ID NO:4. In one example, the isolated nucleic acid molecule contains the sequence of nucleotides set forth in SEQ ID NO:4, an active fragment thereof or the complement thereof. In another example, the isolated nucleic acid molecule has the sequence of nucleotides set forth in SEQ ID NO:4, an active fragment thereof or the complement thereof.

Also provided herein is an isopimaradiene synthase (Iso) polypeptide encoded by any of the nucleic acid molecules provided above encoding an isopimaradiene synthase (Iso) polypeptide or an active fragment thereof.

Also provided herein is a vector containing any of the nucleic acid molecules provided herein above encoding an isopimaradiene synthase (Iso) polypeptide or an active fragment thereof. Also provided is a host cell containing such a vector. The host cell can be a prokaryotic or eukaryotic host cell. For example, the host cell is a bacterial, fungal, plant, insect, amphibian or animal cell, such as an *E. coli* cell or a yeast cell. In examples herein, the host cell is one that produces GGPP. For example, the host cell is transformed with one or more sequences that result in production of GGPP.

Also provided herein is a method of producing isopimaradiene by i) contacting (E,E,E)-geranylgeranyl diphosphate (GGPP) with an isopimaradiene synthase (Iso) polypeptide encoded by any of the nucleic acid molecules provided herein under conditions effective to produce isopimaradiene; and ii) optionally, isolating the isopimaradiene produced in step i). In examples of the methods provided herein, the step of contacting (E,E,E)-geranylgeranyl diphosphate (GGPP) with an isopimaradiene synthase (Iso) polypeptide is effected in vitro or in vivo. In examples of the methods provided herein, the method further includes isolating isopimaradiene.

It is understood that this summary of subject matter provided herein does not necessarily describe all features provided herein.

BRIEF DESCRIPTION OF THE FIGURES

These and other features provided herein will become more apparent from the following description in which reference is made to the appended drawings wherein:

FIG. 1A. Protonation initiated cyclization of GGPP to CPP is catalyzed by the class II active site of LAS- and Iso-type diTPSs. At the class I active site of Iso enzymes, ionization-dependent secondary cyclization of CPP and deprotonation of the resulting sandaracpoimaren-8-yl cation lead to the formation of isopimaradiene. Alternatively, in the class I active site of LAS enzymes, additional proton transfer and methyl migration afford the tertiary abietenyl cation and further deprotonation and hydroxylation (i.e., water capture) result in the formation of the instable 13-hydroxy-8(14)abietene product of the LAS activity. Dehydration of this tertiary diterpene alcohol yields several different diterpene olefins, including abietadiene, levopimaradiene, palustradiene, and neoabietadiene. FIG. 1B. A different reaction sequence is proposed for the formation of the bicyclic diterpene alcohol cis-abienol by the class I/II bifunctional AbCAS enzyme. The class II activity of AbCAS converts GGPP to labda-13-en-8-ol diphosphate via water capture at the C-8 carbon of the labda-13-en-8-yl$^+$ cation. Subsequent ionization of the allylic diphosphate at the class I active site, without additional cyclization, yields cis-abienol.

FIG. 2A. Total ion chromatograms (TIC) of reactions products from in vitro assays with purified recombinant enzymes, as described in Example 3. IS, internal standard 1.6 μM 1-eicosene; 1, palustradiene; 2, levopimaradiene; 3, abietadiene; 4, neoabietadiene; 5 and 6, epimers of 13-hydroxy-8(14)-abietadiene; 7, isopimaradiene; 8, cis-abienol. FIG. 2B Mass spectrum of cis-abienol, produced by recombinant AbdiTPS4 with GGPP as substrate, and comparison to the reference mass spectrum of cis-abienol.

FIG. 5A. Total ion chromatograms (TIC) of reaction products. IS, internal standard 1.6 µM 1-eicosene; PC, plasticizer contamination; 8, cis-abienol; 9, geranylgeraniol; 10, (9S, 10S)-copalol; 11, epi-manoyl oxide; 12, manoyl oxide; 13, labd-13-en-8,15-diol. FIG. 5B. Characteristic mass spectra of (9S,10S)-copalol (upper panel, compound 10) and labd-13-en-8,15-diol (lower panel, compound 13), produced by PaLAS:D611A and AbCAS:D621A, respectively.

FIG. 6A. Superimposed homology models of AbCAS, AbLAS and AbIso resembling the common α-helical folding pattern, comprised of the N-terminal β domain and γ domain and C-terminal α domain. Labda-13-en-8-ol diphosphate is shown in the active sites, with the diphosphate group bound to the $Mg^{2+}$-cluster, which in return is coordinated by the DDxxD (SEQ ID NO:13) and NDxxTxxxE (SEQ ID NO:14) motifs. FIG. 6B. Superimposition of putative catalytic residues in the class II active site of AbLAS, AbIso and AbCAS. Asp348 is located at the posterior of the class II active site, opposite of the DIDD (SEQ ID NO:16) motif, with its side chain protruding towards C-8 of labda-13-en-8-ol diphosphate. FIG. 6C. Leu617 and Phe696 are located in the class I active site cavity upstream of the DDLYD motif (SEQ ID NO:17), creating an expansion of the hydrophobic pocket relative to AbLAS and AbIso. FIG. 6D. Gly723 and Val724 contribute to a change in the hinge region between helix G1 and G2.

FIG. 8A shows the synthesis of (−)-ambroxide from cis-abienol. FIG. 8B shows the synthesis of (−)-ambroxide from cis-abienol through the intermediate sclareolide.

DETAILED DESCRIPTION

Figure 1A:
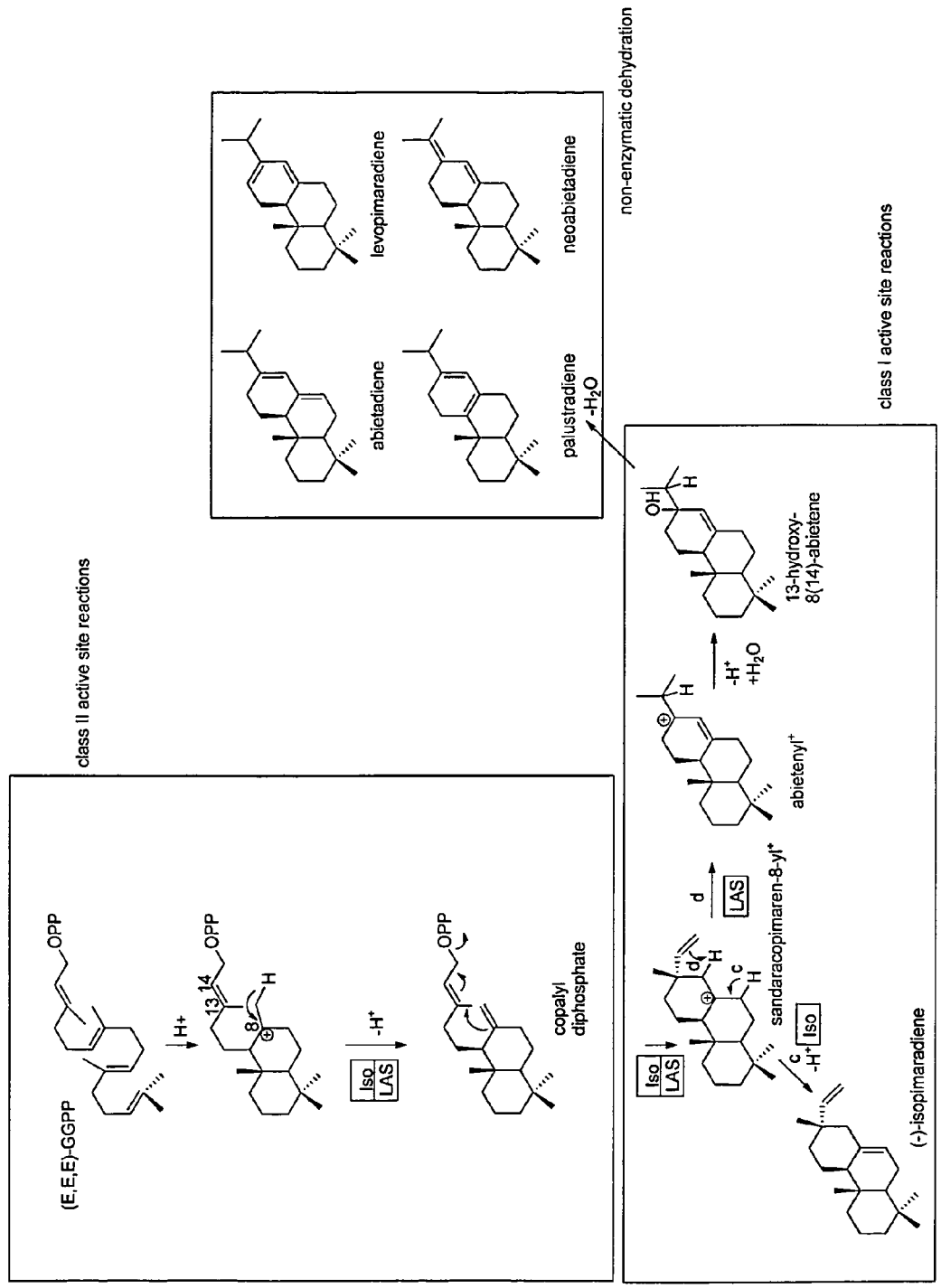
FIGS. 1A-1B show a schematic of the proposed biosynthesis of diterpene olefins and alcohols by class I/II bifunctional diTPSs in conifers. The activity of LAS- and Iso-type diTPSs in the formation of tricyclic diterpenes involves the stepwise cyclization of GGPP via (9S,10S)-CPP (i.e., CPP of normal or (+) stereochemistry).

Outline
   A. Definitions
   B. Bifunctional Class I/II Diterpene Synthase Polypeptides and Diterpenoid Products
      1. Bifunctional Class I/II Diterpene Synthases in Balsam Fir
      2. Biosynthesis of Oleoresin Diterpenoids by diTPSs
         a. Biosynthesis of Tricyclic Diterpene
         b. Biosynthesis of Bicyclic Diterpene
      3. Methods of Producing Diterpenoids
   C. cis-Abienol Synthase and Production of Cis-Abienol
      1. Nucleic Acid and Encoded AbCAS Polypeptides
      2. Methods of producing cis-abienol and ambroxide
         Production of (−)-ambroxide
   D. LAS-type bifunctional class I/II Synthase
   E. Isopimaradiene Synthase
   F. Methods of Producing or Generating Diterpene Synthases, Vectors & Host Cells
      1. Isolation of nucleic acid encoding diterpene synthases
      2. Vectors and Cells
      3. Expression Systems
         a. Prokaryotic cells
         b. Yeast cells
         c. Plants and plant cells
         d. Insects and insect cells
         e. Mammalian expression
      4. Purification
      5. Fusion Proteins
   G. Examples A. Definitions Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the interne can come and go, but equivalent information can be found by searching the internet. Reference thereto evidences the availability and public dissemination of such information.

As used herein, a diterpenoid is an unsaturated hydrocarbon based on the isoprene unit ($C_5H_8$), and having a general formula $C_{5x}H_{8x}$. A diterpene contains 20 carbon atoms, and hence is made up of four isoprene units. A diterpenoid also is a type of diterpene. A diterpenoid can derive from geranylgeranyl pyrophosphate (GGPP). Diterpenoids include diterpene olefins and diterpene alcohols.

As used herein, "diterpene synthase" or "diTPS" as used herein, refers to bifunctional diterpene synthase that is capable of synthesizing diterpene olefins and alcohols by sequential cycloisomerisation of the substrate (E,E,E)-geranylgeranyl diphosphate (GGPP).

As used herein, a bifunctional class I/II diTPS refers to a synthase that contains a class II active site that has a DxDD motif (SEQ ID NO:12) and a class I active site that has a DDxxD motif (SEQ ID NO:13).

As used herein, an active fragment of a synthase polypeptide refers to a contiguous sequence of amino acids of a synthase polypeptide that exhibits synthase activity (e.g. cis-abienol synthase activity, levopimaradiene/abietadiene synthase activity or isopimaradiene synthase activity), but that does not include the full-sequence of the synthase polypeptide. For purposes herein, the active fragment typically includes the class I site and class II site, and thereby contains a class II active site that has a DxDD motif (SEQ ID NO:12) and a class I active site that has a DDxxD motif (SEQ ID NO:13). The active fragment generally contains at least 300, 400, 500, 600, 700, 800 or more amino acid residues.

As used herein, "cis-abienol synthase (CAS) activity" or "AbCAS activity" refers to a synthase polypeptide or an active fragment of a synthase polypeptide that catalyzes the formation of cis-abienol from geranylgeranyl diphosphate (GGPP).

As used herein, "levopimaradiene/abietadiene synthase (LAS) activity" or "AbLAS activity" refers to a synthase polypeptide or an active fragment of a synthase polypeptide that catalyzes the formation of 13-hydroxy-8(14)-abietene from geranylgeranyl diphosphate (GGPP) and the generation of epimers thereof as dehydration products, including abietadiene, levopimaradiene, neoabietadiene and palustradiene.

As used herein, "isopimaradiene synthase activity" or "AbIso" refers to a synthase polypeptide or an active fragment of a synthase polypeptide that catalyzes the formation of isopimaradiene from geranylgeranyl diphosphate (GGPP).

As used herein, a pseudomature polypeptide with reference to a synthase refers to a polypeptide that lacks one or more amino acid residues from the N-terminus of the preprotein, and typically at least 10, 20, 30, 40, 50, 60, 70, 80, 90 or more N-terminal amino acid residues. Typically, a pseudomature polypeptide lacks the plastidial transit peptide. For example, with reference to AbCAS, the plastidial transit polypeptide corresponds to amino acid residues 1-50 of SEQ ID NO:7. Hence, a pseudomature AbCAS polypeptide lacks at least 50, 55, 60, 65, 70, 75, 80, 90 or more N-terminal amino acid residues of the preprotein set forth in SEQ ID NO:7.

As used herein, ambroxide is the compound having the following structure or a mixture of isomers thereof:

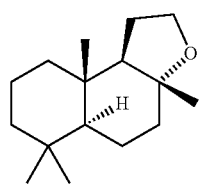

As used herein, corresponding residues refers to residues that occur at aligned loci. Related or variant polypeptides are aligned by any method known to those of skill in the art. Such methods typically maximize matches, and include methods such as manual alignments and those produced by the numerous alignment programs available (for example, BLASTP) and others known to those of skill in the art. By aligning the sequences of polypeptides, one skilled in the art can identify corresponding residues, using conserved and identical amino acid residues as guides. Corresponding positions also can be based on structural alignments, for example by using computer simulated alignments of protein structure.

As used herein, nucleic acids or nucleic acid molecules include DNA, RNA and analogs thereof, including peptide nucleic acids (PNA) and mixtures thereof. Nucleic acids can be single or double-stranded.

As used herein, the term polynucleotide means a single- or double-stranded polymer of deoxyribonucleotides or ribonucleotide bases read from the 5' to the 3' end. Polynucleotides include RNA and DNA, and can be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term nucleotides is used for single- and double-stranded molecules where the context permits. When the term is applied to double-stranded molecules it is used to denote overall length and will be understood to be equivalent to the term base pairs. It will be recognized by those skilled in the art that the two strands of a double-stranded polynucleotide can differ slightly in length and that the ends thereof can be staggered; thus all nucleotides within a double-stranded polynucleotide molecule cannot be paired. Such unpaired ends will, in general, not exceed 20 nucleotides in length.

As used herein, a peptide refers to a polypeptide that is greater than or equal to 2 amino acids in length, and less than or equal to 40 amino acids in length.

As used herein, the amino acids which occur in the various sequences of amino acids provided herein are identified according to their known, three-letter or one-letter abbreviations (Table 1). The nucleotides which occur in the various nucleic acid fragments are designated with the standard single-letter designations used routinely in the art.

As used herein, an "amino acid" is an organic compound containing an amino group and a carboxylic acid group. A polypeptide contains two or more amino acids. For purposes herein, amino acids include the twenty naturally-occurring amino acids, non-natural amino acids and amino acid analogs (i.e., amino acids wherein the α-carbon has a side chain).

As used herein, "amino acid residue" refers to an amino acid formed upon chemical digestion (hydrolysis) of a polypeptide at its peptide linkages. The amino acid residues described herein are presumed to be in the "L" isomeric form. Residues in the "D" isomeric form, which are so designated, can be substituted for any L-amino acid residue as long as the desired functional property is retained by the polypeptide. NH$_2$ refers to the free amino group present at the amino terminus of a polypeptide. COOH refers to the free carboxy group present at the carboxyl terminus of a polypeptide. In keeping with standard polypeptide nomenclature described in J. Biol. Chem. 243:3557-3559 (1968), and adopted 37 C.F.R. §§1.821-1.822, abbreviations for amino acid residues are shown in Table 1:

TABLE 1

Table of Correspondence

| SYMBOL | | |
|---|---|---|
| 1-Letter | 3-Letter | AMINO ACID |
| Y | Tyr | Tyrosine |
| G | Gly | Glycine |
| F | Phe | Phenylalanine |
| M | Met | Methionine |
| A | Ala | Alanine |
| S | Ser | Serine |
| I | Ile | Isoleucine |
| L | Leu | Leucine |
| T | Thr | Threonine |
| V | Val | Valine |
| P | Pro | Proline |
| K | Lys | Lysine |
| H | His | Histidine |
| Q | Gln | Glutamine |
| E | Glu | Glutamic acid |
| Z | Glx | Glu and/or Gln |
| W | Trp | Tryptophan |
| R | Arg | Arginine |
| D | Asp | Aspartic acid |
| N | Asn | Asparagine |
| B | Asx | Asn and/or Asp |
| C | Cys | Cysteine |
| X | Xaa | Unknown or other |

All amino acid residue sequences represented herein by formulae have a left to right orientation in the conventional direction of amino-terminus to carboxyl-terminus. In addition, the phrase "amino acid residue" is defined to include the amino acids listed in the Table of Correspondence (Table 1) and modified and unusual amino acids, such as those referred to in 37 C.F.R. §§1.821-1.822, and incorporated herein by reference. Furthermore, it should be noted that a dash at the beginning or end of an amino acid residue sequence indicates a peptide bond to a further sequence of one or more amino acid residues, to an amino-terminal group such as $NH_2$ or to a carboxyl-terminal group such as COOH.

As used herein, "naturally occurring amino acids" refer to the 20 L-amino acids that occur in polypeptides.

As used herein, "non-natural amino acid" refers to an organic compound containing an amino group and a carboxylic acid group that is not one of the naturally-occurring amino acids listed in Table 1. Non-naturally occurring amino acids thus include, for example, amino acids or analogs of amino acids other than the 20 naturally-occurring amino acids and include, but are not limited to, the D-isostereomers of amino acids. Exemplary non-natural amino acids are known to those of skill in the art.

As used herein, modification is in reference to modification of the primary sequence of amino acids of a polypeptide or a sequence of nucleotides in a nucleic acid molecule and includes deletions, insertions, and replacements and rearrangements of amino acids and nucleotides. Modifications can be made by making conservative amino acid replacements and also non-conservative amino acid substitutions as well as by insertions and other such changes in primary sequence. Modifications also can include post-translational modifications or other changes to the molecule that can occur due to conjugation or linkage, directly or indirectly, to another moiety, but when such modifications are contemplated they are referred to as post-translational modifications or conjugates or other such term as appropriate. Methods of modifying a polypeptide are routine to those of skill in the art, and can be performed by standard methods, such as site directed mutations, amplification methods, and gene shuffling methods.

As used herein, amino acid replacements or substitutions contemplated include, but are not limited to, conservative substitutions, including, but not limited to, those set forth in Table 2. Suitable conservative substitutions of amino acids are known to those of skill in the art and can be made generally without altering the conformation or activity of the polypeptide. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. co., p. 224). Conservative amino acid substitutions are made, for example, in accordance with those set forth in Table 2 as follows:

TABLE 2

| Original residue | Conservative substitution |
|---|---|
| Ala (A) | Gly; Ser |
| Arg (R) | Lys |
| Asn (N) | Gln; His |
| Cys (C) | Ser |
| Gln (Q) | Asn |
| Glu (E) | Asp |
| Gly (G) | Ala; Pro |
| His (H) | Asn; Gln |
| Ile (I) | Leu; Val |
| Leu (L) | Ile; Val |
| Lys (K) | Arg; Gln; Glu |
| Met (M) | Leu; Tyr; Ile |
| Phe (F) | Met; Leu; Tyr |
| Ser (S) | Thr |
| Thr (T) | Ser |
| Trp (W) | Tyr |
| Tyr (Y) | Trp; Phe |
| Val (V) | Ile; Leu; Met |

Other conservative substitutions also are permissible and can be determined empirically or in accord with known conservative substitutions.

As used herein, a DNA construct is a single or double stranded, linear or circular DNA molecule that contains segments of DNA combined and juxtaposed in a manner not found in nature. DNA constructs exist as a result of human manipulation, and include clones and other copies of manipulated molecules.

As used herein, a DNA segment is a portion of a larger DNA molecule having specified attributes. For example, a DNA segment encoding a specified polypeptide is a portion of a longer DNA molecule, such as a plasmid or plasmid fragment, which, when read from the 5' to 3' direction, encodes the sequence of amino acids of the specified polypeptide.

As used herein, "primary sequence" refers to the sequence of amino acid residues in a polypeptide.

As used herein, "similarity" between two proteins or nucleic acids refers to the relatedness between the sequence of amino acids of the proteins or the nucleotide sequences of the nucleic acids. Similarity can be based on the degree of identity and/or homology of sequences of residues and the residues contained therein. Methods for assessing the degree of similarity between proteins or nucleic acids are known to those of skill in the art. For example, in one method of assessing sequence similarity, two amino acid or nucleotide sequences are aligned in a manner that yields a maximal level of identity between the sequences. "Identity" refers to the extent to which the amino acid or nucleotide sequences are invariant. Alignment of amino acid sequences, and to some extent nucleotide sequences, also can take into account conservative differences and/or frequent substitutions in amino acids (or nucleotides). Conservative differences are those that preserve the physico-chemical properties of the residues involved. Alignments can be global (alignment of the compared sequences over the entire length of the sequences and including all residues) or local (the alignment of a portion of the sequences that includes only the most similar region or regions).

As used herein, "sequence identity" refers to the number of identical or similar amino acids or nucleotide bases in a comparison between a test and a reference polypeptide or polynucleotide. Sequence identity can be determined by sequence alignment of nucleic acid or protein sequences to identify regions of similarity or identity. For purposes herein, sequence identity is generally determined by alignment to identify identical residues. The alignment can be local or global. Matches, mismatches and gaps can be identified between compared sequences. Gaps are null amino acids or nucleotides inserted between the residues of aligned sequences so that identical or similar characters are aligned. Generally, there can be internal and terminal gaps. Sequence identity can be determined by taking into account gaps as the number of identical residues/length of the shortest sequence×100. When using gap penalties, sequence identity can be determined with no penalty for end gaps (e.g. terminal gaps are not penalized). Alternatively, sequence identity can be determined without taking into account gaps as the number of identical positions/length of the total aligned sequence×100.

Amino acid sequence similarity or identity can be computed by using the BLASTP and TBLASTN programs which employ the BLAST (basic local alignment search tool) 2.0 algorithm. Techniques for computing amino acid sequence similarity or identity are well known to those skilled in the art, and the use of the BLAST algorithm is described in ALTSCHUL et al. 1990, *J Mol. Biol.* 215: 403-410 and ALTSCHUL et al. (1997), *Nucleic Acids Res.* 25: 3389-3402.

As used herein, the term "identity" represents a comparison between a test and a reference polypeptide or polynucleotide. In one non-limiting example, "at least 90% identical to" refers to percent identities from 90 to 100% relative to the reference polypeptides. Identity at a level of 90% or more is indicative of the fact that, assuming for exemplification purposes a test and reference polypeptide length of 100 amino acids are compared, no more than 10% (i.e., 10 out of 100) of amino acids in the test polypeptide differs from that of the reference polypeptides. Similar comparisons can be made between a test and reference polynucleotides. Such differences can be represented as point mutations randomly distributed over the entire length of an amino acid sequence or they can be clustered in one or more locations of varying length up to the maximum allowable, e.g., 10/100 amino acid difference (approximately 90% identity). Differences also can be due to deletions or truncations of amino acid or nucleotide residues. Differences are defined as nucleic acid or amino acid substitutions, insertions or deletions. Depending on the length of the compared sequences, at the level of homologies or identities above about 85-90%, the result reasonably independent of the program and gap parameters set; such high levels of identity can be assessed readily, often without relying on software.

As used herein, a substantially similar sequence is an amino acid sequence that differs from a reference sequence only by one or more conservative substitutions. Such a sequence can, for example, be functionally homologous to another substantially similar sequence. It will be appreciated by a person of skill in the art the aspects of the individual amino acids in a peptide provided herein that can be substituted.

As used herein, an aligned sequence refers to the use of homology (similarity and/or identity) to align corresponding positions in a sequence of nucleotides or amino acids. Typically, two or more sequences that are related by about or 50% or more identity are aligned. An aligned set of sequences refers to 2 or more sequences that are aligned at corresponding positions and can include aligning sequences derived from RNAs, such as ESTs and other cDNAs, aligned with genomic DNA sequence.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound can, however, be a mixture of stereoisomers or isomers. In such instances, further purification might increase the specific activity of the compound.

As used herein, isolated or purified polypeptide or protein or biologically-active portion thereof is substantially free of cellular material or other contaminating proteins from the cell of tissue from which the protein is derived, or substantially free from chemical precursors or other chemicals when chemically synthesized. Preparations can be determined to be substantially free if they appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as proteolytic and biological activities, of the substance. Methods for purification of the compounds to produce substantially chemically pure compounds are known to those of skill in the art. A substantially chemically pure compound, however, can be a mixture of stereoisomers. In such instances, further purification might increase the specific activity of the compound.

As used herein, substantially free of cellular material includes preparations of diTPSs or diterpene products in which the synthase or product is separated from cellular components of the cells from which it is isolated or produced. In one embodiment, the term substantially free of cellular material includes preparations of having less that about or less than 30%, 20%, 10%, 5% or less (by dry weight) of non-diTPS or diterpene product, including cell culture medium. When the synthase is recombinantly produced, it also is substantially free of culture medium, i.e., culture medium represents less than about or at 20%, 10% or 5% of the volume of the synthase protein preparation.

As used herein, the term substantially free of chemical precursors or other chemicals includes preparations of synthase proteins or diterpene products that is separated from chemical precursors or other chemicals that are involved in the synthesis thereof. The term includes preparations of synthase proteins or diterpene products having less than about or less than 30% (by dry weight), 20%, 10%, 5% or less of chemical precursors or non-synthase chemicals or components.

As used herein, synthetic, with reference to, for example, a synthetic nucleic acid molecule or a synthetic gene or a synthetic peptide refers to a nucleic acid molecule or polypeptide molecule that is produced by recombinant methods and/or by chemical synthesis methods.

As used herein, production by recombinant methods by using recombinant DNA methods refers to the use of the well known methods of molecular biology for expressing proteins encoded by cloned DNA.

As used herein, vector (or plasmid) refers to discrete DNA elements that are used to introduce heterologous nucleic acid into cells for either expression or replication thereof. The vectors typically remain episomal, but can be designed to effect integration of a gene or portion thereof into a chromosome of the genome. Also contemplated are vectors that are artificial chromosomes, such as bacterial artificial chromosomes, yeast artificial chromosomes and mammalian artificial chromosomes. Selection and use of such vehicles are well known to those of skill in the art.

As used herein, expression refers to the process by which nucleic acid is transcribed into mRNA and translated into peptides, polypeptides, or proteins. If the nucleic acid is derived from genomic DNA, expression can, if an appropriate eukaryotic host cell or organism is selected, include processing, such as splicing of the mRNA.

As used herein, an expression vector includes vectors capable of expressing DNA that is operatively linked with regulatory sequences, such as promoter regions, that are capable of effecting expression of such DNA fragments. Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, vector also includes "virus vectors" or "viral vectors." Viral vectors are engineered viruses that are operatively linked to exogenous genes to transfer (as vehicles or shuttles) the exogenous genes into cells. Viral vectors include, but are not limited to, adenoviral vectors, retroviral vectors and vaccinia virus vectors.

As used herein, operably or operatively linked when referring to DNA segments means that the segments are arranged so that they function in concert for their intended purposes, e.g., transcription initiates downstream of the promoter and upstream of any transcribed sequences. The promoter is usually the domain to which the transcriptional machinery binds to initiate transcription and proceeds through the coding segment to the terminator.

As used herein, the term assessing or determining includes quantitative and qualitative determination in the sense of obtaining an absolute value for the activity of a product, and also of obtaining an index, ratio, percentage, visual or other value indicative of the level of the activity. Assessment can be direct or indirect.

As used herein, recitation that a polypeptide "consists essentially" of a recited sequence of amino acids means that only the recited portion, or a fragment thereof, of the full-length polypeptide is present. The polypeptide can optionally and generally will, include additional amino acids from another source or can be inserted into another polypeptide As used herein, the singular forms "a", "an" and "the" include plural referents unless the context clearly dictates otherwise. Thus, for example, reference to polypeptide, comprising "an amino acid replacement" includes polypeptides with one or a plurality of amino acid replacements.

As used herein, ranges and amounts can be expressed as "about" a particular value or range. About also includes the exact amount. Hence "about 5%" means "about 5%" and also "5%."

As used herein, "optional" or "optionally" means that the subsequently described event or circumstance does or does not occur, and that the description includes instances where said event or circumstance occurs and instances where it does not. For example, an optional step of isolating a diterpenoid (e.g. cis-abienol) means that the diterpenoid (e.g. cis-abienol) is isolated or is not isolated.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

For clarity of disclosure, and not by way of limitation, the detailed description is divided into the subsections that follow.

B. Bifunctional Class I/II Diterpene Synthase Polypeptides and Diterpenoid Products The present disclosure provides, in part, diterpene synthase (diTPS) nucleic acid molecules and polypeptides that can, for example, be used in the production of diterpenoids. The disclosure also relates, in part, to vectors containing such sequences, transformed cells, cell lines, and transgenic organisms. The present disclosure also provides methods for producing a diterpene. The present disclosure further relates to a method for producing diterpenoids in a host. The present disclosure also provides compositions, uses, and kits comprising diTPS.

1. Bifunctional Class I/II Diterpene Synthases in Balsam Fir

Varied mechanisms of diTPS-catalyzed cycloisomerization of (E,E,E)-geranylgeranyl diphosphate (GGPP) contribute substantially to the chemical diversity of diterpene metabolites found in the oleoresin of conifers, and in nature, in general. Introduction of hydroxyl functions further increases the diversity of naturally occurring diTPS products. Hydroxylation of conifer diterpenes can result from activity of P450s acting on products of diTPSs (Ro et al. (2005) *Proc. Natl. Acad. Sci. U.S.A.,* 102:8060-8065; Hamberger et al. (2011) *Plant Physiology,* 157:1677-1695); or can result from capture of water by carbocation intermediates during the diTPS reaction (Keeling et al. (2011) *J. Biol. Chem.,* 286: 21145-21153). For example, in general, biosynthesis of oleoresin diterpenoids in conifers involves the sequential cycloisomerization of GGPP, catalyzed by bifunctional class I/II diterpene synthases (diTPSs) of the TPS-d subfamily. Oxygen functionality of conifer oleoresin diterpenes can be introduced by diTPSs (Keeling et al. (2011) *J. Biol. Chem.,* 286: 21145-21153) and/or by separate activity of cytochrome P450 dependent monooxygenases of the CYP720B subfamily (Ro et al. (2005) *Proc. Natl. Acad. Sci. U.S.A.,* 102:8060-8065; Hamberger et al. (2006) *Biochem. Soc. Trans.,* 34:1209-1214; Hamberger et al. (2011) *Plant Physiol,* 157: 1677-1695).

Relatively little is known about diTPSs catalyzing cyclohydration reactions. Reported examples are the biosynthesis of copal-8-ol by a monofunctional class II diTPS from *Cistus creticus* (Falara et al. (2010) *Plant Physiol.,* 154: 301-310), the formation of ent-16α-hydroxy-kaurene as a product of the bifunctional class I/II ent-copalyl diphosphate/ent-kaurene synthase (CPS/KS) from the non-vascular plants *Physcomitrella patens* and *Jungermannia subulata* (Hayashi et al. (2006) *FEBS Lett.*, 580: 6175-6181; Kawaide et al. (2011) *FEBS J.*, 278:123-133), and the biosynthesis of labda-7,13-dien-15-ol catalyzed by a CPS/KS-like diTPS from the lycophyte *Sellaginella moellendorffii* (Mafu et al. (2011) *Chembiochem.*, 12:1984-1987). In addition, a recent study on the product specificity of Norway spruce PaLAS (Keeling et al. (2011) *J. Biol. Chem.*, 286:21145-21153), demonstrated a tricyclic, tertiary diterpene alcohol as the initial, but highly unstable, product of this diTPS. In the case of PaLAS, the allylic diterpenol product dehydrates to a set of diterpene olefins.

Previously characterized conifer diTPSs produce either isopimaradiene and minor amounts of sandaracopimaradiene (Iso-type diTPSs) or epimeric forms of 13-hydroxy-8(14)-abietene (LAS-type diTPSs) (FIG. 1A; see also Stofer Bogel et al. (1996) *J. Biol. Chem.*, 271:23262-23268; Peters et al. (2000) *Biochemistry*, 39:15592-15602; Peters et al. (2001) *J. Am. Chem. Soc.*, 123:8974-8978; Martin et al. (2004) *Plant Physiol.*, 135:1908-1927; Ro et al. (2006) *Phytochemistry*, 67:1572-1578; Keeling et al. (2008) *Proc. Natl. Acad. Sci. U.S.A.*, 105:1085-1090; Keeling et al. (2011) *BMC Plant Biol.*, 11:43; and Keeling et al. (2011) *J. Biol. Chem.*, 286: 21145-21153). In vitro, and perhaps in vivo, 13-hydroxy-8(14)-abietene is readily dehydrated, resulting in a mixture of abietadiene, levopimaradiene, neoabietadiene, and palustradiene (Keeling et al. (2011) *J. Biol. Chem.*, 286:21145-21153).

As described herein from development of a 454-transcriptome resource for balsam fir, which was used in conjunction with terpenoid metabolite profiling, diTPSs were identified that resembled bifunctional class I/II gymnosperm diTPSs of the TPS-d group containing the characteristic DxDD, DDxxD and NSE/DTE motifs (SEQ ID NOS:12-14, respectively) (Martin et al. (2004) *Plant Physiol* 135:1908-1927; Keeling et al. (2011) *BMC Plant Biol* 11:43; Chen et al. (2011) *The Plant Journal* 66:212-229; Peters et al. (2003) *Biochemistry* 42:2700-2707; Peters & Croteau (2002) *Biochemistry* 41:1836-1842; Zhou & Peters (2009) *Phytochemistry* 70:366-369). The identified diTPS synthases are denoted AbdiTPS1 (set forth in SEQ ID NO:2 and encoding the sequence of amino acids set forth in SEQ ID NO:1), AbdiTPS2 (set forth in SEQ ID NO: 4 and encoding the sequence of amino acids set forth in SEQ ID NO:3), AbdiTPS3 (set forth in SEQ ID NO:6 and encoding the sequence of amino acids set forth in SEQ ID NO:5) and AbdiTPS4 (set forth in SEQ ID NO:8 and encoding the sequence of amino acids set forth in SEQ ID NO:7). Identification and functional characterization of pseudomature forms lacking the plastidial transit peptide revealed that AbdiTPS4 is a class I/II gymnosperm cis-abienol synthase (CAS). The same sequence resource also revealed the two additional bifunctional class I/II diTPSs AbdiTPS2 and AbdiTPS1 represent the balsam fir Iso and LAS enzymes, respectively, which form tricyclic diterpenes.

The present disclosure relates to one, or more than one, diterpene synthase (diTPS) nucleic acid molecule and one, or more than one, diTPS polypeptide. The one or more than one, diTPS polypeptides can be a class I/II diTPS. More specifically the one or more than one diTPS polypeptides can be a bifunctional class I/II diTPS. The diTPS can therefore contain a class II active site that has a DxDD motif and/or a class I active site that has a DDxxD motif. The present disclosure provides a nucleic acid containing a nucleotide sequence encoding diterpene synthase (diTPS), for example, LAS diTPS, Iso-type diTPS and CAS diTPS. The nucleotide sequence encoding diTPS can be operatively linked to a regulatory region active in a host.

Also provided herein are variants of any of the nucleic acid sequences provided herein exhibiting substantially the same properties as the sequences provided herein. By this it is meant that nucleic acid sequences need not be identical to the sequence disclosed herein. Variations can be attributable to single or multiple base substitutions, deletions, or insertions or local mutations involving one or more nucleotides not substantially detracting from the properties of the nucleic acid sequence as encoding an enzyme having the activity of the diTPS as provided herein.

One, or more than one, nucleic acid encoding a diTPS are provided. The nucleic acid encoding a diTPS, such as is used in any of the described embodiments herein, can contain a nucleotide sequence that is at least 50% identical to any of SEQ ID NO: 2, 4, 6 or 8, a portion thereof that encodes an active fragment that exhibits diTPS activity or to the complement thereof. For example, the nucleic acid contains a nucleotide sequence that is at least 55%, at least 60%, at least 65%, at least 70%, at least 75%, at least 80%, at least 85%, at least 90%, such as generally at least 95% or at least 98% identical to any of SEQ ID NO: 2, 4, 6 or 8, a portion thereof that encodes an active fragment that exhibits diTPS activity or the complement thereof. The present disclosure provides nucleic acid sequences encoding for a polypeptide having a sequence selected from SEQ ID NO: 1, SEQ ID NO: 3, SEQ ID NO: 5, SEQ ID NO: 7, an active fragment thereof or sequences substantially identical thereto. For example, the provided nucleic acid sequence encodes a pseudomature form of any of SEQ ID NO: 1, SEQ ID NO: 3, SEQ ID NO: 5, SEQ ID NO: 7, or an active fragment thereof. The one, or more than one, nucleic acid can contain the sequence set forth in SEQ ID NO: 2, SEQ ID NO: 4, SEQ ID NO: 6, SEQ ID NO: 8, a portion thereof that encodes an active fragment that exhibits diTPS activity, combinations thereof, or sequences substantially similar thereto. The sequence of the nucleic acid can be changed, for example, to account for codon preference in a particular host cell. In particular examples, the nucleic acid encoding a diTPS contains a nucleotide sequence set forth in any of SEQ ID NO: 2, 4, 6 or 8, a portion thereof that encodes an active fragment or the complement thereof. In other examples, the nucleic acid encoding a diTPS is set forth in any of SEQ ID NO: 2, 4, 6 or 8, a portion thereof that encodes an active fragment or the complement thereof.

Also provided are one, or more than one diTPS polypeptides. The polypeptide having a diTPS activity, such as intended for use in aspects of the methods provided herein, is a polypeptide having an amino acid sequence that is at least 50% identical to any of SEQ ID NO: 1, 3, 5, or 7 or an active fragment thereof that exhibits a diTPS activity. Such polypeptides include pseudomature forms lacking the transit peptide. For examples, among polypeptides provided herein are any that have an amino acid sequence that is at least 55%, at least 60%, at least 65%, at least 70%, at least 75%, at least 80%, at least 85%, at least 90%, such as generally at least 95% or at least 98% identical to any of SEQ ID NO: 1, 3, 5, or 7 or an active fragment thereof that exhibits diTPS activity. The one, or more than one diTPS polypeptides can contain the sequence set forth in SEQ ID NO: 1, SEQ ID NO: 3, SEQ ID NO: 5, SEQ ID NO: 7 or an active fragment thereof that exhibits diTPS activity, or sequences having at least about 80-100% sequence similarity thereto, including any percent similarity within these ranges, such as or at least or greater than 81, 82, 83, 84, 85, 86, 87, 88, 89, 90, 91, 92, 93, 94, 95, 96, 97, 98, 99% sequence similarity thereto. The present disclosure provides nucleic acid sequences encoding for a polypeptide having a sequence selected from SEQ ID NO: 1, SEQ ID NO: 3, SEQ ID NO: 5, SEQ ID NO: 7, an active fragment thereof that exhibits diTPS activity or sequences substantially identical thereto. In examples herein, the polypeptide contains the sequence of amino acids set forth in any of SEQ ID NO: 1, 3, 5, or 7 or an active fragment thereof that exhibits diTPS activity. In other examples, the amino acid sequence for a polypeptide provided herein is set forth in SEQ ID NO: 1, 3, 5, or 7 or an active fragment thereof that exhibits diTPS activity. Also provided herein are pseudomature forms of any of SEQ ID NOS:1, 3, 5 or 7 lacking the transit peptide.

The present study highlights the powers of combined metabolite profiling, tissue-specific deep transcriptome sequencing, and functional (i.e., biochemical) genomics for the successful discovery and characterization of new enzymes of natural product biosynthesis (see also Bleeker et al. (2011) Plant. Mol. Biol., 77:323-336). Of fundamental importance for the success of a genomics- or transcriptomics-based approach to natural products enzyme discovery is the traditional or new knowledge of the occurrence of specialized metabolites associated with particular plant species or particular tissues. Balsam fir was ideally suited for the discovery of CAS, since this species accumulates large amounts of cis-abienol in the oleoresin of bark/phloem tissue (Example 1). Xylem/wood or needles of balsam fir do not contain cis-abienol in relevant amounts, and therefore were not included in the transcriptome sequencing for CAS discovery.

Beyond the selection of species and tissues via metabolite profiling prior to 454 sequencing, another element in the successful discovery strategy of AbCAS was the application of a directed BlastX search of the de novo transcriptome assembly. Specifically, the BlastX search of the de novo transcriptome assembly was directed against a comprehensive sequence database of characterized TPSs. This strategy allowed for the curator-optimized annotation of TPSs genes, which substantially streamlined the efforts of functional gene characterization towards four candidate AbdiTPSs. Of these four candidates, the corresponding enzymes of AbdiTPS1 AbLAS), AbdiTPS2 (AbIso), and AbdiTPS4 (AbCAS) were successfully characterized. Together, the set of three types of bifunctional diTPSs, AbIso, AbLAS and AbCAS, account for the majority of diterpene structures found in the specialized diterpene metabolism of balsam fir bark tissue.

2. Biosynthesis of Oleoresin Diterpenoids by diTPSs

Bifunctional class I/II diTPSs of conifer specialized metabolism are members of the TPS-d group (Martin et al. (2004) Plant Physiol., 135:1908-1927; Keeling et al. (2011) BMC Plant Biol., 11:43; Chen et al. (2011) The Plant Journal, 66:212-229). Within this group, new genes and enzyme functions appear to have evolved from a common ancestor by repeated gene duplication. Neo- or sub-functionalization of members of this gene family involved mutation of specific active site residues (Keeling et al. (2008) Proc. Natl. Acad. Sci., U.S.A., 105:1085-1090; Wilderman et al. (2007) J. Am. Chem. Soc., 129:15736-15737). As shown herein, using mutational analysis of AbCAS and comparative structural analysis of AbCAS with AbIso and AbLAS, distinct catalytic mechanisms were identified. Also, unique residues in the AbCAS class I and class II active sites that are associated with product specificity also were revealed.

Figure 1B:
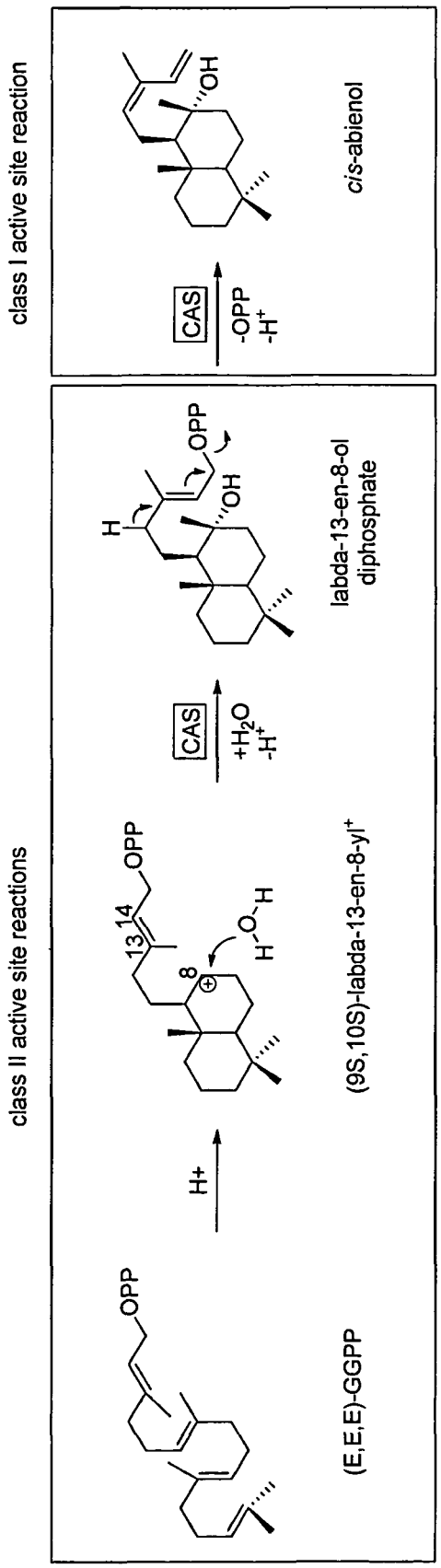

The initial bicyclization of GGPP, resulting in a labda-13-en-8-yl$^+$ intermediate of (9S,10S)-stereochemistry, is likely a common feature of the class II reactions of CAS-, LAS-, and Iso-type diTPSs (FIGS. 1A-1B). Previous work showed that naturally occurring cis-abienol is optically pure and represents the (9S,10S)-stereoisomer (Carman et al. (1993) Aust. J. Chem., 46: 1105-1114). Based on the relatively high protein sequence identity of more than 90% with Abies grandis abietadiene synthase (AgAS), a similar catalytic function was suspected for AbdiTPS1 and AbdiTPS2, while the lower sequence identity of AbdiTPS4 (75%) was indicative of a distinct function. Characterization by sequence identity was confirmed by functional characterization. In a distinct pathway of the class II reaction, it is shown herein that AbCAS then promotes water capture at the C-8 carbon of the carbocation to form labda-13-en-8-ol diphosphate, while the LAS- and Iso-type diTPSs form (9S,10S)-CPP through deprotonation at the C-8 position (FIGS. 1A-1B). In contrast to the well characterized biosynthesis of tricyclic diterpenes by conifer diTPSs of the Iso- and LAS-type, until now a conifer gene or enzyme for the biosynthesis of a bicyclic diterpene cis-abienol has not yet been reported. Thus, AbdiTPS4 (AbCAS) represents a previously unknown diTPS function.

a. Biosynthesis of Tricyclic Diterpene

As shown in FIG. 1A, the reaction mechanism of the Iso- and LAS-type diTPSs involves the initial protonation-initiated bicyclization of GGPP at the class II active site resulting in copalyl diphosphate (CPP) of (9S,10S) configuration (i.e., normal or (+)-configuration). (9S,10S)-CPP then translocates to the class I active site where it undergoes a secondary ionization-dependent cyclization and enzyme-specific rearrangement of intermediate carbocations. In Iso-type diTPSs, direct deprotonation of the sandaracopimarenyl cation results in the formation of isopimaradiene, whereas LAS-type diTPSs catalyze additional rearrangement and water capture at C-13 resulting in 13-hydroxy-8(14)-abietane as the initial product (Keeling et al. (2011) J. Biol. Chem., 286: 21145-21153). This reaction mechanism has been exemplified in the examples herein for the Iso- and LAS-type diTPS provided herein from balsam fir.

Figure 4:
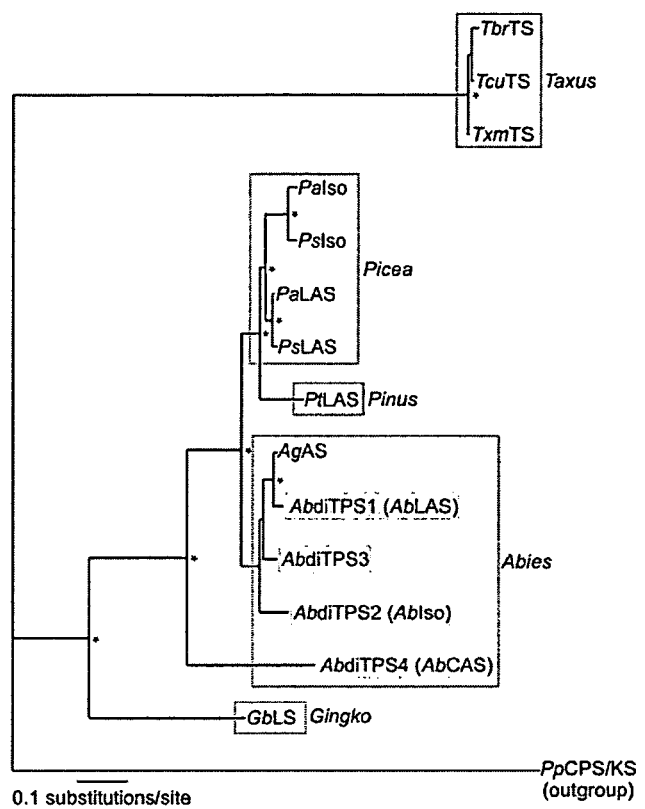
FIG. 4 shows phylogeny of balsam fir diTPSs of the LAS-, Iso- and CAS-type in the context of the TPS-d3 subfamily of conifer diTPSs, including PpCPS/KS, *Physcomitrella patens* ent-copalyl diphosphate/ent-kaurene synthase (NCBI accession no. BAF61135; SEQ ID NO:42); TbrTS, *Taxus brevifolia* taxadiene synthase (NCBI accession no. AAC49310; SEQ ID NO:43); TcuTS, *T. cuspidata* taxadiene synthase (NCBI accession no. ABW82997; SEQ ID NO:44); TxmTS, *T. x media* taxadiene synthase (NCBI accession no. AAS18603; SEQ ID NO:45); PaIso, *Picea abies* isopimaradiene synthase (NCBI accession no. AAS47690; SEQ ID NO:35); PsIso, *Picea sitchensis* isopimaradiene synthase (NCBI accession no. ADZ45512; SEQ ID NO:36); PaLAS, *P. abies* (NCBI accession no. AAS47691; SEQ ID NO:37); PsLAS, *P. sitchensis* levopimaradiene/abietadiene synthase (NCBI accession no. ADZ45517; SEQ ID NO:38); PtLAS, *Pinus taeda* levopimaradiene synthase (NCBI accession no. AY779541; SEQ ID NO:39); AgAS, *Abies grandis* abietadiene synthase (NCBI accession no. AAK83563; SEQ ID NO:40); and GbLS, *Ginkgo biloba* levopimaradiene synthase (NCBI accession no. AAL09965; SEQ ID NO:41). Asterisks indicate nodes supported by >90% bootstrap values.

The functional characterization of AbdiTPS1 (AbLAS) with 13-hydroxy-8(14)-abietene as the initial reaction product, and multiple olefin compounds occurring upon dehydration of the alcohol, substantiates a report of the formation of a tricyclic tertiary C-13 alcohol as the primary product of Norway spruce PaLAS (Keeling et al. (2011) J. Biol. Chem., 286:21145-21153). Likewise, AbdiTPS2 (AbIso) is the first Iso-type diTPS to be characterized outside of the spruce genus (Picea), with phylogenetic patterns indicating that functional divergence of LAS- and Iso-type diTPS occurred independently in the spruce and fir (Abies) lineages (FIG. 4).

b. Biosynthesis of Bicyclic Diterpene

A special feature of AbCAS from other conifer diTPSs is the formation of a bicyclic, tertiary diterpenol, cis-abienol, at the class II active site of a bifunctional class I/II diTPS. As shown herein, the reaction sequence of cis-abienol formation catalyzed by the bifunctional conifer class I/II diTPS (AbCAS) proceeds via water capture of a carbocation intermediate at carbon C-8 and subsequent ionization of the allylic diphosphate group without further cycloisomerization (FIG. 1B). For the fragrance industry, bicyclic hydroxylated diterpenes, such as cis-abienol and sclareol, are of particular value as plant-derived precursors for the sustainable production of Ambrox®, which replaces the controversial use of animal-derived ambergris in perfume formulations.

Structural modeling and molecular docking of labda-13-en-8-ol diphosphate in the class I and class II active sites of AbCAS (see FIG. 6) revealed only one unique amino acid in the class II active site in proximity of the docked intermediate that seems likely to control this particular hydroxylation reaction, namely Asp348 with reference to the sequence set forth in SEQ ID NO:58 (corresponding to Asp349 of SEQ ID NO:7). Located at the posterior of the active site opposite of the DIDD motif and Trp358, which have previously been reported to contribute to the AgAS-catalyzed class II reaction (Peters et al. (2002) *Biochemistry*, 41:1836-1842), the negatively charged side chain of Asp348 appears to stabilize the positive charge at C-8 for water quenching to occur in the formation of labda-13-en-8-ol diphosphate (see FIG. 6B). This local negative charge is not present in any LAS- or Iso-type enzymes, which contain a conserved histidine in this position (FIG. 7).

Figure 5:
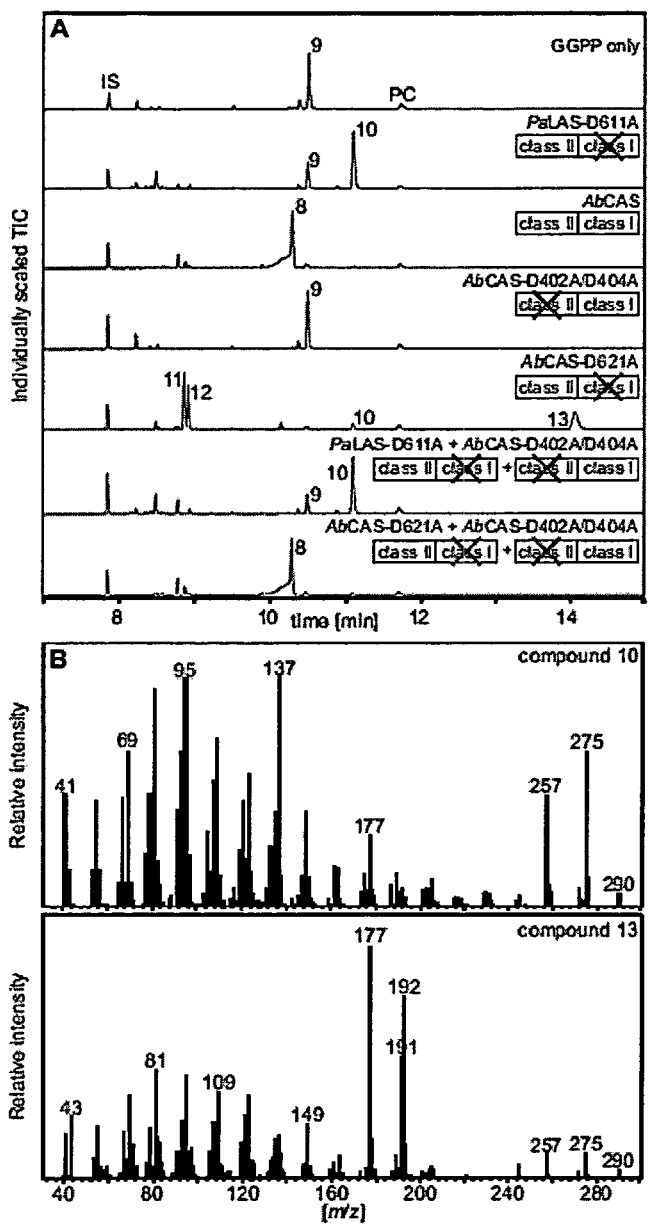
FIG. 5 shows characterization of AbCAS protein variants.

Comparative homology modeling and site directed mutagenesis revealed unique features of cis-abienol biosynthesis that demonstrate a functional divergence in the evolution of CAS relative to the paralogous Iso- and LAS-type conifer diTPSs associated with substitution of key residues in the active sites. Mutational analysis and complementation assays indicate that the class I active site of AbCAS is selective for labda-13-en-8-ol diphosphate as a substrate, but does not convert (9S,10S)-CPP, which is the class I active site substrate of LAS-, and Iso-type diTPSs (FIG. 5). Unlike LAS- and Iso-enzymes, the class I active site of AbCAS catalyzes the ionization of the diphosphate group without cyclization of a C-ring (FIG. 1 FIGS. 1A-1B). Several unique residues were found in a radius of 7 Å around the hydroxy group of labda-13-en-8-ol diphosphate docked within the class I active site of AbCAS that indicate a role in the AbCAS reaction (FIGS. 6C and D). Among these, Leu617, Phe696 and Gly723 with reference to the sequence set forth in SEQ ID NO:58 are of particular interest as they contribute to contour of the active site cavity (corresponding to residues Leu618, Phe697 and Gly724 of SEQ ID NO:7). Leu617 and Phe696 are located in the class I active site cavity upstream of the DDxxD motif on helix D, creating an expansion of the hydrophobic pocket relative to AbLAS and AbIso. Gly723 and Val724 account for a change in the hinge region between helix G1 and G2. These residues are positioned to contribute to the release of a bicyclic product rather than facilitating a secondary cyclization. Interestingly, residues corresponding to Leu617, Phe696 and Gly723 have previously been shown to be critical for the catalytic plasticity of conifer diTPSs (Keeling et al. (2008) *Proc. Natl. Acad. Sci. U.S.A.*, 105:1085-1090; Wilderman et al. (2007) *J. Am. Chem. Soc.*, 129:15736-15737; Peters et al. (2002) *Proc. Natl. Acad. Sci., U.S.A.*, 99:580-584; Leonard et al. (2010) *Proc. Natl. Acad. Sci. U.S.A.*, 107:13654-13659) and thus appear to represent key positions for the functional evolution of these enzymes.

While tricyclic diterpene resin acids are ubiquitously abundant in the pine family (Pinaceae), the oleoresin of balsam fir (*Abies balsamea* (L.) Mill.) contains cis-abienol, a bicyclic, tertiary diterpene alcohol, as the major diterpenoid (Gray et al. (1964) *J. Chem. Soc.*, 5822-5825). The generation of bicyclic, tertiary diterpene alcohols has been demonstrated in non-conifer clades. For example, recently, a monofunctional angiosperm diTPS, catalyzing the formation of a bicyclic oxygen-containing diterpenoid, copal-8-ol diphosphate synthase, from *Cistus creticus* (Cistaceae) has been reported (Falara et al. (2010) *Plant Physiol.*, 154:301-310). This enzyme represents a class II diTPS that catalyzes the protonation-initiated cyclization of GGPP to form the hydroxylated CPP compound. In addition, Mafu et al. ((2011), *Chembiochem*, 12:1984-1987) described a bifunctional class I/II diTPS, SmCPSKSL1, from the lycophyte *Sellaginella moellendorffii* for the formation of labda-7,13-dien-15-ol, where the primary hydroxyl group is introduced in the reaction of the class I active site.

Despite extensive efforts of TPS gene discovery in species of spruce (Martin et al. (2004) *Plant Physiol.*, 135:1908-1927; Keeling et al. (2011) *BMC Plant Biol.*, 11:43; Ralph et al. (2008) *BMC Genomics*, 9:484) and in grand fir (Bohlmann et al. (1999) *Arch. Biochem. Biophys.*, 368:232-243), there is no known gene in any plant species that is closely related (>70% protein identity) to AbCAS. It is therefore possible that a CAS-type bifunctional class I/II diTPS is unique to balsam fir, which is the first conifer species for which three types of functionally distinct diTPSs are now known. A phylogenetic position of AbCAS between Gingko biloba GbLS and other known conifer diTPSs of specialized metabolism in spruce, firs, and pine (FIG. 4) indicates an evolutionary origin of AbCAS by gene duplication prior to speciation within the pine family with its possible loss in some or all of the other species of this comparison.

3. Methods of Producing Diterpenoids

Plant TPSs are useful enzymes for the metabolic engineering of bioproducts and biofuels in yeast and *E. coli* (Bohlmann et al. (2008) *Plant J.*, 54:656-669; Peralta-Yahya et al. (2011) *Nat. Commun.*, 2:483). US Patent Application 2011/0041218 discloses a method for the production of sclareol, a compound useful in the fields of perfumery and flavoring. US Patent Application 2008/0281135 discloses a method for producing terpenes of interest in plants having glandular trichomes. The plants contain a sequence encoding a heterologous terpene synthase under the control of a promoter permitting it to be specifically expressed in the trichomes. Moreover, the pathway for producing endogenous diterpenes is blocked in the trichomes of the plants, to increase the flow in the heterologous pathway. WO 2008/007031 discloses a protein having a syn-copalyl-8-ol diphosphate synthase activity, the nucleotide sequence encoding said protein, as well as a vector and a transgenic non-human organism containing the nucleic acid.

Provided herein are methods of producing diterpenoids in vitro or in vivo using the bifunctional class I/II diTPSs provided herein. Depending on the diTPS used, the diterpenoid that can be produced by the present methods are for example cis-abienol, abietadiene, levopimaradiene, palustradiene, neoabietadiene and/or isopimaradiene.

In one example, the method for producing diterpenoids is carried out in vitro. In this case, (E,E,E)-geranylgeranyl diphosphate (GGPP) is contacted with at least one polypeptide having a diterpene synthase (diTPS) activity under conditions effective to produce diterpenoids. In performing the methods, GGPP can be added to a suspension or solution containing a diterpene synthase polypeptide, which is then incubated at optimal temperature, for example between 15 and 40° C., such as between 25 and 35° C., or at 30° C. The produced diterpenoid can optionally be isolated by methods known in the art. For example, after incubation, the one or more than one diterpene produced can be isolated from the incubated solution by standard isolation procedures, such as solvent extraction and distillation, optionally after removal of polypeptides from the solution. For example, extraction can be effected with pentane, diethyl ether, methyl tertiary butyl ether or other organic solvent. Production and quantification of the amount of the diterpene product (e.g. any one or more of cis-abienol, abietadiene, levopimaradiene, palustradiene, neoabietadiene and/or isopimaradiene) can then be determined using any method known in the art, such as column chromatography, for example liquid chromatography (e.g. LC-MS or HPLC) or gas chromatography (e.g. GC-MS), using an internal standard. For detection of diphosphate intermediates, reaction products can be dephosphorylated prior to extraction by incubation with alkaline phosphatase.

In another example, the method for producing diterpenoids is carried out in vivo. In this case, the method involves introducing into a host capable of producing GGPP, a nucleotide sequence encoding a diterpene synthase (diTPS) operatively linked with a regulatory region active in the host, and growing that host under conditions that permit the expression of the nucleic acid, thereby producing the diterpenoids. Any host cell can be used for expressing the diTPS, such as any host cell described in Section F. For example, the host cell can be a eukaryotic or prokaryotic host cell that produces GGPP or is modified to produce GGPP. Exemplary of host cells are bacterial host cells (e.g. *E. coli*) or fungal host cells (e.g. yeast). In such an example, it is possible to carry out the method in vivo without previously isolating the polypeptide. The reaction occurs directly within the organism or cell transformed to express said nucleic acid. The diterpene product (e.g. any one or more of cis-abienol, abietadiene, levopimaradiene, palustradiene, neoabietadiene and/or isopimaradiene) then can be extracted from the cell culture medium with an organic solvent and subsequently isolated or purified by any known method, such as column chromatography, such as liquid chromatography (e.g. LC-MS or HPLC) or gas chromatography (e.g. GC-MS), and the amount and purity of the recovered product are assessed.

For example cis-abienol, abietadiene, levopimaradiene, palustradiene, neoabietadiene and/or isopimaradiene can be obtained by these in vitro and in vivo methods. Other compounds that can be formed are labda-13-en-8-ol diphosphate, (+)-copalyl diphosphate, sandaracopimaren-8-yl, abientenyl, 13-hydroxy-8(14)abietene and (−)-isopimaradiene, (see FIGS. 1A-1B). The exact product profile is dependent on the conditions in which the method is carried out and the particular diTPS employed.

The quantity of diterpene produced, such as for example cis-abienol, abietadiene, levopimaradiene, palustradiene, neoabietadiene and/or isopimaradiene, can be determined by any known standard chromatographic technique useful for separating and analyzing organic compounds. For example, production can be assayed by any known chromatographic technique useful for the detection and quantification of hydrocarbons, including, but not limited to, gas chromatography mass spectrometry (GC-MS), gas chromatography using a flame ionization detector (GC-FID), capillary GC-MS, liquid chromatography mass spectrometry (LC-MS), high performance liquid chromatography (HPLC) and column chromatography. Typically, these techniques are carried out in the presence of known internal standards which are used to quantify the amount of the terpene produced. For example, diterpenes can be identified by comparison of retention times and mass spectra to those of authentic standards for the particular diterpene in gas chromatography with mass spectrometry detection. In other examples, quantification can be achieved by gas chromatography with flame ionization detection based upon calibration curves with known amounts of authentic standards and normalization to the peak area of an internal standard. These chromatographic techniques allow for the identification of any terpene or diterpene present in the organic layer.

Exemplary provided diTPSs, and methods of use thereof, are described in the following Sections.

C. Cis-Abienol Synthase and Production of Cis-Abienol

Provided herein is a cis-Abienol Synthase (AbTPS4 or AbCAS) polypeptide or active fragment thereof that catalyzes the formation of cis-abienol from geranylgeranyl diphosphate (GGPP). The AbCAS is a bifunctional class I/II diTPS that exhibits class I and class II enzymatic activities to produce a diterpenoid. The nucleic acid or encoded AbCAS polypeptide can be used in methods of producing cis-abienol, which can be used to generate Ambrox® ((−)-ambroxide).

In addition to balsam fir, a gymnosperm tree, only a few angiosperm plant sources such as tobacco (*Nicotiana tabacum*; family Solanaceae) trichomes (Guo et al. (1994) *Archives of Biochemistry and Biophysics*, 308:103-10S; Guo et al. (1995) *Planta*, 197:627-632) or the tuberous roots of Bolivian sunroot (*Polymnia sonchifolia*; family Asteraceae) (Miyazawa et al. (2008) *J. Essent. Oil Res.*, 20:12-14) are known to produce cis-abienol in amounts that are relevant for industrial-scale extraction. Metabolic engineering of microbial hosts or plants to produce oxygenated diterpenoids such as cis-abienol or sclareol, can provide a sustainable production platform for these compounds for the fragrance industry and other applications.

The importance of cis-abienol as a plant-derived precursor for the fragrance and bioproducts industry has spawned an interest in the discovery of the relevant biosynthetic genes and enzymes and their future application in metabolically engineered microbial or plant production systems. Genes for cis-abienol and sclareol biosynthesis have been cloned from angiosperms as described in the patent literature (see e.g. International PCT Application Nos. WO2008/007031; WO2009/044336; WO2009/095366; WO2009/101126). Unlike the bifunctional conifer class I/II diTPSs provided herein, the known angiosperm diTPSs are exclusively monofunctional enzymes (Chen et al. (2011) *The Plant Journal*, 66:212-229). Thus, using the angiosperm enzymes for pathway engineering would require the dual expression and optimization of separate class I and class II enzymes.

In contrast, the use of a bifunctional class I/II diTPS such as AbCAS provided herein requires only expression of a single gene. Optimization of protein expression is also likely to be less complicated for the bifunctional class I/II diTPS (i.e., AbCAS), since the two active sites required for the conversion of GGPP to cis-abienol will be in equal amounts as part of the same protein and will be in very close physical proximity of each other. In essence, for applications of metabolic engineering, the bifunctional class I/II AbCAS offers a scaffolded arrangement of the two active sites. This scaffold evolved in nature for the high volume production of cis-abienol in the oleoresin of balsam fir. Since AbCAS is only very distantly related to angiosperm diTPSs (less than 30% protein sequence identity), this enzyme also is contemplated as the enzyme used for metabolic engineering of cis-abienol production in industrial crops, such as tobacco, as co-suppression effects on endogenous diTPSs are unlikely.

1. Nucleic Acid and Encoded AbCAS Polypeptides

Provided herein are nucleic acid molecules encoding a cis-Abienol Synthase (AbCAS) polypeptide or an active fragment thereof, including pseudomature forms lacking the plastidial transit peptide, and the encoded polypeptides. The AbCAS polypeptide or active fragment thereof catalyzes the formation of cis-abienol from geranylgeranyl diphosphate (GGPP). The polypeptide having an AbCAS activity, such as intended for use in aspects of the methods provided herein, is a polypeptide having an amino acid sequence that is at least 50% identical to SEQ ID NO: 7 or an active fragment thereof.

The AbCAS or active fragment thereof provided herein is a diTPS that is bifunctional and contains a class II active site that has a DxDD motif (SEQ ID NO:12) and a class I active site that has a DDxxD (SEQ ID NO:13) motif. The class II active site is located in the N-terminal beta-gamma domain of the diTPS, encompassing for example residues corresponding to residues Asn87-Glu545 of AbdiTPS4 as set forth in SEQ ID NO: 7 (corresponding to residues Asn86-Glu544 as set forth in SEQ ID NO:58). The DxDD motif corresponds to amino acid residues Asp403-Asp406 as set forth in SEQ ID NO:7 (corresponding to residues Asp402-Asp405 as set forth in SEQ ID NO:58). The class I active site is located in the C-terminal alpha domain of the diTPS, encompassing for example residues corresponding to residues Ser576-Thr867 of AbdiTPS4 as set forth in SEQ ID NO: 7 (corresponding to residues Ser575-Thr866 as set forth in SEQ ID NO:58). The DDxxD motif corresponds to amino acid residues Asp622-Asp626 as set forth in SEQ ID NO:7 (corresponding to residues Asp621-Asp625 as set forth in SEQ ID NO:58). In one example, a diTPS provided herein is an AbCAS polypeptide or active fragment thereof that contains an Asp349 amino acid in the class II active site with reference to SEQ ID NO:7 (corresponding to Asp348 as set forth in SEQ ID NO:58). Furthermore, in some examples, a diTPS provided herein is an AbCAS that contains a Leu618, Phe697 and a Gly724 amino acid in the class I site with reference to amino acid residues set forth in SEQ ID NO:7 (corresponding to Leu617, Phe696 and a Gly723, respectively, as set forth in SEQ ID NO:58).

For example, among polypeptides provided herein are any that have an amino acid sequence that is at least 55%, at least 60%, at least 65%, at least 70%, at least 75%, at least 80%, at least 85%, at least 90%, such as generally at least 95% or at least 98% identical to SEQ ID NO: 7 or an active fragment thereof. The diTPS that is an AbCAS polypeptide can contain the sequence set forth in SEQ ID NO: 7 or an active fragment thereof, or sequences having at least about 80-100% sequence similarity thereto, including any percent similarity within these ranges, such as or at least or greater than 81, 82, 83, 84, 85, 86, 87, 88, 89, 90, 91, 92, 93, 94, 95, 96, 97, 98, 99% sequence similarity thereto. In particular examples, the polypeptide contains the sequence of amino acids set forth in SEQ ID NO: 7 or an active fragment thereof. In other examples, the amino acid sequence for a polypeptide provided herein is set forth in SEQ ID NO: 7 or an active fragment thereof.

Hence, also provided herein are nucleic acid molecules that encode for a polypeptide having a sequence that is at least 50% identical to SEQ ID NO:7 or that has a sequence set forth in SEQ ID NO: 7 or sequences substantially identical thereto, or an active fragment thereof. The nucleic acid encoding a diTPS that is an AbCAS, such as is used in any of the described methods herein, can contain a nucleotide sequence that is at least 50% identical to SEQ ID NO: 8 or a portion thereof that encodes an active fragment having AbCAS activity, or to the complement thereof. For example, the nucleic acid contains a nucleotide sequence that is at least 55%, at least 60%, at least 65%, at least 70%, at least 75%, at least 80%, at least 85%, at least 90%, such as generally at least 95% or at least 98% identical to SEQ ID NO: 8, or a portion thereof that encodes an active fragment having AbCAS activity or the complement thereof. The nucleic acid can contain the sequence set forth in SEQ ID NO: 8 or a portion thereof encoding an active fragment, or sequences substantially similar thereto. The sequence of the nucleic acid can be changed, for example, to account for codon preference in a particular host cell. In particular examples, the nucleic acid encoding a diTPS that is an AbCAS contains a nucleotide sequence set forth in SEQ ID NO: 8, or a portion thereof that encodes an active fragment or the complement thereof. In other examples, the nucleic acid encoding a diTPS that is an AbCAS is set forth in SEQ ID NO: 8 or is a portion thereof that encodes an active fragment or the complement thereof.

For example, AbCAS polypeptides provided herein also include active forms that are pseudomature forms that lack the plastidial transit peptide and that exhibit AbCAS activity to catalyze the formation of cis-abienol from geranylgeranyl diphosphate (GGPP). The plastidial transit peptide of AbCAS corresponds to amino acid residues 1-50 of SEQ ID NO:7 (corresponding to residues 1-49 of SEQ ID NO:58; see also FIG. 7). Exemplary of pseudomature forms are forms that include all or part of the conserved N/KRx6W motif (SEQ ID NO:15), such as the N-terminal sequence K/NREFPP (SEQ ID NO:11; see also FIG. 7). For example, an exemplary pseudomature form of an AbCAS polypeptide provided herein is a polypeptide having an amino acid sequence that is at least 50% identical to SEQ ID NO: 50 or an active fragment thereof. For example, among polypeptides provided herein are any that have an amino acid sequence that is at least or greater than 55%, 60%, 65%, 70%, 75%, 80%, 85%, 86%, 87%, 88%, 89%, 90%, 91%, 92%, 93%, 94%, 95%, 96%, 97%, 98%, 99% or more identical to SEQ ID NO: 50 or an active fragment thereof.

It is understood that the pseudomature form can include fewer or greater amino acids at the N-terminus or less amino acids at the C-terminus as compared to the polypeptide set forth in SEQ ID NO:50 so long as the resulting polypeptide exhibits AbCAS activity to catalyze the formation of cis-abienol from geranylgeranyl diphosphate (GGPP). For example, the AbCAS polypeptide can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60 or more amino acids longer or shorter than the AbCAS polypeptide set forth in SEQ ID NO:50. Also, one or more amino acid variations can occur in the N-terminal or C-terminal domain of the pseudomature form of the AbCAS polypeptide depending on such factors as the cloning procedures employed (e.g. the addition or deletion of amino acids to facilitate cloning procedures), the presence or absence of an N-terminal methionine (e.g. for translation initiation), the presence or absence of a tag or other moiety and other factors well within the knowledge of one of skill in the art. Shortened or lengthened variants with insertions or deletions of amino acids, particularly at either terminus that retain an activity readily can be prepared and the loci for corresponding mutations identified. For example, provided herein is a pseudomature form of AbCAS having an amino acid sequence that is at least 50% identical to SEQ ID NO: 55 or an active fragment thereof. For example, among polypeptides provided herein are any that have an amino acid sequence that is at least or greater than 55%, 60%, 65%, 70%, 75%, 80%, 85%, 86%, 87%, 88%, 89%, 90%, 91%, 92%, 93%, 94%, 95%, 96%, 97%, 98%, 99% or more identical to SEQ ID NO: 55 or an active fragment thereof.

Hence, also provided herein are nucleic acid molecules that encode an AbCAS polypeptide having a sequence of amino acids that is at least 50% identical to the sequence set forth in SEQ ID NO: 50 or SEQ ID NO:55, or an active fragment thereof. The nucleic acid encoding a diTPS that is an AbCAS, such as is used in any of the described methods herein, can contain a nucleotide sequence that is at least 50% identical to SEQ ID NO: 54 or 56 or a portion thereof that encodes an active fragment having AbCAS activity, or to the complement thereof. For example, the nucleic acid contains a nucleotide sequence that is at least 55%, at least 60%, at least 65%, at least 70%, at least 75%, at least 80%, at least 85%, at least 90%, such as generally at least 95% or at least 98% identical to SEQ ID NO: 54 or 56, or a portion thereof that encodes an active fragment having AbCAS activity or the complement thereof. The one, or more than one, nucleic acid can contain the sequence set forth in SEQ ID NO: 54 or 56 or a portion thereof encoding an active fragment, or sequences substantially similar thereto. The sequence of the nucleic acid can be changed, for example, to account for codon preference in a particular host cell. In particular examples, the nucleic acid encoding a diTPS that is an AbCAS contains a nucleotide sequence set forth in SEQ ID NO: 54 or 56, or a portion thereof that encodes an active fragment or the complement thereof. In other examples, the nucleic acid encoding a diTPS that is an AbCAS is set forth in SEQ ID NO: 54 or 56 or is a portion thereof that encodes an active fragment or the complement thereof.

In examples provided herein, amino acid residues in the class I and/or the class II active site of the AbCAS polypeptides or active fragment thereof provided herein can be altered, for example by mutation as compared to any of the sequences set forth in SEQ ID NO: 7, 50 or 55. For example the diTPS polypeptide that is an AbCAS polypeptide or active fragment thereof can contain the sequence as set forth in SEQ ID NO: 7, an active fragment thereof (e.g. such as a pseudomature form as set forth in SEQ ID NO:50 or SEQ ID NO:55), or sequence substantially identical thereto, wherein the amino acid at position 622 is replaced by A, the amino acid at position 403 is replaced by A, the amino acid at position 405 is replaced by A or a combination thereof with reference to amino acid numbering set forth in SEQ ID NO:7. With reference to SEQ ID NO:58, such replacements correspond to amino acids at position 621 replaced by A, amino acid at position 402 replaced by A, amino acid at position 404 replaced by A, or a combination thereof (see for example FIG. 5). Corresponding amino acid residues can be identified by one of skill in the art in other sequence forms of the AbCAS polypeptide by alignment of residues with SEQ ID NO:7 or SEQ ID NO:58. In other examples provided herein, the above amino acid residues are not altered because they are identified herein to change AbCAS activity resulting in a loss of enzymatic activity to produce cis-abienol from GGPP (see Example 5).

Figure 6:
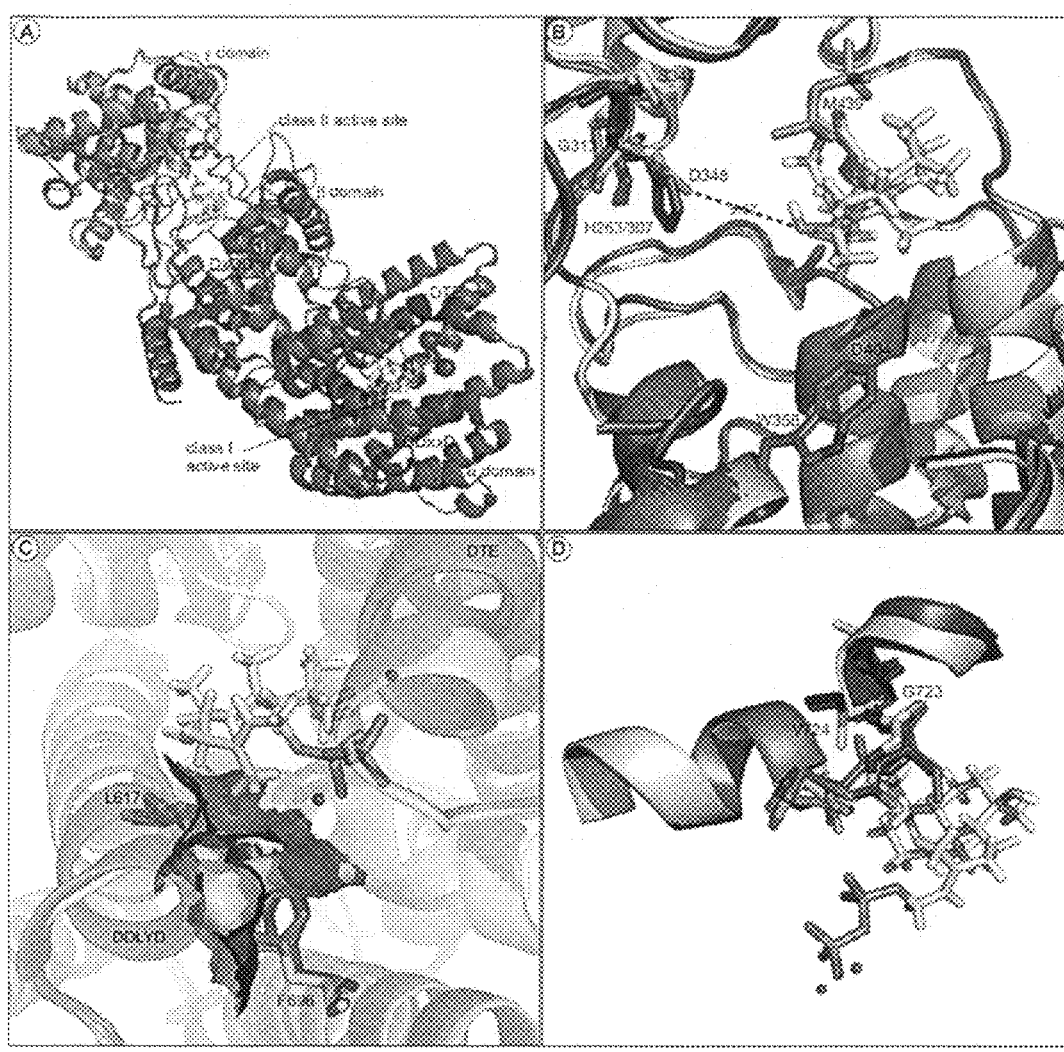
FIG. 6 depicts the unique active site residues of AbCAS (SEQ ID NO:7) relative to AbLAS (SEQ ID NO:1) and AbIso (SEQ ID NO:3) and implication for the formation of cis-abienol.
Figure 7A:
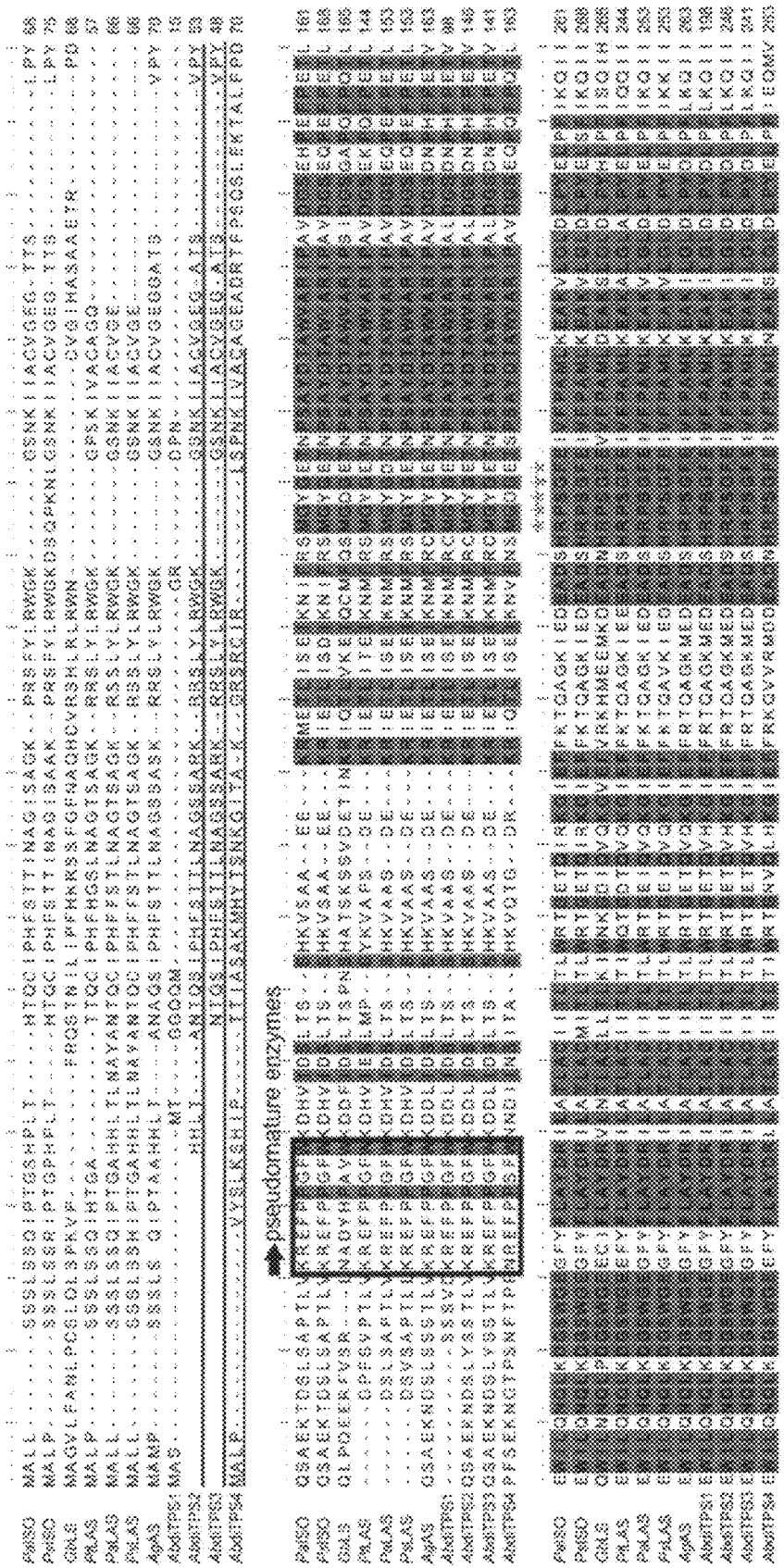
FIG. 7 shows amino acid sequence alignment of bifunctional class I/II conifer diTPSs, including AbdiTPS1 (SEQ ID NO:57), AbdiTPS2 (SEQ ID NO:3), AbdiTPS3 (SEQ ID NO:5) and AbdiTPS4 (SEQ ID NO:58). Grey shading indicates strictly conserved residues. The catalytically relevant aspartate-rich motifs (i.e., DxDD, DDxxD, NDxxTxxxE, (SEQ ID NOS:12-14)) are highlighted. Plastidial transit peptides are underlined. Amino acids identified in a 7 Å radius around the docked reaction intermediates in the N-terminal class II (light asterisks) and C-terminal class I (dark asterisks) active site are highlighted. Additional bifunctional class I/II conifer diTPSs include PaIso, *Picea abies* isopimaradiene synthase (NCBI accession no. AAS47690; SEQ ID NO:35); PsIso, *Picea sitchensis* isopimaradiene synthase (NCBI accession no. ADZ45512; SEQ ID NO:36); PaLAS, *P. abies* (NCBI accession no. AAS47691; SEQ ID NO:37); PsLAS, *P. sitchensis* levopimaradiene/abietadiene synthase (NCBI accession no. ADZ45517; SEQ ID NO:38); PtLAS, *Pinus taeda* levopimaradiene synthase (NCBI accession no. AY779541; SEQ ID NO:39); AgAS, *Abies grandis* abietadiene synthase (NCBI accession no. AAK83563; SEQ ID NO:40); and GbLS, *Ginkgo biloba* levopimaradiene synthase (NCBI accession no. AAL09965; SEQ ID NO:41).
Figure 7B:
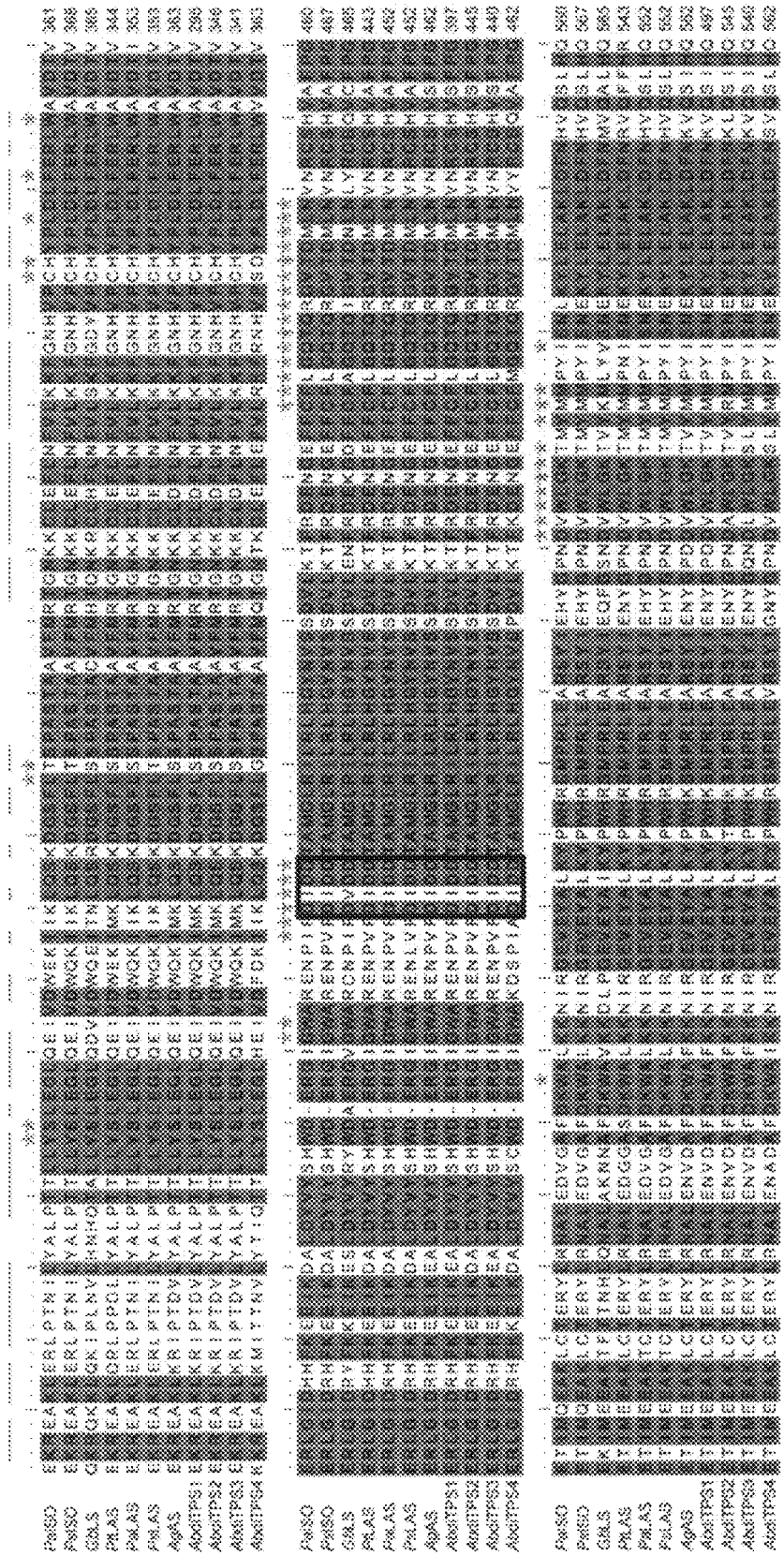
Figure 7C:
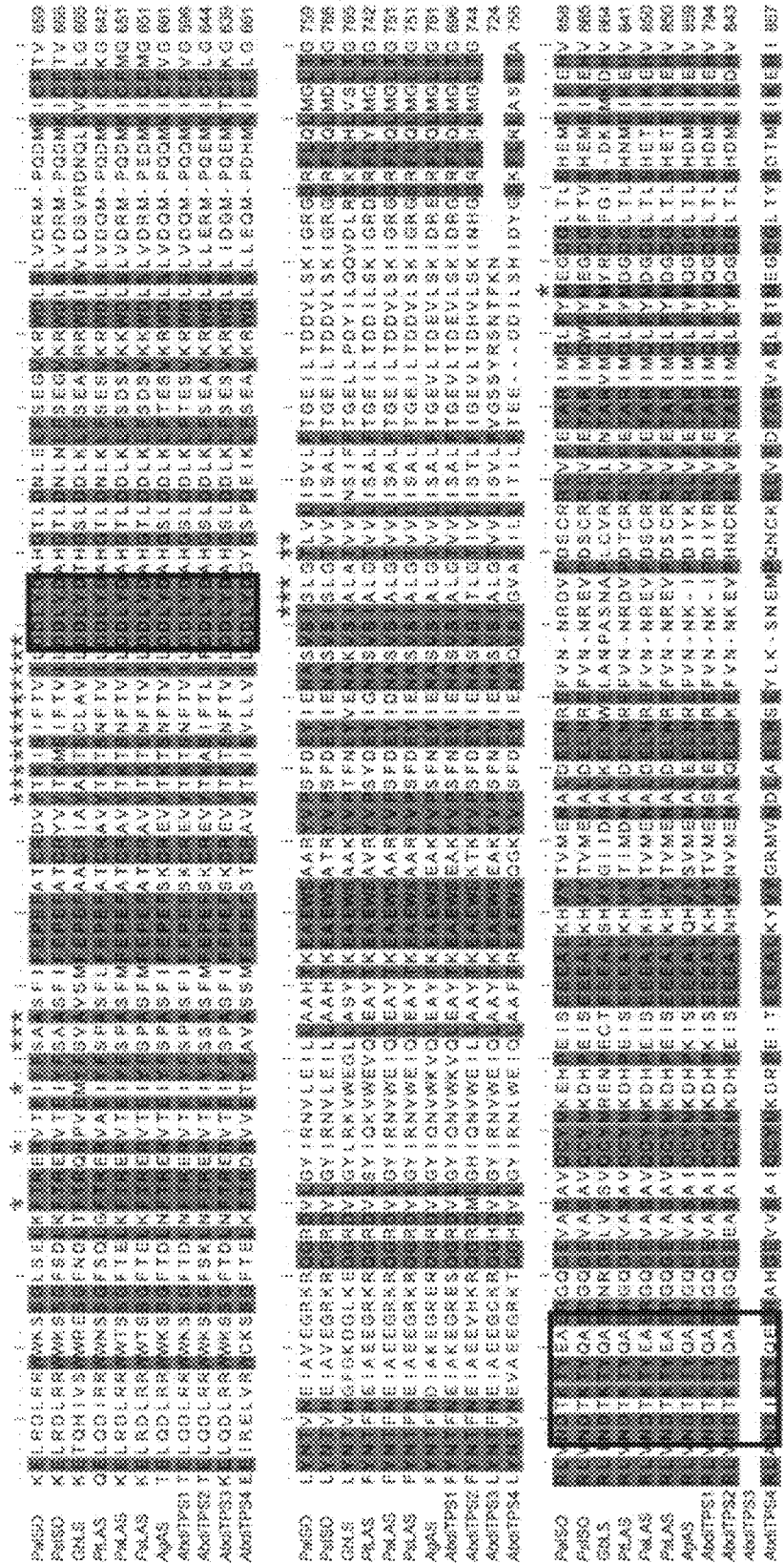
Figure 7D:
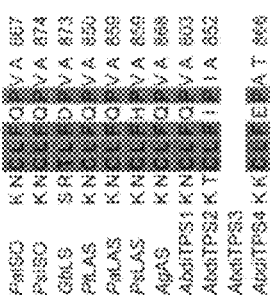

Furthermore, the one or more than one diTPS polypeptides can contain modifications in active site residues as disclosed in FIG. 6 (see also Example 6). For example, the diTPS polypeptide that is an AbCAS polypeptide or active fragment thereof can contain the sequence as set forth in SEQ ID NO: 7, an active fragment thereof (e.g. such as a pseudomature form as set forth in SEQ ID NO:50 or SEQ ID NO:55), or sequence substantially identical thereto, wherein the amino acid at position 618, 697 or 724 or a combination thereof with reference to amino acid numbering set forth in SEQ ID NO:7 is replaced with another amino acid. With reference to SEQ ID NO:58, such replacements correspond to replacement at amino acid position 617, 696 or 723 or a combination thereof with another amino acid. Corresponding amino acid residues can be identified by one of skill in the art in other sequence forms of the AbCAS polypeptide by alignment of residues with SEQ ID NO:7 or SEQ ID NO:58.

2. Methods of Producing Cis-Abienol and Ambroxide

Provided herein are in vitro and in vivo methods of using an AbCAS polypeptide or active fragment thereof provided herein for producing cis-abienol and related products such as (−)-ambroxide (Ambrox®). Among other applications, cis-abienol and other oxygen-containing diterpenoids of plant origin (e.g., sclareol and manool) can be used in the fragrance industry to produce Ambrox®. Ambrox® serves as a sustainable replacement for the use of ambergris in high-end perfume formulations (Barrero et al. (1993) *Tetrahedron*, 49:10405-10412). While Ambrox® is produced from plant terpenoids, ambergris is an animal product secreted from the intestines of sperm whales, which are listed as an endangered species.

In one example, the method for producing the diterpenoid cis-abienol is carried out in vitro. In this case, (E,E,E)-geranylgeranyl diphosphate (GGPP) is contacted with at least one polypeptide having AbCAS activity, such as any described above, under conditions effective to produce cis-abienol. In performing the methods, GGPP can be added to a suspension or solution containing an AbCAS polypeptide or active fragment thereof, such as any provided herein, which is then incubated at optimal temperature, for example between 15 and 40° C., such as between 25 and 35° C., or at 30° C. The cis-abienol diterpenoid can optionally be isolated by methods known in the art. For example, after incubation, the cis-abienol diterpene produced can be isolated from the incubated solution by standard isolation procedures, such as solvent extraction and distillation, optionally after removal of polypeptides from the solution. For example, isolation can be effected by column chromatography, including liquid chromatography methods (e.g. HPLC). Production and quantification of the amount of cis-abienol can be determined using methods as described herein, such as gas chromatography-mass spectroscopy (e.g. GC-MS) or liquid chromatography-mass spectroscopy (e.g. LC-MS), using an internal standard. In some examples, the internal standard can be a cis-abienol authentic standard. In other cases, production can be confirmed by comparison to a reference mass spectrum of cis-abienol as described by Vlad et al. ((1974.) *Khimiya Prirodnykh Soedinenii* 1:30-35) and obtained from the National Institute of Standards and Technology MS library searches (Wiley W9N08).

Figure 2:
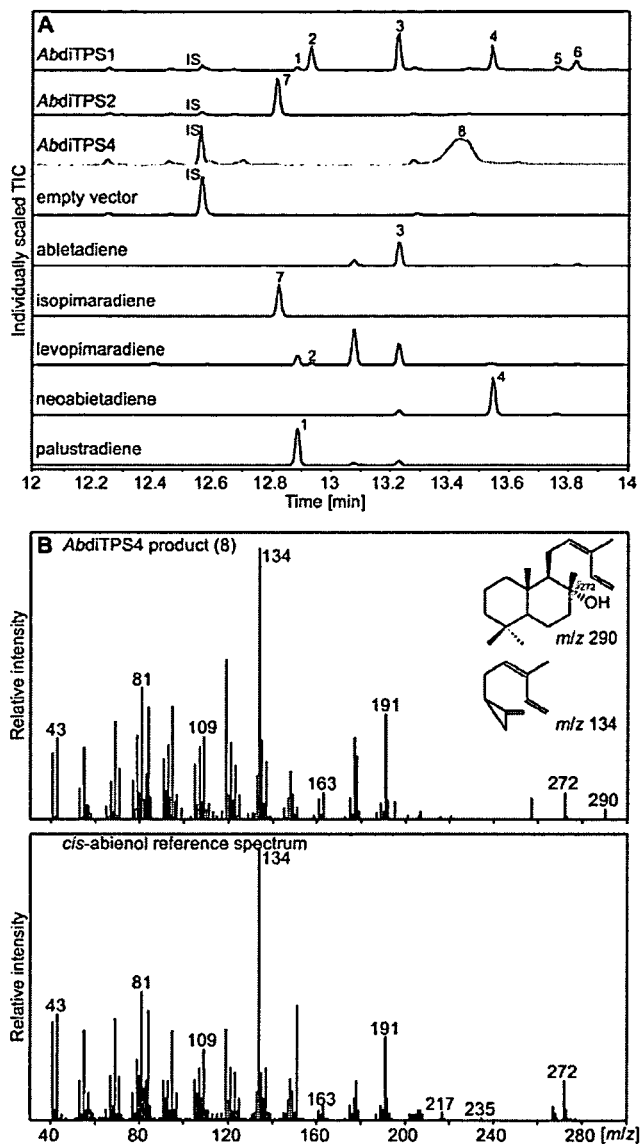
FIG. 2 shows the activity of balsam fir diTPSs AbdiTPS1 (AbLAS; SEQ ID NO:1), AbdiTPS2 (AbIso; SEQ ID NO:3) and AbdiTPS4 (AbCAS; SEQ ID NO:7).

In particular examples of product profiles obtained when the method is carried out in vitro with a Ni-affinity purified polypeptide that is a pseudomature form of sequence SEQ ID NO:7 (e.g. as set forth in SEQ ID NO:55) are provided in FIG. 2. Cis-abienol is the direct product of the enzymatic reaction catalyzed by the diTPS that is an AbCAS polypeptide or active fragment thereof used in the method provided herein.

In another example, the method for producing the diterpenoid cis-abienol is carried out in vivo using any of the nucleic acid molecules encoding an AbCAS polypeptide or active fragment thereof provided herein. In this case, the method involves introducing into a host capable of producing GGPP, a nucleotide sequence encoding an AbCAS polypeptide or active fragment thereof operatively linked with a regulatory region active in the host, and growing that host under conditions that permit the expression of the nucleic acid, thereby producing the cis-abienol diterpenoid. Any host cell can be used for expressing an AbCAS polypeptide or active fragment thereof, such as any host cell described in Section F. For example, the host cell can be a eukaryotic or prokaryotic host cell that produces GGPP or is modified to produce GGPP. Exemplary of host cells are bacterial host cells (e.g. *E. coli*) or fungal host cells (e.g. yeast). In such an example, it is possible to carry out the method in vivo without previously isolating the polypeptide. The reaction occurs directly within the organism or cell transformed to express the nucleic acid. The cis-abienol then can be extracted from the cell culture medium with an organic solvent and subsequently isolated or purified by any known method, such as column chromatography, including liquid chromatography methods (e.g. HPLC) or gas chromatography. The amount and purity of the produced cis-abienol also can be assessed by any known standard chromatographic technique for the detection and quantification of hydrocarbons, including, but not limited to, gas chromatography mass spectrometry (GC-MS), gas chromatography using a flame ionization detector (GC-FID), capillary GC-MS, liquid chromatography mass spectrometry (LC-MS), high performance liquid chromatography (HPLC) and column chromatography using an internal standard or based on a reference mass spectrum as described above.

Production of (−)-Ambroxide

The AbdiTPS4 or AbCAS diterpene synthase polypeptides or active fragments thereof provided herein produce cis-abienol, which can be used to produce (−)-ambroxide. (−)-Ambroxide is used as a base note in the perfume industry as a substitute for ambergris. Conversion of cis-abienol to (−)-ambroxide can be carried out through chemical means (see e.g. Barrero et al. (1993) Tetrahedron 49(45): 10405-10412; Barrero et al. (1994) Tetrahedron 50:6653-6662; Barrero et al., (2004) Synthetic Communications 34(19):3631-3643; and U.S. Pat. No. 5,525,728). In one example, cis-abienol is converted to (−)-ambroxide by chemical methods involving ozonolysis of the side chain followed by reduction and cyclization (see FIG. 8A, Scheme I). In another example, cis-abienol is oxidatively cleaved to form sclareolide (10), which is then converted to (−)-ambroxide by reduction and cyclization (see FIG. 8B, Scheme II) (see, Barrero et al. (1994) Tetrahedron 50:6653-6662; and U.S. Pat. No. 5,525,728). For example, cis-abienol can be treated with $OsO_4$—$NaIO_4$ or $RuO_4$—$NaIO_4$ to form sclareolide.

(−)-Ambroxide can be purified from the reaction mixture by extraction with organic solvents, such as ethers and hydrocarbons, including for example, methyl tert-butyl ether, diethylether, n-hexane and toluene, column chromatography, or extraction with an organic solvent followed by column chromatography. (−)-Ambroxide formation can be confirmed and/or quantified by any of the chromatographic techniques described herein.

D. Las-Type Bifunctional Class I/II Synthase

Provided herein are nucleic acid molecules encoding a levopimaradiene/abietadiene synthase (AbLAS or AbTPS1) polypeptide or active fragment thereof, including pseudomature forms lacking the plastidial transit polypeptide, and the encoded polypeptides. The LAS-type synthase is a bifunctional class I/II dTPS that exhibits class I and class II enzymatic activities to produce diterpenoid products. The polypeptide or active fragment thereof, including pseudomature forms, catalyze the formation of 13-hydroxy-8(14)-abietene from geranylgeranyl diphosphate (GGPP) to effect production of epimers thereof produced as dehydration products of 13-hydroxy-8(14)-abietene, including abietadiene, levopimaradiene, neoabietadiene and palustradiene. The nucleic acid or encoded AbLAS polypeptide can be used in methods to produce a diterpenoid product from among any one or more of abietadiene, levopimaradiene, neoabietadiene and palustradiene.

The AbLAS or active fragment thereof provided herein is a diTPS that is bifunctional and contains a class II active site that has a DxDD motif (SEQ ID NO:12) and a class I active site that has a DDxxD motif (SEQ ID NO:13). The class II active site is located in the N-terminal beta-gamma domain of the diTPS, encompassing for example residues corresponding to residues Lys84-Glu542 of AbdiTPS1 as set forth in SEQ ID NO 1 (corresponding to residues Lys21-Glu479 as set forth in SEQ ID NO:57). The DxDD motif corresponds to amino acid residues Asp400-Asp403 as set forth in SEQ ID NO:1 (corresponding to residues Asp337-Asp340 as set forth in SEQ ID NO:57). The class I active site is located in the C-terminal alpha domain of the diTPS, encompassing for example residues corresponding to amino acid residues Ser573-Ala866 of AbdiTPS1 as set forth in SEQ ID NO: 1 (corresponding to residues Ser510-Ala803 as set forth in SEQ ID NO:57). The DDxxD motif corresponds to amino acid residues Asp619-Asp623 as set forth in SEQ ID NO:1 (corresponding to residues Asp556-Asp560 as set forth in SEQ ID NO:57).

For example among the polypeptides provided herein having AbLAS activity, such as intended for use in aspects of the methods provided herein, is a polypeptide having an amino acid sequence that is at least 50% identical to SEQ ID NO: 1 or an active fragment thereof. For example, among polypeptides provided herein are any that have an amino acid sequence that is at least 55%, at least 60%, at least 65%, at least 70%, at least 75%, at least 80%, at least 85%, at least 90%, such as generally at least 95% or at least 98% identical to SEQ ID NO: 1 or an active fragment thereof. The diTPS that is an AbLAS polypeptide can contain the sequence set forth in SEQ ID NO: 1 or an active fragment thereof, or sequences having at least about 80-100% sequence similarity thereto, including any percent similarity within these ranges, such as or at least or greater than 81, 82, 83, 84, 85, 86, 87, 88, 89, 90, 91, 92, 93, 94, 95, 96, 97, 98, 99% sequence similarity thereto. In particular examples, the polypeptide contains the sequence of amino acids set forth in SEQ ID NO: 1 or an active fragment thereof. In other examples, the amino acid sequence for a polypeptide provided herein is set forth in SEQ ID NO: 1 or an active fragment thereof.

Hence, also provided herein are nucleic acid molecules that encode for a polypeptide having a sequence that is at least 50% identical to SEQ ID NO:1 or that has a sequence set forth in SEQ ID NO:1 or sequences substantially identical thereto, or an active fragment thereof. The nucleic acid encoding a diTPS that is an AbLAS, such as is used in any of the described methods herein, can contain a nucleotide sequence that is at least 50% identical to SEQ ID NO: 2, or a portion thereof that encodes an active fragment having AbLAS activity, or to the complement thereof. For example, the nucleic acid contains a nucleotide sequence that is at least 55%, at least 60%, at least 65%, at least 70%, at least 75%, at least 80%, at least 85%, at least 90%, such as generally at least 95% or at least 98% identical to SEQ ID NO: 2, or a portion thereof that encodes an active fragment having AbLAS activity or the complement thereof. The nucleic acid can contain the sequence set forth in SEQ ID NO: 2 or a portion thereof encoding an active fragment, or sequences substantially similar thereto. The sequence of the nucleic acid can be changed, for example, to account for codon preference in a particular host cell. In particular examples, the nucleic acid encoding a diTPS that is an AbLAS contains a nucleotide sequence set forth in SEQ ID NO: 2, or a portion thereof that encodes an active fragment or the complement thereof. In other examples, the nucleic acid encoding a diTPS that is an AbLAS is set forth in SEQ ID NO: 2 or is a portion thereof that encodes an active fragment or the complement thereof.

For example, AbLAS polypeptides provided herein include active forms that are pseudomature forms that lack the plastidial transit peptide and that exhibit AbLAS activity to catalyze the formation of 13-hydroxy-8(14)-abietene from geranylgeranyl diphosphate (GGPP) to effect production of epimers thereof produced as dehydration products of 13-hydroxy-8(14)-abietene, including abietadiene, levopimaradiene, neoabietadiene and/or palustradiene. Exemplary of pseudomature forms are forms that include all or part of the conserved N/KRx6W motif (SEQ ID NO:15; see also FIG. 7). For example, an exemplary pseudomature form of an AbLAS polypeptide provided herein is a polypeptide having an amino acid sequence that is at least 50% identical to SEQ ID NO: 47 or an active fragment thereof. For examples, among polypeptides provided herein are any that have an amino acid sequence that is at least or greater than 55%, 60%, 65%, 70%, 75%, 80%, 85%, 86%, 87%, 88%, 89%, 90%, 91%, 92%, 93%, 94%, 95%, 96%, 97%, 98%, 99% or more identical to SEQ ID NO: 47 or an active fragment thereof. It is understood that the pseudomature form can include fewer or greater amino acids at the N-terminus or less amino acids at the C-terminus as compared to the polypeptide set forth in SEQ ID NO:47 so long as the resulting polypeptide exhibits AbLAS activity to catalyze the formation of 13-hydroxy-8 (14)-abietene from geranylgeranyl diphosphate (GGPP) to effect production of epimers thereof produced as dehydration products of 13-hydroxy-8(14)-abietene, including abietadiene, levopimaradiene, neoabietadiene and/or palustradiene. For example, the AbLAS polypeptide can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60 or more amino acids longer or shorter than the AbLAS polypeptide set forth in SEQ ID NO:47. Also, one or more amino acid variations can occur in the N-terminal or C-terminal domain of the pseudomature form of the AbLAS polypeptide depending on such factors as the cloning procedures employed (e.g. the addition or deletion of amino acids to facilitate cloning procedures), the presence or absence of an N-terminal methionine (e.g. for translation initiation), the presence or absence of a tag or other moiety and other factors well within the knowledge of one of skill in the art. Shortened or lengthened variants with insertions or deletions of amino acids, particularly at either terminus that retain an activity readily can be prepared and the loci for corresponding mutations identified.

Hence, also provided herein are nucleic acid molecules that encode an AbLAS polypeptide having a sequence of amino acids that is at least 50% identical to the sequence set forth in SEQ ID NO: 47, or an active fragment thereof. The nucleic acid encoding a diTPS that is a AbLAS, such as is used in any of the described methods herein, can contain a nucleotide sequence that is at least 50% identical to SEQ ID NO: 51 or a portion thereof that encodes an active fragment having AbLAS activity, or to the complement thereof. For example, the nucleic acid contains a nucleotide sequence that is at least 55%, at least 60%, at least 65%, at least 70%, at least 75%, at least 80%, at least 85%, at least 90%, such as generally at least 95% or at least 98% identical to SEQ ID NO: 51, or a portion thereof that encodes an active fragment having AbLAS activity or the complement thereof. The one, or more than one, nucleic acid can contain the sequence set forth in SEQ ID NO: 51 or a portion thereof encoding an active fragment, or sequences substantially similar thereto. The sequence of the nucleic acid can be changed, for example, to account for codon preference in a particular host cell. In particular examples, the nucleic acid encoding a diTPS that is an AbLAS contains a nucleotide sequence set forth in SEQ ID NO: 51, or a portion thereof that encodes an active fragment or the complement thereof. In other examples, the nucleic acid encoding a diTPS that is an AbLAS is set forth in SEQ ID NO: 51 or is a portion thereof that encodes an active fragment or the complement thereof.

In examples provided herein, amino acid residues in the class I and/or the class II active site of the AbLAS polypeptides or active fragment thereof provided herein can be altered, for example by mutation as compared to the sequences set forth in SEQ ID NO: 1 or 47.

Also provided herein are in vitro and in vivo methods of using any AbLAS polypeptide or active fragment thereof provided herein for producing an epimer of 13-hydroxy-8 (14)-abietene, such as any one or more of or all of abietadiene, levopimaradiene, neoabietadiene and/or palustradiene or related products.

In one example, the method for producing an AbLAS product is carried out in vitro. In this case, (E,E,E)-geranylgeranyl diphosphate (GGPP) is contacted with at least one polypeptide having AbLAS activity, such as any described above, under conditions effective to produce one or more of abietadiene, levopimaradiene, neoabietadiene and/or palustradiene. In performing the methods, GGPP can be added to a suspension or solution containing an AbLAS polypeptide or active fragment thereof, such as any provided herein, which is then incubated at optimal temperature, for example between 15 and 40° C., such as between 25 and 35° C., or at 30° C. The produced AbLAS diterpenoid or diterpenoids can optionally be isolated by methods known in the art. For example, after incubation, a diterpene product produced can be isolated from the incubated solution by standard isolation procedures, such as solvent extraction and distillation, optionally after removal of polypeptides from the solution. For example, isolation can be effected by column chromatography, including liquid chromatography methods (e.g. HPLC) methods. In such examples, one, two, three or all diterpene products from among any one or more of abietadiene, levopimaradiene, neoabietadiene and/or palustradiene can be isolated. Methods and procedures for individually isolating such products are known to one of skill in the art, for example, by elution profiles using known chromatographic techniques (see e.g. Keeling et al. (2011) *J. Biol. Chem.*, 286:21145-53). Production and quantification of the amount of any one or more of abietadiene, levopimaradiene, neoabietadiene and/or palustradiene can be determined using methods known in the art or as described herein, such as gas chromatography-mass spectroscopy (e.g. GC-MS) or liquid chromatography-mass spectroscopy (e.g. LC-MS) using an internal standard for the particular product.

In another example, the method for producing an AbLAS diterpenoid is carried out in vivo using any of the nucleic acid molecules encoding an AbLAS polypeptide or active fragment thereof provided herein. In this case, the method involves introducing into a host capable of producing GGPP, a nucleotide sequence encoding an AbLAS polypeptide or active fragment thereof operatively linked with a regulatory region active in the host, and growing that host under conditions that permit the expression of the nucleic acid, thereby producing any one or more of abietadiene, levopimaradiene, neoabietadiene and/or palustradiene. Any host cell can be used for expressing an AbLAS polypeptide or active fragment thereof, such as any host cell described in Section F. For example, the host cell can be a eukaryotic or prokaryotic host cell that produces GGPP or is modified to produce GGPP. Exemplary of host cells are bacterial host cells (e.g. *E. coli*) or fungal host cells (e.g. yeast). In such an example, it is possible to carry out the method in vivo without previously isolating the polypeptide. The reaction occurs directly within the organism or cell transformed to express said nucleic acid. The isolated diterpene product or products can be optionally isolated from the cell. For example, the products can be extracted from the cell culture medium with an organic solvent and subsequently isolated or purified by any known methods, such as by known chromatographic techniques including column chromatography methods. In such examples, one, two, three or all diterpene products from among any one or more of one or more of abietadiene, levopimaradiene, neoabietadiene and/or palustradiene can be isolated based on differences in elution profiles as described above and known in the art. Production and quantification of the amount of any one or more of abietadiene, levopimaradiene, neoabietadiene and/or palustradiene can be determined using methods known in the art or as described herein, such as by using any chromatographic technique such as gas chromatography-mass spectroscopy (e.g. GC-MS) or liquid chromatography-mass spectroscopy (e.g. LC-MS) using an internal standard for the particular product.

E. Isopimaradiene Synthase

Provided herein are nucleic acid molecules encoding an isopimaradiene synthase (AbIso or AbTPS2) polypeptide or active fragment thereof, including pseudomature forms lacking the plastidial transit polypeptide, and the encoded polypeptides. AbIso is a bifunctional class I/II dTPS that exhibits class I and class II enzymatic activities to produce diterpene products. The polypeptide or active fragment thereof, including pseudomature forms, catalyze the formation of isopimaradiene from geranylgeranyl diphosphate (GGPP). The nucleic acid or encoded AbIso polypeptide can be used in methods to produce a diterpenoid product that is an isopimaradiene.

The AbIso or active fragment thereof provided herein is a diTPS that is bifunctional and contains a class II active site that has a DxDD motif (SEQ ID NO:12) and a class I active site that has a DDxxD motif (SEQ ID NO:13). The class II active site is located in the N-terminal beta-gamma domain of the diTPS, encompassing for example residues corresponding to residues Lys69-Glu527 of AbdiTPS2 as set forth in SEQ ID NO: 3. The DxDD motif corresponds to amino acid residues Asp385-Asp388. The class I active site is located in the C-terminal alpha domain of the diTPS, encompassing for example residues corresponding to residues Ser558-Ala852 of AbdiTPS2 as set forth in SEQ ID NO:3. The DDxxD motif corresponds to amino acid residues Asp604-Asp608 as set forth in SEQ ID NO:3.

For example among the polypeptides provided herein having AbIso activity, such as intended for use in aspects of the methods provided herein, is a polypeptide having an amino acid sequence that is at least 50% identical to SEQ ID NO: 3 or an active fragment thereof. For example, among polypeptides provided herein are any that have an amino acid sequence that is at least 55%, at least 60%, at least 65%, at least 70%, at least 75%, at least 80%, at least 85%, at least 90%, such as generally at least 95% or at least 98% identical to SEQ ID NO: 3 or an active fragment thereof. The diTPS that is an AbIso polypeptide can contain the sequence set forth in SEQ ID NO: 3 or an active fragment thereof, or sequences having at least about 80-100% sequence similarity thereto, including any percent similarity within these ranges, such as or at least or greater than 81, 82, 83, 84, 85, 86, 87, 88, 89, 90, 91, 92, 93, 94, 95, 96, 97, 98, 99% sequence similarity thereto. In particular examples, the polypeptide contains the sequence of amino acids set forth in SEQ ID NO: 3 or an active fragment thereof. In other examples, the amino acid sequence for a polypeptide provided herein is set forth in SEQ ID NO: 3 or is an active fragment thereof.

Hence, also provided herein are nucleic acid molecules that encode for a polypeptide having a sequence that is at least 50% identical to SEQ ID NO:3 or that has a sequence set forth in SEQ ID NO:3 or sequences substantially identical thereto or an active fragment thereof. The nucleic acid encoding a diTPS that is an AbIso, such as is used in any of the described methods herein, can contain a nucleotide sequence that is at least 50% identical to SEQ ID NO: 4, or a portion thereof that encodes an active fragment having AbISO activity, or to the complement thereof. For example, the nucleic acid contains a nucleotide sequence that is at least 55%, at least 60%, at least 65%, at least 70%, at least 75%, at least 80%, at least 85%, at least 90%, such as generally at least 95% or at least 98% identical to SEQ ID NO: 4, or a portion thereof that encodes an active fragment having AbISO activity or the complement thereof. The nucleic acid can contain the sequence set forth in SEQ ID NO: 4 or a portion thereof encoding an active fragment, or sequences substantially similar thereto. The sequence of the nucleic acid can be changed, for example, to account for codon preference in a particular host cell. In particular examples, the nucleic acid encoding a diTPS that is an AbIso contains a nucleotide sequence set forth in SEQ ID NO: 4, or a portion thereof that encodes an active fragment or the complement thereof. In other examples, the nucleic acid encoding a diTPS that is an AbIso is set forth in SEQ ID NO: 4, or is the portion thereof that encodes an active fragment or the complement thereof.

For example, AbIso polypeptides provided herein include active forms that are pseudomature forms that lack the plastidial transit peptide and that exhibit AbIso activity to catalyze the formation of isopimaradiene from geranylgeranyl diphosphate (GGPP). Exemplary of pseudomature forms are forms that include all or part of the conserved N/KRx6W motif (SEQ ID NO:15; see also FIG. 7). For example, an exemplary pseudomature form of an AbIso polypeptide provided herein is a polypeptide having an amino acid sequence that is at least 50% identical to SEQ ID NO: 48 or an active fragment thereof. For examples, among polypeptides provided herein are any that have an amino acid sequence that is at least or greater than 55%, 60%, 65%, 70%, 75%, 80%, 85%, 86%, 87%, 88%, 89%, 90%, 91%, 92%, 93%, 94%, 95%, 96%, 97%, 98%, 99% or more identical to SEQ ID NO: 48 or an active fragment thereof. It is understood that the pseudomature form can include fewer or greater amino acids at the N-terminus or less amino acids at the C-terminus as compared to the polypeptide set forth in SEQ ID NO:48 so long as the resulting polypeptide exhibits AbIso activity to catalyze the formation of isopimaradiene from geranylgeranyl diphosphate (GGPP). For example, the AbIso polypeptide can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60 or more amino acids longer or shorter than the AbIso polypeptide set forth in SEQ ID NO:48. Also, one or more amino acid variations can occur in the N-terminal or C-terminal domain of the pseudomature form of the AbIso polypeptide depending on such factors as the cloning procedures employed (e.g. the addition or deletion of amino acids to facilitate cloning procedures), the presence or absence of an N-terminal methionine (e.g. for translation initiation), the presence or absence of a tag or other moiety and other factors well within the knowledge of one of skill in the art. Shortened or lengthened variants with insertions or deletions of amino acids, particularly at either terminus that retain an activity readily can be prepared and the loci for corresponding mutations identified.

Hence, also provided herein are nucleic acid molecules that encode an AbIso polypeptide having a sequence of amino acids that is at least 50% identical to the sequence set forth in SEQ ID NO: 48, or an active fragment thereof. The nucleic acid encoding a diTPS that is a AbIso, such as is used in any of the described methods herein, can contain a nucleotide sequence that is at least 50% identical to SEQ ID NO: 52 or a portion thereof that encodes an active fragment having AbIso activity, or to the complement thereof. For example, the nucleic acid contains a nucleotide sequence that is at least 55%, at least 60%, at least 65%, at least 70%, at least 75%, at least 80%, at least 85%, at least 90%, such as generally at least 95% or at least 98% identical to SEQ ID NO: 52, or a portion thereof that encodes an active fragment having AbIso activity or the complement thereof. The nucleic acid can contain the sequence set forth in SEQ ID NO: 52 or a portion thereof encoding an active fragment, or sequences substantially similar thereto. The sequence of the nucleic acid can be changed, for example, to account for codon preference in a particular host cell. In particular examples, the nucleic acid encoding a diTPS that is an AbIso contains a nucleotide sequence set forth in SEQ ID NO: 52, or a portion thereof that encodes an active fragment or the complement thereof. In other examples, the nucleic acid encoding a diTPS that is an AbIso is set forth in SEQ ID NO: 52 or is a portion thereof that encodes an active fragment or the complement thereof.

In examples provided herein, amino acid residues in the class I and/or the class II active site of the AbIso polypeptides or active fragment thereof provided herein can be altered, for example by mutation as compared to the sequences set forth in SEQ ID NO: 3 or 48.

Also provided herein are in vitro and in vivo methods of using an AbIso polypeptide or active fragment thereof provided herein for producing isopimaradiene or a related product. In one example, the method for producing an isopimaradiene product is carried out in vitro. In this case, (E,E,E)-geranylgeranyl diphosphate (GGPP) is contacted with at least one polypeptide having AbIso activity, such as any described above, under conditions effective to produce isopimaradiene. In performing the methods, GGPP can be added to a suspension or solution containing an AbIso polypeptide or active fragment thereof, such as any provided herein, which is then incubated at optimal temperature, for example between 15 and 40° C., such as between 25 and 35° C., or at 30° C. The produced AbIso diterpenoid can optionally be isolated by methods known in the art. For example, after incubation, the diterpene produced can be isolated from the incubated solution by standard isolation procedures, such as solvent extraction and distillation, optionally after removal of polypeptides from the solution. For example, isolation can be effected by column chromatography, including liquid chromatography methods (e.g. HPLC). Production and quantification of the amount of isopimaradiene can be determined using methods as known in the art or as described herein, such as gas chromatography-mass spectroscopy (e.g. GC-MS) or liquid chromatography-mass spectroscopy (e.g. LC-MS) using an internal standard for isopimaradiene.

In another example, the method for producing an AbIso diterpenoid is carried out in vivo using any of the nucleic acid molecules encoding an AbIso polypeptide or active fragment thereof provided herein. In this case, the method involves introducing into a host capable of producing GGPP, a nucleotide sequence encoding an AbIso polypeptide or active fragment thereof operatively linked with a regulatory region active in the host, and growing that host under conditions that permit the expression of the nucleic acid, thereby producing isopimaradiene. Any host cell can be used for expressing an AbIso polypeptide or active fragment thereof, such as any host cell described in Section F. For example, the host cell can be a eukaryotic or prokaryotic host cell that produces GGPP or is modified to produce GGPP. Exemplary of host cells are bacterial host cells (e.g. *E. coli*) or fungal host cells (e.g. yeast). In such an example, it is possible to carry out the method in vivo without previously isolating the AbIso polypeptide. The reaction occurs directly within the organism or cell transformed to express said nucleic acid. The produced isopimaradiene can be isolated from the cell. For example, the isopimaradiene then can be extracted from the cell culture medium with an organic solvent and subsequently isolated or purified by any known method, such as column chromatography, including liquid chromatography methods (e.g. HPLC) or gas chromatography. The amount and purity of the produced isopimaradiene also can be assessed by any known standard chromatographic technique for the detection and quantification of hydrocarbons, including, but not limited to, gas chromatography mass spectrometry (GC-MS), gas chromatography using a flame ionization detector (GC-FID), capillary GC-MS, liquid chromatography mass spectrometry (LC-MS), high performance liquid chromatography (HPLC) and column chromatography using an internal standard as described above.

F. Methods of Producing or Generating Diterpene Synthases, Vectors & Host Cells

Provided herein are polynucleotides encoding any of the diTPS provided herein or the encoded diTPSs polypeptide. As described herein, the nucleic acids and encoding polypeptides are derived from *Abies balsamea*. The polypeptide or the nucleic acid can be used in any of the method provided herein for producing a diterpenoid. Also provided herein are vectors and hosts containing the diTPS and that can be used for producing diterpenoids.

The diTPS to be used in methods provided herein also can be generated synthetically. Standard reference works setting forth the general principles of peptide synthesis technology and methods known to those of skill in the art include, for example: Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwood et al., Oxford University Press, Oxford, United Kingdom, 2000; Sambrook et al., Molecular Cloning: A Laboratory Manual, $3^{rd}$ ed., Cold Spring Harbor Press, Cold Spring Harbor, N.Y. 2001; and Ausubel et al., Current Protocols in Molecular Biology, Greene Publishing Associates and John Wiley & Sons, NY, 1994.

Also provided is a diTPS kit. The kit can contain one or more diTPS nucleic acid molecules. The kit can contain one or more diTPS polypeptides. The kit can contain a synthetic diTPS gene. The kit can contain a vector containing one or more diTPS nucleic acids. The kit can contain a host cell capable of expressing one or more than one diTPS polypeptide.

1. Isolation of Nucleic Acid Encoding Diterpene Synthases

The one or more than one polynucleotide sequences encoding the diTPS as provided herein can be prepared by any method known by the person skilled in the art. For example, the polynucleotide sequence encoding a diTPS can be amplified from a cDNA template, by polymerase chain reaction with specific primers. In such an example the codons of the cDNA can be chosen to favor the expression of said protein in the desired expression system. In other examples, nucleic acids encoding diterpene synthases, including any of the diTPS provided herein, can be cloned or isolated using any available methods known in the art for cloning and isolating nucleic acid molecules. Such methods include PCR amplification of nucleic acids and screening of libraries, including nucleic acid hybridization screening. In some examples, methods for amplification of nucleic acids can be used to isolate nucleic acid molecules encoding a diTPS polypeptide, including for example, polymerase chain reaction (PCR) methods. A nucleic acid containing material can be used as a starting material from which a diTPS-encoding nucleic acid molecule can be isolated. For example, DNA and mRNA preparations from fir (*Abies* sp.), including but not limited to *Abies balsamea*, can be used to obtain diterpene synthase genes.

Nucleic acid libraries also can be used as a source of starting material. Primers can be designed to amplify a diterpene synthase-encoding molecule, such as a diTPS-encoding molecule. For example, primers can be designed based on known nucleic acid sequences encoding a diterpene synthase, such as a class I/class II bifunctional diterpene synthase, such as those set forth in SEQ ID NOS:35-46. Nucleic acid molecules generated by amplification can be sequenced and confirmed to encode a diTPS polypeptide.

Additional nucleotide sequences can be joined to a diTPS-encoding nucleic acid molecule, including linker sequences containing restriction endonuclease sites for the purpose of cloning the synthetic gene into a vector, for example, a protein expression vector or a vector designed for the amplification of the core protein coding DNA sequences. Furthermore, additional nucleotide sequences specifying functional DNA elements can be operatively linked to a diTPS-encoding nucleic acid molecule. Still further, nucleic acid encoding other moieties or domains also can be included so that the resulting synthase is a fusion protein. For example, nucleic acids encoding other enzymes, such as a GGPP synthase, or protein purification tags, such as His or Flag tags.

2. Vectors and Cells

The disclosure also relates, in part, to vectors containing such sequences, transformed cells, cell lines, and transgenic organisms. For recombinant expression of one or more of the diterpene synthase polypeptides provided herein, including diTPS polypeptides, the nucleic acid containing all or a portion of the nucleotide sequence encoding the synthase can be inserted into an appropriate expression vector, i.e., a vector that contains the necessary elements for the transcription and translation of the inserted protein coding sequence. Depending upon the expression system used, the necessary transcriptional and translational signals also can be supplied by the native promoter for a diTPS gene, and/or their flanking regions. For example, vectors containing a polynucleotide sequence encoding a diTPS are provided herein. The vector can be obtained and introduced in a host cell by well-known recombinant DNA and genetic engineering techniques. In some examples, a vector can contain the gene encoding a GGPP synthase, such as the gene encoding the GGPP synthase crtE from *Xanthophyllomyces dendrorhous* (SEQ ID NO:59).

The disclosure also provides a prokaryotic or eukaryotic host cell which is modified by a polynucleotide or a vector as provided herein. The host cell can be prokaryotic, such as bacterial, or eukaryotic, such as fungal (e.g., yeast), plant, Archea, insect, amphibian or animal cell. The host cell can contain a diTPS vector, a synthetic diTPS gene, and/or diTPS nucleic acid. The host cell can be any cell that is capable of being transformed by the vector, synthetic gene, and/or nucleic acid. The host cell can also be any cell that is capable of expressing the diTPS polypeptide. The host cell can be incubated under conditions that allow expression of the diTPS polypeptide.

Several of these organisms do not produce GGPP naturally. To be suitable to carry out the method of the invention, these organisms may need to be transformed with one or more sequences, such as a sequence encoding a GGPP synthase, that result in production of the precursor, GGPP. They can be so transformed either before the modification with the nucleic acid described according to any of the above embodiments, or simultaneously with a nucleotide sequence encoding diTPS, or a vector containing a nucleotide sequence encoding diTPS. Alternatively, in particular examples, the cells are yeast, such as *Saccharomyces cerevisiae*, that express an acyclic pyrophosphate terpene precursor, such as GGPP. The cells are used to produce a diterpene synthase, such as a diTPS polypeptide, by growing the above-described cells under conditions whereby the encoded diTPS is expressed by the cell. In some instances, the expressed synthase is purified. In other instances, the expressed synthase, such as an AbCAS synthase, converts GGPP to one or more terpenes (e.g. cis-abienol) in the host cell.

Any method known to those of skill in the art for the insertion of DNA fragments into a vector can be used to construct expression vectors containing a chimeric gene containing appropriate transcriptional/translational control signals and protein coding sequences. These methods can include in vitro recombinant DNA and synthetic techniques and in vivo recombinants (genetic recombination). Expression of nucleic acid sequences encoding a diTPS polypeptide, or a fragment thereof, can be regulated by a second nucleic acid sequence so that the genes or fragments thereof are expressed in a host transformed with the recombinant DNA molecule(s). For example, expression of the proteins can be controlled by any promoter/enhancer known in the art. In a specific embodiment, the promoter is not native to the genes for a diTPS protein. Promoters that can be used include but are not limited to prokaryotic, yeast, mammalian and plant promoters. The type of promoter depends upon the expression system used, described in more detail below.

In a specific embodiment, a vector is used that contains a promoter operably linked to nucleic acids encoding a diTPS polypeptide, or a fragment thereof, thereof, one or more origins of replication, and optionally, one or more selectable markers (e.g., an antibiotic resistance gene). Vectors and systems for expression of diTPS polypeptides are described, including, for example, the pET28b(+) vector.

3. Expression Systems

Diterpene synthases, including diTPS polypeptides provided herein, can be produced by any methods known in the art for protein production including in vitro and in vivo methods such as, for example, the introduction of nucleic acid molecules encoding the diterpene synthase (e.g. AbIso, AbLAS and AbCAS) into a host cell or host plant for in vivo production or expression from nucleic acid molecules encoding the diterpene synthase (e.g. AbIso, AbLAS and AbCAS) in vitro. Diterpene synthases such as AbIso, AbLAS and AbCAS polypeptides can be expressed in any organism suitable to produce the required amounts and forms of a synthase polypeptide. Expression hosts include prokaryotic and eukaryotic organisms such as *E. coli*, yeast, plants, insect cells, mammalian cells, including human cell lines and transgenic animals. Expression hosts can differ in their protein production levels as well as the types of post-translational modifications that are present on the expressed proteins. The choice of expression host can be made based on these and d other factors, such as regulatory and safety considerations, production costs and the need and methods for purification.

Isolated higher eukaryotic cells, for example cell culture, can also be used, instead of complete organisms, as hosts to carry out the method provided herein in vivo. Suitable eukaryotic cells can be any non-human cell, but are generally plant cells. Representative examples of a plant host cell include for example plants that naturally produce high amounts of terpenes. The plant can be selected from the family of Pinaceae, Funariacea, Solanaceae, Poaceae, Brassicaceae, Fabaceae, Malvaceae, Asteraceae or Lamiaceae. For example, the plant is selected from the genera *Picea* (spruce), *Pinus* (pine), *Abies* (fir), *Physcomitrella, Funariaceae, Nicotiana, Solanum, Sorghum, Arabidopsis, Brassica* (rape), *Medicago* (alfalfa), *Gossypium* (cotton), *Artemisia, Salvia* and *Mentha*. Preferably, the plant belongs to the species of *Nicotiana tabacum, Nicotiana benthamiana* or *Physcomitrella patens*. Additional plants and plant cells include, for example, citrus, corn, rice, algae, and lemna. In other examples, the eukaryotic cells are yeast cells. Representative examples of a yeast host cell include those from the *Saccharomyces* genus (e.g. *Saccharomyces cerevisiae*) and *Pichia* genus (e.g. *Pichia pastoris*). In some examples, insect cells such as *Drosophila* cells and *lepidopteran* cells are used for the expression of a diTPS provided herein. Eukaryotic cells for expression also include mammalian cells lines such as Chinese hamster ovary (CHO) cells or baby hamster kidney (BHK) cells.

Eukaryotic expression hosts also include production in transgenic animals, for example, including production in serum, milk and eggs. There are several methods known in the art for the creation of transgenic host organisms or cells such as plants, fungi, prokaryotes, or cultures of higher eukaryotic cells. Appropriate cloning and expression vectors for use with bacterial, fungal, yeast, plant and mammalian cellular hosts are described, for example, in Pouwels et al., Cloning Vectors: A Laboratory Manual, 1985, Elsevier, New York and Sambrook et al., Molecular Cloning: A Laboratory Manual, $2^{nd}$ edition, 1989, Cold Spring Harbor Laboratory Press. Cloning and expression vectors for higher plants and/or plant cells in particular are available to the skilled person. See for example Schardl et al. (1987) *Gene* 61: 1-11.

Methods for transforming host organisms or cells to harbor transgenic nucleic acids are familiar to the skilled person. For the creation of transgenic plants, for example, current methods include: electroporation of plant protoplasts, liposome-mediated transformation, *agrobacterium*-mediated transformation, polyethylene-glycol-mediated transformation, particle bombardment, microinjection of plant cells, and transformation using viruses.

Many expression vectors are available and known to those of skill in the art for the expression of a diterpene synthase, such as a diTPS provided herein. Exemplary of expression vectors are pET expression vectors, such as pET28b(+). The choice of expression vector is influenced by the choice of host expression system. Such selection is well within the level of skill of the skilled artisan. In general, expression vectors can include transcriptional promoters and optionally enhancers, translational signals, and transcriptional and translational termination signals. Expression vectors that are used for stable transformation typically have a selectable marker which allows selection and maintenance of the transformed cells. In some cases, an origin of replication can be used to amplify the copy number of the vectors in the cells.

Diterpene synthases, including diTPS polypeptides, also can be utilized or expressed as protein fusions. For example, a fusion can be generated to add additional functionality to a polypeptide. Examples of fusion proteins include, but are not limited to, fusions of a signal sequence, a tag such as for localization, e.g. a $his_6$ tag or a myc tag, or a tag for purification, for example, a GST fusion, GFP fusion or CBP fusion, and a sequence for directing protein secretion and/or membrane association. In other examples, diterpene synthases such as diTPS polypeptides provided herein can be fused to GGPP synthase (see, e.g., Brodelius et al. (2002) *Eur. J. Biochem.* 269:3570-3579).

Methods of production of diterpene synthase polypeptides, including AbIso, AbLAS and AbCAS polypeptides, can include co-expression of an acyclic pyrophosphate terpene precursor, such as GGPP, in the host cell. In some instances, the host cell naturally expresses GGPP. Such a cell can be modified to express greater quantities of GGPP (see e.g. U.S. Pat. Nos. 6,531,303, 6,689,593, 7,838,279 and 7,842,497). In other instances, a host cell that does not naturally produce GGPP is modified genetically to produce GGPP.

a. Prokaryotic Cells

Prokaryotes, especially *E. coli*, provide a system for producing large amounts of the diTPS polypeptides provided herein. Transformation of *E. coli* is a simple and rapid technique well known to those of skill in the art. Representative examples of a bacterial host cell include, but are not limited to, *E. coli* strains such as for example *E. coli* BL21DE3-C41 (Miroux and Walker (1996) *J Mol Biol* 260:289-298). Exemplary expression vectors for transformation of *E. coli* cells, include, for example, the pGEM expression vectors, the pQE expression vectors, and the pET expression vectors (see, U.S. Pat. No. 4,952,496; available from Novagen, Madison, Wis.; see, also literature published by Novagen describing the system). Such plasmids include pET11a, which contains the T7lac promoter, T7 terminator, the inducible *E. coli* lac operator, and the lac repressor gene; pET12a-c, which contains the T7 promoter, T7 terminator, and the *E. coli* ompT secretion signal; and pET15b and pET19b (Novagen, Madison, Wis.), which contain a His-Tag™ leader sequence for use in purification with a His column and a thrombin cleavage site that permits cleavage following purification over the column, the T7-lac promoter region and the T7 terminator; and pET28b (Novagen, Madison, Wis.), which contains a His-Tag™ leader sequence for use in purification with a His column and a thrombin cleavage site that permits cleavage following purification over the column, the T7-lac promoter region and the T7 terminator; and the pJET vectors (Thermo Scientific), such as the pJET1.2 vector which contains a lethal gene which is disrupted by ligation of a DNA insert into the cloning site and a T7 promoter for in vitro transcription.

Expression vectors for *E. coli* can contain inducible promoters that are useful for inducing high levels of protein expression and for expressing proteins that exhibit some toxicity to the host cells. Exemplary prokaryotic promoters include, for example, the β-lactamase promoter (Jay et al., (1981) *Proc. Natl. Acad. Sci. USA* 78:5543) and the tac promoter (DeBoer et al., (1983) *Proc. Natl. Acad. Sci. USA* 80:21-25); see also "Useful Proteins from Recombinant Bacteria": in Scientific American 242:79-94 (1980)). Examples of inducible promoters include the lac promoter, the trp promoter, the hybrid tac promoter, the T7 and SP6 RNA promoters and the temperature regulated $\lambda P_L$ promoter.

Diterpene synthases, including diTPS polypeptides provided herein can be expressed in the cytoplasmic environment of *E. coli*. The cytoplasm is a reducing environment and for some molecules, this can result in the formation of insoluble inclusion bodies. Reducing agents such as dithiothreitol and β-mercaptoethanol and denaturants (e.g., such as guanidine-HCl and urea) can be used to resolubilize the proteins. An alternative approach is the expression diTPS polypeptides in the periplasmic space of bacteria which provides an oxidizing environment and chaperonin-like and disulfide isomerases leading to the production of soluble protein. Typically, a leader sequence is fused to the protein to be expressed which directs the protein to the periplasm. The leader is then removed by signal peptidases inside the periplasm. Examples of periplasmic-targeting leader sequences include the pelB leader from the pectate lyase gene and the leader derived from the alkaline phosphatase gene. In some cases, periplasmic expression allows leakage of the expressed protein into the culture medium. The secretion of proteins allows quick and simple purification from the culture supernatant. Proteins that are not secreted can be obtained from the periplasm by osmotic lysis. Similar to cytoplasmic expression, in some cases proteins can become insoluble and denaturants and reducing agents can be used to facilitate solubilization and refolding. Temperature of induction and growth also can influence expression levels and solubility. Typically, temperatures between 25° C. and 37° C. are used. Mutations also can be used to increase solubility of expressed proteins. Typically, bacteria produce aglycosylated proteins.

b. Yeast Cells

Yeast systems, such as, but not limited to, those from the *Saccharomyces* genus (e.g. *Saccharomyces cerevisiae*), *Schizosaccharomyces pombe, Yarrowia lipolytica, Kluyveromyces lactis*, and *Pichia pastoris* can be used to express the diterpene synthases, such as the diTPS polypeptides, provided herein. Yeast expression systems also can be used to produce diterpenes whose reactions are catalyzed by the synthases. Yeast can be transformed with episomal replicating vectors or by stable chromosomal integration by homologous recombination. In some examples, inducible promoters are used to regulate gene expression. Exemplary promoter sequences for expression of diTPS polypeptides in yeast include, among others, promoters for metallothionine, 3-phosphoglycerate kinase (Hitzeman et al. (1980) *J. Biol. Chem.* 255:2073), or other glycolytic enzymes (Hess et al. (1968) *J. Adv. Enzyme Reg.* 7:149; and Holland et al. (1978) *Biochem.* 17:4900), such as enolase, glyceraldehyde phosphate dehydrogenase, hexokinase, pyruvate decarboxylase, phosphofructokinase, glucose phosphate isomerase, 3-phosphoglycerate mutase, pyruvate kinase, triosephosphate isomerase, phosphoglucose isomerase, and glucokinase.

Other suitable vectors and promoters for use in yeast expression are further described in Hitzeman, EPA-73,657 or in Fleer et al. (1991) *Gene,* 107:285-195; and van den Berg et al. (1990) *Bio/Technology,* 8:135-139. Another alternative includes, but is not limited to, the glucose-repressible ADH2 promoter described by Russell et al. (*J. Biol. Chem.* 258: 2674, 1982) and Beier et al. (*Nature* 300:724, 1982), or a modified ADH1 promoter. Shuttle vectors replicable in yeast and *E. coli* can be constructed by, for example, inserting DNA sequences from pBR322 for selection and replication in *E. coli* (Amp$^r$ gene and origin of replication) into a yeast vector.

Yeast expression vectors can include a selectable marker such as LEU2, TRP1, HIS3, and URA3 for selection and maintenance of the transformed DNA. Proteins expressed in yeast are often soluble and co-expression with chaperonins, such as Bip and protein disulfide isomerase, can improve expression levels and solubility. Additionally, proteins expressed in yeast can be directed for secretion using secretion signal peptide fusions such as the yeast mating type alpha-factor secretion signal from *Saccharomyces cerevisiae* and fusions with yeast cell surface proteins such as the Aga2p mating adhesion receptor or the *Arxula adeninivorans* glucoamylase. A protease cleavage site (e.g., the Kex-2 protease) can be engineered to remove the fused sequences from the polypeptides as they exit the secretion pathway.

Yeast naturally express the required proteins, including GGPP synthase (BST1; which can produce GGPP) for the mevalonate-dependent isoprenoid biosynthetic pathway. Thus, expression of the diterpene synthases, including diTPS polypeptides provided herein, in yeast cells can result in the production of diterpenes, such as cis-abienol from GGPP. Exemplary yeast cells for the expression of terpene synthases, including diTPS polypeptides, include yeast modified to express increased levels of FPP and/or GGPP. For example, yeast cells can be modified to produce less squalene synthase or less active squalene synthase (e.g. erg9 mutants; see e.g. U.S. Pat. Nos. 6,531,303 and 6,689,593). This results in accumulation of FPP in the host cell at higher levels compared to wild type yeast cells, which in turn can result in increased yields of GGPP and diterpenes (e.g. cis-abienol, isopimaradiene, abietadiene, levopimaradiene, palustradiene and/or neoabietadiene). In another example, yeast cells can be modified to produce more GGPP synthase by introduction of a GGPP synthase gene, such as BTS1 from *S. cerevisiae*, crtE from *Erwinia uredovora*, crtE from *Xanthophyllomyces dendrorhous*, al-3 from *Neuspora crassa* or ggs from *Giverella fujiuroi* (see U.S. Pat. No. 7,842,497). In some examples, the native GGPP gene in such yeast can be deleted. Other modifications that enable increased production of GGPP in yeast include, for example, but are not limited to, modifications that increase production of acetyl CoA, inactivate genes that encode enzymes that use FPP and GPP as substrate and overexpress of HMG-CoA reductases, as described in U.S. Pat. No. 7,842,497. Exemplary modified yeast cells include, but are not limited to, modified *Saccharomyces cerevisiae* strains CALI5-1 (ura3, leu2, his3, trp1, Δ erg9::HIS3, HMG2cat/TRP1::rDNA, dpp1, sue), ALX7-95 (ura3, his3, trp1, Δerg9:: HIS3, HMG2cat/TRP1::rDNA, dpp1 sue), ALX11-30 (ura3, trp1, erg9$^{def}$25, HMG2cat/TRP1::rDNA, dpp1, sue), which are known and described in one or more of U.S. Pat. Nos. 6,531,303, 6,689,593, 7,838,279, 7,842,497, and published U.S. Pat. Application Serial Nos. 20040249219 and 20110189717.

c. Plants and Plant Cells

Transgenic plant cells and plants can be used for the expression of diterpene synthases, including diTPS polypeptides provided herein. Expression constructs are typically transferred to plants using direct DNA transfer such as microprojectile bombardment and PEG-mediated transfer into protoplasts, and with *agrobacterium*-mediated transformation. Expression vectors can include promoter and enhancer sequences, transcriptional termination elements, and translational control elements. Expression vectors and transformation techniques are usually divided between dicot hosts, such as *Arabidopsis* and tobacco, and monocot hosts, such as corn and rice. Examples of plant promoters used for expression include the cauliflower mosaic virus promoter, the nopaline synthase promoter, the ribose bisphosphate carboxylase promoter and the ubiquitin and UBQ3 promoters. Selectable markers such as hygromycin, phosphomannose isomerase and neomycin phosphotransferase are often used to facilitate selection and maintenance of transformed cells. Transformed plant cells can be maintained in culture as cells, aggregates (callus tissue) or regenerated into whole plants. Transgenic plant cells also can include algae engineered to produce proteins (see, for example, Mayfield et al. (2003) *Proc Natl Acad Sci USA* 100:438-442). Transformed plants include, for example, plants selected from the genera *Picea* (spruce), *Pinus* (pine), *Abies* (fir), *Physcomitrella, Funariaceae, Nicotiana, Solanum, Sorghum, Arabidopsis, Medicago* (alfalfa), *Gossypium* (cotton), *Brassica* (rape), *Artemisia, Salvia* and *Mentha*. In some examples, the plant belongs to the species of *Nicotiana tabacum, Nicotiana benthamiana* or *Physcomitrella patens*, and is transformed with vectors that overexpress a diTPS and optionally a geranylgeranyl diphosphate synthase, such as described in U.S. Pat. Pub. No. 20090123984 and U.S. Pat. No. 7,906,710.

d. Insects and Insect Cells

Insects and insect cells, particularly a baculovirus expression system, can be used for expressing diterpene synthases, including diTPS polypeptides provided herein (see, for example, Muneta et al. (2003) *J. Vet. Med. Sci.* 65(2):219-223). Insect cells and insect larvae, including expression in the haemolymph, express high levels of protein and are capable of most of the post-translational modifications used by higher eukaryotes. Baculoviruses have a restrictive host range which improves the safety and reduces regulatory concerns of eukaryotic expression. Typically, expression vectors use a promoter such as the polyhedrin promoter of baculovirus for high level expression. Commonly used baculovirus systems include baculoviruses such as *Autographa californica* nuclear polyhedrosis virus (AcNPV), and the *Bombyx mori* nuclear polyhedrosis virus (BmNPV) and an insect cell line such as Sf9 derived from *Spodoptera frugiperda*, *Pseudaletia unipuncta* (A7S) and *Danaus plexippus* (DpN1). For high level expression, the nucleotide sequence of the molecule to be expressed is fused immediately downstream of the polyhedrin initiation codon of the virus. Mammalian secretion signals are accurately processed in insect cells and can be used to secrete the expressed protein into the culture medium. In addition, the cell lines *Pseudaletia unipuncta* (A7S) and *Danaus plexippus* (DpN1) produce proteins with glycosylation patterns similar to mammalian cell systems.

An alternative expression system in insect cells is the use of stably transformed cells. Cell lines such as the Schnieder 2 (S2) and Kc cells (*Drosophila melanogaster*) and C7 cells (*Aedes albopictus*) can be used for expression. The *Drosophila* metallothionein promoter can be used to induce high levels of expression in the presence of heavy metal induction with cadmium or copper. Expression vectors are typically maintained by the use of selectable markers such as neomycin and hygromycin.

e. Mammalian Expression

Mammalian expression systems can be used to express diterpene synthases, including diTPS polypeptides provided herein and also can be used to produce diterpenes whose reactions are catalyzed by the synthases. Expression constructs can be transferred to mammalian cells by viral infection such as adenovirus or by direct DNA transfer such as liposomes, calcium phosphate, DEAE-dextran and by physical means such as electroporation and microinjection. Expression vectors for mammalian cells typically include an mRNA cap site, a TATA box, a translational initiation sequence (Kozak consensus sequence) and polyadenylation elements. Such vectors often include transcriptional promoter-enhancers for high level expression, for example the SV40 promoter-enhancer, the human cytomegalovirus (CMV) promoter, and the long terminal repeat of Rous sarcoma virus (RSV). These promoter-enhancers are active in many cell types. Tissue and cell-type promoters and enhancer regions also can be used for expression. Exemplary promoter/enhancer regions include, but are not limited to, those from genes such as elastase I, insulin, immunoglobulin, mouse mammary tumor virus, albumin, alpha-fetoprotein, alpha 1-antitrypsin, beta-globin, myelin basic protein, myosin light chain-2 and gonadotropic releasing hormone gene control. Selectable markers can be used to select for and maintain cells with the expression construct. Examples of selectable marker genes include, but are not limited to, hygromycin B phosphotransferase, adenosine deaminase, xanthine-guanine phosphoribosyl transferase, aminoglycoside phosphotransferase, dihydrofolate reductase and thymidine kinase. Fusion with cell surface signaling molecules such as TCR-ζ and Fc$_\epsilon$RI-γ can direct expression of the proteins in an active state on the cell surface.

Many cell lines are available for mammalian expression including mouse, rat human, monkey, and chicken and hamster cells. Exemplary cell lines include, but are not limited to, BHK (i.e. BHK-21 cells), 293-F, CHO, CHO Express (CHOX; Excellgene), Balb/3T3, HeLa, MT2, mouse NSO (non-secreting) and other myeloma cell lines, hybridoma and heterohybridoma cell lines, lymphocytes, fibroblasts, Sp2/0, COS, NIH3T3, HEK293, 293S, 293T, 2B8, and HKB cells. Cell lines also are available adapted to serum-free media which facilitates purification of secreted proteins from the cell culture media. One such example is the serum free EBNA-1 cell line (Pham et al. (2003) *Biotechnol. Bioeng.* 84:332-342).

4. Purification

Also provided is a method of producing the diTPS polypeptide. The diTPS polypeptide can be purified using standard chromatographic techniques.

The polypeptide to be used when the method is carried out in vitro can be obtained by extraction from any organism expressing it, using standard protein or enzyme extraction technologies. If the host organism is a unicellular organism or cell releasing the polypeptide of the invention into the culture medium, the polypeptide can simply be collected from the culture medium, for example by centrifugation, optionally followed by washing steps and re-suspension in suitable buffer solutions. If the organism or cell accumulates the polypeptide within its cells, the polypeptide can be obtained by disruption or lysis of the cells and further extraction of the polypeptide from the cell lysate.

Methods for purification of diterpene synthases, such as diTPS polypeptides, from host cells depend on the chosen host cells and expression systems. For secreted molecules, proteins are generally purified from the culture media after removing the cells. For intracellular expression, cells can be lysed and the proteins purified from the extract. When transgenic organisms such as transgenic plants and animals are used for expression, tissues or organs can be used as starting material to make a lysed cell extract. Additionally, transgenic animal production can include the production of polypeptides in milk or eggs, which can be collected, and if necessary the proteins can be extracted and further purified using standard methods in the art.

Diterpene synthases, including diTPS polypeptides provided herein, can be purified using standard protein purification techniques known in the art including but not limited to, SDS-PAGE, size fraction and size exclusion chromatography, ammonium sulfate precipitation, chelate chromatography and ionic exchange chromatography. Expression constructs also can be engineered to add an affinity tag such as a myc epitope, GST fusion or His$_6$ and affinity purified with myc antibody, glutathione resin, and Ni-resin, respectively, to a protein. Purity can be assessed by any method known in the art including gel electrophoresis and staining and spectrophotometric techniques. The polypeptides, either in an isolated form or together with other proteins, for example in a crude protein extract obtained from cultured cells or microorganisms, can then be suspended in a buffer solution at optimal pH. If adequate, salts, DTT, BSA and other kinds of enzymatic co-factors, can be added in order to optimize enzyme activity.

5. Fusion Proteins

Fusion proteins containing a diterpene synthase, including diTPS polypeptides, and one or more other polypeptides also are provided. Linkage of a diterpene synthase polypeptide with another polypeptide can be effected directly or indirectly via a linker. In one example, linkage can be by chemical linkage, such as via heterobifunctional agents or thiol linkages or other such linkages. Fusion also can be effected by recombinant means. Fusion of a diterpene synthase, such as a diTPS polypeptide, e.g., AbIso, AbLAS and AbCAS, to another polypeptide can be to the N- or C-terminus of the diTPS polypeptide.

A fusion protein can be produced by standard recombinant techniques. For example, DNA fragments coding for the different polypeptide sequences can be ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel et al. (eds.) Current Protocols in Molecular Biology, John Wiley & Sons, 1992). Moreover, many expression vectors are commercially available that already encode a fusion moiety (e.g., a GST polypeptide). For example, an AbCAS polypeptide-encoding nucleic acid can be cloned into such an expression vector such that nucleic acid encoding AbCAS is linked in-frame to a polypeptide encoding a protein purification tag, such as a His tag. In another example, a nucleic acid molecule encoding a diTPS polypeptide can be linked in-frame to a polypeptide encoding a GGPP synthase. The diTPS polypeptide and additional polypeptide can be linked directly, without a linker, or alternatively, linked indirectly in-frame with a linker.

G. Examples

The following examples are included for illustrative purposes only and are not intended to limit the scope of the invention.

Example 1

Terpenoid Metabolic Profiling of Balsam Fir

A diterpenoid metabolic profile was established for wood and xylem, bark and phloem, and needles of balsam fir sapling trees to determine if it is a suitable tissue source for transcriptome mining of synthase genes involved in diterpenoid biosynthesis. Mono- and sesquiterpenoids were also measured.

A. Methods

1. Plant Material

Two-year old saplings of *Abies balsamea* var. *phanerolepsis* (L.) Mill. were purchased from Arbutus Grove Nursery Ltd. (North Saanich, BC, Canada) and maintained in a greenhouse as previously described in Miller et al. (*Plant Physiol.* 137:369-382 (2005)). Needles, xylem/wood and phloem/bark were harvested from the upper interwhorls and used fresh or flash frozen in liquid $N_2$ for metabolite and RNA extraction, respectively.

2. Diterpene Standards

Authentic diterpene resin acid standards were purchased from Orchid Celmark (New Westminster, BC, Canada). The corresponding diterpene olefins were synthesized from the acids at Best West Labs Inc. (Salt Lake City, Utah, USA) as previously described (Ro et al. (2005) *Proc. Natl. Acad. Sci. USA* 102, 8060-8065).

3. Metabolite Analysis

Terpenoids were extracted from samples of 2 g of pulverized tissue with 1.5 mL of diethyl ether for 16 h at room temperature. Water was removed by addition of anhydrous $Na_2SO_4$, and extracts were passed through 0.22 μm GHP membrane filters (PALL Corporation, De Miniac, QC, Canada). GC-MS analysis was performed on an Agilent 6890N GC (Agilent Technologies Inc, Mississauga, ON, Canada), 7683B series autosampler, and a 5975 Inert XL MS Detector at 70 eV and 1 ml min$^{-1}$ He as carrier gas using a SGE Solgel-Wax column (polyethylene glycol, 30 m, 250 μm i.d., 0.25 μm film) with the following GC temperature program: 40° C. for 5 min, 3° C. min$^{-1}$ to 80° C., 8° C. min$^{-1}$ to 250° C., 10° C. min$^{-1}$ to 270° C., hold 5 min, pulsed splitless injector held at 250° C.

Diterpene resin acids were extracted from samples of approximately 150 mg tissue with 1.5 mL methyl tert-butyl ether following the method described in Lewinsohn et al. (*Plant Physiol.* 101:1021-1028 (1993)) and derivatized with 2 M trimethylsilyl diazomethane (Sigma, Oakville, ON, Canada). GC-MS analysis was performed using an Alltech AT-1000 column (polyethylene glycol-acid modified, 30 m, 250 μm i.d., 0.25 μm film) and GC specifications as follows: 150° C. initial temperature, 1.5° C. min$^{-1}$ to 220° C., 20° C. min$^{-1}$ to 240° C.

Compound identification was achieved by comparison of mass spectra to those of authentic standards and reference mass spectral databases of the National Institute of Standards and Technology (NIST) MS library searches (Wiley W9N08). Quantifications were based on three independent biological replicates.

B. Results

While only trace amounts of terpenoids were detected in wood tissue, bark/phloem and needle samples had similar total amounts of terpenoids, made up mostly of diterpenoids, with lesser amounts of monoterpenoids and relatively minor amounts of sesquiterpenoids (see Table 3 below). Both the bark/phloem and the needle samples contained the diterpene resin acids, abietic acid, isopimaric acid, dehydroabietic acid and palustric acid, as major diterpenoids. These diterpene acids are all commonly abundant in conifers. Cis-abienol was found almost exclusively in the bark/phloem tissue, where it was the most abundant terpenoid metabolite, accounting for more than 25% of the total amount of diterpenoids of balsam fir stem tissue.

TABLE 3

Terpenoid metabolite profiles of Abies balsamea bark/phloem and needle tissues.

| | $\mu g\ g^{-1}$ DW | |
|---|---|---|
| Terpenoid Metabolite | Bark/Phloem | Needles |
| Monoterpenes[1] | | |
| α-Pinene[1] | 126 ± 1 | 72 ± 19 |
| Camphene[1] | 18 ± 15 | 65 ± 12 |
| β-Pinene[1] | 171 ± 41 | 100 ± 36 |
| 3-Carene[1] | 111 ± 36 | 188 ± 23 |
| Myrcene[1] | 11 ± 1 | 10 ± 0 |
| Limonene | 134 ± 17 | 25 ± 5 |
| β-Phellandrene[1] | 67 ± 13 | 20 ± 2 |
| Terpinolene[1] | 15 ± 7 | 15 ± 2 |
| Borneol[1] | 2 ± 1 | 17 ± 7 |
| Bornyl acetate[1] | 130 ± 121 | 305 ± 29 |
| Total | 785 ± 253 | 817 ± 135 |
| Sesquiterpenes[1] | | |
| Longipinene[1] | 11 ± 8 | 5 ± 2 |
| Longifolene[1] | 51 ± 36 | 2 ± 1 |
| α-Humulene[1] | 5 ± 3 | 12 ± 11 |
| β-Bisabolene[1] | 26 ± 13 | 34 ± 19 |
| trans-Caryophyllene[1] | 11 ± 7 | 22 ± 20 |
| Total | 104 ± 67 | 75 ± 53 |
| Diterpenes[1,2] | | |
| Isopimaradiene[1] | 16 ± 1 | traces |
| (epi)-Manoyl oxide[1] | 33 ± 3 | traces |
| Abietadiene[1] | 15 ± 5 | 8 ± 1 |
| cis-abienol[2] | 3287 ± 25 | n.d.* |
| Abietadieneal[1] | 35 ± 20 | 9 ± 2 |

TABLE 3-continued

Terpenoid metabolite profiles of Abies balsamea bark/phloem and needle tissues.

| | μg g$^{-1}$ DW | |
| --- | --- | --- |
| Terpenoid Metabolite | Bark/Phloem | Needles |
| Pimaric acid[2] | traces | n.d.* |
| Isopimaric acid[2] | 1751 ± 422 | 259 ± 244 |
| Sandaracopimaric acid[2] | 437 ± 298 | 160 ± 60 |
| Palustric acid[2] | 1301 ± 1 | 640 ± 243 |
| Levopimaric acid[2] | 682 ± 56 | 1364 ± 704 |
| Abietic acid[2] | 2037 ± 830 | 717 ± 220 |
| Dehydroabietic acid[2] | 1262 ± 742 | 1617 ± 199 |

[1,2]Terpenoid metabolites extracted with diethyl ether[1] or methyl tert-butyl ether[2];
*n.d., not detected

Example 2

Isolation and Sequencing of Diterpene Synthases (diTPS)

Bark/phloem of balsam fir sapling stems was used as source for the preparation of a non-normalized cDNA library and subsequent transcriptome sequencing for identification of diterpene synthases (diTPS).

A. Identification of Candidate diTPS

Total RNA was isolated from samples of 150 mg bark tissue according to the method of Kolosova et al. (*BioTechniques* 36:821-824 (2004)) and mRNA was purified on Dynabeads (Invitrogen, Burlington, ON, Canada). RNA integrity and amounts were determined on a Bioanalyzer 2100 using an RNA Pico Chip (Agilent).

Construction of a non-normalized bark tissue cDNA library and subsequent 454 transcriptome sequencing was conducted at the McGill University and Genome Québec Innovations Centre (Montreal, QC, Canada). The cDNA library was constructed from 200 ng of fragmented mRNA using the cDNA Rapid Library Preparation kit, GS FLX Titanium series (Roche Diagnostics, Laval, QC, Canada) following manufacturer's protocols. Yield of cDNA and the size range of cDNA fragments were assessed using a Bioanalyzer 2100 Pico Chip (Agilent), and 200 ng of the cDNA library were subjected to a half-plate reaction of 454 pyrosequencing using the Roche GS FLX Titanium technology. A half-plate reaction of Roche 454 sequencing generated a total of 797,060 sequence reads with an average GC content of 46% and an average read length of 359 bp.

After adapter trimming, the remaining high quality reads were subjected to a de novo assembly in GS De novo Assembler 2.5 μl with a size exclusion of 45 bp. The assembly contained 85% of all input reads, yielding 14,699 isogroups from 17,122 isotigs of average size of 1,114 nucleotides.

A subset of candidate isotigs were identified by comparing the assembled sequences against 146 known plant TPSs using a BLASTx search (Altschul et al. (1990) *J. Mol. Biol.* 215: 403-410). This resulted in a subset of isotigs that represented candidate genes for nine different putative mono- and sesqui TPSs and five putative diTPSs (see Table 4 below).

TABLE 4

Summary of in silico annotation of putative TPS assemblies.

| Isotig | Reads | BlastX hit | Species | E-value | Identity [%]* |
| --- | --- | --- | --- | --- | --- |
| 04065 (diTPS4) | 170 | Isopimaradiene synthase | P. abies | 0 | 70 |
| 09468 | 170 | δ-Selinene synthase | A. grandis | $1.8^{-155}$ | 92 |
| 00922 (diTPS3) | 167 | Abietadiene synthase | A. grandis | 0 | 94 |
| 01412 | 165 | Myrcene synthase | P. abies | 0 | 70 |
| 00919 (diTPS1) | 163 | Abietadiene synthase | A. grandis | 0 | 97 |
| 00921 (diTPS2) | 162 | Abietadiene synthase | A. grandis | 0 | 92 |
| 04459 | 160 | β-Phellandrene synthase | A. grandis | 0 | 92 |
| 04736 | 157 | α/β-Pinene synthase | A. grandis | 0 | 97 |
| 04513 | 155 | Sabinene synthase | P. sitchensis | 0 | 76 |
| 09269 | 154 | 4S-Limonene synthase | A. grandis | $9.8^{-161}$ | 93 |
| 04902 | 153 | γ-Humulene synthase | A. grandis | 0 | 92 |
| 07269 | 145 | ent-Kaurene synthase | P. sitchensis | 0 | 91 |
| 11523 | 141 | Linalool synthase | P. abies | $1.3^{-113}$ | 80 |
| 14736 | 128 | Limonene synthase | P. sitchensis | $2.2^{-90}$ | 91 |

*Identity is given as amino acid sequence identity between isotig and Blast hit

B. Isolation of Full-Length cDNAs of Bifunctional Class I/II Gymnosperm diTPSs

Of the diTPSs, four candidate isotigs (AbdiTPS1, AbdiTPS2, AbdiTPS3, and AbdiTPS4) resembled bifunctional class I/II gymnosperm diTPSs of the TPS-d group (Martin et al. (2004) *Plant Physiol* 135:1908-1927; Keeling et al. (2011) *BMC Plant Biol* 11:43; Chen et al. (2011) *The Plant Journal* 66:212-229) containing the characteristic DxDD, DDxxD and NSE/DTE motifs (SEQ ID NOS:12-14, respectively) (see Peters et al. (2003) *Biochemistry* 42:2700-2707; Peters & Croteau (2002) *Biochemistry* 41:1836-1842; Zhou & Peters (2009) *Phytochemistry* 70:366-369). Reads corresponding to these four isotigs were reassembled in PHRAP (de la Bastide & McCombie (2007) *Curr Protoc Bioinformatics Chapter* 11, Unit 11.4), from which three unique partial diTPS cDNA sequences (AbdiTPS1, AbdiTPS2, AbdiTPS3) and one FLcDNA sequence (AbdiTPS4) were obtained.

A full length (FL) cDNA clone for AbdiTPS4 was amplified based on the in silico assembled full-length sequence. For the other synthases, synthesis of cDNA as template for PCR amplification of candidate genes was carried out with random hexamer oligonucleotides using the SMARTer cDNA RACE amplification kit (Clontech, Mountain View, Calif., USA). Completion of the 3'-sequences of AbdiTPS1 and AbdiTPS2 was achieved by rapid amplification of cDNA ends (3'-RACE) using the SMARTer cDNA RACE cDNA amplification kit (Clontech) and Phusion DNA-polymerase (New England Biolabs, Pickering, ON, Canada) with primers set forth in Table 5. The following PCR program was used: Initial denaturation at 98° C. for 30 sec, 5 cycles of denaturation at 98° C. for 20 sec and extension at 72° C. for 90 sec, 5 cycles of denaturation at 98° C. for 20 sec, annealing at 70° C. for 20 sec and extension at 72° C. for 90 sec, 27 cycles of denaturation at 98° C. for 20 sec, annealing at 65° C. for 20 sec and extension at 72° C. for 90 sec, and a final extension at 72° C. for 3 min. The obtained amplicons were gel-purified, and ligated into pJET (SEQ ID NO:32) using the CloneJET kit (Clontech).

TABLE 5

Primers for RACE cDNA amplification

| Primer | Sequence | SEQ ID NO |
|---|---|---|
| AbdiTPS1-3'RACE | CTGAGAGAGGTCAAGGTGAGGAGGC TTCTG | 18 |
| AbdiTPS2-3'RACE | CAGAGAGAGGTCAAGGTGAGGTGGC TTCTG | 19 |

Initial sequences of AbdiTPS1, AbdiTPS2, AbdiTPS3, and AbdiTPS4 were obtained based on the initial high-throughput (lower accuracy) transcriptome reads and are set forth in FIG. 7. Higher accuracy Sanger sequencing of the cloned cDNAs was performed on the AbdiTPS1 and AbdiTPS2 to confirm the sequences, which demonstrated some differences in the N-terminal sequences of AbdiTPS1 and AbdiTPS2 compared to that obtained from transcriptome reads. SEQ ID NOS corresponding to the protein and nucleic acid sequences of the isolated balsam fir diterpene synthases are set forth in Table 6 below. AbdiTPS1 and AbdiTPS4 are full length sequences. AbdiTPS2 is a near full-length sequencing lacking 40-50 basepair residues of the plastidial transit peptide and AbdiTPS3 is a partial sequence.

TABLE 6

AbdiTPS Diterpene Synthases

| Diterpene Synthase | Protein SEQ ID NO | Nucleic Acid SEQ ID NO |
|---|---|---|
| AbdiTPS1 | 1 | 2 |
| AbdiTPS2 | 3 | 4 |
| AbdiTPS3 | 5 | 6 |
| AbdiTPS4 | 7 | 8 |

Example 3

Functional Characterization of Balsam Fir diTPSs and Discovery of a Cis-Abienol Synthase A. Cloning and Expression of Pseudomature Enzyme For functional characterization of AbdiTPS1, AbdiTPS2 and AbdiTPS4, pseudomature versions of these diTPSs starting at the conserved N/KRx6W motif (SEQ ID NO:15) were cloned lacking the putative plastidial transit peptide so that expression in *Escherichia coli* (*E. coli*) could be achieved (Keeling et al. (2008) *Proc Natl Acad Sci USA* 105:1085-1090). To generate pseudomature versions, cDNAs described in Example 2.B were amplified using primers set forth in Table 7 to generate products lacking the plastidial transit peptide. In addition, AbdiTPS4 with a less conserved 5' sequence was cloned as a full length gene. For the amplification, the following PCR program was used: initial denaturation at 98° C. for 30 sec followed by 30 cycles of denaturation at 98° C. for 10 sec, annealing at 65-68° C. for 30 sec and extension at 72° C. for 80 sec, and final extension at 72° C. for 10 min. Amplified products were cloned into pJET (SEQ ID NO:32), and subcloned into the NheI/SalI and NotI restriction sites of pET28b(+) (SEQ ID NO:33; EMD Biosciences, San Diego, Calif., USA). Using this expression vector, a 40 amino acid linker (MGRSHHHHHHSSGLVPRGSHMASMTG-GQQMGRDPNSSSVD; SEQ ID NO:23) was added to the 5' end of the gene-specific sequence, including the 6×His-tag, a T7-tag and a thrombin cleavage site. Hence, for the N-terminally tagged expression constructions, a methionine at which translation is initiated was located upstream of the His-tag. All cDNA constructs were sequence verified at the Nucleic Acid Protein Service Unit (NAPS; University of British Columbia, BC, Canada) prior to expression in *E. coli*.

Recombinant proteins were expressed in *E. coli* BL21DE3-C41 cells, $Ni^+$ affinity purified as described elsewhere (Keeling et al. (2008) *Proc Natl Acad Sci USA* 105: 1085-1090), and desalted against 20 mM HEPES (pH 7.2), 150 mM NaCl, 10% glycerol, 5 mM DTT using PD MiniTrap G-25 columns (GE Healthcare, Piscataway, N.J., USA), resulting in soluble proteins of the expected molecular weight of 90 to 91 kDa. SEQ ID NOS corresponding to the protein and encoding nucleic acid sequences of the expressed pseudomature form of AbdiTPS1, AbdiTPS2 and AbdiTPS4 are set forth in Table 8 below.

TABLE 7

Primers for cDNA amplification

| Primer | Sequence | SEQ ID NO |
|---|---|---|
| AbdiTPS4-For-FL-SalI | TAGTCGACATGGCCCTGCCTGTCTATTC | 20 |
| AbdiTPS4-ForΔ85-SalI | TAGTCGACATGCGAGAATTTCCTCCTTC ATTTTG | 21 |
| AbdiTPS4-Rev-NotI | TAGCGGCCGCTTAGGTAGCCGGCTCGAA G | 22 |
| AbdiTPS2-ForΔ68-NheI | TATGTCGACAAACGAGAATTTCCTCCAG GA | 24 |
| AbdiTPS2-Rev-NotI | TGGGCGGCCGCTTACGCAATCGGTATGA AGAG | 25 |
| AbdiTPS1-For-Δ83-SalI | TATGTCGACAAACGAGAATTTCCTCCAG GA | 26 |
| AbdiTPS1-Rev-NotI | TGGGCGGCCGCCTAGGCAACTGGTTGGA AGAG | 27 |

TABLE 8

Pseudomature Versions of diTPSs

| Diterpene Synthase | Protein SEQ ID NO | Nucleic Acid SEQ ID NO |
|---|---|---|
| AbdiTPS1 | 47 | 51 |
| AbdiTPS2 | 48 | 52 |
| AbdiTPS4 | 55 | 56 |

B. Characterization of Enzyme Activity

Enzyme assays with geranylgeranyl pyrophosphate (GGPP) as substrate followed by GC-MS or LC-MS analysis of reaction products against controls and authentic standards was used to identify functions for AbdiTPS1, AbdiTPS2 and AbdiTPS4. Enzyme assays were carried out as described before (Keeling et al. (2008) *Proc Natl Acad Sci USA* 105: 1085-1090). Assays were carried out in 50 mM HEPES (pH 7.2), 10 µM $MgCl_2$, 5% glycerol, 5 mM DTT, using 100 µg of purified protein (100 µg each for coupled assays) and 15 µM of (E,E,E)-GGPP (Sigma) with incubation for 1 h at 30° C. After extraction of reaction products with 500 µL pentane, GC-MS analysis was conducted on an Agilent 7890A GC, 7683B series autosampler, and a 7000A Triple Quad MS Detector at 70 eV and 1.2 ml $min^{-1}$ He flow using a HP5 ms column (5% phenyl methyl siloxane, 30 m, 250 µm i.d., 0.25

μm film) and the following GC temperature program: 40° C. for 2 min, 20° C. min$^{-1}$ to 300° C., hold 2 min; pulsed splitless injection (injector held at 250° C.).

For the detection of diphosphate intermediates, reaction products were dephosphorylated prior to extraction by incubation with 10 U of calf intestinal alkaline phosphatase (Invitrogen) for 16 h at 37° C. and analyzed on a Solgel-Wax column as described above in Example 1 with modified GC parameters: 40° C. for 2 min, 25° C. min$^{-1}$ to 250° C., hold 5 min, pulsed splitless injector held at 250° C. Analysis of reaction products via LC-MS was performed on an Agilent 1100 Series LC/MSD Trap XCT Plus MS with atmospheric pressure chemical ionization (APCI) in positive mode on an Agilent Zorbax RX-Sil silica column (4.6 mm ID×150 mm×5 μm) as previously reported (Keeling et al. (2011) *J. Biol. Chem.* 286, 21145-21153).

Authentic standards of abietadiene, isopimaradiene, levopimaradiene, neoabietadiene and palustradiene were used as positive controls. Empty vector was used as a negative control. As shown in FIG. 2, the authentic standard of abietadiene contained an unknown contamination and the authentic standard of levopimaradiene contained 30% other diterpene isomers, which could not be removed.

Enzymatic activity assays were confirmed with three independent experiments. The product profile results are set forth in FIG. 2, and summarized as follows:

1. AbdiTPS1

The product profile of AbdiTPS1 was identified by GC-MS to be made up of four peaks corresponding to abietadiene, levopimaradiene, neoabietadiene and palustradiene in a ratio of approximately 4:3:2:1 (see FIG. 2). This profile closely matches that previously identified for grand fir *Abies grandis* abietadiene synthase (AgAS) (NCBI accession no. AAK83563, SEQ ID NO:40) (Peters et al. (2002) *Biochemistry* 39:15592-15602). As shown in Example 5 and FIG. 7, AgAS is a diTPS that is 99% identical with AbdiTPS1 on the amino acid level. According to these patterns, AbdiTPS1 can be classified as an LAS-type bifunctional class I/II diTPS (referred to herein also as AbLAS), which appears to be orthologous with AgAS (SEQ ID NO:40).

Figure 3:
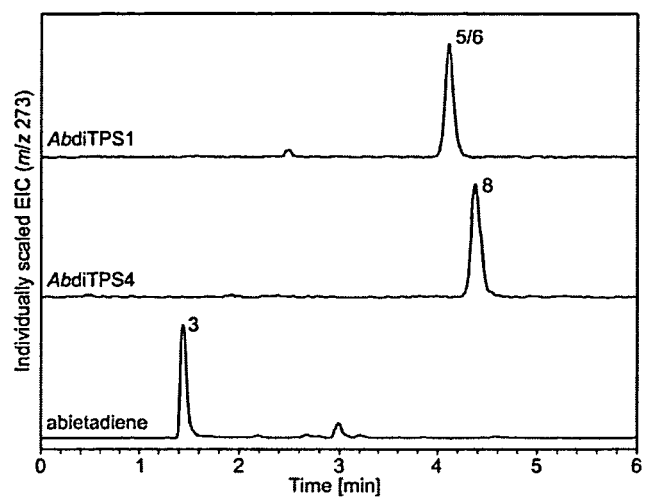
FIG. 3 shows LC-MS analysis of diterpenol products of AbdiTPS1 (AbLAS; SEQ ID NO:1) and AbdiTPS4 (AbCAS; SEQ ID NO:7). Reaction products are shown as extracted ion chromatograms (EIC) of the base peak m/z 273, including 3, abietadiene; 5/6, 13-hydroxy-8(14)-abietadiene epimers; 8, cis-abienol.

Following the recent discovery of epimers of a tertiary alcohol, 13-hydroxy-8(14)-abietene, as the initial enzyme products of Norway spruce *Picea abies* levopimaradiene/abietadiene synthase (PaLAS) (SEQ ID NO:37; Keeling et al. (2011) *J. Biol. Chem.* 286:21145-21153), the product of AbdiTPS1 (AbLAS) by LC-MS was also investigated. As shown in FIG. 3, the detected mass fragment of m/z 273 in the LC-MS analysis corresponds to the dehydration product of 13-hydroxy-8(14)-abietene, and is indicative of dehydration of the unstable diterpene alcohol compounds in the APCI interface, as detailed in Keeling et al. (Keeling et al. (2011) *J. Biol. Chem.* 286:21145-21153). Comparison with abietadiene standard showed separation of olefin compound and the polar hydroxylated diterpenes.

2. AbdiTPS2

The product profile of AbdiTPS2 was identified by GC-MS to be made up of a single peak demonstrating that AbdiTPS2 formed exclusively isopimaradiene (see FIG. 2). This product profile is similar to the previously characterized single-product isopimaradiene synthases from Norway spruce (PaIso; SEQ ID NO:35) and Sitka spruce (PsIso; SEQ ID NO:36) (Martin et al. (2004) *Plant Physiol* 135:1908-1927; Keeling et al. (2008) *Proc Natl Acad Sci USA* 105:1085-1090; Keeling et al. (2011) *BMC Plant Biol* 11:43). AbdiTPS2 was thereby identified as an Iso-type bifunctional class I/II diTPS (referred to herein also as AbIso).

3. AbdiTPS4

The product profile of AbdiTPS4 was identified by GC-MS to be a unique single peak product profile (see FIG. 2 and FIG. 3). The product corresponded to cis-abienol according to retention time consistent with the compound extracted from plant tissue and shared characteristic mass fragments (e.g., m/z 290 [M+], m/z 272 [M+—H2O], and m/z 134) in comparison with reference mass spectra (Vlad et al. (1974) *Khimiya Prirodnykh Soedinenii* 1:30-35) and obtained from the National Institute of Standards and Technology MS library searches (Wiley W9N08). An authentic cis-abienol standard is not commercially available. When the product of AbdiTPS4 was analyzed by GC-MS, under a number of different conditions, poor resolution of the shape of the cis-abienol peak (see FIG. 2) was observed, relative to the peak shape of diterpene olefins, and the occurrence of trace amounts of two additional compounds. This profile is likely due to degradation of cis-abienol during GC-MS as previously reported (Severson et al. (1984) *Journal of Agricultural and Food Chemistry* 32:566-570; Ding et al. (2007) *Chromatographia* 66:529-532; Carman & Duffield (1993) *Aust. J. Chem.* 46:1105-1114). LC-MS analysis confirmed cis-abienol as a single product of AbdiTPS4, with m/z 273 in the LC MS analysis corresponding to the predicted dehydration product of the diterpene alcohol (see FIG. 3). AbdiTPS4 was thereby identified as a bifunctional class I/II cis-abienol synthase (referred to herein also as AbCAS). AbCAS represents a new type of conifer diTPS, producing a bicyclic, tertiary diterpene alcohol, as opposed to tricyclic products of the LAS- and Iso-type diTPSs.

Additional structural and stereochemical analysis by proton and carbon NMR and comparison to previously reported analyses (Ding et al. (2007) *Chromatographia*, 66:529-532; Carman et al. (1993) *Aust. J. Chem.*, 46:1105-1114) confirmed the identity of the AbdiTPS4 product as cis-abienol. For Nuclear magnetic resonance (NMR) analysis, Cis-abienol was prepared from a pool of ten individual enzyme assays as described above using 20 μM GGPP and an incubation time of 2 h to maximize product formation. To enhance product purity, pentane was purified on alumina prior to use and assays were performed in buffer pre-extracted with alumina-purified pentane. Nuclear magnetic resonance (NMR) spectra were recorded on a Bruker Avance 600 equipped with a QNP or TCI cryoprobe (600 MHz) using deuterochloroform (CDCl$_3$) as the solvent, which was neutralized by distillation and filtration through potassium carbonate prior to preparation of the sample. Signal positions (δ) were calculated in parts per million (ppm) as compared to tetramethylsilane (δ 0) and were measured relative to the signal of the solvent (CDCl$_3$: δ 7.26, $^1$H NMR; δ 77.0, $^{13}$C NMR).

Example 4

Phylogenetic Analysis of Bifunctional Class I/II Gymnosperm diTPSs

To perform phylogenetic analysis, the encoded amino acid sequences of AbdiTPS1, AbdiTPS2, AbdiTPS3 and AbdiTPS4 were compared to the amino acid sequence of other synthases. Multiple protein sequence alignments were performed using the CLC bio Main Workbench 5.7.1 (CLC bio, Århus, Denmark). Phylogenetic analyses were conducted on the basis of the maximum likelihood algorithm using PhyML 3.0 (Guindon et al. (2010) *Syst. Biol* 59:307-321) with four rate substitution categories, LG substitution model, BIONJ starting tree and 100 bootstrap repetitions, and displayed as phylogram using treeview32 1.6.6, by rooting with the outgroup *Physcomitrella patens* ent-copalyl diphosphate/ent-kaurene synthase (PpCPS/KS; NCBI accession no. BAF61135; SEQ ID NO:42) and diterpene synthases TbrTS, *Taxus brevifolia* taxadiene synthase (NCBI accession no. AAC49310; SEQ ID NO:43); TcuTS, *T. cuspidata* taxadiene synthase (NCBI accession no. ABW82997; SEQ ID NO:44); TxmTS, *T. x media* taxadiene synthase (NCBI accession no. AAS18603; SEQ ID NO:45); PaIso, *Picea abies* isopimaradiene synthase (NCBI accession no. AAS47690; SEQ ID NO:35); PsIso, *Picea sitchensis* isopimaradiene synthase (NCBI accession no. ADZ45512; SEQ ID NO:36); PaLAS, *P. abies* (NCBI accession no. AAS47691; SEQ ID NO:37); PsLAS, *P. sitchensis* levopimaradiene/abietadiene synthase (NCBI accession no. ADZ45517; SEQ ID NO:38); PtLAS, *Pinus taeda* levopimaradiene synthase (NCBI accession no. AY779541; SEQ ID NO:39); AgAS, *Abies grandis* abietadiene synthase (NCBI accession no. AAK83563; SEQ ID NO:40); and GbLS, *Ginkgo biloba* levopimaradiene synthase (NCBI accession no. AAL09965; SEQ ID NO:41).

The encoded proteins of AbdiTPS1, AbdiTPS2, and AbdiTPS3 showed highest similarity with grand fir (*Abies grandis*) abietadiene synthase (AgAS; SEQ ID NO:40) (Stofer Vogel et al. (1996) *J. Biol. Chem.* 271:23262-23268; Peters et al. (2000) *Biochemistry* 39:15592-15602), with more than 90% protein sequence identity. In contrast, the deduced protein sequence AbdiTPS4 showed highest similarity with Norway spruce (*Picea abies*) isopimaradiene synthase (PaIso; SEQ ID NO:35) (Martin et al. (2004) *Plant Physiol* 135:1908-1927), although on a substantially lower level of sequence identity of only 75%, highlighting AbdiTPS4 as a unique candidate diTPS sequence.

The results of the phylogentic analysis are shown in FIG. 4. The results show that other conifers contain diTPSs of the levopimaradiene synthase (LAS) and isopimaradiene synthase (Iso) types. LAS- or Iso type diTPSs have now been identified in three different genera of the pine family, namely in true firs (*Abies*), spruce (*Picea*), and pine (*Pinus*), which allows for analysis of gene orthology within this family. It appears that gene duplications and neo-functionalization leading to paralogous pairs of LAS and Iso genes occurred independently in *Abies* and *Picea*, after the separation of these genera. Within the spruce genus, the dichotomy of LAS- and Iso-genes happened apparently prior to the speciation of Norway spruce and Sitka spruce.

Within the group of conifer class I/II diTPSs, the AbdiTPS4 (AbCAS) gene is separate from, and appears basal to, the clade of levopimaradiene synthase (LAS) and isopimaradiene synthase (Iso) genes from firs, spruces, and pine. The bifunctional class I/II AbCAS described here has only been cloned from balsam fir, matching the major diterpenoid produced by this species as described in Example 1 (see also Table 3).

Example 5

Analysis of the Reaction Sequence of the Bifunctional Class I/II AbCAS by Site Directed Mutagenesis A mechanism for the formation of cis-abienol requires hydroxylation via water quenching of a labda-13-en-8-yl carbocation at C-8 (see FIG. 1A). In principle, hydroxylation can occur during reactions at the class II active site or at the class I active site. To delineate which of the two active sites of bifunctional AbCAS (AbdiTPS4; SEQ ID NO:7) catalyzed the formation of the tertiary alcohol, a set of alanine substitutions of the DxDD (class II active site) (SEQ ID NO:12) and DDxxD (class I active site) (SEQ ID NO:13) motifs to obtain monofunctional AbCAS variants were generated.

A. Generation of Site Directed Protein Variants of AbdiTPS4 (AbCAS)

Amino acid mutations were generated and tested in the pseudomature form of SEQ ID NO:7 as described in Example 3 (i.e. set forth in SEQ ID NO:55 and encoded by the sequence of nucleotides set forth in SEQ ID NO:56). Alanine substitutions of Asp402, Asp404 or Asp621 of AbdiTPS4 with reference to positions set forth in SEQ ID NO:58 (corresponding to residues Asp403, Asp405 or Asp 622 with reference to SEQ ID NO:7) were generated by QuikChange site directed mutagenesis (Stratagene, Mississauga, ON, Canada) of template cDNA corresponding to the pseudomature form (SEQ ID NO:56) in the vector pET28b(+) (SEQ ID NO:33) using primers as set forth in Table 9 below. Specifically, monofunctional AbCAS variants were generated that contained either a non-functional class II (AbCAS:D402A/D404A) or a non-functional class I (AbCAS:D621A) active site. For the mutagenesis reaction, the following PCR program was used: Initial denaturation at 98° C. for 90 sec followed by 29 cycles of denaturation at 98° C. for 50 sec, annealing at 60° C. for 30 sec and extension at 72° C. for 4 min, and final extension at 72° C. for 10 min.

TABLE 9

Primers for cDNA amplification

| Primer | Sequence | SEQ ID NO |
|---|---|---|
| D402A-D404A-sense | GACAGCCCTATAGCCGCTATTGCTG ATACAGCCATGGGC | 28 |
| D402A-D404A-antisense | GCCCATGGCTGTATCAGCAATAGCG GCTATAGGGCTGTC | 29 |
| D621A-sense | TCTCCTCGTCATTTTAGCCGACCTT TACGATGGG | 30 |
| D621A-antisense | CCCATCGTAAAGGTCGGCTAAAATG ACGAGGAGA | 31 |

B. Activity Analysis of Protein Variants

Activity analysis of protein variants of AbdiTPS4 (AbCAS) was conducted with 20 μM GGPP as substrate and dephosphorylation of the reaction products prior to GC-MS analysis. The results are set forth in FIG. 5. The results showed that AbCAS:D621A converted GGPP (peak 9 in FIG. 5) into trace amounts of CPP (peak 10 in FIG. 5) and a product with a significantly longer retention time, indicative of a hydroxylated diphosphate (peak 13 in FIG. 5). This compound was identified, upon cleavage of the diphosphate group, as labda-13-en-8,15-diol based on characteristic mass fragments (m/z 290 [M+], m/z 275, m/z 257, m/z 192 and m/z 177) as compared to the mass spectrum of the authentic compound (Falara et al. (2010) *Plant Physiol.* 154:301-310). Epi-manoyl oxide and manoyl oxide (peaks 11 and 12 in FIG. 5) were apparently not products of AbCAS, but rather result from ether formation of the dephosphorylated labda-13-en-8-ol diphosphate under GC-MS conditions, as they were not seen in the wild type enzyme product profile and did not occur under different GC conditions. Results from enzyme assays with AbCAS:D621A showed that the class II active site of AbCAS catalyzes protonation-initiated formation of bicyclic labda-13-en-8-ol diphosphate via water quenching of the parental carbocation.

Alanine substitution of Asp402 and Asp404 (AbCAS: D402A/D404A) in the class II active site resulted in complete loss of enzymatic activity with GGPP as substrate. To determine if the activity could be restored, a coupled assay was performed combining the AbCAS:D621A variant with a point mutant of PaLAS (PaLAS:D611A; SEQ ID NO:34) containing a non-functional class I active site that accumulates (9S,10S)-CPP (peak 10 in FIG. 5). Activity of AbCAS: D402A/D404A could not be restored by combining this mutant with a protein variant of PaLAS (PaLAS:D611A). This result shows that, unlike the LAS- and Iso-type enzymes, the class I active site of AbCAS is not active with (9S,10S)-CPP as an intermediate substrate.

Coupled assays also were performed using the two monofunctional AbCAS class I and class II protein variants, AbCAS:D402A/D404A and AbCAS:D621A. Formation of cis-abienol (peak 8 in FIG. 5) from GGPP was restored in coupled assays, confirming that the non-mutated active sites remained functional in the two mutated proteins.

The mutational analysis and complementation assays show that the class I active site of AbCAS is selective for labda-13-en-8-ol diphosphate as a substrate, but does not convert (9S, 10S)-CPP, which is the class I active site substrate of LAS-, and Iso type diTPSs (see FIG. 5). Unlike LAS- and Iso-enzymes, the class I active site of AbCAS catalyzes the ionization of the diphosphate group without cyclization of a C-ring (see FIGS. 1A-1B). Together, the mutational analysis of class I and class II active sites of AbCAS demonstrated a reaction sequence of the bifunctional class I/II enzyme in which both the bicyclization and water capture occur in the class II active site, resulting in an intermediary labda-13-en-8-ol diphosphate, which undergoes cleavage of the diphosphate group and final deprotonation at the class I active site (see FIGS. 1A-1B).

Example 6

Computational Structure Analysis

Homology models of AbLAS (AbTPS1), AbIso (AbTPS2) and AbCAS (AbTPS4) were built using the CPHmodels 3.0 server (Nielsen et al. (2010) *Nucleic Acids Res.* 38:W576-581) based on the tertiary structure of *Taxus brevifolia* taxadiene synthase (TbTXS; PDB-ID 3p5pA, chain A; SEQ ID NO:46) (Kasai et al. (2011) *Nature* 469:116-120). The homology models were certified as high quality exceeding 91% residues assigned to most favored regions in Ramachandran plot statistics using PROCHECK (Laskowski, et al. (1993) *J Applied Crystallography* 26:283-291). Lack of structural errors in the models was validated using the ProSA-web server (Wiederstein & Sippl, (2007) *Nucleic Acids Res.* 35:W407-410). Pairwise comparison of these modeled structures with the DaliLite server (Holm & Park, (2000) *Bioinformatics* 16:566-567) demonstrated a high structural similarity of AbLAS, AbIso, AbCAS and TbTXS with root mean square deviations of ≤1 Å for the βγ domain and the a domain, respectively, thus allowing for a structural comparison of the active sites.

Using Molegro Virtual Docker 2010.4.0.0 (Thomsen & Christensen, (2006) *J. Med. Chem.* 49:3315-3321), a semi-automated docking approach was applied to place labda-13-en-8-ol diphosphate in the class I and class II active site of AbCAS (see FIG. 6). For this purpose, proposed active site cavities were identified using a probe radius of 1.0 Å and a grid resolution of 0.6 Å with further manual optimization. Substrate docking was then restricted to the cavities, inclusive of the required $Mg^{2+}$-complex. Energy minimized PDB coordinates of the ligands were generated using the PRODRG server (Schüttelkopf & van Aalten, (2004) *Acta Crystallogr. D Biol. Crystallogr.* 60:1355-1363).

Structural modeling and molecular docking of labda-13-en-8-ol diphosphate in the class I and class II active sites of AbCAS (FIG. 6) revealed only one unique amino acid in the class II active site, namely Asp348 with reference to numbering set forth in SEQ ID NO:58 (corresponding to Asp349 as set forth in SEQ ID NO:7), in proximity of the docked intermediate. Its locations shows that Asp348 is likely to control this particular hydroxylation reaction. Located at the posterior of the active site opposite of the DIDD motif (SEQ ID NO:16) and Trp358, which have previously been reported to contribute to the AgAS-catalyzed class II reaction (Peters & Croteau (2002) *Biochemistry* 41:1836-1842), the negatively charged side chain of Asp348 is positioned to stabilize the positive charge at C-8 for water quenching to occur in the formation of labda-13-en-8-ol diphosphate (FIG. 6B). This local negative charge is not present in any LAS- or Iso-type enzymes, which contain a conserved histidine in this position (see FIG. 7).

Several unique residues were found in a radius of 7 Å around the hydroxy group of labda-13-en-8 of diphosphate docked within the class I active site of AbCAS that are likely involved in the AbCAS reaction (see FIGS. 6C and 6D). Among these, Leu617, Phe696 and Gly723 with reference to numbering set forth in SEQ ID NO:58 (corresponding to residues Leu618, Phe697 and Gly 724 as set forth in SEQ ID NO:7) are of particular interest as they contribute to contour of the active site cavity. Leu617 and Phe696 are located in the class I active site cavity upstream of the DDxxD motif (SEQ ID NO:13) on helix D, creating an expansion of the hydrophobic pocket relative to AbLAS and AbIso. Gly723 and Val724 account for a change in the hinge region between helix 01 and G2. These residues are likely to contribute to the release of a bicyclic product rather than facilitating a secondary cyclization. Interestingly, residues corresponding to Leu617, Phe696 and Gly723 have previously been shown to be critical for the catalytic plasticity of conifer diTPSs (Keeling et al. (2008) *Proc Natl Acad Sci USA* 105:1085-1090; Wilderman & Peters (2007) *J. Am. Chem. Soc.* 129:15736-15737; Peters & Croteau (2002) *Proc. Natl. Acad. Sci. USA* 99:580-584; Leonard et al. (2010) *Proc. Natl. Acad. Sci. USA* 107:13654-13659), and thus appear to represent positions for the functional evolution of these enzymes.

Example 7

Production of Ambroxide

In this example, cis-abienol is produced from geranylgeranyl diphosphate (GGPP) in the presence of an AbCAS (AbTSP4) as described herein. Then, (−)-ambroxide is produced from the produced cis-abienol as previously described in the art (see, e.g., Barrero et al. (1993) *Tetrahedron* 49(45): 10405-10412; Barrero et al. (1994) *Tetrahedron* 50:6653-6662; Barrero et al., (2004) *Synthetic Communications* 34(19):3631-3643; and U.S. Pat. No. 5,525,728).

A. Scheme 1

Figure 8:
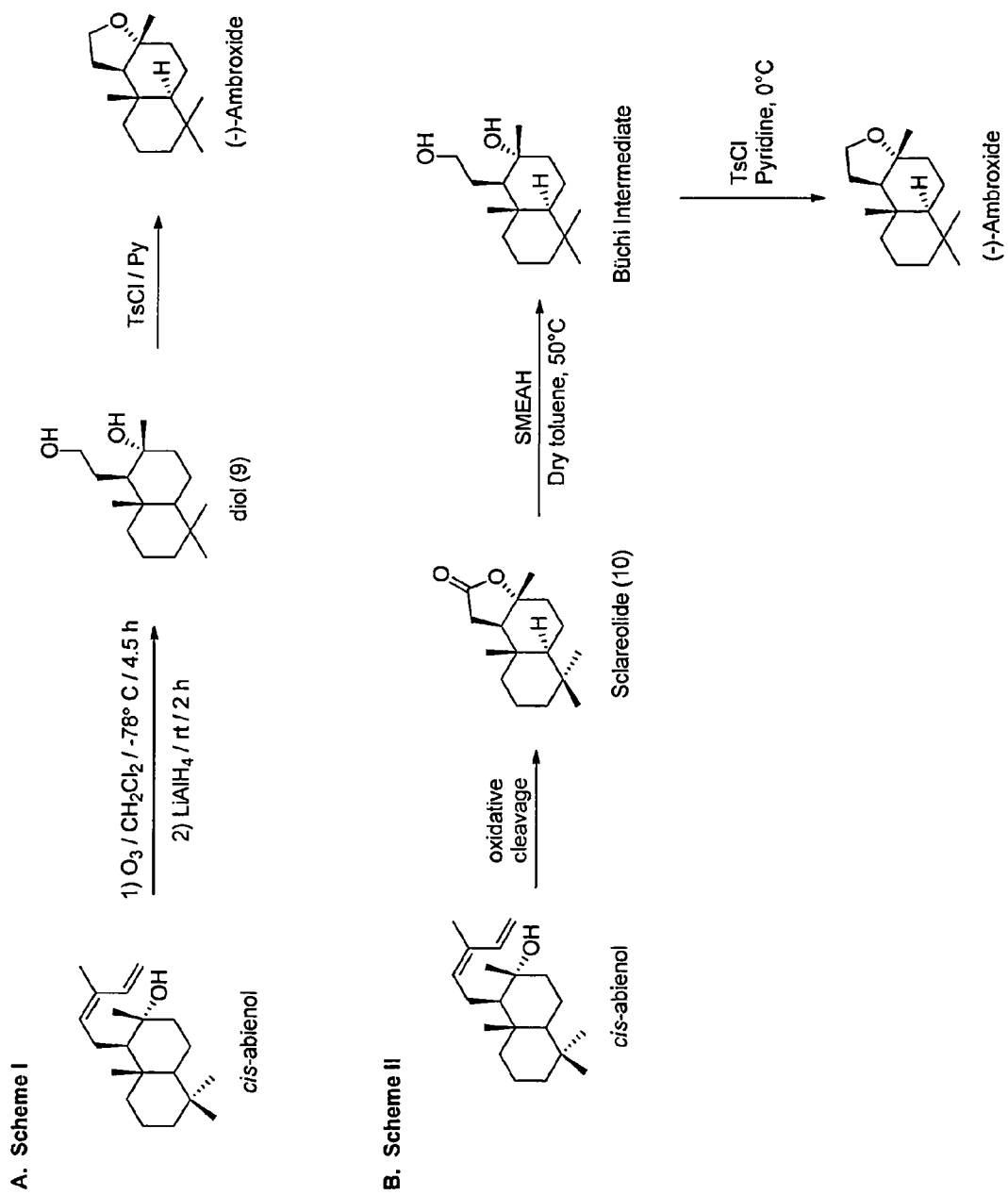
FIG. 8.

As shown in FIG. 8A, Scheme I, cis-abienol is subjected to ozonolysis by reaction with ozone in methylene chloride at −78° C. followed by reduction with lithium aluminum hydride affords the diol (9). The diol (9) is purified by washing the organic phase with 10% HCl, saturated $NaHCO_3$ and water, followed by drying with anhydrous $Na_2SO_4$ and evaporation of the organic solvent. The diol (9) is cyclized in the presence of tosylchloride and the weak base pyridine at room temperature for 1 hour resulting in (−)-ambroxide. (−)-Ambroxide is purified by extraction with organic solvent.

B. Scheme 2

The production of (−)-ambroxide from a starting compound of geranylgeranyl diphosphate (GGPP) is accomplished by converting GGPP to cis-abienol by the diterpene synthase AbCas (SEQ ID NO:7). Cis-abienol is isolated by extraction with organic solvent. Cis-abienol is subjected to ozonolysis by reaction with ozone in methylene chloride at −78° C. followed by reduction with lithium aluminum hydride affords the diol (9). The diol (1) is cyclized in the presence of tosylchloride and the weak base pyridine at room temperature for 1 hour resulting in (−)-ambroxide. (−)-Ambroxide is purified by extraction with organic solvent.

Since modifications will be apparent to those of skill in this art, it is intended that this invention be limited only by the scope of the appended claims.

The invention claimed is:

1. An isolated nucleic acid molecule, comprising a sequence of nucleotides encoding a cis-abienol synthase (CAS) polypeptide selected from among:
   a) the polypeptide whose sequence is set forth in one of SEQ ID NOS:7, 50 and 55;
   b) an active fragment of the polypeptide of a); and
   c) a polypeptide having a sequence of amino acids that has at least 95% sequence identity with a polypeptide of a) or b), wherein:
   the encoded polypeptide or active fragment catalyzes the formation of cis-abienol from geranylgeranyl diphosphate (GGPP); and
   the isolated nucleic acid molecule is cDNA.

2. The isolated nucleic acid molecule of claim 1, wherein the sequence of nucleotides encodes a polypeptide that comprises the sequence of amino acids set forth in one of SEQ ID NOS:7, 50 and 55 or an active fragment thereof.

3. The isolated nucleic acid molecule of claim 1, wherein the sequence of nucleotides encodes a polypeptide that consists of the sequence of amino acids set forth in one of SEQ ID NOS:7, 50 and 55 or an active fragment thereof.

4. The isolated nucleic acid molecule of claim 1, wherein the active fragment is a pseudomature form.

5. The isolated nucleic acid molecule of claim 4, wherein the sequence of nucleotides encodes a cis-abienol synthase (CAS) polypeptide whose sequence is set forth in SEQ ID NO:50 or 55, or encodes a polypeptide whose sequence has at least 95% sequence identity with SEQ ID NO:50 or 55.

6. The isolated nucleic acid molecule of claim 1, comprising a sequence of nucleotides selected from among:
   a) the nucleic acid molecule whose sequence is set forth in one of SEQ ID NOS:8, 54 and 56; and
   b) a nucleic acid molecule whose sequence of nucleotides has at least 95% sequence identity to the sequence of nucleotides set forth in one of SEQ ID NOS:8, 54 and 56 or the complement thereof,
   wherein the sequence of nucleotides encodes a polypeptide that catalyzes the formation of cis-abienol from geranylgeranyl diphosphate (GGPP) or an active fragment of the polypeptide.

7. The isolated nucleic acid molecule of claim 6, comprising the sequence of nucleotides set forth in one of SEQ ID NOS:8, 54 and 56, a portion thereof encoding an active fragment or the complement thereof.

8. The isolated nucleic acid molecule of claim 6, consisting of the sequence of nucleotides set forth in one of SEQ ID NOS:8, 54 and 56, a portion thereof encoding an active fragment or the complement thereof.

9. A vector, comprising the nucleic acid molecule of claim 1.

10. A host cell, comprising a nucleic acid molecule encoding a cis-abienol synthase (CAS) polypeptide selected from among:
   a) the polypeptide whose sequence is set forth in one of SEQ ID NOS:7, 50 and 55;
   b) an active fragment of the polypeptide of a); and
   c) a polypeptide having a sequence of amino acids that has at least 95% sequence identity with a polypeptide of a) or b), wherein:
   the encoded polypeptide or active fragment catalyzes the formation of cis-abienol from geranylgeranyl diphosphate (GGPP); and
   the encoded cis-abienol synthase is heterologous to the host cell.

11. The host cell of claim 10 that is a prokaryotic or eukaryotic host cell.

12. The host cell of claim 10, wherein the host cell is selected from among a bacterial, fungal, plant, insect, amphibian and animal cell.

13. The host cell of claim 10 that is an *E. coli* cell or a yeast cell.

14. The host cell of claim 10 that produces GGPP.

15. A method of producing cis-abienol, comprising:
   i) contacting (E,E,E)-geranylgeranyl diphosphate (GGPP) with a cis-abienol synthase (CAS) polypeptide encoded by the nucleic acid molecule of claim 1 under conditions effective to produce cis-abienol, wherein:
   contacting is effected with an isolated CAS polypeptide, or contacting is effected in a host cell comprising the nucleic acid molecule, and the nucleic acid molecule is heterologous to the host cell; and
   ii) optionally, isolating the cis-abienol produced in step i).

16. The method of claim 15, wherein the step of contacting (E,E,E)-geranylgeranyl diphosphate (GGPP) with the cis-abienol synthase (CAS) polypeptide is effected in vitro.

17. The method of claim 15, comprising isolating the cis-abienol.

18. The method of claim 17, further comprising converting the cis-abienol to (−)-ambroxide.

19. The method of claim 18, comprising isolating the ambroxide.

20. A host cell, comprising a nucleic acid molecule comprising a sequence of nucleotides encoding a cis-abienol synthase (CAS) polypeptide selected from among:
   a) the polypeptide whose sequence is set forth in one of SEQ ID NOS:7, 50 and 55;
   b) an active fragment of the polypeptide of a); and
   c) a polypeptide having a sequence of amino acids that has at least 95% sequence identity with a polypeptide of a) or b), wherein:
   the encoded polypeptide or active fragment catalyzes the formation of cis-abienol from geranylgeranyl diphosphate (GGPP); and
   the host cell is a yeast or bacterial host cell.

21. A host cell, comprising the vector of claim 9.

22. The method of claim 15, wherein the step of contacting (E,E,E)-geranylgeranyl diphosphate (GGPP) with the cis-abienol synthase (CAS) polypeptide is effected in vivo.

* * * * *

SEQUENCE LISTING

<160> NUMBER OF SEQ ID NOS: 59

<210> SEQ ID NO 1
<211> LENGTH: 866
<212> TYPE: PRT
<213> ORGANISM: Abies balsamea
<220> FEATURE:
<223> OTHER INFORMATION: AbdiTPS1

<400> SEQUENCE: 1

Met Ala Ser Met Thr Gly Gly Gln Gln Met Gly Arg Asp Pro Asn Ser
1               5                   10                  15

Ser Ser Val Asp Asn Thr Gln Ser Ile Pro His Phe Ser Thr Thr Leu
            20                  25                  30

Asn Ala Gly Ser Ser Ala Arg Lys Arg Arg Ser Leu Tyr Leu Arg Trp
        35                  40                  45

Gly Lys Gly Ser Asn Lys Ile Ile Ala Cys Val Gly Glu Gly Ala Thr
    50                  55                  60

Ser Val Pro Tyr Gln Ser Ala Glu Lys Asn Asp Ser Leu Tyr Ser Ser
65                  70                  75                  80

Thr Leu Val Lys Arg Glu Phe Pro Pro Gly Phe Trp Lys Asp Asp Leu
                85                  90                  95

Ile Asp Ser Leu Thr Ser Ser His Lys Val Ala Ala Ser Asp Glu Lys
            100                 105                 110

Arg Ile Glu Thr Leu Ile Ser Glu Ile Lys Asn Met Phe Arg Cys Met
        115                 120                 125

Gly Tyr Gly Glu Thr Asn Pro Ser Ala Tyr Asp Thr Ala Trp Val Ala
    130                 135                 140

Arg Ile Pro Ala Leu Asp Gly Ser Asp Asn Pro His Phe Pro Glu Thr
145                 150                 155                 160

Val Glu Trp Ile Leu Gln Asn Gln Leu Lys Asp Gly Ser Trp Gly Glu
                165                 170                 175

Gly Phe Tyr Phe Leu Ala Tyr Asp Arg Ile Leu Ala Thr Leu Ala Cys
            180                 185                 190

Ile Ile Thr Leu Thr Leu Trp Arg Thr Gly Glu Thr Gln Val His Lys
        195                 200                 205

Gly Ile Glu Phe Phe Arg Thr Gln Ala Gly Lys Met Glu Asp Glu Ala
    210                 215                 220

Asp Ser His Arg Pro Ser Gly Phe Glu Ile Val Phe Pro Ala Met Leu
225                 230                 235                 240

Lys Glu Ala Lys Ile Leu Gly Leu Asp Leu Pro Tyr Asp Leu Pro Phe
                245                 250                 255

Leu Lys Gln Ile Ile Glu Lys Arg Glu Ala Lys Leu Lys Arg Ile Pro
            260                 265                 270

Thr Asp Val Leu Tyr Ala Leu Pro Thr Thr Leu Leu Tyr Ser Leu Glu
        275                 280                 285

Gly Leu Gln Glu Ile Val Asp Trp Gln Lys Ile Met Lys Leu Gln Ser

-continued

```
                 290                 295                 300
Lys Asp Gly Ser Phe Leu Ser Ser Pro Ala Ser Thr Ala Ala Val Phe
305                 310                 315                 320

Met Arg Thr Gly Asn Lys Lys Cys Leu Asp Phe Leu Asn Phe Val Leu
                325                 330                 335

Lys Lys Phe Gly Asn His Val Pro Cys His Tyr Pro Leu Asp Leu Phe
                340                 345                 350

Glu Arg Leu Trp Ala Val Asp Thr Val Glu Arg Leu Gly Ile Asp Arg
            355                 360                 365

His Phe Lys Glu Glu Ile Lys Glu Ala Leu Asp Tyr Val Tyr Ser His
        370                 375                 380

Trp Asp Glu Arg Gly Ile Gly Trp Ala Arg Glu Asn Pro Val Pro Asp
385                 390                 395                 400

Ile Asp Asp Thr Ala Met Gly Leu Arg Ile Leu Arg Leu His Gly Tyr
                405                 410                 415

Asn Val Ser Ser Asp Val Leu Lys Thr Phe Arg Asp Glu Asn Gly Glu
                420                 425                 430

Phe Phe Cys Phe Leu Gly Gln Thr Gln Arg Gly Val Thr Asp Met Leu
            435                 440                 445

Asn Val Asn Arg Cys Ser His Val Ser Phe Pro Gly Glu Thr Ile Met
        450                 455                 460

Glu Glu Ala Lys Leu Cys Thr Glu Arg Tyr Leu Arg Asn Ala Leu Glu
465                 470                 475                 480

Asn Val Asp Ala Phe Asp Lys Trp Ala Phe Lys Lys Asn Ile Arg Gly
                485                 490                 495

Glu Val Glu Tyr Ala Leu Lys Tyr Pro Trp His Lys Ser Met Pro Arg
            500                 505                 510

Leu Glu Ala Arg Ser Tyr Ile Glu Asn Tyr Gly Pro Asp Asp Val Trp
        515                 520                 525

Leu Gly Lys Thr Val Tyr Met Met Pro Tyr Ile Ser Asn Glu Lys Tyr
            530                 535                 540

Leu Glu Leu Ala Lys Leu Asp Phe Asn Lys Val Gln Ser Ile His Gln
545                 550                 555                 560

Thr Glu Leu Gln Asp Leu Arg Arg Trp Trp Lys Ser Ser Gly Phe Thr
                565                 570                 575

Asp Leu Asn Phe Thr Arg Glu Arg Val Thr Glu Ile Tyr Phe Ser Pro
            580                 585                 590

Ala Ser Phe Ile Phe Glu Pro Glu Phe Ser Lys Cys Arg Glu Val Tyr
        595                 600                 605

Thr Lys Thr Ser Asn Phe Thr Val Ile Leu Asp Asp Leu Tyr Asp Ala
610                 615                 620

His Gly Ser Leu Asp Asp Leu Lys Leu Phe Thr Glu Ser Val Lys Arg
625                 630                 635                 640

Trp Asp Leu Ser Leu Val Asp Gln Met Pro Gln Gln Met Lys Ile Cys
                645                 650                 655

Phe Val Gly Phe Tyr Asn Thr Phe Asn Glu Ile Ala Lys Glu Gly Arg
            660                 665                 670

Glu Ser Gln Gly Arg Asp Val Leu Gly Tyr Ile Gln Asn Val Trp Lys
        675                 680                 685

Val Gln Leu Glu Ala Tyr Thr Lys Glu Ala Glu Trp Ser Glu Ala Lys
            690                 695                 700

Tyr Val Pro Ser Phe Asn Glu Tyr Ile Glu Asn Ala Ser Val Ser Ile
705                 710                 715                 720
```

| Ala | Leu | Gly | Thr | Val | Leu | Ile | Ser | Ala | Leu | Phe | Thr | Gly | Glu | Val |
|-----|-----|-----|-----|-----|-----|-----|-----|-----|-----|-----|-----|-----|-----|-----|
|     |     |     |     | 725 |     |     |     |     | 730 |     |     |     |     | 735 |

| Leu | Thr | Asp | Glu | Val | Leu | Ser | Lys | Ile | Asp | Arg | Gly | Ser | Arg | Phe | Leu |
|-----|-----|-----|-----|-----|-----|-----|-----|-----|-----|-----|-----|-----|-----|-----|-----|
|     |     |     | 740 |     |     |     |     | 745 |     |     |     |     | 750 |     |     |

| Gln | Leu | Met | Gly | Leu | Thr | Gly | Arg | Leu | Val | Asn | Asp | Thr | Lys | Thr | Tyr |
|-----|-----|-----|-----|-----|-----|-----|-----|-----|-----|-----|-----|-----|-----|-----|-----|
|     |     |     | 755 |     |     |     |     | 760 |     |     |     |     | 765 |     |     |

| Gln | Ala | Glu | Arg | Gly | Gln | Gly | Glu | Val | Ala | Ser | Ala | Ile | Gln | Cys | Tyr |
|-----|-----|-----|-----|-----|-----|-----|-----|-----|-----|-----|-----|-----|-----|-----|-----|
|     | 770 |     |     |     |     | 775 |     |     |     |     | 780 |     |     |     |     |

| Met | Lys | Asp | His | Pro | Lys | Ile | Ser | Glu | Glu | Glu | Ala | Leu | Lys | His | Val |
|-----|-----|-----|-----|-----|-----|-----|-----|-----|-----|-----|-----|-----|-----|-----|-----|
| 785 |     |     |     |     | 790 |     |     |     |     | 795 |     |     |     |     | 800 |

| Tyr | Thr | Val | Met | Glu | Asn | Ser | Leu | Glu | Glu | Leu | Asn | Arg | Glu | Phe | Val |
|-----|-----|-----|-----|-----|-----|-----|-----|-----|-----|-----|-----|-----|-----|-----|-----|
|     |     |     |     | 805 |     |     |     |     | 810 |     |     |     |     | 815 |     |

| Asn | Asn | Lys | Ile | Pro | Asp | Ile | Tyr | Arg | Arg | Leu | Val | Phe | Glu | Thr | Ala |
|-----|-----|-----|-----|-----|-----|-----|-----|-----|-----|-----|-----|-----|-----|-----|-----|
|     |     |     | 820 |     |     |     |     | 825 |     |     |     |     | 830 |     |     |

| Arg | Ile | Met | Gln | Leu | Phe | Tyr | Met | Gln | Gly | Asp | Gly | Leu | Thr | Leu | Ser |
|-----|-----|-----|-----|-----|-----|-----|-----|-----|-----|-----|-----|-----|-----|-----|-----|
|     |     | 835 |     |     |     |     | 840 |     |     |     |     | 845 |     |     |     |

| His | Asp | Met | Glu | Ile | Lys | Glu | His | Val | Lys | Asn | Cys | Leu | Phe | Gln | Pro |
|-----|-----|-----|-----|-----|-----|-----|-----|-----|-----|-----|-----|-----|-----|-----|-----|
| 850 |     |     |     |     | 855 |     |     |     |     | 860 |     |     |     |     |     |

| Val | Ala |
|-----|-----|
| 865 |     |

<210> SEQ ID NO 2
<211> LENGTH: 2601
<212> TYPE: DNA
<213> ORGANISM: Abies balsamea
<220> FEATURE:
<223> OTHER INFORMATION: AbdiTPS1

<400> SEQUENCE: 2

| atggctagca tgactggtgg acagcaaatg ggtcgggatc cgaattcgag ctccgtcgac | 60 |
| aacacacagt ccattccgca tttctccacg acgctgaatg ctggaagcag tgctagaaaa | 120 |
| cggagaagct tgtacctacg atggggtaaa ggttcaaaca agatcattgc ctgtgttgga | 180 |
| gaaggtgcaa cctctgttcc ttatcagtct gctgaaaaga atgattcgct ttattcttct | 240 |
| acattggtga acgagaatt ccctccagga ttttggaagg atgatcttat cgattctctg | 300 |
| acgtcctctc acaaggttgc agcatcagac gagaagcgta tcgagacatt aatatccgag | 360 |
| attaagaata tgtttagatg tatgggctat ggcgaaacga tccctctgc atatgacact | 420 |
| gcttgggtag caaggattcc agcacttgat ggctctgaca ccctcactt tcctgagaca | 480 |
| gttgaatgga ttcttcaaaa tcagttgaaa gatgggtctt ggggtgaagg attctacttc | 540 |
| ttggcatatg acagaatact ggctacactt gcatgtatta ttacgcttac cctctggcgt | 600 |
| actggggaga cacaagtaca caaaggtatt gaattcttca ggcacaagc tggaaagatg | 660 |
| gaagatgaag ctgatagtca taggccaagt ggatttgaaa tagtatttcc tgcaatgcta | 720 |
| aaggaagcta aatcttaggg gttggatctg ccttacgatt tgccattcct gaaacaaatc | 780 |
| atcgaaaagc gggaggctaa gcttaaaagg attcccactg atgttctcta tgcccttcca | 840 |
| acaacgttat tgtattcttt ggaaggtttg caagaaatag tagactggca gaaaataatg | 900 |
| aaacttcaat ccaaggatgg atcatttctc agctctccgg catctacagc ggctgtattc | 960 |
| atgcgtacag ggaacaaaaa gtgcttggat ttcttgaact tgtcttgaa gaaattcgga | 1020 |
| aaccatgtgc ttgtcacta tccgcttgat ctatttgaac gtttgtgggc ggttgatacc | 1080 |
| gttgagcggc taggtatcga tcgccatttc aaagaggaga tcaaggaagc attggattat | 1140 |

```
gtttacagcc attgggacga agaggcatt ggatgggcga gagagaatcc tgttcctgat      1200
attgatgata cagccatggg ccttcgaatc ttgagactac atggatacaa tgtatcctca      1260
gatgttttaa aaacatttag agatgagaat ggtgagttct tttgcttctt gggtcaaaca      1320
cagagaggag ttaccgacat gttaaacgtc aatcgttgtt cacatgtttc atttccggga      1380
gaaacgatca tggaagaagc aaaactctgt accgaaaggt atctgaggaa tgctctggaa      1440
aatgtggatg cctttgacaa atgggctttt aaaaagaata ttcggggaga ggtagagtat      1500
gcactcaaat atccctggca taagagtatg ccaaggttgg aggctagaag ctatattgaa      1560
aactatgggc cagatgatgt gtggcttgga aaaactgtat atatgatgcc atacattccc      1620
aatgaaaagt atttagaact agcgaaactg gacttcaata aggtgcagtc tatacaccaa      1680
acagagcttc aagatcttcg aaggtggtgg aaatcatccg gtttcacgga tctgaatttc      1740
actcgtgagc gtgtgacgga aatatatttc tcaccggcat cctttatctt tgagccggag      1800
ttttctaagt gcagagaagt ttatacaaaa acttccaatt tcactgttat tttagatgat      1860
ctttatgacg cccatggatc tttagacgat cttaagttgt tcacagaatc agtcaaaaga      1920
tgggatctat cattagtgga ccaaatgcca caacaaatga aaatatgctt tgtgggtttc      1980
tacaatactt ttaatgaaat agcaaaagaa ggacgtgaga gccaagggcg cgatgtgcta      2040
ggctacattc aaaatgtttg gaaagtccaa cttgaagctt acactaaaga agcagaatgg      2100
tctgaagcta aatatgtgcc atccttcaat gaatacatag agaacgcgag tgtgtcaata      2160
gcattgggaa cagtggttct cattagtgct cttttcactg gggaagttct tacagatgaa      2220
gtactctcca aaattgatcg cggatctaga tttcttcaac tcatgggctt aacagggcgt      2280
ttggtgaatg acaccaaaac ttatcaggca gagagaggtc aaggtgaggt ggcttctgcc      2340
atacaatgtt atatgaaaga ccatcctaaa atctccgaag aagaagctct caaacatgtc      2400
tatactgtca tggaaaattc cctcgaagag ttgaataggg agtttgtgaa taacaaaata      2460
ccggatattt acagaagact ggttttttgaa actgcaagaa taatgcaact gttttatatg      2520
caaggggatg gtttgacact atcacatgat atggaaatta aagagcatgt caaaaattgc      2580
ctcttccaac cagttgccta g                                                2601
```

<210> SEQ ID NO 3
<211> LENGTH: 852
<212> TYPE: PRT
<213> ORGANISM: Abies balsamea
<220> FEATURE:
<223> OTHER INFORMATION: AbdiTPS2

<400> SEQUENCE: 3

```
His His Leu Thr Ala Asn Thr Gln Ser Ile Pro His Phe Ser Thr Thr
  1               5                  10                  15

Leu Asn Ala Gly Ser Ser Ala Arg Lys Arg Arg Ser Leu Tyr Leu Arg
             20                  25                  30

Trp Gly Lys Gly Ser Asn Lys Ile Ile Ala Cys Val Gly Glu Gly Ala
         35                  40                  45

Thr Ser Val Pro Tyr Gln Ser Ala Glu Lys Asn Asp Ser Leu Tyr Ser
     50                  55                  60

Ser Thr Leu Val Lys Arg Glu Phe Pro Pro Gly Phe Trp Lys Asp Asp
 65                  70                  75                  80

Leu Ile Asp Ser Leu Thr Ser Ser His Lys Val Ala Ala Ser Asp Glu
                 85                  90                  95

Lys Arg Ile Glu Thr Leu Ile Ser Glu Ile Lys Asn Met Phe Arg Cys
```

```
                100                 105                 110
Met Gly Tyr Gly Glu Thr Asn Pro Ser Ala Tyr Asp Thr Ala Trp Val
            115                 120                 125
Ala Arg Ile Pro Ala Leu Asp Gly Ser Asp Asn Pro His Phe Pro Glu
130                 135                 140
Thr Val Glu Trp Ile Leu Gln Asn Gln Leu Lys Asp Gly Ser Trp Gly
145                 150                 155                 160
Glu Gly Phe Tyr Phe Leu Ala Tyr Asp Arg Ile Leu Ala Thr Leu Ala
                165                 170                 175
Cys Ile Ile Thr Leu Thr Leu Trp Arg Thr Gly Glu Thr Gln Val His
                180                 185                 190
Lys Gly Ile Glu Phe Phe Arg Thr Gln Ala Gly Lys Met Glu Asp Glu
            195                 200                 205
Ala Asp Ser His Arg Pro Ser Gly Phe Glu Ile Val Phe Pro Ala Met
            210                 215                 220
Leu Lys Glu Ala Lys Ile Leu Gly Leu Asp Leu Pro Tyr Asp Leu Pro
225                 230                 235                 240
Phe Leu Lys Gln Ile Ile Glu Lys Arg Glu Ala Lys Leu Lys Arg Ile
                245                 250                 255
Pro Thr Asp Val Leu Tyr Ala Leu Pro Thr Thr Leu Leu Tyr Ser Leu
                260                 265                 270
Glu Gly Leu Gln Glu Ile Val Asp Trp Gln Lys Ile Met Lys Leu Gln
            275                 280                 285
Ser Lys Asp Gly Ser Phe Leu Ser Ser Pro Ala Ser Thr Ala Ala Val
            290                 295                 300
Phe Met Arg Thr Gly Asn Lys Lys Cys Leu Asp Phe Leu Asn Phe Val
305                 310                 315                 320
Leu Lys Lys Phe Gly Asn His Val Pro Cys His Tyr Pro Leu Asp Leu
                325                 330                 335
Phe Glu Arg Leu Trp Ala Val Asp Thr Val Glu Arg Leu Gly Ile Asp
                340                 345                 350
Arg His Phe Lys Glu Glu Ile Lys Asp Ala Leu Asp Tyr Val Tyr Ser
            355                 360                 365
His Trp Asp Glu Arg Gly Ile Gly Trp Ala Arg Glu Asn Pro Val Pro
            370                 375                 380
Asp Ile Asp Asp Thr Ala Met Gly Leu Arg Ile Leu Arg Leu His Gly
385                 390                 395                 400
Tyr Asn Val Ser Ser Asp Val Leu Lys Thr Phe Arg Asp Glu Asn Gly
                405                 410                 415
Glu Phe Phe Cys Phe Leu Gly Gln Thr Gln Arg Gly Val Thr Asp Met
                420                 425                 430
Leu Asn Val Asn Arg Cys Ser His Val Ser Phe Pro Gly Glu Thr Ile
            435                 440                 445
Met Glu Glu Ala Lys Leu Cys Thr Glu Arg Tyr Leu Arg Asn Ala Leu
            450                 455                 460
Glu Asn Val Asp Ala Phe Asp Lys Trp Ala Phe Lys Lys Asn Ile Arg
465                 470                 475                 480
Gly Glu Val Glu Tyr Ala Leu Lys Tyr Thr Trp His Lys Ser Met Pro
                485                 490                 495
Arg Leu Glu Ala Arg Ser Tyr Ile Glu Asn Tyr Gly Pro Asn Asp Ala
                500                 505                 510
Trp Leu Gly Lys Thr Val Tyr Arg Met Pro Tyr Ile Ser Asn Glu Lys
            515                 520                 525
```

Tyr Leu Glu Leu Ala Lys Leu Asp Phe Asn Lys Leu Gln Ser Ile His
    530                 535                 540

Gln Thr Glu Leu Gln Asp Leu Arg Arg Trp Trp Lys Ser Ser Gly Phe
545                 550                 555                 560

Ser Lys Leu Asn Phe Thr Arg Glu Arg Val Thr Glu Ile Tyr Phe Ser
            565                 570                 575

Ser Ala Ser Phe Met Phe Glu Pro Glu Phe Ser Lys Cys Arg Glu Val
            580                 585                 590

Tyr Thr Lys Ala Ser Ile Phe Thr Leu Ile Phe Asp Asp Leu Tyr Asp
            595                 600                 605

Ala His Gly Ser Leu Asp Asp Leu Lys Leu Phe Ser Glu Ala Val Lys
    610                 615                 620

Arg Trp Asp Leu Ser Leu Leu Glu Arg Met Pro Gln Glu Met Lys Ile
625                 630                 635                 640

Cys Phe Leu Gly Phe Tyr Asn Thr Phe Asn Glu Ile Ala Glu Glu Val
                645                 650                 655

His Lys Arg Gln Gly Arg Asp Met Leu Gly His Ile Gln Asn Val Trp
            660                 665                 670

Glu Ile Leu Leu Ala Ala Tyr Thr Lys Glu Ala Glu Trp Ser Lys Thr
            675                 680                 685

Lys Tyr Val Pro Ser Phe Asp Glu Tyr Ile Glu Asn Ala Ser Val Ser
    690                 695                 700

Ile Thr Leu Gly Thr Ile Val Leu Ile Ser Thr Leu Phe Ile Gly Glu
705                 710                 715                 720

Val Leu Thr Asp His Val Leu Ser Lys Ile Asn His Gly Ser Arg Phe
                725                 730                 735

Leu His Leu Met Gly Leu Thr Gly Arg Leu Val Asn Asp Thr Lys Thr
            740                 745                 750

Tyr Gln Ala Glu Arg Gly Gln Gly Glu Glu Ala Ser Ala Ile Gln Cys
    755                 760                 765

Tyr Met Lys Asp His Pro Glu Ile Ser Glu Glu Ala Leu Asn His
770                 775                 780

Val Tyr Asn Val Met Glu Asn Ala Leu Gln Glu Leu Asn Lys Glu Phe
785                 790                 795                 800

Val Asn Asn Lys Glu Val Pro Pro Asn Cys Arg Arg Leu Val Phe Asn
                805                 810                 815

Thr Ala Arg Ile Met Gln Leu Phe Tyr Met Gln Gly Asp Gly Leu Thr
            820                 825                 830

Leu Ser His Asp Met Glu Ile Lys Asp His Val Lys Thr Cys Leu Phe
    835                 840                 845

Ile Pro Ile Ala
    850

<210> SEQ ID NO 4
<211> LENGTH: 2559
<212> TYPE: DNA
<213> ORGANISM: Abies balsamea
<220> FEATURE:
<223> OTHER INFORMATION: AbdiTPS2

<400> SEQUENCE: 4
catcatctaa ctgctaacac acagtccatt ccgcatttct ccacgacgct gaatgctgga        60
agcagtgcta gaaacggag aagcttgtac ctacgatggg gtaaaggttc aaacaagatc       120
attgcctgtg ttggagaagg tgcaacctct gttccttatc agtctgctga aaagaatgat       180

```
tcgctttatt cttctacatt ggtgaaacga gaatttcctc caggattttg gaaggatgat    240
cttatcgatt ctctgacgtc ctctcacaag gttgcagcat cagacgagaa gcgtatcgag    300
acattaatat ccgagattaa gaatatgttt agatgtatgg gctatggcga acgaatccc     360 tctgcatatg acactgcttg ggtagcaagg attccagcac ttgatggctc tgacaaccct    420
cactttcctg agacagttga atggattctt caaaatcagt tgaaagatgg gtcttggggt    480
gaaggattct acttcttggc atatgacaga atactggcta cacttgcatg tattattacg    540
cttaccctct ggcgtactgg ggagacacaa gtacacaaag gtattgaatt cttcaggaca    600
caagctggaa agatggaaga tgaagctgat agtcataggc caagtggatt tgaaatagta    660
tttcctgcaa tgctaaagga agctaaaatc ttagggttgg atctgcctta cgatttgcca    720
ttcctgaaac aaatcatcga aaagcgggag gctaagctta aaaggattcc cactgatgtt    780
ctctatgccc ttccaacaac gttattgtat tctttggaag gtttgcaaga aatagtagac    840
tggcagaaaa taatgaaact tcaatccaag gatggatcat ttctcagctc tccggcatct    900
acagcggctg tattcatgcg tacagggaac aaaaagtgct tggatttctt gaactttgtc    960
ttgaagaaat tcggaaacca tgtgccttgt cactatccgc ttgatctatt tgaacgcttg   1020
tgggccgttg atactgttga gcggctaggt atcgatcgcc atttcaaaga ggagatcaag   1080
gacgcattgg attatgttta cagccattgg gacgaaagag gcattggatg ggcgagagag   1140
aatcctgttc ctgatattga tgatacagcc atgggccttc gaatattgag actgcatgga   1200
tacaatgtat cctcagatgt tttaaaaaca tttagagatg agaatgggga gttcttttgc   1260
ttcttgggtc aaacacagag aggagttaca gacatgttaa acgtcaatcg ttgttcacat   1320
gtttcatttc cgggagaaac gatcatgaaa gaagcaaaac tctgcaccga aggtatctg    1380 aggaatgctc tggaaaatgt ggatgccttt gacaaatggg cttttaaaaa gaatattcgg   1440
ggagaggtgg agtacgcact caaatatact tggcataaga gtatgccaag gctggaggct   1500
agaagttaca ttgaaaacta tgggccaaat gatgcgtggc ttggcaaaac tgtatatagg   1560
atgccataca tttccaatga aaagtattta gaactagcaa aactggactt caataagctc   1620
cagtctatac accaaacaga gcttcaagat cttcgaaggt ggtggaaatc atcgggtttc   1680
tcaaagctaa atttcactcg cgagcgtgtc acagaaatat atttttcatc cgcatctttt   1740
atgtttgagc cggagttttc taagtgtaga gaagtttata caaaagcttc catttttcaca  1800 cttattttcg atgatcttta tgacgcccat ggatctttag acgatcttaa gttgttttcc   1860
gaagcagtca aaagatggga tctatcacta ctagagagaa tgccacaaga aatgaaaata   1920
tgcttcctgg gtttctacaa tacatttaat gaaatagctg aagaagtaca caagaggcaa   1980
gggcgtgaca tgctaggtca cattcaaaat gtttgggaaa tcttgctggc agcttacacg   2040
aaagaagcag aatggtctaa aactaaatat gtgccatcct tcgatgaata catagagaat   2100
gcgagtgtgt caataacact gggaacaatt gttctcataa gtactctttt catcggggag   2160
gttcttacag atcatgtact ctccaaaatt aatcatggat ccagatttct acacctcatg   2220
ggcttaacag gcgtttggt gaatgacacc aaaacttatc aggctgagag aggtcaaggt    2280
gaggaggctt ctgccataca atgttatatg aaggaccatc ctgaaatctc tgaagaagaa   2340
gctctgaatc atgtctataa tgtcatggaa aatgctctcc aagagttgaa taaggaattt   2400
gtgaataaca aagaagtccc acccaattgt aggaggttgg ttttaacac tgcaagaatc    2460 atgcagttgt tttatatgca aggggatggt ttgacacttt cacatgacat ggaaattaaa   2520
```
gatcatgtca aaacctgtct cttcataccg attgcgtag        2559

<210> SEQ ID NO 5
<211> LENGTH: 724
<212> TYPE: PRT
<213> ORGANISM: Abies balsamea
<220> FEATURE:
<223> OTHER INFORMATION: AbdiTPS3

<400> SEQUENCE: 5

Asn Thr Gln Ser Ile Pro His Phe Ser Thr Thr Leu Asn Ala Gly Ser
 1               5                  10                  15

Ser Ala Arg Lys Arg Ser Leu Tyr Leu Arg Trp Gly Lys Gly Ser
            20                  25                  30

Asn Lys Ile Ile Ala Cys Val Gly Glu Gly Ala Thr Ser Val Pro Tyr
        35                  40                  45

Gln Ser Ala Glu Lys Asn Asp Ser Leu Tyr Ser Ser Thr Leu Val Lys
    50                  55                  60

Arg Glu Phe Pro Pro Gly Phe Trp Lys Asp Asp Leu Ile Asp Ser Leu
65                  70                  75                  80

Thr Ser Ser His Lys Val Ala Ala Ser Asp Glu Lys Arg Ile Glu Thr
                85                  90                  95

Leu Ile Ser Glu Ile Lys Asn Met Phe Arg Cys Met Gly Tyr Gly Glu
            100                 105                 110

Thr Asn Pro Ser Ala Tyr Asp Thr Ala Trp Val Ala Arg Ile Pro Ala
        115                 120                 125

Leu Asp Gly Ser Asp Asn Pro His Phe Pro Glu Thr Val Glu Trp Ile
    130                 135                 140

Leu Gln Asn Gln Leu Lys Asp Gly Ser Trp Gly Glu Gly Phe Tyr Phe
145                 150                 155                 160

Leu Ala Tyr Asp Arg Ile Leu Ala Thr Leu Ala Cys Ile Ile Thr Leu
                165                 170                 175

Thr Leu Trp Arg Thr Gly Glu Thr Gln Val His Lys Gly Ile Glu Phe
            180                 185                 190

Phe Arg Thr Gln Ala Gly Lys Met Glu Asp Glu Ala Asp Ser His Arg
        195                 200                 205

Pro Ser Gly Phe Glu Ile Val Phe Pro Ala Met Leu Lys Glu Ala Lys
    210                 215                 220

Ile Leu Gly Leu Asp Leu Pro Tyr Asp Leu Pro Phe Leu Lys Gln Ile
225                 230                 235                 240

Ile Glu Lys Arg Glu Ala Lys Leu Lys Arg Ile Pro Thr Asp Val Leu
                245                 250                 255

Tyr Ala Leu Pro Thr Thr Leu Leu Tyr Ser Leu Glu Gly Leu Gln Glu
            260                 265                 270

Ile Val Asp Trp Gln Lys Ile Met Lys Leu Gln Ser Lys Asp Gly Ser
        275                 280                 285

Phe Leu Ser Ser Pro Ala Ser Thr Ala Ala Val Phe Met Arg Thr Gly
    290                 295                 300

Asn Lys Lys Cys Leu Asp Phe Leu Asn Phe Val Leu Lys Lys Phe Gly
305                 310                 315                 320

Asn His Val Pro Cys His Tyr Pro Leu Asp Leu Phe Glu Arg Leu Trp
                325                 330                 335

Ala Val Asp Thr Val Glu Arg Leu Gly Ile Asp Arg His Phe Lys Glu
            340                 345                 350

Glu Ile Lys Glu Ala Leu Asp Tyr Val Tyr Ser His Trp Asp Glu Arg

```
                355                 360                 365
Gly Ile Gly Trp Ala Arg Glu Asn Pro Val Pro Asp Ile Asp Asp Thr
370                 375                 380
Ala Met Gly Leu Arg Ile Leu Arg Leu His Gly Tyr Asn Val Ser Ser
385                 390                 395                 400
Asp Val Leu Lys Thr Phe Arg Asp Glu Asn Gly Glu Phe Phe Cys Phe
                405                 410                 415
Leu Gly Gln Thr Gln Arg Gly Val Thr Asp Met Leu Asn Val Asn Arg
            420                 425                 430
Cys Ser His Val Ser Phe Pro Gly Glu Thr Ile Met Glu Glu Ala Lys
        435                 440                 445
Leu Cys Thr Glu Arg Tyr Leu Arg Asn Ala Leu Glu Asn Val Asp Ala
450                 455                 460
Phe Asp Lys Trp Ala Phe Lys Lys Asn Ile Arg Gly Glu Val Glu Tyr
465                 470                 475                 480
Ala Leu Lys Tyr Pro Trp His Lys Ser Met Pro Arg Leu Glu Ala Arg
                485                 490                 495
Ser Tyr Ile Glu Asn Tyr Gly Gln Asn Asp Leu Trp Leu Gly Lys Ser
            500                 505                 510
Leu Tyr Met Met Pro Tyr Ile Ser Asn Glu Lys Tyr Leu Glu Leu Ala
        515                 520                 525
Lys Leu Asp Phe Asn Lys Val Gln Ser Ile His Gln Lys Glu Leu Gln
530                 535                 540
Asp Leu Arg Arg Trp Trp Lys Ser Ser Gly Phe Thr Asp Leu Asn Phe
545                 550                 555                 560
Thr Arg Glu Arg Val Thr Glu Ile Tyr Phe Ser Pro Ala Ser Phe Ile
                565                 570                 575
Phe Glu Pro Glu Phe Ser Lys Cys Arg Glu Val Tyr Thr Lys Thr Ser
            580                 585                 590
Asn Phe Thr Val Ile Leu Asp Asp Leu Tyr Asp Ala His Gly Ser Leu
        595                 600                 605
Asp Asp Leu Lys Leu Phe Ser Glu Ser Val Lys Arg Trp Asp Leu Ser
610                 615                 620
Leu Ile Asp Gly Met Pro Gln Glu Met Lys Thr Cys Phe Lys Gly Leu
625                 630                 635                 640
Tyr Asn Thr Phe Asn Glu Ile Ala Glu Glu Gly Cys Lys Arg Gln Gly
                645                 650                 655
His Asp Val Leu Gly Tyr Ile Arg Asn Val Trp Glu Ile Gln Leu Ala
            660                 665                 670
Ala Tyr Thr Lys Glu Ala Glu Trp Ser Glu Ala Lys Tyr Val Pro Ser
        675                 680                 685
Phe Asn Glu Tyr Ile Glu Asn Ala Ser Val Ser Ile Ala Leu Gly Thr
        690                 695                 700
Val Val Leu Ile Ser Val Leu Phe Val Gly Ser Ser Tyr Arg Ser Asn
705                 710                 715                 720
Thr Phe Lys Asn

<210> SEQ ID NO 6
<211> LENGTH: 2175
<212> TYPE: DNA
<213> ORGANISM: Abies balsamea
<220> FEATURE:
<223> OTHER INFORMATION: AbdiTPS3

<400> SEQUENCE: 6
```

-continued

```
aacacacagt ccattccgca tttctccacg acgctgaatg ctggaagcag tgctagaaaa      60
cggagaagct tgtacctacg atggggtaaa ggttcaaaca agatcattgc ctgtgttgga     120
gaaggtgcaa cctctgttcc ttatcagtct gctgaaaaga atgattcgct ttattcttct     180
acattggtga aacgagaatt tcctccagga ttttggaagg atgatcttat cgattctctg     240
acgtcctctc acaaggttgc agcatcagac gagaagcgta tcgagacatt aatatccgag     300
attaagaata tgtttagatg tatgggctat ggcgaaacga atccctctgc atatgacact     360
gcttgggtag caaggattcc agcacttgat ggctctgaca accctcactt tcctgagaca     420
gttgaatgga ttcttcaaaa tcagttgaaa gatgggtctt ggggtgaagg attctacttc     480
ttggcatatg acagaatact ggctacactt gcatgtatta ttacgcttac cctctggcgt     540
actggggaga cacaagtaca caaaggtatt gaattcttca ggacacaagc tggaaagatg     600
gaagatgaag ctgatagtca taggccaagt ggatttgaaa tagtatttcc tgcaatgcta     660
aaggaagcta aaatcttagg gttggatctg ccttacgatt tgccattcct gaaacaaatc     720
atcgaaaagc gggaggctaa gcttaaaagg attcccactg atgttctcta tgcccttcca     780
acaacgttat tgtattcttt ggaaggtttg caagaaatag tagactggca gaaaataatg     840
aaacttcaat ccaaggatgg atcatttctc agctctccgg catctacagc ggctgtattc     900
atgcgtacag ggaacaaaaa gtgcttggat tccttgaact ttgtcttgaa gaaattcgga     960
aaccatgtgc cttgtcacta tccgcttgat ctatttgaac gtttgtgggc ggttgatacc    1020
gttgagcggc taggtatcga tcgccatttc aaagaggaga tcaaggaagc attggattat    1080
gtttacagcc attgggacga agaggcattg gatgggcga gagagaatcc tgttcctgat    1140
attgatgata cagccatggg ccttcgaatc ttgagactac atggatacaa tgtatcctca    1200
gatgttttaa aaacatttag agatgagaat ggtgagttct tttgcttctt gggtcaaaca    1260
cagagaggag ttaccgacat gttaaacgtc aatcgttgtt cacatgtttc atttccggga    1320
gaaacgatca tggaagaagc aaaactctgt accgaaaggt atctgaggaa tgctctggaa    1380
aatgtggacg ccttgacaa atgggctttt aaaaagaata ttcggggaga ggtggagtat    1440
gcactcaaat atccttggca taagagtatg ccaaggctgg aggccagaag ctacattgaa    1500
aactatgggc agaatgattt gtggttgggc aaaagtttat atatgatgcc atatatttcc    1560
aatgaaaagt atttagaact agcgaaactg gacttcaata aggtgcagtc tatacaccaa    1620
aaagagcttc aagatcttcg aaggtggtgg aaatcatccg gtttcacgga tctgaatttc    1680
actcgtgagc gtgtgacgga aatatatttc tcaccggcat cctttatttt tgagccggag    1740
ttttctaagt gcagagaagt ttatacaaaa acttccaatt tcacagttat tttagatgat    1800
ctttatgacg cccatggatc tctagacgat cttaagttgt tttccgaatc agtcaaaaga    1860
tgggatctct cactaataga tggaatgcca caagaaatga aaacatgttt caagggttta    1920
tacaatactt tcaatgaaat agcagaagaa ggatgcaaga ggcaggggca tgatgtccta    1980
ggctacatta gaaatgtttg ggaaatccag ttggcagctt acacaaaaga agcagaatgg    2040
tctgaagcta aatatgttcc gtcctttaat gaatacatag agaatgcgag tgtgtcaata    2100
gcactcggaa cggtcgttct cattagtgtt cttttttgtgg ggagttctta cagatcaaat    2160
actttcaaaa attaa                                                      2175
```

<210> SEQ ID NO 7
<211> LENGTH: 867
<212> TYPE: PRT

<213> ORGANISM: Abies balsamea
<220> FEATURE:
<223> OTHER INFORMATION: AbdiTPS4

<400> SEQUENCE: 7

```
Met Ala Leu Pro Val Tyr Ser Leu Lys Ser His Ile Pro Ile Thr Thr
1               5                   10                  15

Ile Ala Ser Ala Lys Met Asn Tyr Thr Pro Asn Lys Gly Met Ile Thr
            20                  25                  30

Ala Asn Gly Arg Ser Arg Arg Ile Arg Leu Ser Pro Asn Lys Ile Val
        35                  40                  45

Ala Cys Ala Gly Glu Ala Asp Arg Thr Phe Pro Ser Gln Ser Leu Glu
    50                  55                  60

Lys Thr Ala Leu Phe Pro Asp Gln Phe Ser Glu Lys Asn Gly Thr Pro
65                  70                  75                  80

Ser Asn Phe Thr Pro Pro Asn Arg Glu Phe Pro Pro Ser Phe Trp Asn
                85                  90                  95

Asn Asp Ile Ile Asn Ser Ile Thr Ala Ser His Lys Val Gln Thr Gly
            100                 105                 110

Asp Arg Lys Arg Ile Gln Thr Leu Ile Ser Glu Ile Lys Asn Val Phe
        115                 120                 125

Asn Ser Met Gly Asp Gly Glu Thr Ser Pro Ser Ala Tyr Asp Thr Ala
    130                 135                 140

Trp Val Ala Arg Ile Pro Ala Val Asp Gly Ser Glu Gln Pro Gln Phe
145                 150                 155                 160

Pro Gln Thr Leu Glu Trp Ile Leu Gln Asn Gln Leu Lys Asp Gly Ser
                165                 170                 175

Trp Gly Glu Glu Phe Tyr Phe Leu Ala Tyr Asp Arg Leu Leu Ala Thr
            180                 185                 190

Leu Ala Cys Ile Ile Thr Leu Thr Ile Trp Arg Thr Gly Asn Val Gln
        195                 200                 205

Leu His Lys Gly Ile Glu Phe Phe Arg Lys Gln Val Val Arg Met Asp
    210                 215                 220

Asp Glu Ala Asp Asn His Arg Pro Ser Gly Phe Glu Ile Val Phe Pro
225                 230                 235                 240

Ala Met Leu Asn Glu Ala Lys Ser Leu Gly Leu Asp Leu Pro Tyr Glu
                245                 250                 255

Leu Pro Phe Ile Glu Gln Met Val Lys Arg Glu Ala Lys Leu Lys
            260                 265                 270

Met Ile Thr Thr Asn Val Leu Tyr Thr Ile Gln Thr Thr Leu Leu Tyr
        275                 280                 285

Ser Leu Glu Gly Leu His Glu Ile Val Asp Phe Asp Lys Ile Ile Lys
    290                 295                 300

Leu Gln Ser Lys Asp Gly Ser Phe Leu Gly Ser Pro Ala Ser Thr Ala
305                 310                 315                 320

Ala Val Phe Met Gln Thr Gly Asn Thr Lys Cys Leu Glu Phe Leu Glu
                325                 330                 335

Phe Val Leu Arg Lys Phe Arg Asn His Val Pro Ser Asp Tyr Pro Leu
            340                 345                 350

Asp Leu Phe Glu Arg Leu Trp Val Asp Thr Val Glu Arg Leu Gly
        355                 360                 365

Ile Asp Arg His Phe Lys Lys Glu Ile Lys Asp Ala Leu Asp Tyr Val
    370                 375                 380

Tyr Ser Cys Trp Asp Glu Arg Gly Ile Gly Trp Ala Lys Asp Ser Pro
```

```
            385                 390                 395                 400
    Ile Ala Asp Ile Asp Asp Thr Ala Met Gly Leu Arg Ile Leu Arg Leu
                    405                 410                 415

His Gly Tyr Asn Val Ser Pro Asp Val Leu Lys Thr Phe Lys Asp Glu
                    420                 425                 430

Asn Gly Glu Phe Phe Cys Phe Met Gly Gln Thr Gln Arg Gly Val Thr
                    435                 440                 445

Asp Met Leu Asn Val Tyr Arg Cys Ser Gln Val Ala Phe Pro Gly Glu
    450                 455                 460

Thr Ile Met Glu Glu Ala Lys Leu Cys Thr Glu Arg Tyr Leu Arg Asn
    465                 470                 475                 480

Ala Leu Glu Asn Ala Asp Ala Phe Asp Lys Trp Ala Ile Lys Lys Asn
                    485                 490                 495

Ile Arg Gly Glu Val Glu Tyr Ala Leu Lys Tyr Pro Trp His Arg Ser
                    500                 505                 510

Met Pro Arg Leu Glu Val Arg Ser Tyr Ile Gly Asn Tyr Gly Pro Asn
                    515                 520                 525

Asp Val Trp Leu Gly Lys Ser Leu Tyr Met Met Pro Tyr Ile Ser Asn
    530                 535                 540

Glu Lys Tyr Leu Glu Leu Ala Lys Leu Asp Phe Asn Ser Val Gln Ser
    545                 550                 555                 560

Leu His Gln Glu Glu Ile Arg Glu Leu Val Arg Trp Cys Lys Ser Ser
                    565                 570                 575

Gly Phe Thr Glu Leu Lys Phe Thr Arg Asp Arg Val Val Glu Thr Tyr
                    580                 585                 590

Phe Ala Val Ala Ser Ser Met Phe Glu Pro Glu Phe Ser Thr Cys Arg
                    595                 600                 605

Ala Val Tyr Thr Lys Ile Ser Val Leu Leu Val Ile Leu Asp Asp Leu
                    610                 615                 620

Tyr Asp Gly Tyr Gly Ser Pro Asp Glu Ile Lys Leu Phe Ser Glu Ala
    625                 630                 635                 640

Val Lys Arg Trp Asp Leu Ser Leu Leu Glu Gln Met Pro Asp His Met
                    645                 650                 655

Lys Ile Cys Phe Leu Gly Leu Tyr Asn Thr Val Asn Glu Val Ala Glu
                    660                 665                 670

Glu Gly Arg Lys Thr Gln Gly His Asp Val Leu Gly Tyr Ile Arg Asn
                    675                 680                 685

Leu Trp Glu Ile Gln Leu Ala Ala Phe Thr Arg Glu Ala Glu Trp Ser
    690                 695                 700

Gln Gly Lys Tyr Val Pro Ser Phe Asp Glu Tyr Ile Glu Asn Ala Gln
    705                 710                 715                 720

Val Ser Ile Gly Val Ala Thr Ile Leu Leu Ile Thr Ile Leu Phe Thr
                    725                 730                 735

Glu Glu Asp Asp Ile Leu Ser His Ile Asp Tyr Gly Ser Lys Phe Leu
                    740                 745                 750

Arg Leu Ala Ser Leu Thr Ala Arg Leu Ala Asn Asp Ile Lys Thr Tyr
                    755                 760                 765

Gln Glu Glu Arg Ala His Gly Glu Val Val Ser Ala Ile Gln Cys Tyr
                    770                 775                 780

Met Lys Asp Arg Pro Glu Ile Thr Glu Glu Ala Leu Lys Tyr Val
    785                 790                 795                 800

Tyr Gly Arg Met Val Asn Asp Leu Ala Glu Leu Asn Ser Glu Tyr Leu
                    805                 810                 815
```

Lys Ser Asn Glu Met Pro Gln Asn Cys Lys Arg Leu Val Phe Asp Thr
              820                 825                 830

Ala Arg Val Ala Gln Leu Phe Thr Met Glu Gly Asp Gly Leu Thr Tyr
              835                 840                 845

Ser Asp Thr Met Glu Ile Lys Glu His Ile Lys Lys Cys Leu Phe Glu
              850                 855                 860

Pro Ala Thr
865

<210> SEQ ID NO 8
<211> LENGTH: 2604
<212> TYPE: DNA
<213> ORGANISM: Abies balsamea
<220> FEATURE:
<223> OTHER INFORMATION: AbdiTPS4

<400> SEQUENCE: 8

```
atggccctgc ctgtctattc gctgaaatcc cacatcccca ttactacaat tgcctctgct      60
aaaatgaatt acacccctaa caagggaatg atcactgcca acgggagaag ccgccgcatc     120
cgattgagtc caaacaagat cgttgcttgt gctggagaag ctgatcgcac atttccttct     180
caatctctcg aaaagaccgc tctgtttccc gatcagtttt ctgaaaagaa tggaactcct     240
tctaatttca caccgcctaa tcgagaattt cctccttcat tttggaataa tgatattatc     300
aattcaataa cggcgtcaca caaggttcaa acaggggacc ggaagcgtat ccagacatta     360
atatctgaaa ttaaaaatgt gtttaattct atgggcgatg agaaacgag tccctctgca      420
tatgacaccg cttgggtagc gaggattcca gcggttgatg gctctgaaca acctcagttt     480
cctcagacac ttgaatggat tctacaaaat cagttgaaag atgggtcttg gggtgaagaa     540
ttctacttct tagcatatga cagattactg gctacccttg catgcattat taccctcacc     600
atatggagaa ctggcaacgt acaactgcat aaaggcattg aattcttcag gaagcaagtt     660
gtaaggatgg atgatgaagc tgataaccac cggccaagtg gatttgaaat agtctttcct     720
gctatgttaa atgaagcaaa aagtttagga ttggatctgc cttatgaatt gccgttcatt     780
gaacaaatgg ttaaaagcg ggaggctaag cttaaaatga ttaccacgaa tgtcctgtat     840
accattcaaa caacattact ttactctctg gaaggcttgc atgaaatagt agactttgat     900
aaaataatca aacttcaatc caaggatgga tcattcctcg gctccccggc atctacagcg     960
gctgtattca tgcaaacagg gaacactaaa tgcttggaat tcttggagtt cgttttaagg    1020
aaatttagaa accatgtgcc tagcgactat cccctcgatc tatttgaacg tctttgggtc    1080
gttgacacgg ttgaacgact agggattgat cgccatttca aaaggagat caaggacgca    1140
ttggattatg tgtacagctg ttgggacgaa agaggcattg gctgggcgaa agacagccct    1200
atagccgata ttgatgatac agccatgggc cttcgaatct tgaggctgca tggatacaat    1260
gtatccccag atgttttaaa aactttcaaa gatgagaatg agagttctt ttgcttcatg    1320
ggtcaaacac agaggggagt tacggacatg ctaaacgttt atcgctgttc acaagttgct    1380
tttccgggag aaacgatcat ggaagaagca aaactctgta ctgaaaggta tctgcgcaac    1440
gctctggaaa atgcggacgc ctttgacaaa tgggctatta aaaagaatat tcgagggag    1500
gtggagtacg cactcaagta tccctggcat agaagtatgc caaggctgga ggtgagaagc    1560
tacattggaa attacgggcc aaacgatgtc tggcttggaa agtctttgta tatgatgcca    1620
tacattagca acgaaaaata tttggaattg gcaaaactgg acttcaatag tgtgcaatct    1680
```

-continued

```
ctacaccaag aggagattcg agagcttgtg aggtggtgta aatcatcagg tttcacagag      1740
ctcaagttca cacgcgaccg tgtagttgaa acatatttcg cagttgcgtc tagtatgttt      1800
gagcccgagt tctctacctg tagagccgtt tatacaaaaa tttccgttct cctcgtcatt      1860
ttagacgacc tttacgatgg gtatggatct ccagacgaaa tcaaactgtt ctcggaagca      1920
gtcaaaagat gggatctctc tttgttagaa caaatgcccg accacatgaa aatctgcttc      1980
ctgggattgt acaacacagt taatgaagta gctgaagaag gacgcaagac acagggccat      2040
gatgtgctag gctacattcg aaacttgtgg gagatccagc tcgcagcttt caccagagaa      2100
gcagaatggt ctcaagggaa atacgtgccg tcttttgatg aatacataga gaacgcccaa      2160
gtatcaatag gtgtagcaac tatacttctt ataactattc ttttcactga agaggatgac      2220
attctctccc atattgatta cggatccaaa tttctccgtc tcgctagctt gacagcacgt      2280
ttagcgaacg acatcaaaac ataccaggag gagagagctc atggcgaggt ggtttcggct      2340
atacagtgtt atatgaagga tcgtcctgaa attacagagg aagaagctct caaatatgtc      2400
tatggtcgaa tggttaacga tctcgcagag ttaaattctg aatacttgaa atctaatgaa      2460
atgccccaaa attgcaagag actggttttt gacactgcaa gagtagcgca gttgtttact      2520
atggagggag acggtttgac atattcagat actatggaaa ttaaagaaca catcaaaaag      2580
tgcctcttcg agccggctac ctaa                                            2604
```

<210> SEQ ID NO 9

<400> SEQUENCE: 9

000

<210> SEQ ID NO 10

<400> SEQUENCE: 10

000

<210> SEQ ID NO 11
<211> LENGTH: 6
<212> TYPE: PRT
<213> ORGANISM: Artificial Sequence
<220> FEATURE:
<223> OTHER INFORMATION: Motif
<220> FEATURE:
<221> NAME/KEY: VARIANT
<222> LOCATION: 1
<223> OTHER INFORMATION: Xaa = Asn or Lys

<400> SEQUENCE: 11

Xaa Arg Glu Phe Pro Pro
1               5

<210> SEQ ID NO 12
<211> LENGTH: 4
<212> TYPE: PRT
<213> ORGANISM: Artificial Sequence
<220> FEATURE:
<223> OTHER INFORMATION: Motif
<220> FEATURE:
<221> NAME/KEY: VARIANT
<222> LOCATION: 2
<223> OTHER INFORMATION: Xaa = any amino acid

<400> SEQUENCE: 12

Asp Xaa Asp Asp
1

<210> SEQ ID NO 13
<211> LENGTH: 5
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: (3)...(4)
<223> OTHER INFORMATION: Xaa = any amino acid

<400> SEQUENCE: 13

Asp Asp Xaa Xaa Asp
1               5

<210> SEQ ID NO 14
<211> LENGTH: 9
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 3, 4, 6, 7, 8
<223> OTHER INFORMATION: Xaa = any amino acid

<400> SEQUENCE: 14

Asn Asp Xaa Xaa Thr Xaa Xaa Xaa Glu
1               5

<210> SEQ ID NO 15
<211> LENGTH: 9
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 1
<223> OTHER INFORMATION: Xaa = Asn or Lys
<220> FEATURE:
<221> NAME/KEY: VARIANT
<222> LOCATION: (3)...(8)
<223> OTHER INFORMATION: Xaa = any amino acid

<400> SEQUENCE: 15

Xaa Arg Xaa Xaa Xaa Xaa Xaa Xaa Trp
1               5

<210> SEQ ID NO 16
<211> LENGTH: 4
<212> TYPE: PRT
<213> ORGANISM: Artificial Sequence
<220> FEATURE:
<223> OTHER INFORMATION: motif

<400> SEQUENCE: 16

Asp Ile Asp Asp
1

<210> SEQ ID NO 17
<211> LENGTH: 5
<212> TYPE: PRT
<213> ORGANISM: Artificial Sequence
<220> FEATURE:
<223> OTHER INFORMATION: motif

<400> SEQUENCE: 17

Asp Asp Leu Tyr Asp
1               5

<210> SEQ ID NO 18
<211> LENGTH: 30
<212> TYPE: DNA
<213> ORGANISM: Artificial Sequence
<220> FEATURE:
<223> OTHER INFORMATION: AbdiTPS1-3'RACE primer

<400> SEQUENCE: 18
ctgagagagg tcaaggtgag gaggcttctg                                    30

<210> SEQ ID NO 19
<211> LENGTH: 30
<212> TYPE: DNA
<213> ORGANISM: Artificial Sequence
<220> FEATURE:
<223> OTHER INFORMATION: AbdiTPS2-3'RACE primer

<400> SEQUENCE: 19
cagagagagg tcaaggtgag gtggcttctg                                    30

<210> SEQ ID NO 20
<211> LENGTH: 28
<212> TYPE: DNA
<213> ORGANISM: Artificial Sequence
<220> FEATURE:
<223> OTHER INFORMATION: AbdiTPS4-For-FL-SalI primer

<400> SEQUENCE: 20
tagtcgacat ggccctgcct gtctattc                                      28

<210> SEQ ID NO 21
<211> LENGTH: 34
<212> TYPE: DNA
<213> ORGANISM: Artificial Sequence
<220> FEATURE:
<223> OTHER INFORMATION: AbdiTPS4-For-delta85-SalI primer

<400> SEQUENCE: 21
tagtcgacat gcgagaattt cctccttcat tttg                               34

<210> SEQ ID NO 22
<211> LENGTH: 29
<212> TYPE: DNA
<213> ORGANISM: Artificial Sequence
<220> FEATURE:
<223> OTHER INFORMATION: AbdiTPS4-Rev-NotI primer

<400> SEQUENCE: 22
tagcggccgc ttaggtagcc ggctcgaag                                     29

<210> SEQ ID NO 23
<211> LENGTH: 40
<212> TYPE: PRT
<213> ORGANISM: Artificial Sequence
<220> FEATURE:
<223> OTHER INFORMATION: 40 amino acid linker containing N-terminal His-
      tag

<400> SEQUENCE: 23

Met Gly Arg Ser His His His His His His Ser Ser Gly Leu Val Pro
1               5                   10                  15

Arg Gly Ser His Met Ala Ser Met Thr Gly Gly Gln Gln Met Gly Arg
            20                  25                  30

Asp Pro Asn Ser Ser Ser Val Asp
              35                  40

<210> SEQ ID NO 24
<211> LENGTH: 30
<212> TYPE: DNA
<213> ORGANISM: Artificial Sequence
<220> FEATURE:
<223> OTHER INFORMATION: AbdiTPS2-For-delta68-SalI primer

<400> SEQUENCE: 24
tatgtcgaca aacgagaatt tcctccagga                               30

<210> SEQ ID NO 25
<211> LENGTH: 32
<212> TYPE: DNA
<213> ORGANISM: Artificial Sequence
<220> FEATURE:
<223> OTHER INFORMATION: AbdiTPS2-Rev-NotI primer

<400> SEQUENCE: 25
tgggcggccg cttacgcaat cggtatgaag ag                            32

<210> SEQ ID NO 26
<211> LENGTH: 30
<212> TYPE: DNA
<213> ORGANISM: Artificial Sequence
<220> FEATURE:
<223> OTHER INFORMATION: AbdiTPS1-For-delta83-SalI primer

<400> SEQUENCE: 26
tatgtcgaca aacgagaatt tcctccagga                               30

<210> SEQ ID NO 27
<211> LENGTH: 32
<212> TYPE: DNA
<213> ORGANISM: Artificial Sequence
<220> FEATURE:
<223> OTHER INFORMATION: AbdiTPS1-Rev-NotI primer

<400> SEQUENCE: 27
tgggcggccg cctaggcaac tggttggaag ag                            32

<210> SEQ ID NO 28
<211> LENGTH: 39
<212> TYPE: DNA
<213> ORGANISM: Artificial Sequence
<220> FEATURE:
<223> OTHER INFORMATION: D402A-D404A-sense primer

<400> SEQUENCE: 28
gacagcccta tagccgctat tgctgataca gccatgggc                     39

<210> SEQ ID NO 29
<211> LENGTH: 39
<212> TYPE: DNA
<213> ORGANISM: Artificial Sequence
<220> FEATURE:
<223> OTHER INFORMATION: D402A-D404A-antisense primer

<400> SEQUENCE: 29
gcccatggct gtatcagcaa tagcggctat agggctgtc                     39

<210> SEQ ID NO 30
<211> LENGTH: 34

```
<212> TYPE: DNA
<213> ORGANISM: Artificial Sequence
<220> FEATURE:
<223> OTHER INFORMATION: D621A-sense primer

<400> SEQUENCE: 30
tctcctcgtc attttagccg acctttacga tggg                                34

<210> SEQ ID NO 31
<211> LENGTH: 34
<212> TYPE: DNA
<213> ORGANISM: Artificial Sequence
<220> FEATURE:
<223> OTHER INFORMATION: D621A-antisense primer

<400> SEQUENCE: 31
cccatcgtaa aggtcggcta aaatgacgag gaga                                34

<210> SEQ ID NO 32
<211> LENGTH: 2974
<212> TYPE: DNA
<213> ORGANISM: Artificial Sequence
<220> FEATURE:
<223> OTHER INFORMATION: pJET vector

<400> SEQUENCE: 32 gccctgcag ccgaattata ttattttgc caaataattt ttaacaaaag ctctgaagtc       60
ttcttcattt aaattcttag atgatacttc atctggaaaa ttgtcccaat tagtagcatc    120
acgctgtgag taagttctaa accatttttt tattgttgta ttatctctaa tcttactact    180
cgatgagttt tcggtattat ctctattttt aacttggagc aggttccatt cattgttttt    240
ttcatcatag tgaataaaat caactgcttt aacacttgtg cctgaacacc atatccatcc    300
ggcgtaatac gactcactat agggagagcg gccgccagat cttccggatg gctcgagttt    360
ttcagcaaga tatctttcta gaagatctcc tacaatattc tcagctgcca tggaaaatcg    420
atgttcttct tttattctct caagattttc aggctgtata ttaaaactta tattaagaac    480
tatgctaacc acctcatcag gaaccgttgt aggtggcgtg ggttttcttg gcaatcgact    540
ctcatgaaaa ctacgagcta aatattcaat atgttcctct tgaccaactt tattctgcat    600 ttttttttgaa cgaggtttag agcaagcttc aggaaactga gacaggaatt ttattaaaaa    660
tttaaatttt gaagaaagtt cagggttaat agcatccatt ttttgctttg caagttcctc    720
agcattctta caaaagacg tctcttttga catgtttaaa gtttaaacct cctgtgtgaa    780
attgttatcc gctcacaatt ccacacatta tacgagccgg aagcataaag tgtaaagcct    840
ggggtgccta atgagtgagc taactcacat taattgcgtt gcgctcactg ccaattgctt    900
tccagtcggg aaacctgtcg tgccagctgc attaatgaat cggccaacgc gcggggagag    960
gcggtttgcg tattgggcgc tcttccgctt cctcgctcac tgactcgctg cgctcggtcg   1020
ttcggctgcg gcgagcggta tcagctcact caaaggcggt aatacggtta tccacagaat   1080
caggggataa cgcaggaaag aacatgtgag caaaaggcca gcaaaggcc aggaaccgta   1140 aaaaggccgc gttgctggcg ttttccata ggctccgccc ccctgacgag catcacaaaa   1200
atcgacgctc aagtcagagg tggcgaaacc cgacaggact ataaagatac caggcgtttc   1260
cccctggaag ctccctcgtg cgctctcctg ttccgaccct gccgcttacc ggatacctgt   1320
ccgcctttct cccttcggga agcgtggcgc tttctcatag ctcacgctgt aggtatctca   1380
gttcggtgta ggtcgttcgc tccaagctgg gctgtgtgca cgaaccccc gttcagcccg   1440
```

| | |
|---|---|
| accgctgcgc cttatccggt aactatcgtc ttgagtccaa cccggtaaga cacgacttat | 1500 |
| cgccactggc agcagccact ggtaacagga ttagcagagc gaggtatgta ggcggtgcta | 1560 |
| cagagttctt gaagtggtgg cctaactacg gctacactag aaggacagta tttggtatct | 1620 |
| gcgctctgct gaagccagtt accttcggaa aaagagttgg tagctcttga tccggcaaac | 1680 |
| aaaccaccgc tggtagcggt ggttttttg tttgcaagca gcagattacg cgcagaaaaa | 1740 |
| aaggatctca agaagatcct ttgatctttt ctacggggtc tgacgctcag tggaacgaaa | 1800 |
| actcacgtta agggattttg gtcatgagat tatcaaaaag gatcttcacc tagatccttt | 1860 |
| taaattaaaa atgaagtttt aaatcaatct aaagtatata tgagtaaact tggtctgaca | 1920 |
| gttaccaatg cttaatcagt gaggcaccta tctcagcgat ctgtctattt cgttcatcca | 1980 |
| tagttgcctg actccccgtc gtgtagataa ctacgatacg ggagggctta ccatctggcc | 2040 |
| ccagtgctgc aatgataccg cgagacccac gctcaccggc tccagattta tcagcaataa | 2100 |
| accagccagc cggaagggcc gagcgcagaa gtggtcctgc aactttatcc gcctccatcc | 2160 |
| agtctattaa ttgttgccgg gaagctagag taagtagttc gccagttaat agtttgcgca | 2220 |
| acgttgttgc cattgctaca ggcatcgtgg tgtcacgctc gtcgtttggt atggcttcat | 2280 |
| tcagctccgg ttcccaacga tcaaggcgag ttacatgatc ccccatgttg tgcaaaaaag | 2340 |
| cggttagctc cttcggtcct ccgatcgttg tcagaagtaa gttggccgca gtgttatcac | 2400 |
| tcatggttat ggcagcactg cataattctc ttactgtcat gccatccgta agatgctttt | 2460 |
| ctgtgactgg tgagtactca accaagtcat tctgagaata gtgtatgcgg cgaccgagtt | 2520 |
| gctcttgccc ggcgtcaata cgggataata ccgcgccaca tagcagaact ttaaaagtgc | 2580 |
| tcatcattgg aaaacgttct tcgggcgaa aactctcaag gatcttaccg ctgttgagat | 2640 |
| ccagttcgat gtaacccact cgtgcaccca actgatcttc agcatctttt actttcacca | 2700 |
| gcgtttctgg gtgagcaaaa acaggaaggc aaaatgccgc aaaaaaggga ataagggcga | 2760 |
| cacggaaatg ttgaatactc atactcttcc tttttcaata ttattgaagc atttatcagg | 2820 |
| gttattgtct catgagcgga tacatatttg aatgtattta gaaaaataaa caaataggggg | 2880 |
| ttccgcgcac atttccccga aaagtgccac ctgacgtcta agaaaccatt attatcatga | 2940 |
| cattaaccta taaaaatagg cgtatcacga ggcc | 2974 |

<210> SEQ ID NO 33
<211> LENGTH: 5368
<212> TYPE: DNA
<213> ORGANISM: Artificial Sequence
<220> FEATURE:
<223> OTHER INFORMATION: pET28b(+) vector

<400> SEQUENCE: 33

| | |
|---|---|
| atccggatat agttcctcct ttcagcaaaa aaccccctcaa gacccgttta gaggccccaa | 60 |
| ggggttatgc tagttattgc tcagcggtgg cagcagccaa ctcagcttcc tttcgggctt | 120 |
| tgttagcagc cggatctcag tggtggtggt ggtggtgctc gagtgcggcc gcaagcttgt | 180 |
| cgacggagct cgaattcgga tcccgaccca tttgctgtcc accagtcatg ctagccatat | 240 |
| ggctgccgcg cggcaccagg ccgctgctgt gatgatgatg atgatggctg ctgcccatgg | 300 |
| tatatctcct tcttaaagtt aaacaaaatt atttctagag gggaattgtt atccgctcac | 360 |
| aattccccta gtgtgagtcg tattaatttc gcggatcga gatctcgatc ctctacgccg | 420 |
| gacgcatcgt ggccggcatc accggcgcca caggtgcggt tgctggcgcc tatatcgccg | 480 |
| acatcaccga tggggaagat cgggctcgcc acttcgggct catgagcgct tgtttcggcg | 540 |

```
tgggtatggt ggcaggcccc gtggccgggg gactgttggg cgccatctcc ttgcatgcac    600
cattccttgc ggcggcggtg ctcaacggcc tcaacctact actgggctgc ttcctaatgc    660
aggagtcgca taagggagag cgtcgagatc ccggacacca tcgaatggcg caaaaccttt    720
cgcggtatgg catgatagcg cccggaagag agtcaattca gggtggtgaa tgtgaaacca    780
gtaacgttat acgatgtcgc agagtatgcc ggtgtctctt atcagaccgt ttccgcgtg     840 gtgaaccagg ccagccacgt ttctgcgaaa acgcgggaaa aagtggaagc ggcgatggcg    900
gagctgaatt acattcccaa ccgcgtggca caacaactgg cgggcaaaca gtcgttgctg    960
attggcgttg ccacctccag tctggccctg cacgcgccgt cgcaaattgt cgcggcgatt    1020
aaatctcgcg ccgatcaact gggtgccagc gtggtggtgt cgatggtaga acgaagcggc    1080
gtcgaagcct gtaaagcggc ggtgcacaat cttctcgcgc aacgcgtcag tgggctgatc    1140
attaactatc cgctggatga ccaggatgcc attgctgtgg aagctgcctg cactaatgtt    1200
ccggcgttat ttcttgatgt ctctgaccag acacccatca acagtattat tttctcccat    1260
gaagacggta cgcgactggg cgtggagcat ctggtcgcat gggtcacca gcaaatcgcg     1320 ctgttagcgg gcccattaag ttctgtctcg gcgcgtctgc gtctggctgg ctggcataaa    1380
tatctcactc gcaatcaaat tcagccgata gcggaacggg aaggcgactg gagtgccatg    1440
tccggttttc aacaaaccat gcaaatgctg aatgagggca tcgttcccac tgcgatgctg    1500
gttgccaacg atcagatggc gctgggcgca atgcgcgcca ttaccgagtc cgggctgcgc    1560
gttggtgcgg atatctcggt agtgggatac gacgataccg aagacagctc atgttatatc    1620
ccgccgttaa ccaccatcaa acaggatttt cgcctgctgg ggcaaaccag cgtggaccgc    1680
ttgctgcaac tctctcaggg ccaggcggtg aagggcaatc agctgttgcc cgtctcactg    1740
gtgaaaagaa aaaccaccct ggcgcccaat acgcaaaccg cctctccccg cgcgttggcc    1800
gattcattaa tgcagctggc acgacaggtt cccgactgg aaagcgggca gtgagcgcaa     1860
cgcaattaat gtaagttagc tcactcatta ggcaccggga tctcgaccga tgcccttgag    1920
agccttcaac ccagtcagct ccttccggtg ggcgcggggc atgactatcg tcgccgcact    1980
tatgactgtc ttctttatca tgcaactcgt aggacaggtg ccggcagcgc tctgggtcat    2040
tttcggcgag gaccgctttc gctggagcgc gacgatgatc ggcctgtcgc ttgcggtatt    2100
cggaatcttg cacgccctcg ctcaagcctt cgtcactggt cccgccacca acgtttcgg    2160 cgagaagcag gccattatcg ccggcatggc ggccccacgg gtgcgcatga tcgtgctcct    2220
gtcgttgagg acccggctag gctggcgggg ttgccttact ggttagcaga atgaatcacc    2280
gatacgcgag cgaacgtgaa gcgactgctg ctgcaaaacg tctgcgacct gagcaacaac    2340
atgaatggtc ttcggtttcc gtgtttcgta aagtctggaa acgcggaagt cagcgccctg    2400
caccattatg ttccggatct gcatcgcagg atgctgctgg ctaccctgtg gaacacctac    2460
atctgtatta acgaagcgct ggcattgacc ctgagtgatt tttctctggt cccgccgcat    2520
ccataccgcc agttgtttac cctcacaacg ttccagtaac cgggcatgtt catcatcagt    2580
aacccgtatc gtgagcatcc tctctcgttt catcggtatc attaccccca tgaacagaaa    2640
tcccccttac acggaggcat cagtgaccaa acaggaaaaa accgccctta acatggcccg    2700
ctttatcaga agccagacat taacgcttct ggagaaactc aacgagctgg acgcggatga    2760
acaggcagac atctgtgaat cgcttcacga ccacgctgat gagctttacc gcagctgcct    2820
cgcgcgtttc ggtgatgacg gtgaaaacct ctgacacatg cagctcccgg agacggtcac    2880
```

```
agcttgtctg taagcggatg ccgggagcag acaagcccgt cagggcgcgt cagcgggtgt    2940
tggcgggtgt cggggcgcag ccatgaccca gtcacgtagc gatagcggag tgtatactgg    3000
cttaactatg cggcatcaga gcagattgta ctgagagtgc accatatatg cggtgtgaaa    3060
taccgcacag atgcgtaagg agaaaatacc gcatcaggcg ctcttccgct tcctcgctca    3120
ctgactcgct gcgctcggtc gttcggctgc ggcgagcggt atcagctcac tcaaaggcgg    3180
taatacggtt atccacagaa tcaggggata acgcaggaaa gaacatgtga gcaaaaggcc    3240
agcaaaaggc caggaaccgt aaaaaggccg cgttgctggc gtttttccat aggctccgcc    3300
cccctgacga gcatcacaaa aatcgacgct caagtcagag gtggcgaaac ccgacaggac    3360
tataaagata ccaggcgttt ccccctggaa gctccctcgt gcgctctcct gttccgaccc    3420
tgccgcttac cggatacctg tccgcctttc tcccttcggg aagcgtggcg ctttctcata    3480
gctcacgctg taggtatctc agttcggtgt aggtcgttcg ctccaagctg ggctgtgtgc    3540
acgaaccccc cgttcagccc gaccgctgcg ccttatccgg taactatcgt cttgagtcca    3600
acccggtaag acacgactta tcgccactgg cagcagccac tggtaacagg attagcagag    3660
cgaggtatgt aggcggtgct acagagttct tgaagtggtg gcctaactac ggctacacta    3720
gaaggacagt atttggtatc tgcgctctgc tgaagccagt taccttcgga aaaagagttg    3780
gtagctcttg atccggcaaa caaaccaccg ctggtagcgg tggtttttt gtttgcaagc    3840 agcagattac gcgcagaaaa aaggatctca agaagatcc tttgatcttt tctacggggt    3900
ctgacgctca gtggaacgaa aactcacgtt aagggatttt ggtcatgaac aataaaactg    3960
tctgcttaca taaacagtaa tacaaggggt gttatgagcc atattcaacg ggaaacgtct    4020
tgctctaggc cgcgattaaa ttccaacatg gatgctgatt tatatgggta taaatgggct    4080
cgcgataatg tcgggcaatc aggtgcgaca atctatcgat tgtatgggaa gcccgatgcg    4140
ccagagttgt ttctgaaaca tggcaaaggt agcgttgcca atgatgttac agatgagatg    4200
gtcagactaa actggctgac ggaatttatg cctcttccga ccatcaagca ttttatccgt    4260
actcctgatg atgcatggtt actcaccact gcgatccccg ggaaaacagc attccaggta    4320
ttagaagaat atcctgattc aggtgaaaat attgttgatg cgctggcagt gttcctgcgc    4380
cggttgcatt cgattcctgt ttgtaattgt ccttttaaca gcgatcgcgt atttcgtctc    4440
gctcaggcgc aatcacgaat gaataacggt ttggttgatg cgagtgattt tgatgacgag    4500
cgtaatggct ggcctgttga acaagtctgg aaagaaatgc ataaactttt gccattctca    4560
ccggattcag tcgtcactca tggtgatttc tcacttgata accttatttt tgacgagggg    4620
aaattaatag gttgtattga tgttggacga gtcggaatcg cagaccgata ccaggatctt    4680
gccatcctat ggaactgcct cggtgagttt tctccttcat tacagaaacg ctttttcaa    4740 aaatatggta ttgataatcc tgatatgaat aaattgcagt ttcatttgat gctcgatgag    4800
tttttctaag aattaattca tgagcggata catatttgaa tgtatttaga aaataaaca    4860 aataggggtt ccgcgcacat ttccccgaaa agtgccacct gaaattgtaa acgttaatat    4920
tttgttaaaa ttcgcgttaa attttgtta atcagctca tttttttaacc aataggccga    4980 aatcggcaaa atcccttata aatcaaaaga atagaccgag atagggttga gtgttgttcc    5040
agtttggaac aagagtccac tattaaagaa cgtggactcc aacgtcaaag ggcgaaaaac    5100
cgtctatcag ggcgatggcc cactacgtga accatcaccc taatcaagtt ttttggggtc    5160
gaggtgccgt aaagcactaa atcggaaccc taaagggagc cccgatttta gagcttgacg    5220
gggaaagccg gcgaacgtgg cgagaaagga agggaagaaa gcgaaaggag cggcgctag    5280
```

```
ggcgctggca agtgtagcgg tcacgctgcg cgtaaccacc acacccgccg cgcttaatgc     5340
gccgctacag ggcgcgtccc attcgcca                                        5368
```

<210> SEQ ID NO 34
<211> LENGTH: 859
<212> TYPE: PRT
<213> ORGANISM: Picea abies
<220> FEATURE:
<223> OTHER INFORMATION: PaLAS D611A variant

<400> SEQUENCE: 34

```
Met Ala Leu Leu Ser Ser Leu Ser Ser Gln Ile Pro Thr Gly Ala
  1               5                  10                  15

His His Leu Thr Leu Asn Ala Tyr Ala Asn Thr Gln Cys Ile Pro His
             20                  25                  30

Phe Phe Ser Thr Leu Asn Ala Gly Thr Ser Ala Gly Lys Arg Ser Ser
         35                  40                  45

Leu Tyr Leu Arg Trp Gly Lys Gly Ser Asn Lys Ile Ile Ala Cys Val
     50                  55                  60

Gly Glu Asp Ser Leu Ser Ala Pro Thr Leu Val Lys Arg Glu Phe Pro
 65                  70                  75                  80

Pro Gly Phe Trp Lys Asp His Val Ile Asp Ser Leu Thr Ser Ser His
                 85                  90                  95

Lys Val Ala Ala Ser Asp Glu Lys Arg Ile Glu Thr Leu Ile Ser Glu
            100                 105                 110

Ile Lys Asn Met Phe Arg Ser Met Gly Tyr Gly Asp Thr Asn Pro Ser
        115                 120                 125

Ala Tyr Asp Thr Ala Trp Val Ala Arg Ile Pro Ala Val Asp Gly Ser
    130                 135                 140

Glu Gln Pro Glu Phe Pro Glu Thr Leu Glu Trp Ile Leu Gln Asn Gln
145                 150                 155                 160

Leu Lys Asp Gly Ser Trp Gly Glu Gly Phe Tyr Phe Leu Ala Tyr Asp
                165                 170                 175

Arg Ile Leu Ala Thr Leu Ala Cys Ile Ile Thr Leu Thr Leu Trp Arg
            180                 185                 190

Thr Gly Glu Ile Gln Val Gln Lys Gly Ile Glu Phe Phe Lys Thr Gln
        195                 200                 205

Ala Gly Lys Ile Glu Asp Glu Ala Asp Ser His Arg Pro Ser Gly Phe
    210                 215                 220

Glu Ile Val Phe Pro Ala Met Leu Lys Glu Ala Lys Val Leu Gly Leu
225                 230                 235                 240

Asp Leu Pro Tyr Glu Leu Pro Phe Ile Lys Gln Ile Ile Glu Lys Arg
                245                 250                 255

Glu Ala Lys Leu Glu Arg Leu Pro Thr Asn Ile Leu Tyr Ala Leu Pro
            260                 265                 270

Thr Thr Leu Leu Tyr Ser Leu Glu Gly Leu Gln Glu Ile Val Asp Trp
        275                 280                 285

Gln Lys Ile Ile Lys Leu Gln Ser Lys Asp Gly Ser Phe Leu Ser Ser
    290                 295                 300

Pro Ala Ser Thr Ala Ala Val Phe Met Arg Thr Gly Asn Lys Lys Cys
305                 310                 315                 320

Leu Glu Phe Leu Asn Phe Val Leu Lys Lys Phe Gly Asn His Val Pro
                325                 330                 335

Cys His Tyr Pro Leu Asp Leu Phe Glu Arg Leu Trp Ala Val Asp Thr
```

```
                340                 345                 350
Ile Glu Arg Leu Gly Ile Asp Arg His Phe Lys Glu Glu Ile Lys Asp
            355                 360                 365

Ala Leu Asp Tyr Val Tyr Ser His Trp Asp Glu Arg Gly Ile Gly Trp
370                 375                 380

Ala Arg Glu Asn Pro Val Pro Asp Ile Asp Asp Thr Ala Met Gly Leu
385                 390                 395                 400

Arg Ile Leu Arg Leu His Gly Tyr Asn Val Ser Ser Asp Val Leu Lys
                405                 410                 415

Thr Phe Arg Asp Glu Asn Gly Glu Phe Phe Cys Phe Leu Gly Gln Thr
            420                 425                 430

Gln Arg Gly Val Thr Asp Met Leu Asn Val Asn Arg Cys Ser His Val
        435                 440                 445

Ala Phe Pro Gly Glu Thr Ile Met Glu Glu Ala Lys Thr Cys Thr Glu
    450                 455                 460

Arg Tyr Leu Arg Asn Ala Leu Glu Asp Val Gly Ala Phe Asp Lys Trp
465                 470                 475                 480

Ala Leu Lys Lys Asn Ile Arg Gly Glu Val Glu Tyr Ala Leu Lys Tyr
                485                 490                 495

Pro Trp His Arg Ser Met Pro Arg Leu Glu Ala Arg Ser Tyr Ile Glu
            500                 505                 510

His Tyr Gly Pro Asn Asp Val Trp Leu Gly Lys Thr Met Tyr Met Met
        515                 520                 525

Pro Tyr Ile Ser Asn Glu Lys Tyr Leu Glu Leu Ala Lys Leu Asp Phe
    530                 535                 540

Asn His Val Gln Ser Leu His Gln Lys Glu Leu Arg Asp Leu Arg Arg
545                 550                 555                 560

Trp Trp Thr Ser Ser Gly Phe Thr Glu Leu Lys Phe Thr Arg Glu Arg
                565                 570                 575

Val Thr Glu Ile Tyr Phe Ser Pro Ala Ser Phe Met Phe Glu Pro Glu
            580                 585                 590

Phe Ala Thr Cys Arg Ala Val Tyr Thr Lys Thr Ser Asn Phe Thr Val
        595                 600                 605

Ile Leu Ala Asp Leu Tyr Asp Ala His Gly Thr Leu Asp Asp Leu Lys
    610                 615                 620

Leu Phe Ser Asp Ser Val Lys Lys Trp Asp Leu Ser Leu Val Asp Arg
625                 630                 635                 640

Met Pro Gln Asp Met Lys Ile Cys Phe Met Gly Phe Tyr Asn Thr Phe
                645                 650                 655

Asn Glu Ile Ala Glu Glu Gly Arg Lys Arg Gln Gly Arg Asp Val Leu
            660                 665                 670

Gly Tyr Ile Arg Asn Val Trp Glu Ile Gln Leu Glu Ala Tyr Thr Lys
        675                 680                 685

Glu Ala Glu Trp Ser Ala Ala Arg Tyr Val Pro Ser Phe Asp Glu Tyr
    690                 695                 700

Ile Asp Asn Ala Ser Val Ser Ile Ala Leu Gly Thr Val Val Leu Ile
705                 710                 715                 720

Ser Ala Leu Phe Thr Gly Glu Ile Leu Thr Asp Val Leu Ser Lys
                725                 730                 735

Ile Gly Arg Gly Ser Arg Phe Leu Gln Leu Met Gly Leu Thr Gly Arg
            740                 745                 750

Leu Val Asn Asp Thr Lys Thr Tyr Glu Ala Glu Arg Gly Gln Gly Glu
        755                 760                 765
```

```
Val Ala Ser Ala Val Gln Cys Tyr Met Lys Asp His Pro Glu Ile Ser
            770                 775                 780

Glu Glu Glu Ala Leu Lys His Val Tyr Thr Val Met Glu Asn Ala Leu
785                 790                 795                 800

Asp Glu Leu Asn Arg Glu Phe Val Asn Asn Arg Glu Val Pro Asp Ser
                805                 810                 815

Cys Arg Arg Leu Val Phe Glu Thr Ala Arg Ile Met Gln Leu Phe Tyr
                820                 825                 830

Met Asp Gly Asp Gly Leu Thr Leu Ser His Glu Thr Glu Ile Lys Glu
                835                 840                 845

His Val Lys Asn Cys Leu Phe Gln Pro Val Ala
            850                 855

<210> SEQ ID NO 35
<211> LENGTH: 867
<212> TYPE: PRT
<213> ORGANISM: Picea abies
<220> FEATURE:
<223> OTHER INFORMATION: Isopimaradiene synthase
<300> PUBLICATION INFORMATION:
<308> DATABASE ACCESSION NUMBER: Genbank AAS47690
<309> DATABASE ENTRY DATE: 2009-04-08

<400> SEQUENCE: 35

Met Ala Leu Leu Ser Ser Leu Ser Ser Gln Ile Pro Thr Gly Ser
1               5                   10                  15

His Pro Leu Thr His Thr Gln Cys Ile Pro His Phe Ser Thr Thr Ile
            20                  25                  30

Asn Ala Gly Ile Ser Ala Gly Lys Pro Arg Ser Phe Tyr Leu Arg Trp
            35                  40                  45

Gly Lys Gly Ser Asn Lys Ile Ile Ala Cys Val Gly Glu Gly Thr Thr
50                  55                  60

Ser Leu Pro Tyr Gln Ser Ala Glu Lys Thr Asp Ser Leu Ser Ala Pro
65                  70                  75                  80

Thr Leu Val Lys Arg Glu Phe Pro Pro Gly Phe Trp Lys Asp His Val
                85                  90                  95

Ile Asp Ser Leu Thr Ser Ser His Lys Val Ser Ala Ala Glu Glu Lys
            100                 105                 110

Arg Met Glu Thr Leu Ile Ser Glu Ile Lys Asn Ile Phe Arg Ser Met
            115                 120                 125

Gly Tyr Gly Glu Thr Asn Pro Ser Ala Tyr Asp Thr Ala Trp Val Ala
130                 135                 140

Arg Ile Pro Ala Val Asp Gly Ser Glu His Pro Glu Phe Pro Glu Thr
145                 150                 155                 160

Leu Glu Trp Ile Leu Gln Asn Gln Leu Lys Asp Gly Ser Trp Gly Glu
                165                 170                 175

Gly Phe Tyr Phe Leu Ala Tyr Asp Arg Ile Leu Ala Thr Leu Ala Cys
            180                 185                 190

Ile Ile Thr Leu Thr Leu Trp Arg Thr Gly Glu Thr Gln Ile Arg Lys
            195                 200                 205

Gly Ile Glu Phe Lys Thr Gln Ala Gly Lys Ile Glu Asp Glu Ala
            210                 215                 220

Asp Ser His Arg Pro Ser Gly Phe Glu Ile Val Phe Pro Ala Met Leu
225                 230                 235                 240

Lys Glu Ala Lys Val Leu Gly Leu Asp Leu Pro Tyr Glu Leu Pro Phe
                245                 250                 255
```

```
Ile Lys Gln Ile Ile Glu Lys Arg Glu Ala Lys Leu Glu Arg Leu Pro
            260                 265                 270

Thr Asn Ile Leu Tyr Ala Leu Pro Thr Thr Leu Leu Tyr Ser Leu Glu
            275                 280                 285

Gly Leu Gln Glu Ile Val Asp Trp Glu Lys Ile Ile Lys Leu Gln Ser
            290                 295                 300

Lys Asp Gly Ser Phe Leu Thr Ser Pro Ala Ser Thr Ala Ala Val Phe
305                 310                 315                 320

Met Arg Thr Gly Asn Lys Lys Cys Leu Glu Phe Leu Asn Phe Val Leu
            325                 330                 335

Lys Lys Phe Gly Asn His Val Pro Cys His Tyr Pro Leu Asp Leu Phe
            340                 345                 350

Glu Arg Leu Trp Ala Val Asp Thr Val Glu Arg Leu Gly Ile Asp His
            355                 360                 365

His Phe Lys Glu Glu Ile Lys Asp Ala Leu Asp Tyr Val Tyr Ser His
            370                 375                 380

Trp Asp Glu Arg Gly Ile Gly Trp Ala Arg Glu Asn Pro Ile Pro Asp
385                 390                 395                 400

Ile Asp Asp Thr Ala Met Gly Leu Arg Ile Leu Arg Leu His Gly Tyr
            405                 410                 415

Asn Val Ser Ser Asp Val Leu Lys Thr Phe Arg Asp Glu Asn Gly Glu
            420                 425                 430

Phe Phe Cys Phe Leu Gly Gln Thr Gln Arg Gly Val Thr Asp Met Leu
            435                 440                 445

Asn Val Asn Arg Cys Ser His Val Ala Phe Pro Gly Glu Thr Ile Met
450                 455                 460

Gln Glu Ala Lys Leu Cys Thr Glu Arg Tyr Leu Arg Asn Ala Leu Glu
465                 470                 475                 480

Asp Val Gly Ala Phe Asp Lys Trp Ala Leu Lys Lys Asn Ile Arg Gly
            485                 490                 495

Glu Val Glu Tyr Ala Leu Lys Tyr Pro Trp His Arg Ser Met Pro Arg
            500                 505                 510

Leu Glu Ala Arg Ser Tyr Ile Glu His Tyr Gly Pro Asn Asp Val Trp
            515                 520                 525

Leu Gly Lys Thr Met Tyr Met Met Pro Tyr Ile Ser Asn Leu Lys Tyr
            530                 535                 540

Leu Glu Leu Ala Lys Leu Asp Phe Asn His Val Gln Ser Leu His Gln
545                 550                 555                 560

Lys Glu Leu Arg Asp Leu Arg Arg Trp Trp Lys Ser Ser Gly Leu Ser
            565                 570                 575

Glu Leu Lys Phe Thr Arg Glu Arg Val Thr Glu Ile Tyr Phe Ser Ala
            580                 585                 590

Ala Ser Phe Ile Phe Glu Pro Glu Phe Ala Thr Cys Arg Asp Val Tyr
            595                 600                 605

Thr Lys Ile Ser Ile Phe Thr Val Ile Leu Asp Asp Leu Tyr Asp Ala
            610                 615                 620

His Gly Thr Leu Asp Asn Leu Glu Leu Phe Ser Glu Gly Val Lys Arg
625                 630                 635                 640

Trp Asp Leu Ser Leu Val Asp Arg Met Pro Gln Asp Met Lys Ile Cys
            645                 650                 655

Phe Thr Val Leu Tyr Asn Thr Val Asn Glu Ile Ala Val Glu Gly Arg
            660                 665                 670
```

```
Lys Arg Gln Gly Arg Asp Val Leu Gly Tyr Ile Arg Asn Val Leu Glu
            675                 680                 685

Ile Leu Leu Ala Ala His Thr Lys Glu Ala Glu Trp Ser Ala Ala Arg
690                 695                 700

Tyr Val Pro Ser Phe Asp Glu Tyr Ile Glu Asn Ala Ser Val Ser Ile
705                 710                 715                 720

Ser Leu Gly Thr Leu Val Leu Ile Ser Val Leu Phe Thr Gly Glu Ile
                725                 730                 735

Leu Thr Asp Asp Val Leu Ser Lys Ile Gly Arg Gly Ser Arg Phe Leu
            740                 745                 750

Gln Leu Met Gly Leu Thr Gly Arg Leu Val Asn Asp Thr Lys Thr Tyr
        755                 760                 765

Glu Ala Glu Arg Gly Gln Gly Glu Val Ala Ser Ala Val Gln Cys Tyr
    770                 775                 780

Met Lys Glu His Pro Glu Ile Ser Glu Glu Ala Leu Lys His Val
785                 790                 795                 800

Tyr Thr Val Met Glu Asn Ala Leu Asp Glu Leu Asn Arg Glu Phe Val
                805                 810                 815

Asn Asn Arg Asp Val Pro Asp Ser Cys Arg Arg Leu Val Phe Glu Thr
            820                 825                 830

Ala Arg Ile Met Gln Leu Phe Tyr Met Glu Gly Asp Gly Leu Thr Leu
        835                 840                 845

Ser His Glu Met Glu Ile Lys Glu His Val Lys Asn Cys Leu Phe Gln
    850                 855                 860

Pro Val Ala
865

<210> SEQ ID NO 36
<211> LENGTH: 874
<212> TYPE: PRT
<213> ORGANISM: Picea sitchensis
<220> FEATURE:
<223> OTHER INFORMATION: Isopimaradiene synthase
<300> PUBLICATION INFORMATION:
<308> DATABASE ACCESSION NUMBER: Genbank ADZ45512
<309> DATABASE ENTRY DATE: 2011-03-16

<400> SEQUENCE: 36

Met Ala Leu Pro Ser Ser Leu Ser Ser Arg Ile Pro Thr Gly Pro
1               5                   10                  15

His Pro Leu Thr His Thr Gln Cys Ile Pro His Phe Ser Thr Thr Ile
                20                  25                  30

Asn Ala Gly Ile Ser Ala Ala Lys Pro Arg Ser Phe Tyr Leu Arg Trp
            35                  40                  45

Gly Lys Asp Ser Gln Pro Lys Asn Leu Gly Ser Asn Lys Ile Ile Ala
        50                  55                  60

Cys Val Gly Glu Gly Thr Thr Ser Leu Pro Tyr Gln Ser Ala Glu Lys
65                  70                  75                  80

Thr Asp Ser Leu Ser Ala Pro Thr Leu Val Lys Arg Glu Phe Pro Pro
                85                  90                  95

Gly Phe Trp Lys Asp His Val Ile Asp Ser Leu Thr Ser Ser His Lys
            100                 105                 110

Val Ser Ala Ala Glu Glu Lys Arg Ile Glu Thr Leu Ile Ser Asp Ile
        115                 120                 125

Lys Asn Ile Phe Arg Ser Met Gly Tyr Gly Glu Thr Asn Pro Ser Ala
    130                 135                 140
```

-continued

```
Tyr Asp Thr Ala Trp Val Ala Arg Ile Pro Ala Val Asp Gly Ser Glu
145                 150                 155                 160

Gln Pro Glu Phe Pro Glu Thr Leu Glu Trp Ile Leu Gln Asn Gln Leu
            165                 170                 175

Lys Asp Gly Ser Trp Gly Glu Gly Phe Tyr Phe Leu Ala Tyr Asp Arg
        180                 185                 190

Ile Leu Ala Thr Leu Ala Cys Met Ile Thr Leu Thr Leu Trp Arg Thr
    195                 200                 205

Gly Glu Thr Gln Ile Arg Lys Gly Ile Glu Phe Phe Lys Thr Gln Ala
210                 215                 220

Gly Lys Ile Glu Asp Glu Ala Asp Ser His Arg Pro Ser Gly Phe Glu
225                 230                 235                 240

Ile Val Phe Pro Ala Met Leu Lys Glu Ala Lys Val Leu Gly Leu Asp
                245                 250                 255

Leu Pro Tyr Glu Leu Ser Phe Ile Lys Gln Ile Ile Glu Lys Arg Glu
            260                 265                 270

Ala Lys Leu Glu Arg Leu Pro Thr Asn Ile Leu Tyr Ala Leu Pro Thr
        275                 280                 285

Thr Leu Leu Tyr Ser Leu Glu Gly Leu Gln Glu Ile Val Asp Trp Gln
    290                 295                 300

Lys Ile Ile Lys Leu Gln Ser Lys Asp Gly Ser Phe Leu Thr Ser Pro
305                 310                 315                 320

Ala Ser Thr Ala Ala Val Phe Met Arg Thr Gly Asn Lys Lys Cys Leu
                325                 330                 335

Glu Phe Leu Asn Phe Val Leu Lys Lys Phe Gly Asn His Val Pro Cys
            340                 345                 350

His Tyr Pro Leu Asp Leu Phe Glu Arg Leu Trp Ala Val Asp Thr Val
        355                 360                 365

Glu Arg Leu Gly Ile Asp Arg His Phe Lys Glu Glu Ile Lys Asp Ala
    370                 375                 380

Leu Asp Tyr Val Tyr Ser His Trp Asp Glu Arg Gly Ile Gly Trp Ala
385                 390                 395                 400

Arg Glu Asn Pro Val Pro Asp Ile Asp Asp Thr Ala Met Gly Leu Arg
                405                 410                 415

Ile Leu Arg Leu His Gly Tyr Asn Val Ser Ser Asp Val Leu Lys Thr
            420                 425                 430

Phe Arg Asp Glu Asn Gly Glu Phe Phe Cys Phe Leu Gly Gln Thr Gln
        435                 440                 445

Arg Gly Val Thr Asp Met Leu Asn Val Asn Arg Cys Ser His Val Ala
450                 455                 460

Phe Pro Gly Glu Thr Ile Met Gln Glu Ala Lys Leu Cys Thr Glu Arg
465                 470                 475                 480

Tyr Leu Arg Asn Ala Leu Glu Asp Val Gly Ala Phe Asp Lys Trp Ala
                485                 490                 495

Leu Lys Lys Asn Ile Arg Gly Val Glu Tyr Ala Leu Lys Tyr Pro
            500                 505                 510

Trp His Arg Ser Met Pro Arg Leu Glu Ala Arg Ser Tyr Ile Glu His
        515                 520                 525

Tyr Gly Pro Asn Asp Val Trp Leu Gly Lys Thr Met Tyr Met Met Pro
    530                 535                 540

Tyr Ile Ser Asn Glu Lys Tyr Leu Glu Leu Ala Lys Leu Asp Phe Asn
545                 550                 555                 560

His Val Gln Ser Leu His Gln Lys Glu Leu Arg Asp Leu Arg Arg Trp
```

```
                       565                 570                 575
Trp Lys Ser Ser Gly Phe Ser Asp Leu Lys Phe Thr Arg Glu Arg Val
                580                 585                 590
Thr Glu Ile Tyr Phe Ser Ala Ala Ser Phe Ile Phe Glu Pro Glu Phe
            595                 600                 605
Ala Thr Cys Arg Tyr Val Tyr Thr Lys Met Ser Ile Phe Thr Val Ile
        610                 615                 620
Leu Asp Asp Leu Tyr Asp Ala His Gly Thr Leu Asp Asn Leu Asn Leu
625                 630                 635                 640
Phe Ser Glu Gly Val Lys Arg Trp Asp Leu Ser Leu Val Asp Arg Met
                645                 650                 655
Pro Gln Asp Met Lys Ile Cys Phe Thr Val Leu Tyr Asn Thr Val Asn
                660                 665                 670
Glu Ile Ala Val Glu Gly Arg Lys Arg Gln Gly Arg Asp Val Leu Gly
                675                 680                 685
Tyr Ile Arg Asn Val Leu Glu Ile Leu Leu Ala Ala His Thr Lys Glu
        690                 695                 700
Ala Glu Trp Ser Ala Thr Arg Tyr Val Pro Ser Phe Asp Glu Tyr Ile
705                 710                 715                 720
Glu Asn Ala Ser Val Ser Ile Ser Leu Gly Thr Val Val Leu Ile Ser
                725                 730                 735
Ala Leu Phe Thr Gly Glu Ile Leu Thr Asp Asp Val Leu Ser Lys Ile
                740                 745                 750
Gly Arg Gly Ser Arg Phe Leu Gln Leu Met Asp Leu Thr Gly Arg Leu
                755                 760                 765
Val Asn Asp Thr Lys Thr Tyr Gln Ala Glu Arg Gly Gln Gly Glu Val
                770                 775                 780
Ala Ser Ala Val Gln Cys Tyr Met Lys Asp His Pro Glu Ile Ser Glu
785                 790                 795                 800
Glu Glu Ala Leu Lys His Val Tyr Thr Val Met Glu Asn Ala Leu Asp
                805                 810                 815
Glu Leu Asn Arg Glu Phe Val Asn Asn Arg Glu Val Pro Asp Ser Cys
                820                 825                 830
Arg Arg Leu Val Phe Glu Thr Ala Arg Ile Met Gln Trp Phe Tyr Met
                835                 840                 845
Glu Gly Asp Gly Phe Thr Val Ser His Glu Met Glu Ile Lys Glu His
                850                 855                 860
Val Lys Asn Cys Leu Phe Gln Pro Val Ala
865                 870

<210> SEQ ID NO 37
<211> LENGTH: 859
<212> TYPE: PRT
<213> ORGANISM: Picea abies
<220> FEATURE:
<223> OTHER INFORMATION: levopimaradiene/abietadiene synthase
<300> PUBLICATION INFORMATION:
<308> DATABASE ACCESSION NUMBER: Genbank AAS47691
<309> DATABASE ENTRY DATE: 2009-04-08

<400> SEQUENCE: 37

Met Ala Leu Leu Ser Ser Ser Leu Ser Ser Gln Ile Pro Thr Gly Ala
 1               5                  10                  15
His His Leu Thr Leu Asn Ala Tyr Ala Asn Thr Gln Cys Ile Pro His
                20                  25                  30
Phe Phe Ser Thr Leu Asn Ala Gly Thr Ser Ala Gly Lys Arg Ser Ser
```

```
                35                  40                  45
Leu Tyr Leu Arg Trp Gly Lys Gly Ser Asn Lys Ile Ile Ala Cys Val
 50                  55                  60

Gly Glu Asp Ser Leu Ser Ala Pro Thr Leu Val Lys Arg Glu Phe Pro
 65                  70                  75                  80

Pro Gly Phe Trp Lys Asp His Val Ile Asp Ser Leu Thr Ser Ser His
                 85                  90                  95

Lys Val Ala Ala Ser Asp Glu Lys Arg Ile Glu Thr Leu Ile Ser Glu
                100                 105                 110

Ile Lys Asn Met Phe Arg Ser Met Gly Tyr Gly Asp Thr Asn Pro Ser
            115                 120                 125

Ala Tyr Asp Thr Ala Trp Val Ala Arg Ile Pro Ala Val Asp Gly Ser
130                 135                 140

Glu Gln Pro Glu Phe Pro Glu Thr Leu Glu Trp Ile Leu Gln Asn Gln
145                 150                 155                 160

Leu Lys Asp Gly Ser Trp Gly Glu Gly Phe Tyr Phe Leu Ala Tyr Asp
                165                 170                 175

Arg Ile Leu Ala Thr Leu Ala Cys Ile Ile Thr Leu Thr Leu Trp Arg
            180                 185                 190

Thr Gly Glu Ile Gln Val Gln Lys Gly Ile Glu Phe Phe Lys Thr Gln
        195                 200                 205

Ala Gly Lys Ile Glu Asp Glu Ala Asp Ser His Arg Pro Ser Gly Phe
210                 215                 220

Glu Ile Val Phe Pro Ala Met Leu Lys Glu Ala Lys Val Leu Gly Leu
225                 230                 235                 240

Asp Leu Pro Tyr Glu Leu Pro Phe Ile Lys Gln Ile Ile Glu Lys Arg
                245                 250                 255

Glu Ala Lys Leu Glu Arg Leu Pro Thr Asn Ile Leu Tyr Ala Leu Pro
            260                 265                 270

Thr Thr Leu Leu Tyr Ser Leu Glu Gly Leu Gln Glu Ile Val Asp Trp
        275                 280                 285

Gln Lys Ile Ile Lys Leu Gln Ser Lys Asp Gly Ser Phe Leu Ser Ser
290                 295                 300

Pro Ala Ser Thr Ala Ala Val Phe Met Arg Thr Gly Asn Lys Lys Cys
305                 310                 315                 320

Leu Glu Phe Leu Asn Phe Val Leu Lys Lys Phe Gly Asn His Val Pro
                325                 330                 335

Cys His Tyr Pro Leu Asp Leu Phe Glu Arg Leu Trp Ala Val Asp Thr
            340                 345                 350

Ile Glu Arg Leu Gly Ile Asp Arg His Phe Lys Glu Glu Ile Lys Asp
        355                 360                 365

Ala Leu Asp Tyr Val Tyr Ser His Trp Asp Glu Arg Gly Ile Gly Trp
370                 375                 380

Ala Arg Glu Asn Pro Val Pro Asp Ile Asp Asp Thr Ala Met Gly Leu
385                 390                 395                 400

Arg Ile Leu Arg Leu His Gly Tyr Asn Val Ser Ser Asp Val Leu Lys
                405                 410                 415

Thr Phe Arg Asp Glu Asn Gly Glu Phe Phe Cys Phe Leu Gly Gln Thr
            420                 425                 430

Gln Arg Gly Val Thr Asp Met Leu Asn Val Asn Arg Cys Ser His Val
        435                 440                 445

Ala Phe Pro Gly Glu Thr Ile Met Glu Glu Ala Lys Thr Cys Thr Glu
450                 455                 460
```

Arg Tyr Leu Arg Asn Ala Leu Glu Asp Val Gly Ala Phe Asp Lys Trp
465                 470                 475                 480

Ala Leu Lys Lys Asn Ile Arg Gly Glu Val Glu Tyr Ala Leu Lys Tyr
                485                 490                 495

Pro Trp His Arg Ser Met Pro Arg Leu Glu Ala Arg Ser Tyr Ile Glu
            500                 505                 510

His Tyr Gly Pro Asn Asp Val Trp Leu Gly Lys Thr Met Tyr Met Met
        515                 520                 525

Pro Tyr Ile Ser Asn Glu Lys Tyr Leu Glu Leu Ala Lys Leu Asp Phe
    530                 535                 540

Asn His Val Gln Ser Leu His Gln Lys Glu Leu Arg Asp Leu Arg Arg
545                 550                 555                 560

Trp Trp Thr Ser Ser Gly Phe Thr Glu Leu Lys Phe Thr Arg Glu Arg
                565                 570                 575

Val Thr Glu Ile Tyr Phe Ser Pro Ala Ser Phe Met Phe Glu Pro Glu
            580                 585                 590

Phe Ala Thr Cys Arg Ala Val Tyr Thr Lys Thr Ser Asn Phe Thr Val
        595                 600                 605

Ile Leu Asp Asp Leu Tyr Asp Ala His Gly Thr Leu Asp Asp Leu Lys
    610                 615                 620

Leu Phe Ser Asp Ser Val Lys Lys Trp Asp Leu Ser Leu Val Asp Arg
625                 630                 635                 640

Met Pro Gln Asp Met Lys Ile Cys Phe Met Gly Phe Tyr Asn Thr Phe
                645                 650                 655

Asn Glu Ile Ala Glu Glu Gly Arg Lys Arg Gln Gly Arg Asp Val Leu
            660                 665                 670

Gly Tyr Ile Arg Asn Val Trp Glu Ile Gln Leu Glu Ala Tyr Thr Lys
        675                 680                 685

Glu Ala Glu Trp Ser Ala Ala Arg Tyr Val Pro Ser Phe Asp Glu Tyr
    690                 695                 700

Ile Asp Asn Ala Ser Val Ser Ile Ala Leu Gly Thr Val Val Leu Ile
705                 710                 715                 720

Ser Ala Leu Phe Thr Gly Glu Ile Leu Thr Asp Asp Val Leu Ser Lys
                725                 730                 735

Ile Gly Arg Gly Ser Arg Phe Leu Gln Leu Met Gly Leu Thr Gly Arg
            740                 745                 750

Leu Val Asn Asp Thr Lys Thr Tyr Glu Ala Glu Arg Gly Gln Gly Glu
        755                 760                 765

Val Ala Ser Ala Val Gln Cys Tyr Met Lys Asp His Pro Glu Ile Ser
    770                 775                 780

Glu Glu Glu Ala Leu Lys His Val Tyr Thr Val Met Glu Asn Ala Leu
785                 790                 795                 800

Asp Glu Leu Asn Arg Glu Phe Val Asn Asn Arg Glu Val Pro Asp Ser
                805                 810                 815

Cys Arg Arg Leu Val Phe Glu Thr Ala Arg Ile Met Gln Leu Phe Tyr
            820                 825                 830

Met Asp Gly Asp Gly Leu Thr Leu Ser His Glu Thr Glu Ile Lys Glu
        835                 840                 845

His Val Lys Asn Cys Leu Phe Gln Pro Val Ala
    850                 855

<210> SEQ ID NO 38
<211> LENGTH: 859

<212> TYPE: PRT
<213> ORGANISM: Picea sitchensis
<220> FEATURE:
<223> OTHER INFORMATION: levopimaradiene/abietadiene synthase
<300> PUBLICATION INFORMATION:
<308> DATABASE ACCESSION NUMBER: Genbank ADZ45517
<309> DATABASE ENTRY DATE: 2011-03-16

<400> SEQUENCE: 38

```
Met Ala Leu Leu Ser Ser Leu Ser Ser His Ile Pro Thr Gly Ala
  1               5                  10                  15

His His Leu Thr Leu Asn Ala Tyr Ala Asn Thr Gln Cys Ile Pro His
             20                  25                  30

Phe Phe Ser Thr Leu Asn Ala Gly Thr Ser Ala Gly Lys Arg Ser Ser
         35                  40                  45

Leu Tyr Leu Arg Trp Gly Lys Gly Ser Asn Lys Ile Ile Ala Cys Val
     50                  55                  60

Gly Glu Asp Ser Val Ser Ala Pro Thr Leu Leu Lys Arg Glu Phe Pro
 65                  70                  75                  80

Pro Gly Phe Trp Lys Asp His Val Ile Asp Ser Leu Thr Ser Ser His
                 85                  90                  95

Lys Val Ala Ala Ser Asp Glu Lys Arg Ile Glu Thr Leu Ile Ser Glu
            100                 105                 110

Ile Lys Asn Met Phe Arg Ser Met Gly Tyr Gly Glu Thr Asn Pro Ser
        115                 120                 125

Ala Tyr Asp Thr Ala Trp Val Ala Arg Ile Pro Ala Val Asp Gly Ser
    130                 135                 140

Glu Gln Pro Glu Phe Pro Glu Thr Leu Glu Trp Ile Leu Gln Asn Gln
145                 150                 155                 160

Leu Lys Asp Gly Ser Trp Gly Glu Gly Phe Tyr Phe Leu Ala Tyr Asp
                165                 170                 175

Arg Ile Leu Ala Thr Leu Ala Cys Ile Ile Thr Leu Thr Leu Trp Arg
            180                 185                 190

Thr Gly Glu Ile Gln Val Gln Lys Gly Ile Glu Phe Phe Lys Thr Gln
        195                 200                 205

Ala Val Lys Ile Glu Asp Glu Ala Asp Ser His Arg Pro Ser Gly Phe
    210                 215                 220

Glu Ile Val Phe Pro Ala Met Leu Lys Glu Ala Lys Val Leu Gly Leu
225                 230                 235                 240

Asp Leu Pro Tyr Glu Leu Pro Phe Ile Lys Lys Ile Glu Lys Arg
                245                 250                 255

Glu Ala Lys Leu Glu Arg Leu Pro Thr Asn Ile Leu Tyr Ala Leu Pro
            260                 265                 270

Thr Thr Leu Leu Tyr Ser Leu Glu Gly Leu Gln Glu Ile Val Asp Trp
        275                 280                 285

Gln Lys Ile Ile Lys Leu Gln Ser Lys Asp Gly Ser Phe Leu Thr Ser
    290                 295                 300

Pro Ala Ser Thr Ala Ala Val Phe Met Arg Thr Gly Asn Lys Lys Cys
305                 310                 315                 320

Leu Glu Phe Leu Asn Phe Val Leu Lys Lys Phe Gly Asn His Val Pro
                325                 330                 335

Cys His Tyr Pro Leu Asp Leu Phe Glu Arg Leu Trp Ala Val Asp Thr
            340                 345                 350

Val Glu Arg Leu Gly Ile Asp Arg His Phe Lys Glu Glu Ile Lys Asp
        355                 360                 365
```

```
Ala Leu Asp Tyr Val Tyr Ser His Trp Asp Glu Arg Gly Ile Gly Trp
    370             375                 380
Ala Arg Glu Asn Leu Val Pro Asp Ile Asp Asp Thr Ala Met Gly Leu
385             390                 395                 400
Arg Ile Leu Arg Leu His Gly Tyr Asn Val Ser Ser Asp Val Leu Lys
                405                 410                 415
Thr Phe Arg Asp Glu Asn Gly Glu Phe Phe Cys Phe Leu Gly Gln Thr
            420                 425                 430
Gln Arg Gly Val Thr Asp Met Leu Asn Val Asn Arg Cys Ser His Val
        435                 440                 445
Ala Phe Pro Gly Glu Thr Ile Met Glu Glu Ala Lys Thr Cys Thr Glu
    450                 455                 460
Arg Tyr Leu Arg Asn Ala Leu Glu Asp Val Gly Ala Phe Asp Lys Trp
465                 470                 475                 480
Ala Leu Lys Lys Asn Ile Arg Gly Glu Val Glu Tyr Ala Leu Lys Tyr
                485                 490                 495
Pro Trp His Arg Ser Met Pro Arg Leu Glu Ala Arg Ser Tyr Ile Glu
            500                 505                 510
His Tyr Gly Pro Asn Asp Val Trp Leu Gly Lys Thr Met Tyr Met Met
        515                 520                 525
Pro Tyr Ile Ser Asn Glu Lys Tyr Leu Glu Leu Ala Lys Leu Asp Phe
    530                 535                 540
Asn His Val Gln Ser Leu His Gln Lys Glu Leu Arg Asp Leu Arg Arg
545                 550                 555                 560
Trp Trp Thr Ser Ser Gly Phe Thr Glu Leu Lys Phe Thr Arg Glu Arg
                565                 570                 575
Val Thr Glu Ile Tyr Phe Ser Pro Ala Ser Phe Met Phe Glu Pro Glu
            580                 585                 590
Phe Ala Thr Cys Arg Ala Val Tyr Thr Lys Thr Ser Asn Phe Thr Val
        595                 600                 605
Ile Leu Asp Asp Leu Tyr Asp Ala His Gly Thr Leu Asp Asp Leu Lys
    610                 615                 620
Leu Phe Ser Asp Ser Val Lys Lys Trp Asp Leu Ser Leu Val Asp Arg
625                 630                 635                 640
Met Pro Glu Asp Met Lys Ile Cys Phe Met Gly Phe Tyr Asn Thr Phe
                645                 650                 655
Asn Glu Ile Ala Glu Glu Gly Arg Lys Arg Gln Gly Arg Asp Val Leu
            660                 665                 670
Gly Tyr Ile Arg Asn Val Trp Glu Ile Gln Leu Glu Ala Tyr Thr Lys
        675                 680                 685
Glu Ala Glu Trp Ser Ala Ala Arg Tyr Val Pro Ser Phe Asp Glu Tyr
    690                 695                 700
Ile Glu Asn Ala Ser Val Ser Ile Ala Leu Gly Thr Val Val Leu Ile
705                 710                 715                 720
Ser Ala Leu Phe Thr Gly Glu Ile Leu Thr Asp Asp Val Leu Ser Lys
                725                 730                 735
Ile Gly Arg Gly Ser Arg Phe Leu Gln Leu Met Gly Leu Thr Gly Arg
            740                 745                 750
Leu Val Asn Asp Thr Lys Thr Tyr Glu Ala Glu Arg Gly Gln Gly Glu
        755                 760                 765
Val Ala Ser Ala Val Gln Cys Tyr Met Lys Asp His Pro Glu Ile Ser
    770                 775                 780
Glu Glu Glu Ala Leu Lys His Val Tyr Thr Val Met Glu Asn Ala Leu
```

```
                785                 790                 795                 800
Asp Glu Leu Asn Arg Glu Phe Val Asn Asn Arg Glu Val Pro Asp Ser
                    805                 810                 815

Cys Arg Arg Leu Val Phe Glu Thr Ala Arg Ile Met Gln Leu Phe Tyr
                820                 825                 830

Met Asp Gly Asp Gly Leu Thr Leu Ser His Glu Thr Glu Ile Lys Glu
                835                 840                 845

His Val Lys Asn Cys Leu Phe His Pro Val Ala
                850                 855

<210> SEQ ID NO 39
<211> LENGTH: 850
<212> TYPE: PRT
<213> ORGANISM: Pinus taeda
<220> FEATURE:
<223> OTHER INFORMATION: diterpene synthase
<300> PUBLICATION INFORMATION:
<308> DATABASE ACCESSION NUMBER: Genbank AAX07435
<309> DATABASE ENTRY DATE: 2005-06-02

<400> SEQUENCE: 39

Met Ala Leu Pro Ser Ser Leu Ser Ser Gln Ile His Thr Gly Ala
 1               5                  10                  15

Thr Thr Gln Cys Ile Pro His Phe His Gly Ser Leu Asn Ala Gly Thr
                20                  25                  30

Ser Ala Gly Lys Arg Arg Ser Leu Tyr Leu Arg Trp Gly Lys Gly Pro
            35                  40                  45

Ser Lys Ile Val Ala Cys Ala Gly Gln Asp Pro Phe Ser Val Pro Thr
        50                  55                  60

Leu Val Lys Arg Glu Phe Pro Pro Gly Phe Trp Lys Asp His Val Ile
 65                 70                  75                  80

Glu Ser Leu Met Pro Ser Tyr Lys Val Ala Pro Ser Asp Glu Lys Arg
                85                  90                  95

Ile Glu Thr Leu Ile Thr Glu Ile Lys Asn Met Phe Arg Ser Met Gly
            100                 105                 110

Tyr Gly Glu Thr Asn Pro Ser Ala Tyr Asp Thr Ala Trp Val Ala Arg
        115                 120                 125

Ile Pro Ala Val Asp Gly Ser Glu Lys Pro Gln Phe Pro Glu Thr Leu
    130                 135                 140

Glu Trp Ile Leu Gln Asn Gln Leu Lys Asp Gly Ser Trp Gly Glu Glu
145                 150                 155                 160

Phe Tyr Phe Leu Ala Tyr Asp Arg Ile Leu Ala Thr Leu Ala Cys Ile
                165                 170                 175

Ile Thr Leu Thr Ile Trp Gln Thr Gly Asp Thr Gln Val Gln Lys Gly
            180                 185                 190

Ile Glu Phe Phe Lys Thr Gln Ala Gly Lys Ile Glu Glu Glu Ala Asp
        195                 200                 205

Ser His Arg Pro Ser Gly Phe Glu Ile Val Phe Pro Ala Met Leu Lys
    210                 215                 220

Glu Ala Lys Ala Leu Gly Leu Ala Leu Pro Tyr Glu Leu Pro Phe Ile
225                 230                 235                 240

Gln Gln Ile Ile Glu Lys Arg Glu Ala Lys Leu Gln Arg Leu Pro Pro
                245                 250                 255

Asp Leu Leu Tyr Ala Leu Pro Thr Thr Leu Leu Tyr Ser Leu Glu Gly
            260                 265                 270

Leu Gln Glu Ile Val Asp Trp Glu Lys Ile Met Lys Leu Gln Ser Lys
```

```
                    275                 280                 285
Asp Gly Ser Phe Leu Ser Ser Pro Ala Ser Thr Ala Ala Val Phe Met
290                 295                 300

Arg Thr Gly Asn Lys Lys Cys Leu Glu Phe Leu Asn Phe Val Leu Lys
305                 310                 315                 320

Lys Phe Gly Asn His Val Pro Cys His Tyr Pro Leu Asp Leu Phe Glu
                    325                 330                 335

Arg Leu Trp Ala Val Asp Thr Val Arg Leu Gly Ile Asp His His
                340                 345                 350

Phe Lys Glu Glu Ile Lys Asp Ala Leu Asp Tyr Val Tyr Ser His Trp
                355                 360                 365

Asp Glu Arg Gly Ile Gly Trp Ala Arg Glu Asn Pro Val Pro Asp Ile
370                 375                 380

Asp Asp Thr Ala Met Gly Leu Arg Ile Leu Arg Leu His Gly Tyr Asn
385                 390                 395                 400

Val Ser Ser Asp Val Leu Lys Thr Phe Arg Asp Glu Asn Gly Glu Phe
                405                 410                 415

Phe Cys Phe Leu Gly Gln Thr Gln Arg Gly Val Thr Asp Met Leu Asn
                420                 425                 430

Val Asn Arg Cys Ser His Val Ala Phe Pro Gly Glu Thr Ile Met Glu
                435                 440                 445

Glu Ala Lys Leu Cys Thr Glu Arg Tyr Leu Arg Asn Ala Leu Glu Asp
450                 455                 460

Gly Gly Ala Ser Asp Lys Trp Ala Leu Lys Lys Asn Ile Arg Gly Glu
465                 470                 475                 480

Val Glu Tyr Ala Leu Lys Tyr Pro Trp His Arg Ser Met Pro Arg Leu
                485                 490                 495

Glu Ala Arg Ser Tyr Ile Glu Asn Tyr Gly Pro Asn Asp Val Trp Leu
                500                 505                 510

Gly Lys Thr Met Tyr Met Met Pro Asn Ile Ser Asn Glu Lys Tyr Leu
                515                 520                 525

Glu Leu Ala Lys Leu Asp Phe Asn Arg Val Gln Phe Phe His Arg Gln
530                 535                 540

Glu Leu Gln Asp Ile Arg Arg Trp Trp Asn Ser Ser Gly Phe Ser Gln
545                 550                 555                 560

Leu Gly Phe Thr Arg Glu Arg Val Ala Glu Ile Tyr Phe Ser Pro Ala
                565                 570                 575

Ser Phe Leu Phe Glu Pro Glu Phe Ala Thr Cys Arg Ala Val Tyr Thr
                580                 585                 590

Lys Thr Ser Asn Phe Thr Val Ile Leu Asp Asp Leu Tyr Asp Ala His
                595                 600                 605

Gly Thr Leu Asp Asn Leu Lys Leu Phe Ser Glu Ser Val Lys Arg Trp
                610                 615                 620

Asp Leu Ser Leu Val Asp Gln Met Pro Gln Asp Met Lys Ile Cys Phe
625                 630                 635                 640

Lys Gly Phe Tyr Asn Thr Phe Asn Glu Ile Ala Glu Glu Gly Arg Lys
                645                 650                 655

Arg Gln Gly Arg Asp Val Leu Ser Tyr Ile Gln Lys Val Trp Glu Val
                660                 665                 670

Gln Leu Glu Ala Tyr Thr Lys Glu Ala Glu Trp Ser Ala Val Arg Tyr
                675                 680                 685

Val Pro Ser Tyr Asp Glu Tyr Ile Gly Asn Ala Ser Val Ser Ile Ala
690                 695                 700
```

```
Leu Gly Thr Val Val Leu Ile Ser Ala Leu Phe Thr Gly Glu Ile Leu
705                 710                 715                 720

Thr Asp Asp Ile Leu Ser Lys Ile Gly Arg Asp Ser Arg Phe Leu Tyr
                725                 730                 735

Leu Met Gly Leu Thr Gly Arg Leu Val Asn Asp Thr Lys Thr Tyr Gln
        740                 745                 750

Ala Glu Arg Gly Gln Gly Glu Val Ala Ser Val Gln Cys Tyr Met
            755                 760                 765

Lys Asp His Pro Glu Ile Ser Glu Glu Ala Leu Lys His Val Tyr
        770                 775                 780

Thr Ile Met Asp Asn Ala Leu Asp Glu Leu Asn Arg Glu Phe Val Asn
785                 790                 795                 800

Asn Arg Asp Val Pro Asp Thr Cys Arg Arg Leu Val Phe Glu Thr Ala
                805                 810                 815

Arg Ile Met Gln Leu Phe Tyr Met Asp Gly Asp Gly Leu Thr Leu Ser
                820                 825                 830

His Asn Met Glu Ile Lys Glu His Val Lys Asn Cys Leu Phe Gln Pro
        835                 840                 845

Val Ala
    850
```

<210> SEQ ID NO 40
<211> LENGTH: 853
<212> TYPE: PRT
<213> ORGANISM: Abies grandis
<220> FEATURE:
<223> OTHER INFORMATION: abietadiene synthase
<300> PUBLICATION INFORMATION:
<308> DATABASE ACCESSION NUMBER: Genbank AAK83563
<309> DATABASE ENTRY DATE: 2001-08-03

<400> SEQUENCE: 40

```
Ala His His Leu Thr Ala Asn Thr Gln Ser Ile Pro His Phe Ser Thr
  1               5                  10                  15

Thr Leu Asn Ala Gly Ser Ser Ala Ser Lys Arg Arg Ser Leu Tyr Leu
            20                  25                  30

Arg Trp Gly Lys Gly Ser Asn Lys Ile Ile Ala Cys Val Gly Glu Gly
        35                  40                  45

Gly Ala Thr Ser Val Pro Tyr Gln Ser Ala Glu Lys Asn Asp Ser Leu
    50                  55                  60

Ser Ser Ser Thr Leu Val Lys Arg Glu Phe Pro Pro Gly Phe Trp Lys
65                  70                  75                  80

Asp Asp Leu Ile Asp Ser Leu Thr Ser Ser His Lys Val Ala Ala Ser
                85                  90                  95

Asp Glu Lys Arg Ile Glu Thr Leu Ile Ser Glu Ile Lys Asn Met Phe
            100                 105                 110

Arg Cys Met Gly Tyr Gly Glu Thr Asn Pro Ser Ala Tyr Asp Thr Ala
        115                 120                 125

Trp Val Ala Arg Ile Pro Ala Val Asp Gly Ser Asp Asn Pro His Phe
    130                 135                 140

Pro Glu Thr Val Glu Trp Ile Leu Gln Asn Gln Leu Lys Asp Gly Ser
145                 150                 155                 160

Trp Gly Glu Gly Phe Tyr Phe Leu Ala Tyr Asp Arg Ile Leu Ala Thr
                165                 170                 175

Leu Ala Cys Ile Ile Thr Leu Thr Leu Trp Arg Thr Gly Glu Thr Gln
            180                 185                 190
```

```
            -continued

Val Gln Lys Gly Ile Glu Ser Phe Arg Thr Gln Ala Gly Lys Met Glu
            195                 200                 205

Asp Glu Ala Asp Ser His Arg Pro Ser Gly Phe Glu Ile Val Phe Pro
    210                 215                 220

Ala Met Leu Lys Glu Ala Lys Ile Leu Gly Leu Asp Leu Pro Tyr Asp
225                 230                 235                 240

Leu Pro Phe Leu Lys Gln Ile Ile Glu Lys Arg Glu Ala Lys Leu Lys
                245                 250                 255

Arg Ile Pro Thr Asp Val Leu Tyr Ala Leu Pro Thr Thr Leu Leu Tyr
            260                 265                 270

Ser Leu Glu Gly Leu Gln Glu Ile Val Glu Trp Glu Lys Ile Met Lys
        275                 280                 285

Leu Gln Ser Lys Asp Gly Ser Phe Leu Ser Ser Pro Ala Ser Thr Ala
    290                 295                 300

Ala Val Phe Met Arg Thr Gly Asn Lys Lys Cys Leu Asp Phe Leu Asn
305                 310                 315                 320

Phe Val Leu Lys Lys Phe Gly Asn His Val Pro Cys His Tyr Pro Leu
                325                 330                 335

Asp Leu Phe Glu Arg Leu Trp Ala Val Asp Thr Val Glu Arg Leu Gly
            340                 345                 350

Ile Asp Arg His Phe Lys Glu Glu Ile Lys Glu Ala Leu Asp Tyr Val
        355                 360                 365

Tyr Ser His Trp Asp Glu Arg Gly Ile Gly Trp Ala Arg Glu Asn Pro
    370                 375                 380

Val Pro Asp Ile Asp Asp Thr Ala Met Gly Leu Arg Ile Leu Arg Leu
385                 390                 395                 400

His Gly Tyr Asn Val Ser Ser Asp Val Leu Lys Thr Phe Arg Asp Glu
                405                 410                 415

Asn Gly Glu Phe Phe Cys Phe Leu Gly Gln Thr Gln Arg Gly Val Thr
            420                 425                 430

Asp Met Leu Asn Val Asn Arg Cys Ser His Val Ser Phe Pro Gly Glu
        435                 440                 445

Thr Ile Met Glu Glu Ala Lys Leu Cys Thr Arg Tyr Leu Arg Asn
    450                 455                 460

Ala Leu Glu Asn Val Asp Ala Phe Asp Lys Trp Ala Phe Lys Lys Asn
465                 470                 475                 480

Ile Arg Gly Glu Val Glu Tyr Ala Leu Lys Tyr Pro Trp His Lys Ser
                485                 490                 495

Met Pro Arg Leu Glu Ala Arg Ser Tyr Ile Glu Asn Tyr Gly Pro Asp
            500                 505                 510

Asp Val Trp Leu Gly Lys Thr Val Tyr Met Met Pro Tyr Ile Ser Asn
        515                 520                 525

Glu Lys Tyr Leu Glu Leu Ala Lys Leu Asp Phe Asn Lys Leu Gln Ser
    530                 535                 540

Ile His Gln Thr Glu Leu Gln Asp Leu Arg Arg Trp Trp Lys Ser Ser
545                 550                 555                 560

Gly Phe Thr Glu Leu Asn Phe Thr Arg Glu Arg Val Thr Glu Ile Tyr
                565                 570                 575

Phe Ser Pro Ala Ser Phe Ile Phe Glu Pro Glu Phe Ser Lys Cys Arg
            580                 585                 590

Glu Val Tyr Thr Lys Thr Ser Asn Phe Thr Val Ile Leu Asp Asp Leu
        595                 600                 605
```

```
Tyr Asp Ala His Gly Ser Leu Asp Asp Leu Lys Leu Phe Thr Glu Ser
    610             615                 620

Val Lys Arg Trp Asp Leu Ser Leu Val Asp Gln Met Pro Lys Gln Met
625             630                 635                 640

Lys Ile Cys Phe Val Gly Phe Tyr Asn Thr Phe Asn Asp Ile Ala Lys
                645                 650                 655

Glu Gly Arg Glu Arg Gln Gly Arg Asp Val Leu Gly Tyr Ile Gln Asn
            660                 665                 670

Val Trp Lys Val Gln Leu Glu Ala Tyr Thr Lys Glu Ala Glu Trp Ser
        675                 680                 685

Glu Ala Lys Tyr Val Pro Ser Phe Asn Glu Tyr Ile Glu Asn Ala Ser
    690                 695                 700

Val Ser Ile Ala Leu Gly Thr Val Val Leu Ile Ser Ala Leu Phe Thr
705             710                 715                 720

Gly Glu Val Leu Thr Asp Glu Val Leu Ser Lys Ile Asp Arg Glu Ser
                725                 730                 735

Arg Phe Leu Gln Leu Met Gly Leu Thr Gly Arg Leu Val Asn Asp Thr
            740                 745                 750

Lys Thr Tyr Gln Ala Glu Arg Gly Gln Gly Glu Val Ala Ser Ala Ile
        755                 760                 765

Gln Cys Tyr Met Lys Asp His Pro Lys Ile Ser Glu Glu Glu Ala Leu
    770                 775                 780

Gln His Val Tyr Ser Val Met Glu Asn Ala Leu Glu Glu Leu Asn Arg
785             790                 795                 800

Glu Phe Val Asn Asn Lys Ile Pro Asp Ile Tyr Lys Arg Leu Val Phe
                805                 810                 815

Glu Thr Ala Arg Ile Met Gln Leu Phe Tyr Met Gln Gly Asp Gly Leu
            820                 825                 830

Thr Leu Ser His Asp Met Glu Ile Lys Glu His Val Lys Asn Cys Leu
        835                 840                 845

Phe Gln Pro Val Ala
    850

<210> SEQ ID NO 41
<211> LENGTH: 873
<212> TYPE: PRT
<213> ORGANISM: Ginkgo biloba
<220> FEATURE:
<223> OTHER INFORMATION: levopimaradiene synthase
<300> PUBLICATION INFORMATION:
<308> DATABASE ACCESSION NUMBER: Genbank AAL09965
<309> DATABASE ENTRY DATE: 2001-10-03

<400> SEQUENCE: 41

Met Ala Gly Val Leu Phe Ala Asn Leu Pro Cys Ser Leu Gln Leu Ser
1               5                   10                  15

Pro Lys Val Pro Phe Arg Gln Ser Thr Asn Ile Leu Ile Pro Phe His
            20                  25                  30

Lys Arg Ser Ser Phe Gly Phe Asn Ala Gln His Cys Val Arg Ser His
        35                  40                  45

Leu Arg Leu Arg Trp Asn Cys Val Gly Ile His Ala Ser Ala Ala Glu
    50                  55                  60

Thr Arg Pro Asp Gln Leu Pro Gln Glu Glu Arg Phe Val Ser Arg Leu
65                  70                  75                  80

Asn Ala Asp Tyr His Pro Ala Val Trp Lys Asp Asp Phe Ile Asp Ser
                85                  90                  95
```

```
Leu Thr Ser Pro Asn Ser His Ala Thr Ser Lys Ser Ser Val Asp Glu
            100                 105                 110

Thr Ile Asn Lys Arg Ile Gln Thr Leu Val Lys Glu Ile Gln Cys Met
            115                 120                 125

Phe Gln Ser Met Gly Asp Gly Glu Thr Asn Pro Ser Ala Tyr Asp Thr
            130                 135                 140

Ala Trp Val Ala Arg Ile Pro Ser Ile Asp Gly Ser Gly Ala Pro Gln
145                 150                 155                 160

Phe Pro Gln Thr Leu Gln Trp Ile Leu Asn Asn Gln Leu Pro Asp Gly
                165                 170                 175

Ser Trp Gly Glu Glu Cys Ile Phe Leu Ala Tyr Asp Arg Val Leu Asn
                180                 185                 190

Thr Leu Ala Cys Leu Leu Thr Leu Lys Ile Trp Asn Lys Gly Asp Ile
                195                 200                 205

Gln Val Gln Lys Gly Val Glu Phe Val Arg Lys His Met Glu Glu Met
            210                 215                 220

Lys Asp Glu Ala Asp Asn His Arg Pro Ser Gly Phe Glu Val Val Phe
225                 230                 235                 240

Pro Ala Met Leu Asp Glu Ala Lys Ser Leu Gly Leu Asp Leu Pro Tyr
                245                 250                 255

His Leu Pro Phe Ile Ser Gln Ile His Gln Lys Arg Gln Lys Lys Leu
                260                 265                 270

Gln Lys Ile Pro Leu Asn Val Leu His Asn His Gln Thr Ala Leu Leu
                275                 280                 285

Tyr Ser Leu Glu Gly Leu Gln Asp Val Val Asp Trp Gln Glu Ile Thr
            290                 295                 300

Asn Leu Gln Ser Arg Asp Gly Ser Phe Leu Ser Ser Pro Ala Ser Thr
305                 310                 315                 320

Ala Cys Val Phe Met His Thr Gln Asn Lys Arg Cys Leu His Phe Leu
                325                 330                 335

Asn Phe Val Leu Ser Lys Phe Gly Asp Tyr Val Pro Cys His Tyr Pro
                340                 345                 350

Leu Asp Leu Phe Glu Arg Leu Trp Ala Val Asp Thr Val Glu Arg Leu
                355                 360                 365

Gly Ile Asp Arg Tyr Phe Lys Lys Glu Ile Lys Glu Ser Leu Asp Tyr
            370                 375                 380

Val Tyr Arg Tyr Trp Asp Ala Glu Arg Gly Val Gly Trp Ala Arg Cys
385                 390                 395                 400

Asn Pro Ile Pro Asp Val Asp Asp Thr Ala Met Gly Leu Arg Ile Leu
                405                 410                 415

Arg Leu His Gly Tyr Asn Val Ser Ser Asp Val Leu Glu Asn Phe Arg
                420                 425                 430

Asp Glu Lys Gly Asp Phe Phe Cys Phe Ala Gly Gln Thr Gln Ile Gly
            435                 440                 445

Val Thr Asp Asn Leu Asn Leu Tyr Arg Cys Ser Gln Val Cys Phe Pro
450                 455                 460

Gly Glu Lys Ile Met Glu Glu Ala Lys Thr Phe Thr Thr Asn His Leu
465                 470                 475                 480

Gln Asn Ala Leu Ala Lys Asn Asn Ala Phe Asp Lys Trp Ala Val Lys
                485                 490                 495

Lys Asp Leu Pro Gly Glu Val Glu Tyr Ala Ile Lys Tyr Pro Trp His
            500                 505                 510

Arg Ser Met Pro Arg Leu Glu Ala Arg Ser Tyr Ile Glu Gln Phe Gly
```

```
            515                 520                 525
Ser Asn Asp Val Trp Leu Gly Lys Thr Val Tyr Lys Met Leu Tyr Val
530                 535                 540

Ser Asn Glu Lys Tyr Leu Glu Leu Ala Lys Leu Asp Phe Asn Met Val
545                 550                 555                 560

Gln Ala Leu His Gln Lys Glu Thr Gln His Ile Val Ser Trp Trp Arg
                565                 570                 575

Glu Ser Gly Phe Asn Asp Leu Thr Phe Thr Arg Gln Arg Pro Val Glu
                580                 585                 590

Met Tyr Phe Ser Val Ala Val Ser Met Phe Glu Pro Glu Phe Ala Ala
                595                 600                 605

Cys Arg Ile Ala Tyr Ala Lys Thr Ser Cys Leu Ala Val Ile Leu Asp
610                 615                 620

Asp Leu Tyr Asp Thr His Gly Ser Leu Asp Asp Leu Lys Leu Phe Ser
625                 630                 635                 640

Glu Ala Val Arg Arg Trp Asp Ile Ser Val Leu Asp Ser Val Arg Asp
                645                 650                 655

Asn Gln Leu Lys Val Cys Phe Leu Gly Leu Tyr Asn Thr Val Asn Gly
                660                 665                 670

Phe Gly Lys Asp Gly Leu Lys Glu Gln Gly Arg Asp Val Leu Gly Tyr
                675                 680                 685

Leu Arg Lys Val Trp Glu Gly Leu Leu Ala Ser Tyr Thr Lys Glu Ala
690                 695                 700

Glu Trp Ser Ala Ala Lys Tyr Val Pro Thr Phe Asn Glu Tyr Val Glu
705                 710                 715                 720

Asn Ala Lys Val Ser Ile Ala Leu Ala Thr Val Leu Asn Ser Ile
                725                 730                 735

Phe Phe Thr Gly Glu Leu Leu Pro Asp Tyr Ile Leu Gln Gln Val Asp
                740                 745                 750

Leu Arg Ser Lys Phe Leu His Leu Val Ser Leu Thr Gly Arg Leu Ile
                755                 760                 765

Asn Asp Thr Lys Thr Tyr Gln Ala Glu Arg Asn Arg Gly Glu Leu Val
                770                 775                 780

Ser Ser Val Gln Cys Tyr Met Arg Glu Asn Pro Glu Cys Thr Glu Glu
785                 790                 795                 800

Glu Ala Leu Ser His Val Tyr Gly Ile Ile Asp Asn Ala Leu Lys Glu
                805                 810                 815

Leu Asn Trp Glu Leu Ala Asn Pro Ala Ser Asn Ala Pro Leu Cys Val
                820                 825                 830

Arg Arg Leu Leu Phe Asn Thr Ala Arg Val Met Gln Leu Phe Tyr Met
                835                 840                 845

Tyr Arg Asp Gly Phe Gly Ile Ser Asp Lys Glu Met Lys Asp His Val
                850                 855                 860

Ser Arg Thr Leu Phe Asp Pro Val Ala
865                 870

<210> SEQ ID NO 42
<211> LENGTH: 881
<212> TYPE: PRT
<213> ORGANISM: Physcomitrella patens
<220> FEATURE:
<223> OTHER INFORMATION: ent-kaurene synthase
<300> PUBLICATION INFORMATION:
<308> DATABASE ACCESSION NUMBER: Genbank BAF61135
<309> DATABASE ENTRY DATE: 2007-05-09
```

```
<400> SEQUENCE: 42

Met Ala Ser Ser Thr Leu Ile Gln Asn Arg Ser Cys Gly Val Thr Ser
 1               5                  10                  15

Ser Met Ser Ser Phe Gln Ile Phe Arg Gly Gln Pro Leu Arg Phe Pro
            20                  25                  30

Gly Thr Arg Thr Pro Ala Ala Val Gln Cys Leu Lys Lys Arg Arg Cys
        35                  40                  45

Leu Arg Pro Thr Glu Ser Val Leu Glu Ser Ser Pro Gly Ser Gly Ser
    50                  55                  60

Tyr Arg Ile Val Thr Gly Pro Ser Gly Ile Asn Pro Ser Ser Asn Gly
65                  70                  75                  80

His Leu Gln Glu Gly Ser Leu Thr His Arg Leu Pro Ile Pro Met Glu
                85                  90                  95

Lys Ser Ile Asp Asn Phe Gln Ser Thr Leu Tyr Val Ser Asp Ile Trp
            100                 105                 110

Ser Glu Thr Leu Gln Arg Thr Glu Cys Leu Leu Gln Val Thr Glu Asn
        115                 120                 125

Val Gln Met Asn Glu Trp Ile Glu Glu Ile Arg Met Tyr Phe Arg Asn
    130                 135                 140

Met Thr Leu Gly Glu Ile Ser Met Ser Pro Tyr Asp Thr Ala Trp Val
145                 150                 155                 160

Ala Arg Val Pro Ala Leu Asp Gly Ser His Gly Pro Gln Phe His Arg
                165                 170                 175

Ser Leu Gln Trp Ile Ile Asp Asn Gln Leu Pro Asp Gly Asp Trp Gly
            180                 185                 190

Glu Pro Ser Leu Phe Leu Gly Tyr Asp Arg Val Cys Asn Thr Leu Ala
        195                 200                 205

Cys Val Ile Ala Leu Lys Thr Trp Gly Val Gly Ala Gln Asn Val Glu
    210                 215                 220

Arg Gly Ile Gln Phe Leu Gln Ser Asn Ile Tyr Lys Met Glu Glu Asp
225                 230                 235                 240

Asp Ala Asn His Met Pro Ile Gly Phe Glu Ile Val Phe Pro Ala Met
                245                 250                 255

Met Glu Asp Ala Lys Ala Leu Gly Leu Asp Leu Pro Tyr Asp Ala Thr
            260                 265                 270

Ile Leu Gln Gln Ile Ser Ala Glu Arg Glu Lys Lys Met Lys Lys Ile
        275                 280                 285

Pro Met Ala Met Val Tyr Lys Tyr Pro Thr Thr Leu Leu His Ser Leu
    290                 295                 300

Glu Gly Leu His Arg Glu Val Asp Trp Asn Lys Leu Leu Gln Leu Gln
305                 310                 315                 320

Ser Glu Asn Gly Ser Phe Leu Tyr Ser Pro Ala Ser Thr Ala Cys Ala
                325                 330                 335

Leu Met Tyr Thr Lys Asp Val Lys Cys Phe Asp Tyr Leu Asn Gln Leu
            340                 345                 350

Leu Ile Lys Phe Asp His Ala Cys Pro Asn Val Tyr Pro Val Asp Leu
        355                 360                 365

Phe Glu Arg Leu Trp Met Val Asp Arg Leu Gln Arg Leu Gly Ile Ser
    370                 375                 380

Arg Tyr Phe Glu Arg Glu Ile Arg Asp Cys Leu Gln Tyr Val Tyr Arg
385                 390                 395                 400

Tyr Trp Lys Asp Cys Gly Ile Gly Trp Ala Ser Asn Ser Ser Val Gln
                405                 410                 415
```

```
Asp Val Asp Asp Thr Ala Met Ala Phe Arg Leu Leu Arg Thr His Gly
            420                 425                 430

Phe Asp Val Lys Glu Asp Cys Phe Arg Gln Phe Phe Lys Asp Gly Glu
            435                 440                 445

Phe Phe Cys Phe Ala Gly Gln Ser Ser Gln Ala Val Thr Gly Met Phe
450                 455                 460

Asn Leu Ser Arg Ala Ser Gln Thr Leu Phe Pro Gly Glu Ser Leu Leu
465                 470                 475                 480

Lys Lys Ala Arg Thr Phe Ser Arg Asn Phe Leu Arg Thr Lys His Glu
            485                 490                 495

Asn Asn Glu Cys Phe Asp Lys Trp Ile Ile Thr Lys Asp Leu Ala Gly
            500                 505                 510

Glu Val Glu Tyr Asn Leu Thr Phe Pro Trp Tyr Ala Ser Leu Pro Arg
            515                 520                 525

Leu Glu His Arg Thr Tyr Leu Asp Gln Tyr Gly Ile Asp Asp Ile Trp
            530                 535                 540

Ile Gly Lys Ser Leu Tyr Lys Met Pro Ala Val Thr Asn Glu Val Phe
545                 550                 555                 560

Leu Lys Leu Ala Lys Ala Asp Phe Asn Met Cys Gln Ala Leu His Lys
            565                 570                 575

Lys Glu Leu Glu Gln Val Ile Lys Trp Asn Ala Ser Cys Gln Phe Arg
            580                 585                 590

Asp Leu Glu Phe Ala Arg Gln Lys Ser Val Glu Cys Tyr Phe Ala Gly
            595                 600                 605

Ala Ala Thr Met Phe Glu Pro Glu Met Val Gln Ala Arg Leu Val Trp
            610                 615                 620

Ala Arg Cys Cys Val Leu Thr Thr Val Leu Asp Asp Tyr Phe Asp His
625                 630                 635                 640

Gly Thr Pro Val Glu Glu Leu Arg Val Phe Val Gln Ala Val Arg Thr
            645                 650                 655

Trp Asn Pro Glu Leu Ile Asn Gly Leu Pro Glu Gln Ala Lys Ile Leu
            660                 665                 670

Phe Met Gly Leu Tyr Lys Thr Val Asn Thr Ile Ala Glu Glu Ala Phe
            675                 680                 685

Met Ala Gln Lys Arg Asp Val His His Leu Lys His Tyr Trp Asp
            690                 695                 700

Lys Leu Ile Thr Ser Ala Leu Lys Glu Ala Glu Trp Ala Glu Ser Gly
705                 710                 715                 720

Tyr Val Pro Thr Phe Asp Glu Tyr Met Glu Val Ala Glu Ile Ser Val
            725                 730                 735

Ala Leu Glu Pro Ile Val Cys Ser Thr Leu Phe Phe Ala Gly His Arg
            740                 745                 750

Leu Asp Glu Asp Val Leu Asp Ser Tyr Asp Tyr His Leu Val Met His
            755                 760                 765

Leu Val Asn Arg Val Gly Arg Ile Leu Asn Asp Ile Gln Gly Met Lys
            770                 775                 780

Arg Glu Ala Ser Gln Gly Lys Ile Ser Ser Val Gln Ile Tyr Met Glu
785                 790                 795                 800

Glu His Pro Ser Val Pro Ser Glu Ala Met Ala Ile Ala His Leu Gln
            805                 810                 815

Glu Leu Val Asp Asn Ser Met Gln Gln Leu Thr Tyr Glu Val Leu Arg
            820                 825                 830
```

```
Phe Thr Ala Val Pro Lys Ser Cys Lys Arg Ile His Leu Asn Met Ala
            835                 840                 845

Lys Ile Met His Ala Phe Tyr Lys Asp Thr Asp Gly Phe Ser Ser Leu
850                 855                 860

Thr Ala Met Thr Gly Phe Val Lys Lys Val Leu Phe Glu Pro Val Pro
865                 870                 875                 880

Glu

<210> SEQ ID NO 43
<211> LENGTH: 862
<212> TYPE: PRT
<213> ORGANISM: Taxus brevifolia
<220> FEATURE:
<223> OTHER INFORMATION: taxadiene synthase
<300> PUBLICATION INFORMATION:
<308> DATABASE ACCESSION NUMBER: Genbank AAC49310
<309> DATABASE ENTRY DATE: 1996-06-05

<400> SEQUENCE: 43

Met Ala Gln Leu Ser Phe Asn Ala Ala Leu Lys Met Asn Ala Leu Gly
1               5                   10                  15

Asn Lys Ala Ile His Asp Pro Thr Asn Cys Arg Ala Lys Ser Glu Arg
            20                  25                  30

Gln Met Met Trp Val Cys Ser Arg Ser Gly Arg Thr Arg Val Lys Met
        35                  40                  45

Ser Arg Gly Ser Gly Gly Pro Gly Pro Val Val Met Met Ser Ser Ser
50                  55                  60

Thr Gly Thr Ser Lys Val Val Ser Glu Thr Ser Ser Thr Ile Val Asp
65                  70                  75                  80

Asp Ile Pro Arg Leu Ser Ala Asn Tyr His Gly Asp Leu Trp His His
                85                  90                  95

Asn Val Ile Gln Thr Leu Glu Thr Pro Phe Arg Glu Ser Ser Thr Tyr
            100                 105                 110

Gln Glu Arg Ala Asp Glu Leu Val Val Lys Ile Lys Asp Met Phe Asn
        115                 120                 125

Ala Leu Gly Asp Gly Asp Ile Ser Pro Ser Ala Tyr Asp Thr Ala Trp
130                 135                 140

Val Ala Arg Leu Ala Thr Ile Ser Ser Asp Gly Ser Glu Lys Pro Arg
145                 150                 155                 160

Phe Pro Gln Ala Leu Asn Trp Val Phe Asn Asn Gln Leu Gln Asp Gly
                165                 170                 175

Ser Trp Gly Ile Glu Ser His Phe Ser Leu Cys Asp Arg Leu Leu Asn
            180                 185                 190

Thr Thr Asn Ser Val Ile Ala Leu Ser Val Trp Lys Thr Gly His Ser
        195                 200                 205

Gln Val Gln Gln Gly Ala Glu Phe Ile Ala Glu Asn Leu Arg Leu Leu
210                 215                 220

Asn Glu Glu Asp Glu Leu Ser Pro Asp Phe Gln Ile Ile Phe Pro Ala
225                 230                 235                 240

Leu Leu Gln Lys Ala Lys Ala Leu Gly Ile Asn Leu Pro Tyr Asp Leu
                245                 250                 255

Pro Phe Ile Lys Tyr Leu Ser Thr Thr Arg Glu Ala Arg Leu Thr Asp
            260                 265                 270

Val Ser Ala Ala Ala Asp Asn Ile Pro Ala Asn Met Leu Asn Ala Leu
        275                 280                 285

Glu Gly Leu Glu Glu Val Ile Asp Trp Asn Lys Ile Met Arg Phe Gln
```

```
                290                 295                 300
Ser Lys Asp Gly Ser Phe Leu Ser Ser Pro Ala Ser Thr Ala Cys Val
305                 310                 315                 320

Leu Met Asn Thr Gly Asp Glu Lys Cys Phe Thr Phe Leu Asn Asn Leu
                325                 330                 335

Leu Asp Lys Phe Gly Gly Cys Val Pro Cys Met Tyr Ser Ile Asp Leu
                340                 345                 350

Leu Glu Arg Leu Ser Leu Val Asp Asn Ile Glu His Leu Gly Ile Gly
                355                 360                 365

Arg His Phe Lys Gln Glu Ile Lys Gly Ala Leu Asp Tyr Val Tyr Arg
                370                 375                 380

His Trp Ser Glu Arg Gly Ile Gly Trp Gly Arg Asp Ser Leu Val Pro
385                 390                 395                 400

Asp Leu Asn Thr Thr Ala Leu Gly Leu Arg Thr Leu Arg Met His Gly
                405                 410                 415

Tyr Asn Val Ser Ser Asp Val Leu Asn Asn Phe Lys Asp Glu Asn Gly
                420                 425                 430

Arg Phe Phe Ser Ser Ala Gly Gln Thr His Val Glu Leu Arg Ser Val
                435                 440                 445

Val Asn Leu Phe Arg Ala Ser Asp Leu Ala Phe Pro Asp Glu Arg Ala
450                 455                 460

Met Asp Asp Ala Arg Lys Phe Ala Glu Pro Tyr Leu Arg Glu Ala Leu
465                 470                 475                 480

Ala Thr Lys Ile Ser Thr Asn Thr Lys Leu Phe Lys Glu Ile Glu Tyr
                485                 490                 495

Val Val Glu Tyr Pro Trp His Met Ser Ile Pro Arg Leu Glu Ala Arg
                500                 505                 510

Ser Tyr Ile Asp Ser Tyr Asp Asn Tyr Val Trp Gln Arg Lys Thr
                515                 520                 525

Leu Tyr Arg Met Pro Ser Leu Ser Asn Ser Lys Cys Leu Glu Leu Ala
                530                 535                 540

Lys Leu Asp Phe Asn Ile Val Gln Ser Leu His Gln Glu Glu Leu Lys
545                 550                 555                 560

Leu Leu Thr Arg Trp Trp Lys Glu Ser Gly Met Ala Asp Ile Asn Phe
                565                 570                 575

Thr Arg His Arg Val Ala Glu Val Tyr Phe Ser Ser Ala Thr Phe Glu
                580                 585                 590

Pro Glu Tyr Ser Ala Thr Arg Ile Ala Phe Thr Lys Ile Gly Cys Leu
                595                 600                 605

Gln Val Leu Phe Asp Asp Met Ala Asp Ile Phe Ala Thr Leu Asp Glu
                610                 615                 620

Leu Lys Ser Phe Thr Glu Gly Val Lys Arg Trp Asp Thr Ser Leu Leu
625                 630                 635                 640

His Glu Ile Pro Glu Cys Met Gln Thr Cys Phe Lys Val Trp Phe Lys
                645                 650                 655

Leu Met Glu Glu Val Asn Asn Asp Val Val Lys Val Gln Gly Arg Asp
                660                 665                 670

Met Leu Ala His Ile Arg Lys Pro Trp Glu Leu Tyr Phe Asn Cys Tyr
                675                 680                 685

Val Gln Glu Arg Glu Trp Leu Glu Ala Gly Tyr Ile Pro Thr Phe Glu
                690                 695                 700

Glu Tyr Leu Lys Thr Tyr Ala Ile Ser Val Gly Leu Gly Pro Cys Thr
705                 710                 715                 720
```

```
Leu Gln Pro Ile Leu Leu Met Gly Glu Leu Val Lys Asp Asp Val Val
                725                 730                 735

Glu Lys Val His Tyr Pro Ser Asn Met Phe Glu Leu Val Ser Leu Ser
            740                 745                 750

Trp Arg Leu Thr Asn Asp Thr Lys Thr Tyr Gln Ala Glu Lys Ala Arg
        755                 760                 765

Gly Gln Gln Ala Ser Gly Ile Ala Cys Tyr Met Lys Asp Asn Pro Gly
    770                 775                 780

Ala Thr Glu Glu Asp Ala Ile Lys His Ile Cys Arg Val Val Asp Arg
785                 790                 795                 800

Ala Leu Lys Glu Ala Ser Phe Glu Tyr Phe Lys Pro Ser Asn Asp Ile
                805                 810                 815

Pro Met Gly Cys Lys Ser Phe Ile Phe Asn Leu Arg Leu Cys Val Gln
            820                 825                 830

Ile Phe Tyr Lys Phe Ile Asp Gly Tyr Gly Ile Ala Asn Glu Glu Ile
        835                 840                 845

Lys Asp Tyr Ile Arg Lys Val Tyr Ile Asp Pro Ile Gln Val
    850                 855                 860

<210> SEQ ID NO 44
<211> LENGTH: 343
<212> TYPE: PRT
<213> ORGANISM: Taxus cuspidata
<220> FEATURE:
<223> OTHER INFORMATION: taxadiene synthase
<300> PUBLICATION INFORMATION:
<308> DATABASE ACCESSION NUMBER: Genbank ABW82997
<309> DATABASE ENTRY DATE: 2009-08-13

<400> SEQUENCE: 44

Met Ala Gln Leu Ser Phe Asn Ala Ala Leu Lys Met Asn Ala Leu Gly
  1               5                  10                  15

Asn Lys Ala Ile His Asp Pro Thr Asn Cys Arg Ala Lys Ser Glu Gly
                20                  25                  30

Gln Met Met Trp Val Cys Ser Lys Ser Gly Arg Thr Arg Val Lys Met
            35                  40                  45

Ser Arg Gly Ser Gly Gly Pro Gly Val Val Met Met Ser Ser Ser
    50                  55                  60

Thr Gly Thr Ser Lys Val Val Ser Glu Thr Ser Ser Thr Ile Val Asp
65                  70                  75                  80

Asp Ile Pro Arg Leu Ser Ala Asn Tyr His Gly Asp Leu Trp His His
                85                  90                  95

Asn Val Ile Gln Thr Leu Glu Thr Pro Phe Arg Glu Ser Ser Thr Phe
                100                 105                 110

Gln Lys Arg Ala Asp Glu Leu Val Val Lys Ile Lys Asp Met Phe Asn
            115                 120                 125

Ala Leu Gly Asp Gly Asp Ile Ser Pro Ser Ala Tyr Asp Thr Ala Trp
    130                 135                 140

Val Ala Arg Val Ala Thr Ile Ser Ser Asp Gly Ser Glu Lys Pro Arg
145                 150                 155                 160

Phe Pro Gln Ala Leu Asn Trp Val Phe Asn Gln Leu Gln Asp Gly
                165                 170                 175

Ser Trp Gly Ile Glu Ser His Phe Ser Leu Cys Asp Arg Leu Leu Asn
            180                 185                 190

Thr Thr Asn Ser Val Ile Ala Leu Ser Val Trp Lys Thr Gly His Ser
        195                 200                 205
```

```
Gln Val Glu Gln Gly Thr Glu Phe Ile Ala Glu Asn Leu Arg Leu Leu
    210                 215                 220

Asn Glu Glu Asp Glu Leu Ser Pro Asp Phe Glu Ile Ile Phe Pro Ala
225                 230                 235                 240

Leu Leu Gln Lys Ala Lys Ala Leu Gly Ile Asn Leu Pro Tyr Asp Leu
                245                 250                 255

Pro Phe Ile Lys Ser Leu Ser Thr Thr Arg Glu Ala Arg Leu Thr Asp
                260                 265                 270

Val Ser Ala Ala Asp Asn Ile Pro Ala Asn Met Leu Asn Ala Leu
        275                 280                 285

Glu Gly Leu Glu Glu Val Ile Asp Trp Asn Lys Ile Met Arg Phe Gln
290                 295                 300

Ser Lys Asp Gly Ser Phe Leu Ser Ser Pro Ala Ser Thr Ala Cys Val
305                 310                 315                 320

Leu Met Asn Thr Gly Asp Glu Lys Cys Phe Thr Phe Leu Asn Asn Leu
                325                 330                 335

Leu Asp Lys Phe Gly Gly Cys
                340
```

```
<210> SEQ ID NO 45
<211> LENGTH: 862
<212> TYPE: PRT
<213> ORGANISM: Taxus x media
<220> FEATURE:
<223> OTHER INFORMATION: taxadiene synthase
<300> PUBLICATION INFORMATION:
<308> DATABASE ACCESSION NUMBER: Genbank AAS18603
<309> DATABASE ENTRY DATE: 2007-08-17

<400> SEQUENCE: 45
```

```
Met Ala Gln Leu Ser Phe Asn Ala Ala Leu Lys Met Asn Ala Leu Gly
  1               5                  10                  15

Asn Lys Ala Ile His Asp Pro Thr Asn Cys Arg Ala Lys Ser Glu Gly
                 20                  25                  30

Gln Met Met Trp Val Cys Ser Lys Ser Gly Arg Thr Arg Val Lys Met
             35                  40                  45

Ser Arg Gly Ser Gly Gly Pro Gly Pro Val Val Met Met Ser Ser Ser
 50                  55                  60

Thr Gly Thr Ser Lys Val Val Ser Glu Thr Ser Ser Thr Ile Val Asp
 65                  70                  75                  80

Asp Ile Pro Arg Leu Ser Ala Asn Tyr His Gly Asp Leu Trp His His
                 85                  90                  95

Asn Val Ile Gln Thr Leu Glu Thr Pro Phe Arg Glu Ser Ser Thr Phe
                100                 105                 110

Gln Glu Arg Ala Asp Glu Leu Val Val Lys Ile Lys Asp Met Phe Asn
            115                 120                 125

Ala Leu Gly Asp Gly Asp Ile Ser Pro Ser Ala Tyr Asp Thr Ala Trp
        130                 135                 140

Val Ala Arg Val Ala Thr Val Ser Ser Asp Gly Ser Glu Lys Pro Arg
145                 150                 155                 160

Phe Pro Gln Ala Leu Asn Trp Val Leu Asn Asn Gln Leu Gln Asp Gly
                165                 170                 175

Ser Trp Gly Ile Glu Ser His Phe Ser Leu Cys Asp Arg Leu Leu Asn
                180                 185                 190

Thr Val Asn Ser Val Ile Ala Leu Ser Val Trp Lys Thr Gly His Ser
            195                 200                 205
```

```
Gln Val Glu Gln Gly Thr Glu Phe Ile Ala Glu Asn Leu Arg Leu Leu
    210                 215                 220

Asn Glu Glu Asp Glu Leu Ser Pro Asp Phe Glu Ile Ile Phe Pro Ala
225                 230                 235                 240

Leu Leu Gln Lys Ala Lys Ala Leu Gly Ile Asn Leu Pro Tyr Asp Leu
                245                 250                 255

Pro Phe Ile Lys Ser Leu Ser Thr Thr Arg Glu Ala Arg Leu Thr Asp
                260                 265                 270

Val Ser Ala Val Ala Asp Asn Ile Pro Ala Asn Met Leu Asn Ala Leu
            275                 280                 285

Glu Gly Leu Glu Glu Val Ile Asp Trp Asn Lys Ile Met Arg Phe Gln
        290                 295                 300

Ser Lys Asp Gly Ser Phe Leu Ser Ser Pro Ala Ser Thr Ala Cys Val
305                 310                 315                 320

Leu Met Asn Thr Gly Asp Glu Lys Cys Phe Thr Leu Leu Asn Asn Leu
                325                 330                 335

Leu Asp Lys Phe Gly Gly Cys Val Pro Cys Met Tyr Ser Ile Asp Leu
                340                 345                 350

Leu Glu Arg Leu Ser Leu Val Asp Asn Ile Glu His Leu Gly Ile Gly
            355                 360                 365

Arg His Phe Lys Gln Glu Ile Lys Val Ala Leu Asp Tyr Val Tyr Arg
        370                 375                 380

His Trp Ser Glu Arg Gly Ile Gly Trp Gly Arg Asp Ser Leu Val Pro
385                 390                 395                 400

Asp Leu Asn Thr Thr Ala Leu Gly Leu Arg Thr Leu Arg Thr His Gly
                405                 410                 415

Tyr Asp Val Ser Ser Asp Val Leu Asn Asn Phe Lys Asp Glu Asn Gly
                420                 425                 430

Arg Phe Phe Ser Ser Ala Gly Gln Thr His Val Glu Leu Arg Ser Val
            435                 440                 445

Val Asn Leu Phe Arg Ala Ser Asp Leu Ala Phe Pro Asp Glu Gly Ala
    450                 455                 460

Met Asp Asp Ala Arg Lys Phe Ala Glu Pro Tyr Leu Arg Asp Ala Leu
465                 470                 475                 480

Ala Thr Lys Ile Ser Thr Asn Thr Lys Leu Tyr Lys Glu Ile Glu Tyr
                485                 490                 495

Val Val Glu Tyr Pro Trp His Met Ser Ile Pro Arg Leu Glu Ala Arg
                500                 505                 510

Ser Tyr Ile Asp Ser Tyr Asp Asp Tyr Val Trp Gln Arg Lys Thr
    515                 520                 525

Leu Tyr Arg Met Pro Ser Leu Ser Asn Ser Lys Cys Leu Glu Leu Ala
    530                 535                 540

Lys Leu Asp Phe Asn Ile Val Gln Ser Leu His Gln Glu Glu Leu Lys
545                 550                 555                 560

Leu Leu Thr Arg Trp Trp Lys Glu Ser Gly Met Ala Asp Ile Asn Phe
                565                 570                 575

Thr Arg His Arg Val Ala Glu Val Tyr Phe Ser Ser Ala Thr Phe Glu
                580                 585                 590

Pro Glu Tyr Ser Ala Thr Arg Ile Ala Phe Thr Lys Ile Gly Cys Leu
            595                 600                 605

Gln Val Leu Phe Asp Asp Met Ala Asp Ile Phe Ala Thr Leu Asp Glu
    610                 615                 620
```

-continued

Leu Lys Ser Phe Thr Glu Gly Val Lys Arg Trp Asp Thr Ser Leu Leu
625                 630                 635                 640

His Glu Ile Pro Glu Cys Met Gln Thr Cys Phe Lys Val Trp Phe Lys
            645                 650                 655

Leu Met Glu Glu Val Asn Asn Asp Val Val Lys Val Gln Gly Arg Asp
        660                 665                 670

Met Leu Ala His Ile Arg Lys Pro Trp Glu Leu Tyr Phe Asn Cys Tyr
    675                 680                 685

Val Gln Glu Arg Glu Trp Leu Glu Ala Gly Tyr Ile Pro Thr Phe Glu
690                 695                 700

Glu Tyr Leu Lys Thr Tyr Ala Ile Ser Val Gly Leu Gly Pro Cys Thr
705                 710                 715                 720

Leu Gln Pro Ile Leu Leu Met Gly Glu Leu Val Lys Asp Asp Val Val
                725                 730                 735

Glu Lys Val His Tyr Pro Ser Asn Met Phe Glu Leu Val Ser Leu Ser
            740                 745                 750

Trp Arg Leu Thr Asn Asp Thr Lys Thr Tyr Gln Ala Glu Lys Ala Arg
        755                 760                 765

Gly Gln Gln Ala Ser Gly Ile Ala Cys Tyr Met Lys Asp Asn Pro Gly
770                 775                 780

Ala Thr Glu Glu Asp Ala Ile Lys His Ile Cys Arg Val Val Asp Arg
785                 790                 795                 800

Ala Leu Lys Glu Ala Ser Phe Glu Tyr Phe Lys Pro Ser Asn Asp Ile
                805                 810                 815

Pro Met Gly Cys Lys Ser Phe Ile Phe Asn Leu Arg Leu Cys Val Gln
            820                 825                 830

Ile Phe Tyr Lys Phe Ile Asp Gly Tyr Gly Ile Ala Asn Glu Glu Ile
        835                 840                 845

Lys Asp Tyr Ile Arg Lys Val Tyr Ile Asp Pro Ile Gln Val
850                 855                 860

<210> SEQ ID NO 46
<211> LENGTH: 764
<212> TYPE: PRT
<213> ORGANISM: Taxus brevifolia
<220> FEATURE:
<223> OTHER INFORMATION: taxadiene synthase
<300> PUBLICATION INFORMATION:
<308> DATABASE ACCESSION NUMBER: PDB 3p5pa
<309> DATABASE ENTRY DATE: 2012-10-10

<400> SEQUENCE: 46

Met Glu Ser Ser Thr Tyr Gln Glu Arg Ala Asp Glu Leu Val Val Lys
1               5                   10                  15

Ile Lys Asp Met Phe Asn Ala Leu Gly Asp Gly Asp Ile Ser Pro Ser
            20                  25                  30

Ala Tyr Asp Thr Ala Trp Val Ala Arg Leu Ala Thr Ile Ser Ser Asp
        35                  40                  45

Gly Ser Glu Lys Pro Arg Phe Pro Gln Ala Leu Asn Trp Val Phe Asn
    50                  55                  60

Asn Gln Leu Gln Asp Gly Ser Trp Gly Ile Glu Ser His Phe Ser Leu
65                  70                  75                  80

Cys Asp Arg Leu Leu Asn Thr Thr Asn Ser Val Ile Ala Leu Ser Val
                85                  90                  95

Trp Lys Thr Gly His Ser Gln Val Gln Gln Gly Ala Glu Phe Ile Ala
            100                 105                 110

```
Glu Asn Leu Arg Leu Leu Asn Glu Glu Asp Glu Leu Ser Pro Asp Phe
            115                 120                 125
Gln Ile Ile Phe Pro Ala Leu Leu Gln Lys Ala Lys Ala Leu Gly Ile
        130                 135                 140
Asn Leu Pro Tyr Asp Leu Pro Phe Ile Lys Tyr Leu Ser Thr Thr Arg
145                 150                 155                 160
Glu Ala Arg Leu Thr Asp Val Ser Ala Ala Asp Asn Ile Pro Ala
                165                 170                 175
Asn Met Leu Asn Ala Leu Glu Gly Leu Glu Glu Val Ile Asp Trp Asn
            180                 185                 190
Lys Ile Met Arg Phe Gln Ser Lys Asp Gly Ser Phe Leu Ser Ser Pro
        195                 200                 205
Ala Ser Thr Ala Cys Val Leu Met Asn Thr Gly Asp Glu Lys Cys Phe
    210                 215                 220
Thr Phe Leu Asn Asn Leu Leu Asp Lys Phe Gly Gly Cys Val Pro Cys
225                 230                 235                 240
Met Tyr Ser Ile Asp Leu Leu Glu Arg Leu Ser Leu Val Asp Asn Ile
                245                 250                 255
Glu His Leu Gly Ile Gly Arg His Phe Lys Gln Glu Ile Lys Gly Ala
            260                 265                 270
Leu Asp Tyr Val Tyr Arg His Trp Ser Glu Arg Gly Ile Gly Trp Gly
        275                 280                 285
Arg Asp Ser Leu Val Pro Asp Leu Asn Thr Thr Ala Leu Gly Leu Arg
    290                 295                 300
Thr Leu Arg Met His Gly Tyr Asn Val Ser Ser Asp Val Leu Asn Asn
305                 310                 315                 320
Phe Lys Asp Glu Asn Gly Arg Phe Phe Ser Ser Ala Gly Gln Thr His
                325                 330                 335
Val Glu Leu Arg Ser Val Val Asn Leu Phe Arg Ala Ser Asp Leu Ala
            340                 345                 350
Phe Pro Asp Glu Arg Ala Met Asp Asp Ala Arg Lys Phe Ala Glu Pro
        355                 360                 365
Tyr Leu Arg Glu Ala Leu Ala Thr Lys Ile Ser Thr Asn Thr Lys Leu
    370                 375                 380
Phe Lys Glu Ile Glu Tyr Val Glu Tyr Pro Trp His Met Ser Ile
385                 390                 395                 400
Pro Arg Leu Glu Ala Arg Ser Tyr Ile Asp Ser Tyr Asp Asp Asn Tyr
                405                 410                 415
Val Trp Gln Arg Lys Thr Leu Tyr Arg Met Pro Ser Leu Ser Asn Ser
            420                 425                 430
Lys Cys Leu Glu Leu Ala Lys Leu Asp Phe Asn Ile Val Gln Ser Leu
        435                 440                 445
His Gln Glu Glu Leu Lys Leu Leu Thr Arg Trp Trp Lys Glu Ser Gly
    450                 455                 460
Met Ala Asp Ile Asn Phe Thr Arg His Arg Val Ala Glu Val Tyr Phe
465                 470                 475                 480
Ser Ser Ala Thr Phe Glu Pro Glu Tyr Ser Ala Thr Arg Ile Ala Phe
                485                 490                 495
Thr Lys Ile Gly Cys Leu Gln Val Leu Phe Asp Asp Met Ala Asp Ile
            500                 505                 510
Phe Ala Thr Leu Asp Glu Leu Lys Ser Phe Thr Glu Gly Val Lys Arg
        515                 520                 525
Trp Asp Thr Ser Leu Leu His Glu Ile Pro Glu Cys Met Gln Thr Cys
```

```
                   530               535               540
Phe Lys Val Trp Phe Lys Leu Met Glu Glu Val Asn Asn Asp Val Val
545                 550                 555                 560

Lys Val Gln Gly Arg Asp Met Leu Ala His Ile Arg Lys Pro Trp Glu
                565                 570                 575

Leu Tyr Phe Asn Cys Tyr Val Gln Glu Arg Glu Trp Leu Glu Ala Gly
                580                 585                 590

Tyr Ile Pro Thr Phe Glu Glu Tyr Leu Lys Thr Tyr Ala Ile Ser Val
            595                 600                 605

Gly Leu Gly Pro Cys Thr Leu Gln Pro Ile Leu Leu Met Gly Glu Leu
            610                 615                 620

Val Lys Asp Asp Val Val Glu Lys Val His Tyr Pro Ser Asn Met Phe
625                 630                 635                 640

Glu Leu Val Ser Leu Ser Trp Arg Leu Thr Asn Asp Thr Lys Thr Tyr
                645                 650                 655

Gln Ala Glu Lys Ala Arg Gly Gln Gln Ala Ser Gly Ile Ala Cys Tyr
                660                 665                 670

Met Lys Asp Asn Pro Gly Ala Thr Glu Glu Asp Ala Ile Lys His Ile
                675                 680                 685

Cys Arg Val Val Asp Arg Ala Leu Lys Glu Ala Ser Phe Glu Tyr Phe
                690                 695                 700

Lys Pro Ser Asn Asp Ile Pro Met Gly Cys Lys Ser Phe Ile Phe Asn
705                 710                 715                 720

Leu Arg Leu Cys Val Gln Ile Phe Tyr Lys Phe Ile Asp Gly Tyr Gly
                725                 730                 735

Ile Ala Asn Glu Glu Ile Lys Asp Tyr Ile Arg Lys Val Tyr Ile Asp
                740                 745                 750

Pro Ile Gln Val Gly Ser His His His His His
            755                 760

<210> SEQ ID NO 47
<211> LENGTH: 783
<212> TYPE: PRT
<213> ORGANISM: Abies balsamea
<220> FEATURE:
<223> OTHER INFORMATION: pseudomature AbdiTPS1

<400> SEQUENCE: 47

Lys Arg Glu Phe Pro Pro Gly Phe Trp Lys Asp Asp Leu Ile Asp Ser
1               5                   10                  15

Leu Thr Ser Ser His Lys Val Ala Ala Ser Asp Glu Lys Arg Ile Glu
                20                  25                  30

Thr Leu Ile Ser Glu Ile Lys Asn Met Phe Arg Cys Met Gly Tyr Gly
            35                  40                  45

Glu Thr Asn Pro Ser Ala Tyr Asp Thr Ala Trp Val Ala Arg Ile Pro
50                  55                  60

Ala Leu Asp Gly Ser Asp Asn Pro His Phe Pro Glu Thr Val Glu Trp
65                  70                  75                  80

Ile Leu Gln Asn Gln Leu Lys Asp Gly Ser Trp Gly Glu Gly Phe Tyr
                85                  90                  95

Phe Leu Ala Tyr Asp Arg Ile Leu Ala Thr Leu Ala Cys Ile Ile Thr
                100                 105                 110

Leu Thr Leu Trp Arg Thr Gly Glu Thr Gln Val His Lys Gly Ile Glu
            115                 120                 125

Phe Phe Arg Thr Gln Ala Gly Lys Met Glu Asp Glu Ala Asp Ser His
```

```
            130                 135                 140
Arg Pro Ser Gly Phe Glu Ile Val Phe Pro Ala Met Leu Lys Glu Ala
145                 150                 155                 160

Lys Ile Leu Gly Leu Asp Leu Pro Tyr Asp Leu Pro Phe Leu Lys Gln
                165                 170                 175

Ile Ile Glu Lys Arg Glu Ala Lys Leu Lys Arg Ile Pro Thr Asp Val
                180                 185                 190

Leu Tyr Ala Leu Pro Thr Thr Leu Leu Tyr Ser Leu Glu Gly Leu Gln
            195                 200                 205

Glu Ile Val Asp Trp Gln Lys Ile Met Lys Leu Gln Ser Lys Asp Gly
        210                 215                 220

Ser Phe Leu Ser Ser Pro Ala Ser Thr Ala Ala Val Phe Met Arg Thr
225                 230                 235                 240

Gly Asn Lys Lys Cys Leu Asp Phe Leu Asn Phe Val Leu Lys Lys Phe
                245                 250                 255

Gly Asn His Val Pro Cys His Tyr Pro Leu Asp Leu Phe Glu Arg Leu
                260                 265                 270

Trp Ala Val Asp Thr Val Glu Arg Leu Gly Ile Asp Arg His Phe Lys
            275                 280                 285

Glu Glu Ile Lys Glu Ala Leu Asp Tyr Val Tyr Ser His Trp Asp Glu
290                 295                 300

Arg Gly Ile Gly Trp Ala Arg Glu Asn Pro Val Pro Asp Ile Asp Asp
305                 310                 315                 320

Thr Ala Met Gly Leu Arg Ile Leu Arg Leu His Gly Tyr Asn Val Ser
                325                 330                 335

Ser Asp Val Leu Lys Thr Phe Arg Asp Glu Asn Gly Glu Phe Phe Cys
                340                 345                 350

Phe Leu Gly Gln Thr Gln Arg Gly Val Thr Asp Met Leu Asn Val Asn
            355                 360                 365

Arg Cys Ser His Val Ser Phe Pro Gly Glu Thr Ile Met Glu Glu Ala
        370                 375                 380

Lys Leu Cys Thr Glu Arg Tyr Leu Arg Asn Ala Leu Glu Asn Val Asp
385                 390                 395                 400

Ala Phe Asp Lys Trp Ala Phe Lys Lys Asn Ile Arg Gly Glu Val Glu
                405                 410                 415

Tyr Ala Leu Lys Tyr Pro Trp His Lys Ser Met Pro Arg Leu Glu Ala
                420                 425                 430

Arg Ser Tyr Ile Glu Asn Tyr Gly Pro Asp Asp Val Trp Leu Gly Lys
            435                 440                 445

Thr Val Tyr Met Met Pro Tyr Ile Ser Asn Glu Lys Tyr Leu Glu Leu
        450                 455                 460

Ala Lys Leu Asp Phe Asn Lys Val Gln Ser Ile His Gln Thr Glu Leu
465                 470                 475                 480

Gln Asp Leu Arg Arg Trp Trp Lys Ser Ser Gly Phe Thr Asp Leu Asn
                485                 490                 495

Phe Thr Arg Glu Arg Val Thr Glu Ile Tyr Phe Ser Pro Ala Ser Phe
                500                 505                 510

Ile Phe Glu Pro Glu Phe Ser Lys Cys Arg Glu Val Tyr Thr Lys Thr
            515                 520                 525

Ser Asn Phe Thr Val Ile Leu Asp Asp Leu Tyr Asp Ala His Gly Ser
        530                 535                 540

Leu Asp Asp Leu Lys Leu Phe Thr Glu Ser Val Lys Arg Trp Asp Leu
545                 550                 555                 560
```

```
Ser Leu Val Asp Gln Met Pro Gln Met Lys Ile Cys Phe Val Gly
            565                 570                 575

Phe Tyr Asn Thr Phe Asn Glu Ile Ala Lys Glu Gly Arg Glu Ser Gln
                580                 585                 590

Gly Arg Asp Val Leu Gly Tyr Ile Gln Asn Val Trp Lys Val Gln Leu
        595                 600                 605

Glu Ala Tyr Thr Lys Glu Ala Glu Trp Ser Glu Ala Lys Tyr Val Pro
    610                 615                 620

Ser Phe Asn Glu Tyr Ile Glu Asn Ala Ser Val Ser Ile Ala Leu Gly
625                 630                 635                 640

Thr Val Val Leu Ile Ser Ala Leu Phe Thr Gly Glu Val Leu Thr Asp
                645                 650                 655

Glu Val Leu Ser Lys Ile Asp Arg Gly Ser Arg Phe Leu Gln Leu Met
                660                 665                 670

Gly Leu Thr Gly Arg Leu Val Asn Asp Thr Lys Thr Tyr Gln Ala Glu
            675                 680                 685

Arg Gly Gln Gly Glu Val Ala Ser Ala Ile Gln Cys Tyr Met Lys Asp
        690                 695                 700

His Pro Lys Ile Ser Glu Glu Ala Leu Lys His Val Tyr Thr Val
705                 710                 715                 720

Met Glu Asn Ser Leu Glu Glu Leu Asn Arg Glu Phe Val Asn Lys
                725                 730                 735

Ile Pro Asp Ile Tyr Arg Arg Leu Val Phe Glu Thr Ala Arg Ile Met
                740                 745                 750

Gln Leu Phe Tyr Met Gln Gly Asp Gly Leu Thr Leu Ser His Asp Met
            755                 760                 765

Glu Ile Lys Glu His Val Lys Asn Cys Leu Phe Gln Pro Val Ala
770                 775                 780

<210> SEQ ID NO 48
<211> LENGTH: 784
<212> TYPE: PRT
<213> ORGANISM: Abies balsamea
<220> FEATURE:
<223> OTHER INFORMATION: pseudomature AbdiTPS2

<400> SEQUENCE: 48

Lys Arg Glu Phe Pro Pro Gly Phe Trp Lys Asp Asp Leu Ile Asp Ser
1               5                   10                  15

Leu Thr Ser Ser His Lys Val Ala Ala Ser Asp Glu Lys Arg Ile Glu
                20                  25                  30

Thr Leu Ile Ser Glu Ile Lys Asn Met Phe Arg Cys Met Gly Tyr Gly
            35                  40                  45

Glu Thr Asn Pro Ser Ala Tyr Asp Thr Ala Trp Val Ala Arg Ile Pro
        50                  55                  60

Ala Leu Asp Gly Ser Asp Asn Pro His Phe Pro Glu Thr Val Glu Trp
65                  70                  75                  80

Ile Leu Gln Asn Gln Leu Lys Asp Gly Ser Trp Gly Glu Gly Phe Tyr
                85                  90                  95

Phe Leu Ala Tyr Asp Arg Ile Leu Ala Thr Leu Ala Cys Ile Ile Thr
            100                 105                 110

Leu Thr Leu Trp Arg Thr Gly Glu Thr Gln Val His Lys Gly Ile Glu
        115                 120                 125

Phe Phe Arg Thr Gln Ala Gly Lys Met Glu Asp Glu Ala Asp Ser His
    130                 135                 140
```

```
Arg Pro Ser Gly Phe Glu Ile Val Phe Pro Ala Met Leu Lys Glu Ala
145                 150                 155                 160

Lys Ile Leu Gly Leu Asp Leu Pro Tyr Asp Leu Pro Phe Leu Lys Gln
            165                 170                 175

Ile Ile Glu Lys Arg Glu Ala Lys Leu Lys Arg Ile Pro Thr Asp Val
        180                 185                 190

Leu Tyr Ala Leu Pro Thr Thr Leu Leu Tyr Ser Leu Glu Gly Leu Gln
    195                 200                 205

Glu Ile Val Asp Trp Gln Lys Ile Met Lys Leu Gln Ser Lys Asp Gly
210                 215                 220

Ser Phe Leu Ser Ser Pro Ala Ser Thr Ala Ala Val Phe Met Arg Thr
225                 230                 235                 240

Gly Asn Lys Lys Cys Leu Asp Phe Leu Asn Phe Val Leu Lys Lys Phe
                245                 250                 255

Gly Asn His Val Pro Cys His Tyr Pro Leu Asp Leu Phe Glu Arg Leu
            260                 265                 270

Trp Ala Val Asp Thr Val Glu Arg Leu Gly Ile Asp Arg His Phe Lys
        275                 280                 285

Glu Glu Ile Lys Asp Ala Leu Asp Tyr Val Tyr Ser His Trp Asp Glu
290                 295                 300

Arg Gly Ile Gly Trp Ala Arg Glu Asn Pro Val Pro Asp Ile Asp Asp
305                 310                 315                 320

Thr Ala Met Gly Leu Arg Ile Leu Arg Leu His Gly Tyr Asn Val Ser
                325                 330                 335

Ser Asp Val Leu Lys Thr Phe Arg Asp Glu Asn Gly Glu Phe Phe Cys
            340                 345                 350

Phe Leu Gly Gln Thr Gln Arg Gly Val Thr Asp Met Leu Asn Val Asn
        355                 360                 365

Arg Cys Ser His Val Ser Phe Pro Gly Glu Thr Ile Met Glu Glu Ala
370                 375                 380

Lys Leu Cys Thr Glu Arg Tyr Leu Arg Asn Ala Leu Glu Asn Val Asp
385                 390                 395                 400

Ala Phe Asp Lys Trp Ala Phe Lys Lys Asn Ile Arg Gly Glu Val Glu
                405                 410                 415

Tyr Ala Leu Lys Tyr Thr Trp His Lys Ser Met Pro Arg Leu Glu Ala
            420                 425                 430

Arg Ser Tyr Ile Glu Asn Tyr Gly Pro Asn Asp Ala Trp Leu Gly Lys
        435                 440                 445

Thr Val Tyr Arg Met Pro Tyr Ile Ser Asn Glu Lys Tyr Leu Glu Leu
    450                 455                 460

Ala Lys Leu Asp Phe Asn Lys Leu Gln Ser Ile His Gln Thr Glu Leu
465                 470                 475                 480

Gln Asp Leu Arg Arg Trp Trp Lys Ser Ser Gly Phe Ser Lys Leu Asn
                485                 490                 495

Phe Thr Arg Glu Arg Val Thr Glu Ile Tyr Phe Ser Ser Ala Ser Phe
            500                 505                 510

Met Phe Glu Pro Glu Phe Ser Lys Cys Arg Glu Val Tyr Thr Lys Ala
        515                 520                 525

Ser Ile Phe Thr Leu Ile Phe Asp Asp Leu Tyr Asp Ala His Gly Ser
    530                 535                 540

Leu Asp Asp Leu Lys Leu Phe Ser Glu Ala Val Lys Arg Trp Asp Leu
545                 550                 555                 560
```

```
Ser Leu Leu Glu Arg Met Pro Gln Glu Met Lys Ile Cys Phe Leu Gly
            565                 570                 575

Phe Tyr Asn Thr Phe Asn Glu Ile Ala Glu Glu Val His Lys Arg Gln
            580                 585                 590

Gly Arg Asp Met Leu Gly His Ile Gln Asn Val Trp Glu Ile Leu Leu
            595                 600                 605

Ala Ala Tyr Thr Lys Glu Ala Glu Trp Ser Lys Thr Lys Tyr Val Pro
            610                 615                 620

Ser Phe Asp Glu Tyr Ile Glu Asn Ala Ser Val Ser Ile Thr Leu Gly
625                 630                 635                 640

Thr Ile Val Leu Ile Ser Thr Leu Phe Ile Gly Glu Val Leu Thr Asp
                    645                 650                 655

His Val Leu Ser Lys Ile Asn His Gly Ser Arg Phe Leu His Leu Met
            660                 665                 670

Gly Leu Thr Gly Arg Leu Val Asn Asp Thr Lys Thr Tyr Gln Ala Glu
            675                 680                 685

Arg Gly Gln Gly Glu Glu Ala Ser Ala Ile Gln Cys Tyr Met Lys Asp
            690                 695                 700

His Pro Glu Ile Ser Glu Glu Ala Leu Asn His Val Tyr Asn Val
705                 710                 715                 720

Met Glu Asn Ala Leu Gln Glu Leu Asn Lys Glu Phe Val Asn Asn Lys
                    725                 730                 735

Glu Val Pro Pro Asn Cys Arg Arg Leu Val Phe Asn Thr Ala Arg Ile
                    740                 745                 750

Met Gln Leu Phe Tyr Met Gln Gly Asp Gly Leu Thr Leu Ser His Asp
            755                 760                 765

Met Glu Ile Lys Asp His Val Lys Thr Cys Leu Phe Ile Pro Ile Ala
770                 775                 780

<210> SEQ ID NO 49
<211> LENGTH: 661
<212> TYPE: PRT
<213> ORGANISM: Abies balsamea
<220> FEATURE:
<223> OTHER INFORMATION: pseudomature AbdiTPS3

<400> SEQUENCE: 49

Lys Arg Glu Phe Pro Pro Gly Phe Trp Lys Asp Asp Leu Ile Asp Ser
1               5                   10                  15

Leu Thr Ser Ser His Lys Val Ala Ala Ser Asp Glu Lys Arg Ile Glu
            20                  25                  30

Thr Leu Ile Ser Glu Ile Lys Asn Met Phe Arg Cys Met Gly Tyr Gly
            35                  40                  45

Glu Thr Asn Pro Ser Ala Tyr Asp Thr Ala Trp Val Ala Arg Ile Pro
50                  55                  60

Ala Leu Asp Gly Ser Asp Asn Pro His Phe Pro Glu Thr Val Glu Trp
65                  70                  75                  80

Ile Leu Gln Asn Gln Leu Lys Asp Gly Ser Trp Gly Glu Gly Phe Tyr
                    85                  90                  95

Phe Leu Ala Tyr Asp Arg Ile Leu Ala Thr Leu Ala Cys Ile Ile Thr
            100                 105                 110

Leu Thr Leu Trp Arg Thr Gly Glu Thr Gln Val His Lys Gly Ile Glu
            115                 120                 125

Phe Phe Arg Thr Gln Ala Gly Lys Met Glu Asp Glu Ala Asp Ser His
            130                 135                 140
```

```
Arg Pro Ser Gly Phe Glu Ile Val Phe Pro Ala Met Leu Lys Glu Ala
145                 150                 155                 160

Lys Ile Leu Gly Leu Asp Leu Pro Tyr Asp Leu Pro Phe Leu Lys Gln
            165                 170                 175

Ile Ile Glu Lys Arg Glu Ala Lys Leu Lys Arg Ile Pro Thr Asp Val
        180                 185                 190

Leu Tyr Ala Leu Pro Thr Thr Leu Leu Tyr Ser Leu Glu Gly Leu Gln
    195                 200                 205

Glu Ile Val Asp Trp Gln Lys Ile Met Lys Leu Gln Ser Lys Asp Gly
210                 215                 220

Ser Phe Leu Ser Ser Pro Ala Ser Thr Ala Ala Val Phe Met Arg Thr
225                 230                 235                 240

Gly Asn Lys Lys Cys Leu Asp Phe Leu Asn Phe Val Leu Lys Lys Phe
            245                 250                 255

Gly Asn His Val Pro Cys His Tyr Pro Leu Asp Leu Phe Glu Arg Leu
        260                 265                 270

Trp Ala Val Asp Thr Val Glu Arg Leu Gly Ile Asp Arg His Phe Lys
    275                 280                 285

Glu Glu Ile Lys Glu Ala Leu Asp Tyr Val Tyr Ser His Trp Asp Glu
290                 295                 300

Arg Gly Ile Gly Trp Ala Arg Glu Asn Pro Val Pro Asp Ile Asp Asp
305                 310                 315                 320

Thr Ala Met Gly Leu Arg Ile Leu Arg Leu His Gly Tyr Asn Val Ser
            325                 330                 335

Ser Asp Val Leu Lys Thr Phe Arg Asp Glu Asn Gly Glu Phe Phe Cys
        340                 345                 350

Phe Leu Gly Gln Thr Gln Arg Gly Val Thr Asp Met Leu Asn Val Asn
    355                 360                 365

Arg Cys Ser His Val Ser Phe Pro Gly Glu Thr Ile Met Glu Glu Ala
370                 375                 380

Lys Leu Cys Thr Glu Arg Tyr Leu Arg Asn Ala Leu Glu Asn Val Asp
385                 390                 395                 400

Ala Phe Asp Lys Trp Ala Phe Lys Lys Asn Ile Arg Gly Glu Val Glu
            405                 410                 415

Tyr Ala Leu Lys Tyr Pro Trp His Lys Ser Met Pro Arg Leu Glu Ala
        420                 425                 430

Arg Ser Tyr Ile Glu Asn Tyr Gly Gln Asn Asp Leu Trp Leu Gly Lys
    435                 440                 445

Ser Leu Tyr Met Met Pro Tyr Ile Ser Asn Glu Lys Tyr Leu Glu Leu
450                 455                 460

Ala Lys Leu Asp Phe Asn Lys Val Gln Ser Ile His Gln Lys Glu Leu
465                 470                 475                 480

Gln Asp Leu Arg Arg Trp Trp Lys Ser Ser Gly Phe Thr Asp Leu Asn
            485                 490                 495

Phe Thr Arg Glu Arg Val Thr Glu Ile Tyr Phe Ser Pro Ala Ser Phe
        500                 505                 510

Ile Phe Glu Pro Glu Phe Ser Lys Cys Arg Glu Val Tyr Thr Lys Thr
    515                 520                 525

Ser Asn Phe Thr Val Ile Leu Asp Asp Leu Tyr Asp Ala His Gly Ser
530                 535                 540

Leu Asp Asp Leu Lys Leu Phe Ser Glu Ser Val Lys Arg Trp Asp Leu
545                 550                 555                 560

Ser Leu Ile Asp Gly Met Pro Gln Glu Met Lys Thr Cys Phe Lys Gly
```

```
              565                 570                 575
Leu Tyr Asn Thr Phe Asn Glu Ile Ala Glu Glu Gly Cys Lys Arg Gln
            580                 585                 590

Gly His Asp Val Leu Gly Tyr Ile Arg Asn Val Trp Glu Ile Gln Leu
        595                 600                 605

Ala Ala Tyr Thr Lys Glu Ala Glu Trp Ser Glu Ala Lys Tyr Val Pro
610                 615                 620

Ser Phe Asn Glu Tyr Ile Glu Asn Ala Ser Val Ser Ile Ala Leu Gly
625                 630                 635                 640

Thr Val Val Leu Ile Ser Val Leu Phe Val Gly Ser Ser Tyr Arg Ser
                645                 650                 655

Asn Thr Phe Lys Asn
            660

<210> SEQ ID NO 50
<211> LENGTH: 781
<212> TYPE: PRT
<213> ORGANISM: Abies balsamea
<220> FEATURE:
<223> OTHER INFORMATION: pseudomature AbdiTPS4

<400> SEQUENCE: 50

Asn Arg Glu Phe Pro Pro Ser Phe Trp Asn Asn Asp Ile Ile Asn Ser
1               5                   10                  15

Ile Thr Ala Ser His Lys Val Gln Thr Gly Asp Arg Lys Arg Ile Gln
            20                  25                  30

Thr Leu Ile Ser Glu Ile Lys Asn Val Phe Asn Ser Met Gly Asp Gly
        35                  40                  45

Glu Thr Ser Pro Ser Ala Tyr Asp Thr Ala Trp Val Ala Arg Ile Pro
50                  55                  60

Ala Val Asp Gly Ser Glu Gln Pro Gln Phe Pro Gln Thr Leu Glu Trp
65                  70                  75                  80

Ile Leu Gln Asn Gln Leu Lys Asp Gly Ser Trp Gly Glu Glu Phe Tyr
                85                  90                  95

Phe Leu Ala Tyr Asp Arg Leu Leu Ala Thr Leu Ala Cys Ile Ile Thr
            100                 105                 110

Leu Thr Ile Trp Arg Thr Gly Asn Val Gln Leu His Lys Gly Ile Glu
        115                 120                 125

Phe Phe Arg Lys Gln Val Val Arg Met Asp Asp Glu Ala Asp Asn His
130                 135                 140

Arg Pro Ser Gly Phe Glu Ile Val Phe Pro Ala Met Leu Asn Glu Ala
145                 150                 155                 160

Lys Ser Leu Gly Leu Asp Leu Pro Tyr Glu Leu Pro Phe Ile Glu Gln
                165                 170                 175

Met Val Lys Lys Arg Glu Ala Lys Leu Lys Met Ile Thr Thr Asn Val
            180                 185                 190

Leu Tyr Thr Ile Gln Thr Thr Leu Leu Tyr Ser Leu Glu Gly Leu His
        195                 200                 205

Glu Ile Val Asp Phe Asp Lys Ile Ile Lys Leu Gln Ser Lys Asp Gly
210                 215                 220

Ser Phe Leu Gly Ser Pro Ala Ser Thr Ala Ala Val Phe Met Gln Thr
225                 230                 235                 240

Gly Asn Thr Lys Cys Leu Glu Phe Leu Glu Phe Val Leu Arg Lys Phe
                245                 250                 255

Arg Asn His Val Pro Ser Asp Tyr Pro Leu Asp Leu Phe Glu Arg Leu
```

```
                260                 265                 270
Trp Val Val Asp Thr Val Glu Arg Leu Gly Ile Asp Arg His Phe Lys
            275                 280                 285
Lys Glu Ile Lys Asp Ala Leu Asp Tyr Val Tyr Ser Cys Trp Asp Glu
            290                 295                 300
Arg Gly Ile Gly Trp Ala Lys Asp Ser Pro Ile Ala Asp Ile Asp Asp
305                 310                 315                 320
Thr Ala Met Gly Leu Arg Ile Leu Arg Leu His Gly Tyr Asn Val Ser
                325                 330                 335
Pro Asp Val Leu Lys Thr Phe Lys Asp Glu Asn Gly Glu Phe Phe Cys
                340                 345                 350
Phe Met Gly Gln Thr Gln Arg Gly Val Thr Asp Met Leu Asn Val Tyr
                355                 360                 365
Arg Cys Ser Gln Val Ala Phe Pro Gly Glu Thr Ile Met Glu Glu Ala
                370                 375                 380
Lys Leu Cys Thr Glu Arg Tyr Leu Arg Asn Ala Leu Glu Asn Ala Asp
385                 390                 395                 400
Ala Phe Asp Lys Trp Ala Ile Lys Lys Asn Ile Arg Gly Glu Val Glu
                405                 410                 415
Tyr Ala Leu Lys Tyr Pro Trp His Arg Ser Met Pro Arg Leu Glu Val
                420                 425                 430
Arg Ser Tyr Ile Gly Asn Tyr Gly Pro Asn Asp Val Trp Leu Gly Lys
                435                 440                 445
Ser Leu Tyr Met Met Pro Tyr Ile Ser Asn Glu Lys Tyr Leu Glu Leu
                450                 455                 460
Ala Lys Leu Asp Phe Asn Ser Val Gln Ser Leu His Gln Glu Glu Ile
465                 470                 475                 480
Arg Glu Leu Val Arg Trp Cys Lys Ser Ser Gly Phe Thr Glu Leu Lys
                485                 490                 495
Phe Thr Arg Asp Arg Val Val Glu Thr Tyr Phe Ala Val Ala Ser Ser
                500                 505                 510
Met Phe Glu Pro Glu Phe Ser Thr Cys Arg Ala Val Tyr Thr Lys Ile
                515                 520                 525
Ser Val Leu Leu Val Ile Leu Asp Asp Leu Tyr Asp Gly Tyr Gly Ser
                530                 535                 540
Pro Asp Glu Ile Lys Leu Phe Ser Glu Ala Val Lys Arg Trp Asp Leu
545                 550                 555                 560
Ser Leu Leu Glu Gln Met Pro Asp His Met Lys Ile Cys Phe Leu Gly
                565                 570                 575
Leu Tyr Asn Thr Val Asn Glu Val Ala Glu Glu Gly Arg Lys Thr Gln
                580                 585                 590
Gly His Asp Val Leu Gly Tyr Ile Arg Asn Leu Trp Glu Ile Gln Leu
                595                 600                 605
Ala Ala Phe Thr Arg Glu Ala Glu Trp Ser Gln Gly Lys Tyr Val Pro
                610                 615                 620
Ser Phe Asp Glu Tyr Ile Glu Asn Ala Gln Val Ser Ile Gly Val Ala
625                 630                 635                 640
Thr Ile Leu Leu Ile Thr Ile Leu Phe Thr Glu Glu Asp Ile Leu
                645                 650                 655
Ser His Ile Asp Tyr Gly Ser Lys Phe Leu Arg Leu Ala Ser Leu Thr
                660                 665                 670
Ala Arg Leu Ala Asn Asp Ile Lys Thr Tyr Gln Glu Glu Arg Ala His
                675                 680                 685
```

```
Gly Glu Val Val Ser Ala Ile Gln Cys Tyr Met Lys Asp Arg Pro Glu
            690                 695                 700

Ile Thr Glu Glu Ala Leu Lys Tyr Val Tyr Gly Arg Met Val Asn
705                 710                 715                 720

Asp Leu Ala Glu Leu Asn Ser Glu Tyr Leu Lys Ser Asn Glu Met Pro
                725                 730                 735

Gln Asn Cys Lys Arg Leu Val Phe Asp Thr Ala Arg Val Ala Gln Leu
            740                 745                 750

Phe Thr Met Glu Gly Asp Gly Leu Thr Tyr Ser Asp Thr Met Glu Ile
        755                 760                 765

Lys Glu His Ile Lys Lys Cys Leu Phe Glu Pro Ala Thr
770                 775                 780

<210> SEQ ID NO 51
<211> LENGTH: 2352
<212> TYPE: DNA
<213> ORGANISM: Abies balsamea
<220> FEATURE:
<223> OTHER INFORMATION: pseudomature AbdiTPS1

<400> SEQUENCE: 51
```

| | | | | | |
|---|---|---|---|---|---|
| aaacgagaat | tcctccagg | attttggaag | gatgatctta | tcgattctct | gacgtcctct | 60 |
| cacaaggttg | cagcatcaga | cgagaagcgt | atcgagacat | taatatccga | gattaagaat | 120 |
| atgtttagat | gtatgggcta | tggcgaaacg | aatccctctg | catatgacac | tgcttgggta | 180 |
| gcaaggattc | cagcacttga | tggctctgac | aaccctcact | ttcctgagac | agttgaatgg | 240 |
| attcttcaaa | atcagttgaa | agatgggtct | tggggtgaag | gattctactt | cttggcatat | 300 |
| gacagaatac | tggctacact | tgcatgtatt | attacgctta | ccctctggcg | tactggggag | 360 |
| acacaagtac | acaaaggtat | tgaattcttc | aggacacaag | ctggaaagat | ggaagatgaa | 420 |
| gctgatagtc | ataggccaag | tggatttgaa | atagtatttc | ctgcaatgct | aaaggaagct | 480 |
| aaaatcttag | ggttggatct | gccttacgat | ttgccattcc | tgaaacaaat | catcgaaaag | 540 |
| cgggaggcta | agcttaaaag | gattcccact | gatgttctct | atgcccttcc | aacaacgtta | 600 |
| ttgtattctt | tggaaggttt | gcaagaaata | gtagactggc | agaaaataat | gaaacttcaa | 660 |
| tccaaggatg | gatcatttct | cagctctccg | gcatctacag | cggctgtatt | catgcgtaca | 720 |
| gggaacaaaa | agtgcttgga | tttcttgaac | tttgtcttga | agaaattcgg | aaaccatgtg | 780 |
| ccttgtcact | atccgcttga | tctatttgaa | cgtttgtggg | cggttgatac | cgttgagcgg | 840 |
| ctaggtatcg | atcgccattt | caagaggag | atcaaggaag | cattggatta | tgtttacagc | 900 |
| cattgggacg | aaagaggcat | tggatgggcg | agagagaatc | ctgttcctga | tattgatgat | 960 |
| acagccatgg | gccttcgaat | cttgagacta | catggataca | atgtatcctc | agatgtttta | 1020 |
| aaaacattta | gagatgagaa | tggtgagttc | ttttgcttct | tgggtcaaac | acagagagga | 1080 |
| gttaccgaca | tgtaaacgt | caatcgttgt | tcacatgttt | catttccggg | agaaacgatc | 1140 |
| atggaagaag | caaaactctg | taccgaaagg | tatctgagga | atgctctgga | aaatgtggat | 1200 |
| gcctttgaca | aatgggcttt | taaaaagaat | attcggggag | aggtagagta | tgcactcaaa | 1260 |
| tatccctggc | ataagagtat | gccaaggttg | gaggctagaa | gctatattga | aaactatggg | 1320 |
| ccagatgatg | tgtggcttgg | aaaaactgta | tatatgatgc | catacatttc | caatgaaaag | 1380 |
| tatttagaac | tagcgaaact | ggacttcaat | aaggtgcagt | ctatacacca | aacagagctt | 1440 |
| caagatcttc | gaaggtggtg | gaaatcatcc | ggtttcacgg | atctgaattt | cactcgtgag | 1500 |

```
cgtgtgacgg aaatatattt ctcaccggca tcctttatct ttgagccgga gttttctaag   1560
tgcagagaag tttatacaaa aacttccaat ttcactgtta ttttagatga tctttatgac   1620
gcccatggat ctttagacga tcttaagttg ttcacagaat cagtcaaaag atgggatcta   1680
tcattagtgg accaaatgcc acaacaaatg aaaatatgct ttgtgggttt ctacaatact   1740
tttaatgaaa tagcaaaaga aggacgtgag agccaagggc gcgatgtgct aggctacatt   1800
caaaatgttt ggaaagtcca acttgaagct tacactaaag aagcagaatg gtctgaagct   1860
aaatatgtgc catccttcaa tgaatacata gagaacgcga gtgtgtcaat agcattggga   1920
acagtggttc tcattagtgc tcttttcact ggggaagttc ttacagatga agtactctcc   1980
aaaattgatc gcggatctag atttcttcaa ctcatgggct taacagggcg tttggtgaat   2040
gacaccaaaa cttatcaggc agagagaggt caaggtgagg tggcttctgc catacaatgt   2100
tatatgaaag accatcctaa aatctccgaa gaagaagctc tcaaacatgt ctatactgtc   2160
atggaaaatt ccctcgaaga gttgaatagg gagtttgtga ataacaaaat accggatatt   2220
tacagaagac tggtttttga aactgcaaga ataatgcaac tgttttatat gcaaggggat   2280

ggtttgacac tatcacatga tatggaaatt aaagagcatg tcaaaaattg cctcttccaa   2340
ccagttgcct ag                                                       2352
```

<210> SEQ ID NO 52
<211> LENGTH: 2355
<212> TYPE: DNA
<213> ORGANISM: Abies balsamea
<220> FEATURE:
<223> OTHER INFORMATION: pseudomature AbdiTPS2

<400> SEQUENCE: 52

```
aaacgagaat ttcctccagg attttggaag gatgatctta tcgattctct gacgtcctct     60
cacaaggttg cagcatcaga cgagaagcgt atcgagacat taatatccga gattaagaat    120
atgtttagat gtatgggcta tggcgaaacg aatccctctg catatgacac tgcttgggta    180
gcaaggattc cagcacttga tggctctgac aaccctcact ttcctgagac agttgaatgg    240
attcttcaaa atcagttgaa agatgggtct tggggtgaag gattctactt cttggcatat    300
gacagaatac tggctacact tgcatgtatt attacgctta ccctctggcg tactggggag    360
acacaagtac acaaaggtat tgaattcttc aggacacaag ctggaaagat ggaagatgaa    420
gctgatagtc ataggccaag tggatttgaa atagtatttc ctgcaatgct aaaggaagct    480
aaaatcttag ggttggatct gccttacgat ttgccattcc tgaaacaaat catcgaaaag    540
cgggaggcta agcttaaaag gattcccact gatgttctct atgcccttcc aacaacgtta    600
ttgtattctt tggaaggttt gcaagaaata gtagactggc agaaaataat gaaacttcaa    660
tccaaggatg gatcatttct cagctctccg gcatctacag cggctgtatt catgcgtaca    720
gggaacaaaa agtgcttgga tttcttgaac tttgtcttga agaaattcgg aaaccatgtg    780
ccttgtcact atccgcttga tctatttgaa cgcttgtggg ccgttgatac tgttgagcgg    840
ctaggtatcg atcgccattt caaagaggag atcaaggacg cattggatta tgtttacagc    900
cattgggacg aaagaggcat tggatgggcg agagagaatc ctgttcctga tattgatgat    960
acagccatgg gccttcgaat attgagactg catggataca atgtatcctc agatgtttta   1020
aaaacattta gagatgagaa tggggagttc ttttgcttct tgggtcaaac acagagagga   1080
gttacagaca tgttaaacgt caatcgttgt tcacatgttt catttccggg agaaacgatc   1140
atggaagaag caaaactctg caccgaaagg tatctgagga atgctctgga aaatgtggat   1200
```

```
gcctttgaca aatgggcttt taaaaagaat attcggggag aggtggagta cgcactcaaa    1260
tatacttggc ataagagtat gccaaggctg gaggctagaa gttacattga aaactatggg    1320
ccaaatgatg cgtggcttgg caaaactgta tataggatgc catacatttc caatgaaaag    1380
tatttagaac tagcaaaact ggacttcaat aagctccagt ctatacacca aacagagctt    1440
caagatcttc gaaggtggtg gaaatcatcg ggtttctcaa agctaaattt cactcgcgag    1500
cgtgtcacag aaatatattt ttcatccgca tctttatgt ttgagccgga gttttctaag    1560
tgtagagaag tttatacaaa agcttccatt ttcacactta ttttcgatga tctttatgac    1620
gcccatggat ctttagacga tcttaagttg ttttccgaag cagtcaaaag atgggatcta    1680
tcactactag agagaatgcc acaagaaatg aaaatatgct tcctgggttt ctacaataca    1740
tttaatgaaa tagctgaaga agtacacaag aggcaagggc gtgacatgct aggtcacatt    1800
caaaatgttt gggaaatctt gctggcagct tacacgaaag aagcagaatg gtctaaaact    1860
aaatatgtgc catccttcga tgaatacata gagaatgcga gtgtgtcaat aacactggga    1920
acaattgttc tcataagtac tcttttcatc ggggaggttc ttacagatca tgtactctcc    1980
aaaattaatc atggatccag atttctacac ctcatgggct taacagggcg tttggtgaat    2040
gacaccaaaa cttatcaggc tgagagaggt caaggtgagg aggcttctgc catacaatgt    2100
tatatgaagg accatcctga aatctctgaa gaagaagctc tgaatcatgt ctataatgtc    2160
atggaaaatg ctctccaaga gttgaataag gaatttgtga ataacaaaga agtcccaccc    2220
aattgtagga ggttggtttt taacactgca agaatcatgc agttgtttta tatgcaaggg    2280
gatggtttga cactttcaca tgacatggaa attaaagatc atgtcaaaac ctgtctcttc    2340
ataccgattg cgtag                                                    2355

<210> SEQ ID NO 53
<211> LENGTH: 1986
<212> TYPE: DNA
<213> ORGANISM: Abies balsamea
<220> FEATURE:
<223> OTHER INFORMATION: pseudomature AbdiTPS3

<400> SEQUENCE: 53
aaacgagaat tcctccagg attttggaag gatgatctta tcgattctct gacgtcctct      60
cacaaggttg cagcatcaga cgagaagcgt atcgagacat taatatccga gattaagaat    120
atgtttagat gtatgggcta tggcgaaacg aatccctctg catatgacac tgcttgggta    180
gcaaggattc cagcacttga tggctctgac aaccctcact ttcctgagac agttgaatgg    240
attcttcaaa atcagttgaa agatgggtct tggggtgaag gattctactt cttggcatat    300
gacagaatac tggctacact tgcatgtatt attacgctta ccctctggcg tactggggag    360
acacaagtac acaaaggtat tgaattcttc aggacacaag ctggaaagat ggaagatgaa    420
gctgatagtc ataggccaag tggatttgaa atagtatttc ctgcaatgct aaaggaagct    480
aaaatcttag ggttggatct gccttacgat ttgccattcc tgaaacaaat catcgaaaag    540
cgggaggcta agcttaaaag gattcccact gatgttctct atgcccttcc aacaacgtta    600
ttgtattctt tggaaggttt gcaagaaata gtagactggc agaaaataat gaaacttcaa    660
tccaaggatg gatcatttct cagctctccg gcatctacag cggctgtatt catgcgtaca    720
gggaacaaaa agtgcttgga tttcttgaac tttgtcttga gaaattcgg aaaccatgtg    780 ccttgtcact atccgcttga tctatttgaa cgtttgtggg cggttgatac cgttgagcgg    840
```

```
ctaggtatcg atcgccattt caaagaggag atcaaggaag cattggatta tgtttacagc      900
cattgggacg aaagaggcat tggatgggcg agagagaatc ctgttcctga tattgatgat      960
acagccatgg gccttcgaat cttgagacta catggataca atgtatcctc agatgtttta     1020
aaaacattta gagatgagaa tggtgagttc ttttgcttct tgggtcaaac acagagagga     1080
gttaccgaca tgttaaacgt caatcgttgt tcacatgttt catttccggg agaaacgatc     1140
atggaagaag caaaactctg taccgaaagg tatctgagga atgctctgga aaatgtggac     1200
gcctttgaca aatgggcttt taaaaagaat attcggggag aggtggagta tgcactcaaa     1260
tatccttggc ataagagtat gccaaggctg gaggccagaa gctacattga aaactatggg     1320
cagaatgatt tgtggttggg caaaagttta tatatgatgc catatatttc caatgaaaag     1380
tatttagaac tagcgaaact ggacttcaat aaggtgcagt ctatacacca aaaagagctt     1440
caagatcttc gaaggtggtg gaaatcatcc ggtttcacgg atctgaattt cactcgtgag     1500
cgtgtgacgg aaatatattt ctcaccggca tcctttattt ttgagccgga gttttctaag     1560
tgcagagaag tttatacaaa aacttccaat ttcacagtta ttttagatga tctttatgac     1620
gcccatggat ctctagacga tcttaagttg ttttccgaat cagtcaaaag atgggatctc     1680
tcactaatag atgggaatgcc acaagaaatg aaaacatgtt tcaagggttt atacaatact     1740
ttcaatgaaa tagcgaaaga aggatgcaag aggcaggggc atgatgtcct aggctacatt     1800
agaaatgttt gggaaatcca gttggcagct tacacaaaag aagcagaatg gtctgaagct     1860
aaatatgttc cgtcctttaa tgaatacata gagaatgcga gtgtgtcaat agcactcgga     1920
acggtcgttc tcattagtgt tcttttttgtg gggagttctt acagatcaaa tactttcaaa     1980
aattaa                                                               1986
```

<210> SEQ ID NO 54
<211> LENGTH: 2346
<212> TYPE: DNA
<213> ORGANISM: Abies balsamea
<220> FEATURE:
<223> OTHER INFORMATION: pseudomature AbdiTPS4

<400> SEQUENCE: 54

```
aatcgagaat tcctccttc attttggaat aatgatatta tcaattcaat aacggcgtca       60
cacaaggttc aaacagggga ccggaagcgt atccagacat taatatctga aattaaaaat      120
gtgtttaatt ctatgggcga tggagaaacg agtccctctg catatgacac cgcttgggta      180
gcgaggattc cagcggttga tggctctgaa caacctcagt ttcctcagac acttgaatgg      240
attctacaaa atcagttgaa agatgggtct tggggtgaag aattctactt cttagcatat      300
gacagattac tggctacccct tgcatgcatt attaccctca ccatatggag aactggcaac      360
gtacaactgc ataaaggcat tgaattcttc aggaagcaag ttgtaaggat ggatgatgaa      420
gctgataacc accggccaag tggatttgaa atagtctttc ctgctatgtt aaatgaagca      480
aaaagtttag gattggatct gccttatgaa ttgccgttca ttgaacaaat ggttaaaaag      540
cgggaggcta agcttaaaat gattaccacg aatgtcctgt ataccattca acaacatta      600 ctttactctc tggaaggctt gcatgaaata gtagactttg ataaaataat caaacttcaa      660
tccaaggatg gatcattcct cggctccccg gcatctacag cggctgtatt catgcaaaca      720
gggaacacta aatgcttgga attcttggag ttcgttttaa ggaaatttag aaaccatgtg      780
cctagcgact atccctcga tctatttgaa cgtctttggg tcgttgacac ggttgaacga      840
ctagggattg atcgccattt caaaaaggag atcaaggacg cattggatta tgtgtacagc      900
```

```
tgttgggacg aaagaggcat tggctgggcg aaagacagcc ctatagccga tattgatgat    960
acagccatgg gccttcgaat cttgaggctg catggataca atgtatcccc agatgtttta   1020
aaaactttca aagatgagaa tggagagttc ttttgcttca tgggtcaaac acagagggga   1080
gttacggaca tgctaaacgt ttatcgctgt tcacaagttg cttttccggg agaaacgatc   1140
atggaagaag caaaactctg tactgaaagg tatctgcgca acgctctgga aaatgcggac   1200
gcctttgaca atgggctat  taaaaagaat attcgagggg aggtgagta  cgcactcaag   1260
tatccctggc atagaagtat gccaaggctg gaggtgagaa gctacattgg aaattacggg   1320
ccaaacgatg tctggcttgg aaagtctttg tatatgatgc catacattag caacgaaaaa   1380
tatttggaat tggcaaaact ggacttcaat agtgtgcaat ctctacacca agaggagatt   1440
cgagagcttg tgaggtggtg taaatcatca ggtttcacag agctcaagtt cacacgcgac   1500
cgtgtagttg aaacatattt cgcagttgcg tctagtatgt ttgagcccga gttctctacc   1560
tgtagagccg tttatacaaa aatttccgtt ctcctcgtca ttttagacga cctttacgat   1620
gggtatggat ctccagacga aatcaaactg ttctcggaag cagtcaaaag atgggatctc   1680
tctttgttag aacaaatgcc cgaccacatg aaaatctgct tcctgggatt gtacaacaca   1740
gttaatgaag tagctgaaga aggacgcaag acacagggcc atgatgtgct aggctacatt   1800
cgaaacttgt gggagatcca gctcgcagct ttcaccagag aagcagaatg gtctcaaggg   1860
aaatacgtgc cgtcttttga tgaatacata gagaacgccc aagtatcaat aggtgtagca   1920
actatacttc ttataactat tcttttcact gaagaggatg acattctctc ccatattgat   1980
tacggatcca aatttctccg tctcgctagc ttgacagcac gtttagcgaa cgacatcaaa   2040
acataccagg aggagagagc tcatggcgag gtggtttcgg ctatacagtg ttatatgaag   2100
gatcgtcctg aaattacaga ggaagaagct ctcaaatatg tctatggtcg aatggttaac   2160
gatctcgcag agttaaattc tgaatacttg aaatctaatg aaatgcccca aaattgcaag   2220
agactggttt ttgacactgc aagagtagcg cagttgttta ctatggaggg agacggtttg   2280
acatattcag atactatgga aattaaagaa cacatcaaaa agtgcctctt cgagccggct   2340
acctaa                                                              2346
```

<210> SEQ ID NO 55
<211> LENGTH: 781
<212> TYPE: PRT
<213> ORGANISM: Abies balsamea
<220> FEATURE:
<223> OTHER INFORMATION: pseudomature AbdiTPS4

<400> SEQUENCE: 55

```
Met Arg Glu Phe Pro Pro Ser Phe Trp Asn Asn Asp Ile Ile Asn Ser
 1               5                  10                  15

Ile Thr Ala Ser His Lys Val Gln Thr Gly Asp Arg Lys Arg Ile Gln
            20                  25                  30

Thr Leu Ile Ser Glu Ile Lys Asn Val Phe Asn Ser Met Gly Asp Gly
        35                  40                  45

Glu Thr Ser Pro Ser Ala Tyr Asp Thr Ala Trp Val Ala Arg Ile Pro
    50                  55                  60

Ala Val Asp Gly Ser Glu Gln Pro Gln Phe Pro Gln Thr Leu Glu Trp
65                  70                  75                  80

Ile Leu Gln Asn Gln Leu Lys Asp Gly Ser Trp Gly Glu Glu Phe Tyr
                85                  90                  95
```

```
Phe Leu Ala Tyr Asp Arg Leu Leu Ala Thr Leu Ala Cys Ile Ile Thr
            100                 105                 110
Leu Thr Ile Trp Arg Thr Gly Asn Val Gln Leu His Lys Gly Ile Glu
        115                 120                 125
Phe Phe Arg Lys Gln Val Val Arg Met Asp Asp Glu Ala Asp Asn His
    130                 135                 140
Arg Pro Ser Gly Phe Glu Ile Val Phe Pro Ala Met Leu Asn Glu Ala
145                 150                 155                 160
Lys Ser Leu Gly Leu Asp Leu Pro Tyr Glu Leu Pro Phe Ile Glu Gln
                165                 170                 175
Met Val Lys Lys Arg Glu Ala Lys Leu Lys Met Ile Thr Thr Asn Val
            180                 185                 190
Leu Tyr Thr Ile Gln Thr Thr Leu Leu Tyr Ser Leu Glu Gly Leu His
        195                 200                 205
Glu Ile Val Asp Phe Asp Lys Ile Ile Lys Leu Gln Ser Lys Asp Gly
    210                 215                 220
Ser Phe Leu Gly Ser Pro Ala Ser Thr Ala Ala Val Phe Met Gln Thr
225                 230                 235                 240
Gly Asn Thr Lys Cys Leu Glu Phe Leu Glu Phe Val Leu Arg Lys Phe
                245                 250                 255
Arg Asn His Val Pro Ser Asp Tyr Pro Leu Asp Leu Phe Glu Arg Leu
            260                 265                 270
Trp Val Val Asp Thr Val Glu Arg Leu Gly Ile Asp Arg His Phe Lys
        275                 280                 285
Lys Glu Ile Lys Asp Ala Leu Asp Tyr Val Tyr Ser Cys Trp Asp Glu
    290                 295                 300
Arg Gly Ile Gly Trp Ala Lys Asp Ser Pro Ile Ala Asp Ile Asp Asp
305                 310                 315                 320
Thr Ala Met Gly Leu Arg Ile Leu Arg Leu His Gly Tyr Asn Val Ser
                325                 330                 335
Pro Asp Val Leu Lys Thr Phe Lys Asp Glu Asn Gly Glu Phe Phe Cys
            340                 345                 350
Phe Met Gly Gln Thr Gln Arg Gly Val Thr Asp Met Leu Asn Val Tyr
        355                 360                 365
Arg Cys Ser Gln Val Ala Phe Pro Gly Glu Thr Ile Met Glu Glu Ala
    370                 375                 380
Lys Leu Cys Thr Glu Arg Tyr Leu Arg Asn Ala Leu Glu Asn Ala Asp
385                 390                 395                 400
Ala Phe Asp Lys Trp Ala Ile Lys Lys Asn Ile Arg Gly Glu Val Glu
                405                 410                 415
Tyr Ala Leu Lys Tyr Pro Trp His Arg Ser Met Pro Arg Leu Glu Val
            420                 425                 430
Arg Ser Tyr Ile Gly Asn Tyr Gly Pro Asn Asp Val Trp Leu Gly Lys
        435                 440                 445
Ser Leu Tyr Met Met Pro Tyr Ile Ser Asn Glu Lys Tyr Leu Glu Leu
    450                 455                 460
Ala Lys Leu Asp Phe Asn Ser Val Gln Ser Leu His Gln Glu Glu Ile
465                 470                 475                 480
Arg Glu Leu Val Arg Trp Cys Lys Ser Ser Gly Phe Thr Glu Leu Lys
                485                 490                 495
Phe Thr Arg Asp Arg Val Val Glu Thr Tyr Phe Ala Val Ala Ser Ser
            500                 505                 510
Met Phe Glu Pro Glu Phe Ser Thr Cys Arg Ala Val Tyr Thr Lys Ile
```

```
            515                 520                 525
Ser Val Leu Leu Val Ile Leu Asp Asp Leu Tyr Asp Gly Tyr Gly Ser
    530                 535                 540

Pro Asp Glu Ile Lys Leu Phe Ser Glu Ala Val Lys Arg Trp Asp Leu
545                 550                 555                 560

Ser Leu Leu Glu Gln Met Pro Asp His Met Lys Ile Cys Phe Leu Gly
                565                 570                 575

Leu Tyr Asn Thr Val Asn Glu Val Ala Glu Gly Arg Lys Thr Gln
            580                 585                 590

Gly His Asp Val Leu Gly Tyr Ile Arg Asn Leu Trp Glu Ile Gln Leu
            595                 600                 605

Ala Ala Phe Thr Arg Glu Ala Glu Trp Ser Gln Gly Lys Tyr Val Pro
    610                 615                 620

Ser Phe Asp Glu Tyr Ile Glu Asn Ala Gln Val Ser Ile Gly Val Ala
625                 630                 635                 640

Thr Ile Leu Leu Ile Thr Ile Leu Phe Thr Glu Glu Asp Asp Ile Leu
                645                 650                 655

Ser His Ile Asp Tyr Gly Ser Lys Phe Leu Arg Leu Ala Ser Leu Thr
            660                 665                 670

Ala Arg Leu Ala Asn Asp Ile Lys Thr Tyr Gln Glu Arg Ala His
    675                 680                 685

Gly Glu Val Val Ser Ala Ile Gln Cys Tyr Met Lys Asp Arg Pro Glu
    690                 695                 700

Ile Thr Glu Glu Glu Ala Leu Lys Tyr Val Tyr Gly Arg Met Val Asn
705                 710                 715                 720

Asp Leu Ala Glu Leu Asn Ser Glu Tyr Leu Lys Ser Asn Glu Met Pro
                725                 730                 735

Gln Asn Cys Lys Arg Leu Val Phe Asp Thr Ala Arg Val Ala Gln Leu
            740                 745                 750

Phe Thr Met Glu Gly Asp Gly Leu Thr Tyr Ser Asp Thr Met Glu Ile
                755                 760                 765

Lys Glu His Ile Lys Lys Cys Leu Phe Glu Pro Ala Thr
770                 775                 780

<210> SEQ ID NO 56
<211> LENGTH: 2346
<212> TYPE: DNA
<213> ORGANISM: Abies balsamea
<220> FEATURE:
<223> OTHER INFORMATION: pseudomature AbdiTPS4

<400> SEQUENCE: 56
atgcgagaat tcctccttc attttggaat aatgatatta tcaattcaat aacggcgtca      60
cacaaggttc aaacagggga ccggaagcgt atccagacat taatatctga aattaaaaat     120
gtgtttaatt ctatgggcga tggagaaacg agtccctctg catatgacac cgcttggta      180 gcgaggattc cagcggttga tggctctgaa caacctcagt tcctcagac acttgaatgg      240 attctacaaa atcagttgaa agatgggtct tggggtgaag aattctactt cttagcatat     300
gacagattac tggctaccct tgcatgcatt attaccctca ccatatggag aactggcaac     360
gtacaactgc ataaaggcat tgaattcttc aggaagcaag ttgtaaggat ggatgatgaa     420
gctgataacc accggccaag tggatttgaa atagtctttc ctgctatgtt aaatgaagca     480
aaaagtttag gattggatct gccttatgaa ttgccgttca ttgaacaaat ggttaaaaag     540
cgggaggcta agcttaaaat gattaccacg aatgtcctgt ataccattca acaacatta     600
```

```
ctttactctc tggaaggctt gcatgaaata gtagactttg ataaaataat caaacttcaa    660
tccaaggatg gatcattcct cggctccccg gcatctacag cggctgtatt catgcaaaca    720
gggaacacta aatgcttgga attcttggag ttcgttttaa ggaaatttag aaaccatgtg    780
cctagcgact atcccctcga tctatttgaa cgtctttggg tcgttgacac ggttgaacga    840
ctagggattg atcgccattt caaaaaggag atcaaggacg cattggatta tgtgtacagc    900
tgttgggacg aaagaggcat tggctgggcg aaagacagcc ctatagccga tattgatgat    960
acagccatgg gccttcgaat cttgaggctg catggataca atgtatcccc agatgtttta   1020
aaaactttca agatgagaa tggagagttc ttttgcttca tgggtcaaac acagagggga   1080
gttacggaca tgctaaacgt ttatcgctgt tcacaagttg cttttccggg agaaacgatc   1140
atggaagaag caaaactctg tactgaaagg tatctgcgca acgctctgga aaatgcggac   1200
gcctttgaca aatgggctat taaaaagaat attcgagggg aggtggagta cgcactcaag   1260
tatccctggc atagaagtat gccaaggctg gaggtgagaa gctacattgg aaattacggg   1320
ccaaacgatg tctggcttgg aaagtctttg tatatgatgc catacattag caacgaaaaa   1380
tatttggaat tggcaaaact ggacttcaat agtgtgcaat ctctacacca agaggagatt   1440
cgagagcttg tgaggtggtg taaatcatca ggtttcacag agctcaagtt cacacgcgac   1500
cgtgtagttg aaacatattt cgcagttgcg tctagtatgt ttgagcccga gttctctacc   1560
tgtagagccg tttatacaaa aatttccgtt ctcctcgtca ttttagacga cctttacgat   1620
gggtatggat ctccagacga aatcaaactg ttctcggaag cagtcaaaag atgggatctc   1680
tctttgttag aacaaatgcc cgaccacatg aaaatctgct tcctgggatt gtacaacaca   1740
gttaatgaag tagctgaaga aggacgcaag acacagggcc atgatgtgct aggctacatt   1800
cgaaacttgt gggagatcca gctcgcagct ttcaccagag aagcagaatg gtctcaaggg   1860
aaatacgtgc cgtctttttga tgaatacata gagaacgccc aagtatcaat aggtgtagca   1920
actatacttc ttataactat tcttttcact gaagaggatg acattctctc ccatattgat   1980
tacggatcca aatttctccg tctcgctagc ttgacagcac gtttagcgaa cgacatcaaa   2040
acataccagg aggagagagc tcatggcgag gtggtttcgg ctatacagtg ttatatgaag   2100
gatcgtcctg aaattacaga ggaagaagct ctcaaatatg tctatggtcg aatggttaac   2160
gatctcgcag agttaaattc tgaatacttg aaatctaatg aaatgcccca aaattgcaag   2220
agactggttt ttgacactgc aagagtagcg cagttgttta ctatggaggg agacggtttg   2280
acatattcag atactatgga aattaaagaa cacatcaaaa agtgcctctt cgagccggct   2340
acctaa                                                             2346
```

<210> SEQ ID NO 57
<211> LENGTH: 803
<212> TYPE: PRT
<213> ORGANISM: Abies balsamea
<220> FEATURE:
<223> OTHER INFORMATION: AbdiTPS1 transcriptome sequence

<400> SEQUENCE: 57

Met Ala Ser Met Thr Gly Gly Gln Gln Met Gly Arg Asp Pro Asn Ser
 1               5                  10                  15

Ser Ser Val Asp Lys Arg Glu Phe Pro Pro Gly Phe Trp Lys Asp Asp
                20                  25                  30

Leu Ile Asp Ser Leu Thr Ser Ser His Lys Val Ala Ala Ser Asp Glu
            35                  40                  45

-continued

```
Lys Arg Ile Glu Thr Leu Ile Ser Glu Ile Lys Asn Met Phe Arg Cys
 50                  55                  60

Met Gly Tyr Gly Glu Thr Asn Pro Ser Ala Tyr Asp Thr Ala Trp Val
 65                  70                  75                  80

Ala Arg Ile Pro Ala Leu Asp Gly Ser Asp Asn Pro His Phe Pro Glu
                 85                  90                  95

Thr Val Glu Trp Ile Leu Gln Asn Gln Leu Lys Asp Gly Ser Trp Gly
                100                 105                 110

Glu Gly Phe Tyr Phe Leu Ala Tyr Asp Arg Ile Leu Ala Thr Leu Ala
            115                 120                 125

Cys Ile Ile Thr Leu Thr Leu Trp Arg Thr Gly Glu Thr Gln Val His
        130                 135                 140

Lys Gly Ile Glu Phe Phe Arg Thr Gln Ala Gly Lys Met Glu Asp Glu
145                 150                 155                 160

Ala Asp Ser His Arg Pro Ser Gly Phe Glu Ile Val Phe Pro Ala Met
                165                 170                 175

Leu Lys Glu Ala Lys Ile Leu Gly Leu Asp Leu Pro Tyr Asp Leu Pro
            180                 185                 190

Phe Leu Lys Gln Ile Ile Glu Lys Arg Glu Ala Lys Leu Lys Arg Ile
        195                 200                 205

Pro Thr Asp Val Leu Tyr Ala Leu Pro Thr Thr Leu Leu Tyr Ser Leu
    210                 215                 220

Glu Gly Leu Gln Glu Ile Val Asp Trp Gln Lys Ile Met Lys Leu Gln
225                 230                 235                 240

Ser Lys Asp Gly Ser Phe Leu Ser Ser Pro Ala Ser Thr Ala Ala Val
                245                 250                 255

Phe Met Arg Thr Gly Asn Lys Lys Cys Leu Asp Phe Leu Asn Phe Val
            260                 265                 270

Leu Lys Lys Phe Gly Asn His Val Pro Cys His Tyr Pro Leu Asp Leu
        275                 280                 285

Phe Glu Arg Leu Trp Ala Val Asp Thr Val Glu Arg Leu Gly Ile Asp
    290                 295                 300

Arg His Phe Lys Glu Glu Ile Lys Glu Ala Leu Asp Tyr Val Tyr Ser
305                 310                 315                 320

His Trp Asp Glu Arg Gly Ile Gly Trp Ala Arg Glu Asn Pro Val Pro
                325                 330                 335

Asp Ile Asp Asp Thr Ala Met Gly Leu Arg Ile Leu Arg Leu His Gly
            340                 345                 350

Tyr Asn Val Ser Ser Asp Val Leu Lys Thr Phe Arg Asp Glu Asn Gly
        355                 360                 365

Glu Phe Phe Cys Phe Leu Gly Gln Thr Gln Arg Gly Val Thr Asp Met
    370                 375                 380

Leu Asn Val Asn Arg Cys Ser His Val Ser Phe Pro Gly Glu Thr Ile
385                 390                 395                 400

Met Glu Glu Ala Lys Leu Cys Thr Glu Arg Tyr Leu Arg Asn Ala Leu
                405                 410                 415

Glu Asn Val Asp Ala Phe Asp Lys Trp Ala Phe Lys Lys Asn Ile Arg
            420                 425                 430

Gly Glu Val Glu Tyr Ala Leu Lys Tyr Pro Trp His Lys Ser Met Pro
        435                 440                 445

Arg Leu Glu Ala Arg Ser Tyr Ile Glu Asn Tyr Gly Pro Asp Asp Val
    450                 455                 460
```

Trp Leu Gly Lys Thr Val Tyr Met Met Pro Tyr Ile Ser Asn Glu Lys
465                 470                 475                 480

Tyr Leu Glu Leu Ala Lys Leu Asp Phe Asn Lys Val Gln Ser Ile His
            485                 490                 495

Gln Thr Glu Leu Gln Asp Leu Arg Arg Trp Lys Ser Ser Gly Phe
        500                 505                 510

Thr Asp Leu Asn Phe Thr Arg Glu Arg Val Thr Glu Ile Tyr Phe Ser
            515                 520                 525

Pro Ala Ser Phe Ile Phe Glu Pro Glu Phe Ser Lys Cys Arg Glu Val
530                 535                 540

Tyr Thr Lys Thr Ser Asn Phe Thr Val Ile Leu Asp Asp Leu Tyr Asp
545                 550                 555                 560

Ala His Gly Ser Leu Asp Asp Leu Lys Leu Phe Thr Glu Ser Val Lys
            565                 570                 575

Arg Trp Asp Leu Ser Leu Val Asp Gln Met Pro Gln Gln Met Lys Ile
            580                 585                 590

Cys Phe Val Gly Phe Tyr Asn Thr Phe Asn Glu Ile Ala Lys Glu Gly
            595                 600                 605

Arg Glu Ser Gln Gly Arg Asp Val Leu Gly Tyr Ile Gln Asn Val Trp
610                 615                 620

Lys Val Gln Leu Glu Ala Tyr Thr Lys Glu Ala Glu Trp Ser Glu Ala
625                 630                 635                 640

Lys Tyr Val Pro Ser Phe Asn Glu Tyr Ile Glu Asn Ala Ser Val Ser
            645                 650                 655

Ile Ala Leu Gly Thr Val Val Leu Ile Ser Ala Leu Phe Thr Gly Glu
            660                 665                 670

Val Leu Thr Asp Glu Val Leu Ser Lys Ile Asp Arg Gly Ser Arg Phe
            675                 680                 685

Leu Gln Leu Met Gly Leu Thr Gly Arg Leu Val Asn Asp Thr Lys Thr
690                 695                 700

Tyr Gln Ala Glu Arg Gly Gln Gly Glu Val Ala Ser Ala Ile Gln Cys
705                 710                 715                 720

Tyr Met Lys Asp His Pro Lys Ile Ser Glu Glu Ala Leu Lys His
            725                 730                 735

Val Tyr Thr Val Met Glu Asn Ser Leu Glu Glu Leu Asn Arg Glu Phe
            740                 745                 750

Val Asn Asn Lys Ile Pro Asp Ile Tyr Arg Arg Leu Val Phe Glu Thr
            755                 760                 765

Ala Arg Ile Met Gln Leu Phe Tyr Met Gln Gly Asp Gly Leu Thr Leu
770                 775                 780

Ser His Asp Met Glu Ile Lys Glu His Val Lys Asn Cys Leu Phe Gln
785                 790                 795                 800

Pro Val Ala

<210> SEQ ID NO 58
<211> LENGTH: 866
<212> TYPE: PRT
<213> ORGANISM: Abies balsamea
<220> FEATURE:
<223> OTHER INFORMATION: AbdiTPS4 transcriptome sequence

<400> SEQUENCE: 58

Met Ala Leu Pro Val Cys Ser Ile Lys Ser His Ile Pro Ile Thr Thr
1               5                   10                  15

Ile Ala Ser Ala Lys Met His Tyr Thr Ser Asn Lys Gly Ile Thr Ala

-continued

```
                20                  25                  30
Lys Gly Arg Ser Arg Cys Ile Arg Leu Ser Pro Asn Lys Ile Val Ala
            35                  40                  45
Cys Ala Gly Glu Ala Asp Arg Thr Phe Pro Ser Gln Ser Leu Glu Lys
        50                  55                  60
Thr Ala Leu Phe Pro Asp Pro Phe Ser Glu Lys Asn Gly Thr Pro Ser
65                  70                  75                  80
Asn Phe Thr Pro Pro Asn Arg Glu Phe Pro Ser Phe Trp Asn Asn
                85                  90                  95
Asp Ile Ile Asn Ser Ile Thr Ala Ser His Lys Val Gln Thr Gly Asp
                100                 105                 110
Arg Lys Arg Ile Gln Thr Leu Ile Ser Glu Ile Lys Asn Val Phe Asn
            115                 120                 125
Ser Met Gly Asp Gly Glu Thr Ser Pro Ser Ala Tyr Asp Thr Ala Trp
        130                 135                 140
Val Ala Arg Ile Pro Ala Val Asp Gly Ser Glu Gln Pro Gln Phe Pro
145                 150                 155                 160
Gln Thr Leu Glu Trp Ile Leu Gln Asn Gln Leu Lys Asp Gly Ser Trp
                165                 170                 175
Gly Glu Glu Phe Tyr Phe Leu Ala Tyr Asp Arg Leu Leu Ala Thr Leu
                180                 185                 190
Ala Cys Ile Ile Thr Leu Thr Ile Trp Arg Thr Gly Asn Val Gln Leu
            195                 200                 205
His Lys Gly Ile Glu Phe Phe Arg Lys Gln Val Val Arg Met Asp Asp
        210                 215                 220
Glu Ala Asp Asn His Arg Pro Ser Gly Phe Glu Ile Val Phe Pro Ala
225                 230                 235                 240
Met Leu Asn Glu Ala Lys Ser Leu Gly Leu Asp Leu Pro Tyr Glu Leu
                245                 250                 255
Pro Phe Ile Glu Gln Met Val Lys Lys Arg Glu Ala Lys Leu Lys Met
                260                 265                 270
Ile Thr Thr Asn Val Leu Tyr Thr Ile Gln Thr Thr Leu Leu Tyr Ser
            275                 280                 285
Leu Glu Gly Leu His Glu Ile Val Asp Phe Asp Lys Ile Ile Lys Leu
        290                 295                 300
Gln Ser Lys Asp Gly Ser Phe Leu Gly Ser Pro Ala Ser Thr Ala Ala
305                 310                 315                 320
Val Phe Met Gln Thr Gly Asn Thr Lys Cys Leu Glu Phe Leu Glu Phe
                325                 330                 335
Val Leu Arg Lys Phe Arg Asn His Val Pro Ser Asp Tyr Pro Leu Asp
                340                 345                 350
Leu Phe Glu Arg Leu Trp Val Val Asp Thr Val Glu Arg Leu Gly Ile
            355                 360                 365
Asp Arg His Phe Lys Lys Glu Ile Lys Asp Ala Leu Asp Tyr Val Tyr
        370                 375                 380
Ser Cys Trp Asp Glu Arg Gly Ile Gly Trp Ala Lys Asp Ser Pro Ile
385                 390                 395                 400
Ala Asp Ile Asp Asp Thr Ala Met Gly Leu Arg Ile Leu Arg Leu His
                405                 410                 415
Gly Tyr Asn Val Ser Pro Asp Val Leu Lys Thr Phe Lys Asp Glu Asn
                420                 425                 430
Gly Glu Phe Phe Cys Phe Met Gly Gln Thr Gln Arg Gly Val Thr Asp
            435                 440                 445
```

-continued

```
Met Leu Asn Val Tyr Arg Cys Ser Gln Val Ala Phe Pro Gly Glu Thr
            450                 455                 460

Ile Met Glu Glu Ala Lys Leu Cys Thr Glu Arg Tyr Leu Arg Asn Ala
465                 470                 475                 480

Leu Glu Asn Ala Asp Ala Phe Asp Lys Trp Ala Ile Lys Lys Asn Ile
                485                 490                 495

Arg Gly Glu Val Glu Tyr Ala Leu Lys Tyr Pro Trp His Arg Ser Met
                500                 505                 510

Pro Arg Leu Glu Val Arg Ser Tyr Ile Gly Asn Tyr Gly Pro Asn Asp
            515                 520                 525

Val Trp Leu Gly Lys Ser Leu Tyr Met Met Pro Tyr Ile Ser Asn Glu
            530                 535                 540

Lys Tyr Leu Glu Leu Ala Lys Leu Asp Phe Asn Ser Val Gln Ser Leu
545                 550                 555                 560

His Gln Glu Glu Ile Arg Glu Leu Val Arg Trp Cys Lys Ser Ser Gly
                565                 570                 575

Phe Thr Glu Leu Lys Phe Thr Arg Asp Arg Val Val Glu Thr Tyr Phe
                580                 585                 590

Ala Val Ala Ser Ser Met Phe Glu Pro Glu Phe Ser Thr Cys Arg Ala
            595                 600                 605

Val Tyr Thr Lys Ile Ser Val Leu Leu Val Ile Leu Asp Asp Leu Tyr
            610                 615                 620

Asp Gly Tyr Gly Ser Pro Asp Glu Ile Lys Leu Phe Ser Glu Ala Val
625                 630                 635                 640

Lys Arg Trp Asp Leu Ser Leu Leu Glu Gln Met Pro Asp His Met Lys
                645                 650                 655

Ile Cys Phe Leu Gly Leu Tyr Asn Thr Val Asn Glu Val Ala Glu Glu
                660                 665                 670

Gly Arg Lys Thr Gln Gly His Asp Val Leu Gly Tyr Ile Arg Asn Leu
            675                 680                 685

Trp Glu Ile Gln Leu Ala Ala Phe Thr Arg Glu Ala Glu Trp Ser Gln
690                 695                 700

Gly Lys Tyr Val Pro Ser Phe Asp Glu Tyr Ile Glu Asn Ala Gln Val
705                 710                 715                 720

Ser Ile Gly Val Ala Thr Ile Leu Ile Thr Ile Leu Phe Thr Glu
                725                 730                 735

Glu Asp Asp Ile Leu Ser His Ile Asp Tyr Gly Ser Lys Phe Leu Arg
                740                 745                 750

Leu Ala Ser Leu Thr Ala Arg Leu Ala Asn Asp Ile Lys Thr Tyr Gln
            755                 760                 765

Glu Glu Arg Ala His Gly Glu Val Val Ser Ala Ile Gln Cys Tyr Met
            770                 775                 780

Lys Asp Arg Pro Glu Ile Thr Glu Glu Ala Leu Lys Tyr Val Tyr
785                 790                 795                 800

Gly Arg Met Val Asn Asp Leu Ala Glu Leu Asn Ser Glu Tyr Leu Lys
                805                 810                 815

Ser Asn Glu Met Pro Gln Asn Cys Lys Arg Leu Val Phe Asp Thr Ala
                820                 825                 830

Arg Val Ala Gln Leu Phe Thr Met Glu Gly Asp Gly Leu Thr Tyr Ser
            835                 840                 845

Asp Thr Met Glu Ile Lys Glu His Ile Lys Lys Cys Leu Phe Glu Pro
850                 855                 860
```

Ala Thr
865

<210> SEQ ID NO 59
<211> LENGTH: 1131
<212> TYPE: DNA
<213> ORGANISM: Xanthophyllomyces dendrorhous
<220> FEATURE:
<223> OTHER INFORMATION: crtE GGPP synthase

<400> SEQUENCE: 59

```
atggattacg cgaacatcct cacagcaatt ccactcgagt ttactcctca ggatgatatc      60
gtgctccttg aaccgtatca ctacctagga agaaccctg gaaaagaaat tcgatcacaa     120
ctcatcgagg ctttcaacta ttggttggat gtcaagaagg aggatctcga ggtcatccag    180
aacgttgttg gcatgctaca taccgctagc ttattaatgg acgatgtgga ggattcatcg    240
gtcctcaggc gtgggtcgcc tgtggcccat ctaatttacg ggattccgca gacaataaac    300
actgcaaact acgtctactt tctggcttat caagagatct tcaagcttcg cccaacaccg    360
atacccatgc ctgtaattcc tccttcatct gcttcgcttc aatcatccgt ctcctctgca    420
tcctcctcct cctcggcctc gtctgaaaac gggggcacgt caactcctaa ttcgcagatt    480
ccgttctcga aagatacgta tcttgataaa gtgatcacag acgagatgct ttccctccat    540
agagggcaag gcctggagct attctggaga gatagtctga cgtgtcctag cgaagaggaa    600
tatgtgaaaa tggttcttgg aaagacggga ggtttgttcc gtatagcggt cagattgatg    660
atggcaaagt cagaatgtga catagacttt gtccagcttg tcaacttgat ctcaatatac    720
ttccagatca gggatgacta tatgaacctt cagtcttctg agtatgccca taataagaat    780
tttgcagagg acctcacaga aggaaaattc agtttcccca ctatccactc gattcatgcc    840
aaccctcat cgagactcgt catcaatacg ttgcagaaga aatcgacctc tcctgagatc    900
cttcaccact gtgtaaacta catgcgcaca gaaacccact cattcgaata tactcaggaa    960
gtcctcaaca ccttgtcagg tgcactcgag agagaactag gaaggcttca aggagagttc   1020
gcagaagcta actcaaagat tgatcttgga gacgtagagt cggaaggaag aacggggaag   1080
aacgtcaaat tggaagcgat cctgaaaaag ctagccgata tccctctgtg a            1131
```